US009290546B2

(12) United States Patent
Weiner et al.

(10) Patent No.: US 9,290,546 B2
(45) Date of Patent: Mar. 22, 2016

(54) HTERT SEQUENCES AND METHODS FOR USING THE SAME

(71) Applicant: The Trustees of the University of Pennsylvania, Philadelphia, PA (US)

(72) Inventors: David B. Weiner, Merion, PA (US); Jian Yan, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 8 days.

(21) Appl. No.: 14/139,660

(22) Filed: Dec. 23, 2013

(65) Prior Publication Data
US 2014/0186384 A1   Jul. 3, 2014

Related U.S. Application Data

(62) Division of application No. 13/458,013, filed on Apr. 27, 2012, now Pat. No. 8,697,084, which is a division of application No. 12/375,518, filed as application No. PCT/US2007/074769 on Jul. 30, 2007, now Pat. No. 8,168,769.

(60) Provisional application No. 60/890,352, filed on Feb. 16, 2007, provisional application No. 60/833,856, filed on Jul. 28, 2006, provisional application No. 60/833,861, filed on Jul. 28, 2006.

(51) Int. Cl.
| C07K 14/005 | (2006.01) |
| A61K 39/00 | (2006.01) |
| A61K 39/12 | (2006.01) |
| A61K 39/21 | (2006.01) |
| C12N 7/00 | (2006.01) |
| A61K 38/00 | (2006.01) |

(52) U.S. Cl.
CPC ........... *C07K 14/005* (2013.01); *A61K 39/0011* (2013.01); *A61K 39/12* (2013.01); *A61K 39/21* (2013.01); *C12N 7/00* (2013.01); *A61K 38/00* (2013.01); *A61K 39/00* (2013.01); *A61K 2039/523* (2013.01); *A61K 2039/53* (2013.01); *A61K 2039/54* (2013.01); *A61K 2039/55538* (2013.01); *A61K 2039/585* (2013.01); *C12N 2710/20034* (2013.01); *C12N 2740/16034* (2013.01); *C12N 2740/16122* (2013.01); *C12N 2740/16134* (2013.01); *C12N 2740/16222* (2013.01); *C12N 2740/16234* (2013.01); *C12N 2740/16322* (2013.01); *C12N 2740/16334* (2013.01); *C12N 2760/16134* (2013.01); *C12N 2770/24234* (2013.01)

(58) Field of Classification Search
None
See application file for complete search history.

(56) References Cited

U.S. PATENT DOCUMENTS

| 4,510,245 A | 4/1985 | Cousens et al. |
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | Davis et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III |
| 5,389,368 A | 2/1995 | Curtiss, III |
| 5,424,065 A | 6/1995 | Curtiss, III et al. |
| 5,451,499 A | 9/1995 | Cochran |
| 5,453,364 A | 9/1995 | Paoletti |

(Continued)

FOREIGN PATENT DOCUMENTS

| GB | 2317891 | 4/1998 |
| WO | WO94/16737 | 8/1994 |

(Continued)

OTHER PUBLICATIONS

Ehrhardt et al., Blood, 2003;102:2403-2411.*

(Continued)

*Primary Examiner* — Nicole Kinsey White
(74) *Attorney, Agent, or Firm* — Riverside Law LLP

(57) ABSTRACT

Improved anti-HIV immunogens and nucleic acid molecules that encode them are disclosed. Immunogens disclosed include those having consensus sequences for HIV Subtype A Envelope protein, those having consensus sequences for HIV Subtype B Envelope protein, those having consensus sequences for HIV Subtype C Envelope protein, those having consensus sequences for HIV Subtype D Envelope protein, those having consensus sequences for HIV Subtype B consensus Nef-Rev protein, and those having consensus sequences form HIV Gag protein subtypes A, B, C and D. Improved anti-HPV immunogens and nucleic acid molecules that encode them; improved anti-HCV immunogens and nucleic acid molecules that encode them; improved hTERT immunogens and nucleic acid molecules that encode them; and improved anti-Influenza immunogens and nucleic acid molecules that encode them are disclosed as well methods of inducing an immune response in an individual against HIV, HPV, HCV, hTERT and Influenza are disclosed.

12 Claims, 50 Drawing Sheets

(56) References Cited

U.S. PATENT DOCUMENTS

| | | | |
|---|---|---|---|
| 5,462,734 | A | 10/1995 | Letchworth, III |
| 5,470,734 | A | 11/1995 | Sondermeijer et al. |
| 5,474,935 | A | 12/1995 | Chatterjee et al. |
| 5,482,713 | A | 1/1996 | Paoletti |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,156,319 | A | 12/2000 | Cohen et al. |
| 6,342,224 | B1 | 1/2002 | Bruck et al. |
| 6,468,982 | B1 | 10/2002 | Weiner et al. |
| 6,589,529 | B1 | 7/2003 | Choi et al. |
| 7,262,288 | B1* | 8/2007 | Cech et al. .............. 536/23.5 |
| 2004/0005711 | A1 | 1/2004 | Regts et al. |
| 2004/0106100 | A1 | 6/2004 | Weiner et al. |
| 2007/0041941 | A1 | 2/2007 | Weiner et al. |
| 2007/0106062 | A1 | 5/2007 | Ayyavoo et al. |
| 2008/0090778 | A1* | 4/2008 | Scarselli et al. .............. 514/44 |

FOREIGN PATENT DOCUMENTS

| | | |
|---|---|---|
| WO | 98/36772 | 8/1998 |
| WO | 2004/037175 | 5/2004 |
| WO | 2005/028625 | 3/2005 |
| WO | 2005028634 | 3/2005 |

OTHER PUBLICATIONS

Gao, F. et al., "Antigenicity and immunogenicity of a synthetic human immunodeficiency virus type 1 group m consensus envelope glycoprotein", J. Virol., 2005, 79:1154-1163.

Scriba, T.J. et al., "Functionally-inactive and immunogenic Tat, Rev and Nef DNA vaccines derived from sub-Saharan subtype C human immunodeficiency virus type 1 consensus sequences", Vaccine, 2005, 23:1158-1169.

Doria-Rose, N.A. et al., "Human Immunodeficiency Virus Type 1 subtype B Ancestral Envelope Protein is Functional and Elicits Neutralizing Antibodies in Rabbits Similar to Those Elicited by a Circulating Subtype B Envelope", J. Virol., 2005, 79:11214-11224.

Gao, F. et al., "Centralized immunogens as a vaccine strategy to overcome HIV-1 diversity", Expert Rev. Vaccines, 2004, 3:S161-S168.

Mullins, J.I. et al., "Immunogen sequence: the fourth tier of AIDS vaccine design", Expert Rev. Vaccines, 2004, 3: S151-S159.

Nickle, D.C. et al., "Consensus and ancestral state HIV vaccines", Science, 2003, 299:1515-1517.

Derdeyn, C.A. et al., "Envelope-constrained neutralization-sensitive HIV-1 after heterosexual transmission", Science, 2004, 303:2019-2022.

Chohan, B. et al., "Selection for Human Immunodeficiency Virus Type 1 envelope glycosylation variants with shorter V1-V2 loop sequences occurs during transmission of certain genetic subtypes and may impact viral RNA levels", J. Virol., 2005, 79:6528-6531.

Pickora, C. et al., "Identification of two N-linked glycosylation sites within the core of the Simian Immunodeficiency virus glycoprotein whose removal enhances sensitivity to soluble CD4", J. Virol., 2005, 79:12575-12583.

Andre, S. et al., "Increased immune response elicited by DNA vaccination with a synthetic gp120 sequence with optimized codon usage", J. Virol., 1998, 72:1497-1503.

Deml, L. et al., "Multiple effects of codon usage optimization on expression and immunogenicity of DNA candidate vaccines encoding the human immunodeficiency virus type 1 gag protein", J. Virol., 2001, 75:10991-11001.

Muthumani, K. et al., "Novel engineered HIV-1 East African Clade-A gp160 plasmid construct induces strong humoral and cell-mediated immune responses in vivo", Virology, 2003, 314:134-146.

Schneider, R.M. et al., "Inactivation of the human immunodefiency virus type 1 inhibitory elements allows Rev-independent expression of Gag and Gag/protease and particle formation", J. Virol., 1997, 71:4892-4903.

Yang, J.S. et al., "Induction of potent Th1-Type immune responses from a novel DNA vaccine for West Nile Virus New York Isolate (WNV-NY1999)", J. Infect Diseases, 2001, 184:809-816.

Altschul et al., "Gapped BLAST and PSI-BLAST: a new generation of protein database search programs", Nuc. Acids Res., 1997, 25:3389-3402.

Altschul et al., "Basic local alignment search tool", J. Mol. Biol., 1990, 215:403-410.

Henikoff et al., "Amino acid substitution matrices from protein blocks", Proc. Natl. Acad. Sci. USA, 1992, 89:10915-10919.

Karlin et al., "Applications and statistics for multiple high-scoring segments in molecular sequences", Proc. Natl. Acad. Sci. USA, 1993, 90:5873-5787.

Thompson, J.D. et al., "The CLUSTAL_X windows interface: flexible strategies for multiple sequence alignment aided by quality analysis tools", Nucleic Acids Research,1997, 25:4876-4882.

Kuiken, C. et al., "HIV Sequence Databases", AIDS Rev., 2003, 5:52-61.

Berlioz-Torrent, C. et al., "Interactions of the cytoplasmic domains of human and simian retroviral transmembrane proteins with components of the clathrin adaptor complexes modulate intracellular and cell surface expression of envelope glycoproteins", J. Virol., 1999, 73:1350-1359.

Bultmann, A. et al., "Identification of two sequences in the cytoplasmic tail of the human immunodeficiency virus type 1 envelope glycoprotein that inhibit cell surface expression", J. Virol., 2001, 75:5263-5276.

Puffer, B.A. et al., "CD4 independent of Simian Immunodeficiency Virus Envs is associated with macrophage tropism, neutralization sensitivity, and attenuated pathogenicity", J. Virol., 2002, 76:2595-2605.

Kolchinsky, P. et al., "Increased neutrlization sensitity of CD4-independent Human Immunodeficiency Virus variants", J. Virol., 2001, 75:2041-2050.

Edwards, T.G. et al., "Relationships between CD4 independence, neutralization sensitivity, and exposure of a CD4-induced epitope in a Human Immunodeficiency Virus type 1 envelope protein", J. Virol., 2001, 75:5230-5239.

Almond, N. et al., "Protection by attenuated simian immunodeficiency virus in macaques against challenge with virus-infected cells", Lancet, 1995, 345:1342-1344.

Berman, P.W. et al., "Protection of MN-rgp120-immunized chimpanzees from heterologous HIV-1 challenge by DNA vaccination", J Infect Dis, 1996, 173:52-59.

Boyer, J. et al., "Protection of chimpanzees from high-dose heterologous HIV-1 challenge by DNA vaccination", Nat Med, 1997, 3:526-532.

Daniel, M.C. et al., "Protective effects of a live attenuated SIV vaccine with a deletion in the nef gene", Science, 1992, 258:1938-1941.

Gaschen et al., "Diversity considerations in HIV-1 vaccine selection," Science (2002) 296:2354-2360.

Yan et al., "Enhanced cellular immune responses elicited by an engineered HIV-1 subtype B consensus-based envelope DNA vaccine," Molecular Therapy (2007) 15(2):411-421.

Kothe et al., "Ancestral and consensus envelope immunogens for HIV-1 subtype C," Virology (2006) 352:438-449.

Kumar et al., "Immunogenicity testing of a novel engineered HIV-1 envelope gp140 DNA vaccine construct," DNA Cell Biol (2006) 25(7):383-392.

(56) References Cited

OTHER PUBLICATIONS

Reichenback, D. et al. "Efficacy of a novel engineered HPV-16 plasmid DNA vaccine encoding a E6/E7 fusion gene", Proceedings of the American Association for Cancer Research Annual Meeting, 2006, 47:330.
Raghunath, M. et al., "Carboxy-terminal conversion of profibrillin to fibrillin at a basic site by PACE/furin-like activity required to incorporation in the matrix", Journal of Cell Science, 1999, 112:1093-1100.
Yan, J. et al., "Induction of antitumor immunity in vivo following delivery of a novel HPV-16 DNA vaccine encoding an E6/E7 fusion antigen", Vaccine, Elsevier Ltd, GB LNKD-DOI:10.1016/J.Vaccine, 2009, 27:431-440.
Database Geneseq [Online], Dec. 15, 2005, "HPV 16 E7 variatn protein sequence", retrieved from EBI Accession No. GSP:AED13079, Database Accession No. AED 13079.
Database EMBL [online], Dec. 17, 2008, "Sequence from Patent WO2006117671", retrieved from EBI accession No. GM010652, Database Accession No. GM010652.
Database Geneseq [online], Apr. 6, 2006, "hTERT opti mRNA", retrieved from EBI accession No. GSNAEF70095, Database Accession No. AEF70095.
Ray, S.C. et al., "Divergent and convergent evolution after a common-source outbreak of hepatitis C virus", The Journal of Experimental Medicine, 2005, 201(11):1753-1759.
Longfei, Huo et al., "Cellular & Molecular Immunology 1 Cancer Immunotherapy Targeting the Telomerase Reverse Transcriptase", Cellular & Molecular Immunology, 2006, 3:1-9.
Matthews et al, "AIDS Research and Human Retroviruses," (1987) 3(1):197-206.
Burton et al., "Why do we not have an HIV vaccine and how can we make one?," Nature Medicine (1998) 4 (5):495-498.
Desrosiers "Prospects for an AIDS vaccine," Nature Medicine (2004) 10(3):221-223.
GenBank Accession No. AX029189, Sep. 15, 2000.
GenBank Accession No. AAE90044, Apr. 20, 2002.
GenBank Accession No. AEC98783, Dec. 1, 2005.

* cited by examiner

SEQUENCE LISTING

```
<160> NUMBER OF SEQ ID NOS: 44

<210> SEQ ID NO 1
<211> LENGTH: 2142
<212> TYPE: DNA
<213> ORGANISM: Artificial Sequence
<220> FEATURE:
<223> OTHER INFORMATION: Subtype A consensus Envelope DNA sequence
      construct

<400> SEQUENCE: 1
ggatccatgg actggacctg gattctgttc ctggtggccg ccgccaccag agtgcacagc      60
agagtgatgg gcatccagcg gaattgccag cacctgtgga gatggggcac catgatcctg     120
ggcatgatca tcatctgctc tgccgccgag aacctgtggg tgaccgtgta ctacggcgtg     180
cctgtgtgga aggacgccga gaccaccctg ttctgcgcca gcgacgccaa ggcctacgat     240
accgaagtgc acaatgtgtg ggccaccac gcctgcgtgc ctaccgatcc caaccccag      300 gagatcaacc tggagaacgt gaccgaggag ttcaacatgt ggaagaacaa catggtggag     360
cagatgcaca ccgacatcat cagcctgtgg gaccagagcc tgaagccttg cgtgaagctg     420
acccctctgt gcgtgaccct gaactgcagc aacgtgaacg tgaccaccaa catcatgaag     480
ggcgagatca agaactgcag cttcaacatg accaccgagc tgcgggacaa gaagcagaaa     540
gtgtacagcc tgttctacaa gctggacgtg gtgcagatca acaagagcaa cagcagcagc     600
cagtaccggc tgatcaactg caacaccagc gccatcaccc aggcctgccc caaagtgagc     660
ttcgagccca tccccatcca ctactgcgcc cctgccggct tcgccatcct gaagtgcaag     720
gacaaggagt taacggcac cggcccctgc aagaatgtga gcaccgtgca gtgcacccac     780
ggcatcaagc ccgtggtgtc cacccagctg ctgctgaacg gcagcctggc cgaggaggaa     840
gtgatgatcc ggagcgagaa catcaccaac aacgccaaga acatcatcgt gcagctgacc     900
aagcccgtga agatcaattg cacccggccc aacaacaaca cccggaagag catcagaatc     960
ggccctggcc aggccttcta cgccaccggc gacatcatcg gcgatatcag gcaggcccac    1020
tgcaatgtga gccggaccga gtggaacgag accctgcaga agtggccaa gcagctgcgg     1080 aagtacttca caacaagac catcatcttc accaacagca gcggcggcag actgagaatc    1140
accacccaca gcttcaattg tggcggcgag ttcttctact gcaatacctc cggcctgttc    1200
aacagcacct ggaacggcaa cggcaccaag aagaagaaca gcaccgagag caacgacacc    1260
atcaccctgc cctgccggat caagcagatc atcaatatgt ggcagagggt gggccaggcc    1320
atgtacgccc ctcccatcca gggcgtgatc agatgcgaga gcaacatcac cggcctgctg    1380
ctgaccagag atggcggcga caacaacagc aagaacgaga ccttcagacc tggcggcgga    1440
gacatgaggg acaactggcg gagcgagctg tacaagtaca aagtggtgaa gatcgagccc    1500
ctgggcgtgg cccccaccaa ggccaagaga agagtggtgg agcgggagaa gagagctgtg    1560
ggcatcggcg ccgtgttcct gggcttcctg ggagccgccg gaagcaccat gggagccgcc    1620
agcatcaccc tgaccgtgca ggccagacag ctgctgagcg gcattgtgca gcagcagagc    1680
```

```
aacctgctga gagccatcga ggcccagcag cacctgctga agctgacagt gtggggcatc   1740
aaacagctgc aggcccgcgt gctggccgtg gagagatacc tgaaggacca gcagctgctg   1800
ggcatctggg gctgcagcgg caagctgatc tgcaccacca acgtgccctg gaatagcagc   1860
tggagcaaca agagccagag cgagatctgg gacaacatga cctggctgca gtgggacaag   1920
gagatcagca actacaccga tatcatctac aacctgatcg aggagagcca gaaccagcag   1980
gagaagaacg agcaggatct gctggccctg gacaagtggg ccaacctgtg gaactggttc   2040
gacatcagca actggctgtg gtacatcaag atcttcatca tgattgtggg cggcctgatc   2100
ggcctgagaa tcgtgttcgc cgtgctgtct gtgtgactcg ag                       2142
```

```

<210> SEQ ID NO 2
<211> LENGTH: 709
<212> TYPE: PRT
<213> ORGANISM: Artificial Sequence
<220> FEATURE:
<223> OTHER INFORMATION: Subtype A consensus Envelope protein sequence
      construct

<400> SEQUENCE: 2

Met Asp Trp Thr Trp Ile Leu Phe Leu Val Ala Ala Ala Thr Arg Val
1               5                   10                  15

His Ser Arg Val Met Gly Ile Gln Arg Asn Cys Gln His Leu Trp Arg
            20                  25                  30

Trp Gly Thr Met Ile Leu Gly Met Ile Ile Ile Cys Ser Ala Ala Glu
        35                  40                  45

Asn Leu Trp Val Thr Val Tyr Tyr Gly Val Pro Val Trp Lys Asp Ala
    50                  55                  60

Glu Thr Thr Leu Phe Cys Ala Ser Asp Ala Lys Ala Tyr Asp Thr Glu
65                  70                  75                  80

Val His Asn Val Trp Ala Thr His Ala Cys Val Pro Thr Asp Pro Asn
                85                  90                  95

Pro Gln Glu Ile Asn Leu Glu Asn Val Thr Glu Glu Phe Asn Met Trp
            100                 105                 110

Lys Asn Asn Met Val Glu Gln Met His Thr Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Ser Asn Val Asn Val Thr Thr Asn Ile Met Lys Gly Glu
145                 150                 155                 160

Ile Lys Asn Cys Ser Phe Asn Met Thr Thr Glu Leu Arg Asp Lys Lys
                165                 170                 175

Gln Lys Val Tyr Ser Leu Phe Tyr Lys Leu Asp Val Val Gln Ile Asn
            180                 185                 190

Lys Ser Asn Ser Ser Ser Gln Tyr Arg Leu Ile Asn Cys Asn Thr Ser
        195                 200                 205

Ala Ile Thr Gln Ala Cys Pro Lys Val Ser Phe Glu Pro Ile Pro Ile
    210                 215                 220

His Tyr Cys Ala Pro Ala Gly Phe Ala Ile Leu Lys Cys Lys Asp Lys
225                 230                 235                 240

Glu Phe Asn Gly Thr Gly Pro Cys Lys Asn Val Ser Thr Val Gln Cys
                245                 250                 255

Thr His Gly Ile Lys Pro Val Val Ser Thr Gln Leu Leu Leu Asn Gly
            260                 265                 270
```

```
Ser Leu Ala Glu Glu Val Met Ile Arg Ser Glu Asn Ile Thr Asn
        275                 280                 285

Asn Ala Lys Asn Ile Ile Val Gln Leu Thr Lys Pro Val Lys Ile Asn
    290                 295                 300

Cys Thr Arg Pro Asn Asn Asn Thr Arg Lys Ser Ile Arg Ile Gly Pro
305                 310                 315                 320

Gly Gln Ala Phe Tyr Ala Thr Gly Asp Ile Ile Gly Asp Ile Arg Gln
                325                 330                 335

Ala His Cys Asn Val Ser Arg Thr Glu Trp Asn Glu Thr Leu Gln Lys
            340                 345                 350

Val Ala Lys Gln Leu Arg Lys Tyr Phe Asn Asn Lys Thr Ile Ile Phe
        355                 360                 365

Thr Asn Ser Ser Gly Gly Arg Leu Arg Ile Thr Thr His Ser Phe Asn
370                 375                 380

Cys Gly Gly Glu Phe Phe Tyr Cys Asn Thr Ser Gly Leu Phe Asn Ser
385                 390                 395                 400

Thr Trp Asn Gly Asn Gly Thr Lys Lys Lys Asn Ser Thr Glu Ser Asn
                405                 410                 415

Asp Thr Ile Thr Leu Pro Cys Arg Ile Lys Gln Ile Ile Asn Met Trp
            420                 425                 430

Gln Arg Val Gly Gln Ala Met Tyr Ala Pro Pro Ile Gln Gly Val Ile
        435                 440                 445

Arg Cys Glu Ser Asn Ile Thr Gly Leu Leu Leu Thr Arg Asp Gly Gly
    450                 455                 460

Asp Asn Asn Ser Lys Asn Glu Thr Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Glu
            500                 505                 510

Arg Glu Lys Arg Ala Val Gly Ile Gly Ala Val Phe Leu Gly Phe Leu
        515                 520                 525

Gly Ala Ala Gly Ser Thr Met Gly Ala Ala Ser Ile Thr Leu Thr Val
    530                 535                 540

Gln Ala Arg Gln Leu Leu Ser Gly Ile Val Gln Gln Gln Ser Asn Leu
545                 550                 555                 560

Leu Arg Ala Ile Glu Ala Gln Gln His Leu Leu Lys Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
        595                 600                 605

Cys Thr Thr Asn Val Pro Trp Asn Ser Ser Trp Ser Asn Lys Ser Gln
    610                 615                 620

Ser Glu Ile Trp Asp Asn Met Thr Trp Leu Gln Trp Asp Lys Glu Ile
625                 630                 635                 640

Ser Asn Tyr Thr Asp Ile Ile Tyr Asn Leu Ile Glu Glu Ser Gln Asn
                645                 650                 655

Gln Gln Glu Lys Asn Glu Gln Asp Leu Leu Ala Leu Asp Lys Trp Ala
            660                 665                 670

Asn Leu Trp Asn Trp Phe Asp Ile Ser Asn Trp Leu Trp Tyr Ile Lys
        675                 680                 685

Ile Phe Ile Met Ile Val Gly Gly Leu Ile Gly Leu Arg Ile Val Phe
```

Ala Val Leu Ser Val
705

<210> SEQ ID NO 3
<211> LENGTH: 2734
<212> TYPE: DNA
<213> ORGANISM: Artificial Sequence
<220> FEATURE:
<223> OTHER INFORMATION: Subtype B consensus Envelope DNA sequence construct

<400> SEQUENCE: 3

| | |
|---|---|
| ggatccgcca ccatggactg gacctggatt ctgttcctgg tggccgccgc caccagagtg | 60 |
| cacagcagag tgaagggcat ccggaagaac taccagcacc tgtggagatg ggcaccatg | 120 |
| ctgctgggca tgctgatgat ctgttctgcc gccgagaagc tgtgggtgac cgtgtactac | 180 |
| ggcgtgcctg tgtggaagga ggccaccacc accctgttct gcgccagcga cgccaaggcc | 240 |
| tacgataccg aagtgcacaa tgtgtgggcc acccacgcct gcgtgcctac cgatcccaac | 300 |
| cctcaggaag tggtgctgga gaacgtgacc gagaacttca acatgtggaa gaacaacatg | 360 |
| gtggagcaga tgcacgagga catcatcagc ctgtgggacc agagcctgaa gccttgcgtg | 420 |
| aagctgaccc ctctgtgcgt gaccctgaac tgcaccgacc tgagcggcga agatggag | 480 |
| aagggcgaga tcaagaactg cagcttcaac atcaccacct ccatccggga caaagtgcag | 540 |
| aaggagtacg ccctgttcta caagctggac gtggtgccca tcgacaacga caacaccagc | 600 |
| taccggctga tcagctgcaa caccagcgtg atcacccagg cctgccccaa agtgagcttc | 660 |
| gagcccatcc ccatccacta ctgcgcccct gccggcttcg ccatcctgaa gtgcaacgac | 720 |
| aagaagttca cggcaccgg cccttgcacc aatgtgagca ccgtgcagtg cacccacggc | 780 |
| atcagacccg tggtgtccac ccagctgctg ctgaacggca gcctggccga ggaagaagtg | 840 |
| gtgatccgga gcgagaattt caccaacaac gccaagacca tcatcgtgca gctgaacgag | 900 |
| agcgtggaga tcaactgcac ccggcccaac aacatacc ggaagagcat ccacatcggc | 960 |
| cctggccagg ccttctacac caccggcgag atcatcggcg atatcaggca ggcccactgc | 1020 |
| aatatcagcc gggccaagtg aacaacacc ctgaagcaga tcgtgaagaa gctgcgggag | 1080 |
| cagttcggca caagaccat cgtgttcaac cagagcagcg gcggcagacc tagaatcgtg | 1140 |
| atgcacagct tcaactgtgg cggcgagttc ttctactgca cacaacccca gctgttcaac | 1200 |
| agcacctgga cgtgaacgg gacctggaac aacaacaccg agggcaacga caccatcacc | 1260 |
| ctgccctgcc ggatcaagca gatcatcaat atgtggcagg aggtgggcaa ggccatgtac | 1320 |
| gccctccca tcagaggcca gatccggtgc agcagcaata tcaccggcct gctgctgacc | 1380 |
| agagatggcg gcaacaataa caccaacgag accgagatct tagacctgg cggcggagac | 1440 |
| atgagggaca ctggcggag cgagctgtac aagtacaaag tggtgaagat cgagcccctg | 1500 |
| ggcgtggccc ccaccaaggc caagagaaga gtggtgcagc gggagaagag agctgtgggc | 1560 |
| atcggcgcca tgtttctggg ctttctggga gccgccggaa gcaccatggg agccgccagc | 1620 |
| atgaccctga ccgtgcaggc cagacagctg ctgagcggca tcgtgcagca gcagaacaac | 1680 |
| ctgctgagag ccatcgaggc ccagcagcac ctgctgcagc tgacagtgtg ggcatcaag | 1740 |
| cagctgcagg cccgcgtgct ggccgtggag agatacctga aggaccagca gctgctggga | 1800 |
| atctggggct gcagcggcaa gctgatctgc accaccaccg tgccctgaa cgccagctgg | 1860 |
| agcaacaaga gcctggacga gatctgggac aacatgacct ggatggagtg ggagcgggag | 1920 |

```
atcgacaact acaccagcct gatctacacc ctgatcgagg agagccagaa ccagcaggag    1980
aagaacgagc aggagctgct ggagctggac aagtgggcca gcctgtggaa ctggttcgac    2040
atcaccaact ggctgtggta catcaagatc ttcatcatga ttgtgggcgg cctgatcggc    2100
ctgagaatcg tgttcgccgt gctgagcatc taccoctacg acgtgcccga ttacgcctga    2160
gaattcgtaa gtaagtgtca tatgggagag ctcgactaga ctggacagcc aatgacgggt    2220
aagagagtga catttctcac taacctaaga caggagggcc gtcaaagcta ctgcctaatc    2280
caatgacggg taatagtgac aagaaatgta tcactccaac ctaagacagg cgcagcctcc    2340
gagggatgtg tcttttgttt tttataatta aaaagggtga catgtccgga gccgtgctgc    2400
ccggatgatg tcttggcctc tgtttgctac cggtatcgat gttaacgtcg accccgggct    2460
cgaggtaagt aagtgtcata tgggagagct cgactagact ggacagccaa tgacgggtaa    2520
gagagtgaca tttctcacta acctaagaca ggagggccgt caaagctact gcctaatcca    2580
atgacgggta atagtgacaa gaaatgtatc actccaacct aagacaggcg cagcctccga    2640
gggatgtgtc ttttgttttt tataattaaa aagggtgaca tgtccggagc cgtgctgccc    2700
ggatgatgtc ttggcctctg tttgctgcgg ccgc                                2734

<210> SEQ ID NO 4
<211> LENGTH: 715
<212> TYPE: PRT
<213> ORGANISM: Artificial Sequence
<220> FEATURE:
<223> OTHER INFORMATION: Subtype B consensus Envelope protein sequence
      construct

<400> SEQUENCE: 4

Met Asp Trp Thr Trp Ile Leu Phe Leu Val Ala Ala Thr Arg Val
1               5                   10                  15

His Ser Arg Val Lys Gly Ile Arg Lys Asn Tyr Gln His Leu Trp Arg
                20                  25                  30

Trp Gly Thr Met Leu Leu Gly Met Leu Met Ile Cys Ser Ala Ala Glu
            35                  40                  45

Lys Leu Trp Val Thr Val Tyr Tyr Gly Val Pro Val Trp Lys Glu Ala
        50                  55                  60

Thr Thr Thr Leu Phe Cys Ala Ser Asp Ala Lys Ala Tyr Asp Thr Glu
65                  70                  75                  80

Val His Asn Val Trp Ala Thr His Ala Cys Val Pro Thr Asp Pro Asn
                85                  90                  95

Pro Gln Glu Val Val Leu Glu Asn Val Thr Glu Asn Phe Asn Met Trp
            100                 105                 110

Lys Asn Asn Met Val Glu Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Thr Asp Leu Ser Gly Glu Lys Met Glu Lys Gly Glu Ile
145                 150                 155                 160

Lys Asn Cys Ser Phe Asn Ile Thr Thr Ser Ile Arg Asp Lys Val Gln
                165                 170                 175

Lys Glu Tyr Ala Leu Phe Tyr Lys Leu Asp Val Val Pro Ile Asp Asn
            180                 185                 190

Asp Asn Thr Ser Tyr Arg Leu Ile Ser Cys Asn Thr Ser Val Ile Thr
        195                 200                 205
```

-continued

```
Gln Ala Cys Pro Lys Val Ser Phe Glu Pro Ile Pro Ile His Tyr Cys
    210                 215                 220
Ala Pro Ala Gly Phe Ala Ile Leu Lys Cys Asn Asp Lys Lys Phe Asn
225                 230                 235                 240
Gly Thr Gly Pro Cys Thr Asn Val Ser Thr Val Gln Cys Thr His Gly
                245                 250                 255
Ile Arg Pro Val Val Ser Thr Gln Leu Leu Leu Asn Gly Ser Leu Ala
            260                 265                 270
Glu Glu Glu Val Val Ile Arg Ser Glu Asn Phe Thr Asn Asn Ala Lys
        275                 280                 285
Thr Ile Ile Val Gln Leu Asn Glu Ser Val Glu Ile Asn Cys Thr Arg
290                 295                 300
Pro Asn Asn Asn Thr Arg Lys Ser Ile His Ile Gly Pro Gly Gln Ala
305                 310                 315                 320
Phe Tyr Thr Thr Gly Glu Ile Ile Gly Asp Ile Arg Gln Ala His Cys
                325                 330                 335
Asn Ile Ser Arg Ala Lys Trp Asn Asn Thr Leu Lys Gln Ile Val Lys
            340                 345                 350
Lys Leu Arg Glu Gln Phe Gly Asn Lys Thr Ile Val Phe Asn Gln Ser
        355                 360                 365
Ser Gly Gly Arg Pro Arg Ile Val Met His Ser Phe Asn Cys Gly Gly
370                 375                 380
Glu Phe Phe Tyr Cys Asn Thr Thr Gln Leu Phe Asn Ser Thr Trp Asn
385                 390                 395                 400
Val Asn Gly Thr Trp Asn Asn Asn Thr Glu Gly Asn Asp Thr Ile Thr
                405                 410                 415
Leu Pro Cys Arg Ile Lys Gln Ile Ile Asn Met Trp Gln Glu Val Gly
            420                 425                 430
Lys Ala Met Tyr Ala Pro Pro Ile Arg Gly Gln Ile Arg Cys Ser Ser
        435                 440                 445
Asn Ile Thr Gly Leu Leu Leu Thr Arg Asp Gly Gly Asn Asn Asn Thr
450                 455                 460
Asn Glu Thr Glu Ile Phe Arg Pro Gly Gly Gly Asp Met Arg Asp Asn
465                 470                 475                 480
Trp Arg Ser Glu Leu Tyr Lys Tyr Lys Val Val Lys Ile Glu Pro Leu
                485                 490                 495
Gly Val Ala Pro Thr Lys Ala Lys Arg Arg Val Val Gln Arg Glu Lys
            500                 505                 510
Arg Ala Val Gly Ile Gly Ala Met Phe Leu Gly Phe Leu Gly Ala Ala
        515                 520                 525
Gly Ser Thr Met Gly Ala Ala Ser Met Thr Leu Thr Val Gln Ala Arg
530                 535                 540
Gln Leu Leu Ser Gly Ile Val Gln Gln Asn Asn Leu Leu Arg Ala
545                 550                 555                 560
Ile Glu Ala Gln Gln His Leu Leu Gln Leu Thr Val Trp Gly Ile Lys
                565                 570                 575
Gln Leu Gln Ala Arg Val Leu Ala Val Glu Arg Tyr Leu Lys Asp Gln
            580                 585                 590
Gln Leu Leu Gly Ile Trp Gly Cys Ser Gly Lys Leu Ile Cys Thr Thr
        595                 600                 605
Thr Val Pro Trp Asn Ala Ser Trp Ser Asn Lys Ser Leu Asp Glu Ile
610                 615                 620
Trp Asp Asn Met Thr Trp Met Glu Trp Glu Arg Glu Ile Asp Asn Tyr
```

```
                625                  630                  635                  640
Thr Ser Leu Ile Tyr Thr Leu Ile Glu Glu Ser Gln Asn Gln Gln Glu
                    645                  650                  655

Lys Asn Glu Gln Glu Leu Leu Glu Leu Asp Lys Trp Ala Ser Leu Trp
                    660                  665                  670

Asn Trp Phe Asp Ile Thr Asn Trp Leu Trp Tyr Ile Lys Ile Phe Ile
                    675                  680                  685

Met Ile Val Gly Gly Leu Ile Gly Leu Arg Ile Val Phe Ala Val Leu
                    690                  695                  700

Ser Ile Tyr Pro Tyr Asp Val Pro Asp Tyr Ala
705                 710                  715

<210> SEQ ID NO 5
<211> LENGTH: 2140
<212> TYPE: DNA
<213> ORGANISM: Artificial Sequence
<220> FEATURE:
<223> OTHER INFORMATION: Subtype C consensus Envelope DNA sequence
      construct

<400> SEQUENCE: 5
ggatccgcca ccatggattg gacctggatt ctgttcctgg tggccgccgc cacaagagtg     60
cacagcagag tgcggggcat cctgagaaat tgccagcagt ggtggatctg gggcattctg    120
gggttctgga tgctgatgat ctgcaacgtg atgggcaacc tgtgggtgac cgtgtactac    180
ggcgtgcctg tgtggaagga ggccaagacc accctgttct gtgccagcga tgccaaggcc    240
tacgagaccg aggtgcacaa tgtgtgggcc acccacgcct gtgtgcccac cgatcccaac    300
cctcaggaga tggtgctgga aacgtgacc gagaacttca acatgtggaa gaacgacatg    360
gtggaccaga tgcacgagga catcatcagc ctgtgggacc agagcctgaa gccttgcgtg    420
aagctgaccc ctctgtgcgt gaccctgaac tgccggaaca cgtgaacaa caacaacacc    480 atgaaggagg agatcaagaa ctgcagcttc aacatcacca ccgagctgcg ggacaagaag    540
cagaaggtgt acgccctgtt ctaccggctg acatcgtgc ccctgaacga agaacaac      600 agcaacgact accggctgat caactgcaac ccagcgcca tcacccaggc ctgtcccaag    660
gtgtccttcg accccatccc catccactat tgtgcccctg ccggctacgc catcctgaag    720
tgcaacaaca gaccttcaa cggcaccggc cctgcaata atgtgagcac cgtgcagtgt    780
acccacggca tcaagcctgt ggtgtccacc cagctgctgc tgaatggcag cctggccgag    840
gaggagatta tcatccggag cgagaacctg accaacaacg ccaagaccat cattgtgcac    900
ctgaatgaga gcgtggagat cgtgtgtacc cggcccaaca caatacccg gaagagcatc    960 agaatcggcc ctggccagac cttttacgcc accggcgaca tcatcggcga tatcaggcag   1020
gcccactgca atatcagcga ggagaagtgg aacaagaccc tgcagcgggt gtccgagaag   1080
ctgaaggagc acttccccaa taagaccatc aagttcgccc ctagcagcgg cggcagactg   1140
gagatcacca cccacagctt caactgcagg ggcgagttct tctactgcaa taccagcaag   1200
ctgttcaaca gcacctacat gcccaacagc accaacaata ccaacaccac catcaccctg   1260
ccctgccgga tcaagcagat catcaatatg tggcaggaag tggcagagc catgtacgcc   1320 cctcccatcg agggcaacat cacctgcaag tccaacatca ccggcctgct gctgacaaga   1380
gatggcggca gaacgacac caatgacacc gagaccttca gcctggcgg cggagacatg   1440 agggacaact ggcggagcga gctgtacaag tacaaggtgg tggagatcaa gcctctgggc   1500
gtggccccta ccaaggccaa gaggagagtg gtggagaggg agaagagagc cgtgggcatc   1560
```

-continued

```
ggcgccgtgt ttctgggctt tctgggagcc gccggatcta caatgggagc cgccagcatc    1620
acactgaccg tgcaggccag acagctgctg agcggcatcg tgcagcagca gagcaatctg    1680
ctgagagcca tcgaggccca gcagcacatg ctgcagctga cagtgtgggg catcaagcag    1740
ctgcagacca gagtgctggc catcgagcgc tacctgaagg atcagcagct gctgggcatc    1800
tggggctgta gcggcaagct gatctgtacc accgccgtgc cttggaatag cagctggagc    1860
aacaagagcc aggaggacat ctgggacaac atgacctgga tgcagtggga ccggagatc     1920 agcaactaca ccgacaccat ctacaggctg ctggaggaca gccagaacca gcaggagaag    1980
aacgagaagg acctgctggc cctggacagc tggaagaacc tgtggaactg gttcgacatc    2040
accaactggc tgtggtacat caagatcttc atcatgattg tgggcggcct gatcggcctg    2100
agaatcatct tcgccgtgct gagcatctga tagcggccgc                          2140
```

<210> SEQ ID NO 6
<211> LENGTH: 705
<212> TYPE: PRT
<213> ORGANISM: Artificial Sequence
<220> FEATURE:
<223> OTHER INFORMATION: Subtype C consensus Envelope protein sequence construct

<400> SEQUENCE: 6

```
Met Asp Trp Thr Trp Ile Leu Phe Leu Val Ala Ala Thr Arg Val
1               5                   10                  15

His Ser Arg Val Arg Gly Ile Leu Arg Asn Cys Gln Gln Trp Trp Ile
            20                  25                  30

Trp Gly Ile Leu Gly Phe Trp Met Leu Met Ile Cys Asn Val Met Gly
        35                  40                  45

Asn Leu Trp Val Thr Val Tyr Tyr Gly Val Pro Val Trp Lys Glu Ala
    50                  55                  60

Lys Thr Thr Leu Phe Cys Ala Ser Asp Ala Lys Ala Tyr Glu Thr Glu
65                  70                  75                  80

Val His Asn Val Trp Ala Thr His Ala Cys Val Pro Thr Asp Pro Asn
                85                  90                  95

Pro Gln Glu Met Val Leu Glu Asn Val Thr Glu Asn Phe Asn Met Trp
            100                 105                 110

Lys Asn Asp Met Val Asp Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Arg Asn Val Asn Asn Asn Thr Met Lys Glu Glu
145                 150                 155                 160

Ile Lys Asn Cys Ser Phe Asn Ile Thr Thr Glu Leu Arg Asp Lys Lys
                165                 170                 175

Gln Lys Val Tyr Ala Leu Phe Tyr Arg Leu Asp Ile Val Pro Leu Asn
            180                 185                 190

Glu Lys Asn Asn Ser Asn Asp Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255
```

```
Thr His Gly Ile Lys Pro Val Ser Thr Gln Leu Leu Asn Gly
            260                 265                 270

Ser Leu Ala Glu Glu Ile Ile Arg Ser Glu Asn Leu Thr Asn
            275                 280                 285

Asn Ala Lys Thr Ile Ile Val His Leu Asn Glu Ser Val Glu Ile Val
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Ile Ser Glu Glu Lys Trp Asn Lys Thr Leu Gln Arg
            340                 345                 350

Val Ser Glu Lys Leu Lys Glu His Phe Pro Asn Lys Thr Ile Lys Phe
            355                 360                 365

Ala Pro Ser Ser Gly Gly Arg Leu Glu Ile Thr Thr His Ser Phe Asn
            370                 375                 380

Cys Arg Gly Glu Phe Phe Tyr Cys Asn Thr Ser Lys Leu Phe Asn Ser
385                 390                 395                 400

Thr Tyr Met Pro Asn Ser Thr Asn Asn Thr Asn Thr Thr Ile Thr Leu
                405                 410                 415

Pro Cys Arg Ile Lys Gln Ile Ile Asn Met Trp Gln Glu Val Gly Arg
            420                 425                 430

Ala Met Tyr Ala Pro Pro Ile Glu Gly Asn Ile Thr Cys Lys Ser Asn
            435                 440                 445

Ile Thr Gly Leu Leu Leu Thr Arg Asp Gly Gly Lys Asn Asp Thr Asn
            450                 455                 460

Asp Thr Glu Thr Phe Arg Pro Gly Gly Gly Asp Met Arg Asp Asn Trp
465                 470                 475                 480

Arg Ser Glu Leu Tyr Lys Tyr Lys Val Val Glu Ile Lys Pro Leu Gly
                485                 490                 495

Val Ala Pro Thr Lys Ala Lys Arg Arg Val Val Glu Arg Glu Lys Arg
            500                 505                 510

Ala Val Gly Ile Gly Ala Val Phe Leu Gly Phe Leu Gly Ala Ala Gly
            515                 520                 525

Ser Thr Met Gly Ala Ala Ser Ile Thr Leu Thr Val Gln Ala Arg Gln
            530                 535                 540

Leu Leu Ser Gly Ile Val Gln Gln Gln Ser Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Thr Arg Val Leu Ala Ile Glu Arg Tyr Leu Lys Asp Gln Gln
            580                 585                 590

Leu Leu Gly Ile Trp Gly Cys Ser Gly Lys Leu Ile Cys Thr Thr Ala
            595                 600                 605

Val Pro Trp Asn Ser Ser Trp Ser Asn Lys Ser Gln Glu Asp Ile Trp
            610                 615                 620

Asp Asn Met Thr Trp Met Gln Trp Asp Arg Glu Ile Ser Asn Tyr Thr
625                 630                 635                 640

Asp Thr Ile Tyr Arg Leu Leu Glu Asp Ser Gln Asn Gln Gln Glu Lys
                645                 650                 655

Asn Glu Lys Asp Leu Leu Ala Leu Asp Ser Trp Lys Asn Leu Trp Asn
            660                 665                 670
```

```
Trp Phe Asp Ile Thr Asn Trp Leu Trp Tyr Ile Lys Ile Phe Ile Met
        675                 680                 685

Ile Val Gly Gly Leu Ile Gly Leu Arg Ile Ile Phe Ala Val Leu Ser
    690                 695                 700

Ile
705

<210> SEQ ID NO 7
<211> LENGTH: 2089
<212> TYPE: DNA
<213> ORGANISM: Artificial Sequence
<220> FEATURE:
<223> OTHER INFORMATION: Subtype D consensus Envelope DNA sequence
      construct

<400> SEQUENCE: 7
```

| | | | | |
|---|---|---|---|---|
| gggcatcaag | cggaattacc | agcacctgtg | gaagtggggc | accatgctgc tgggcatgct | 60 |
| gatgaccctgc | agcgtggccg | agaacctgtg | ggtgaccgtg | tactacgccg tgcctgtgtg | 120 |
| gaaggaagcc | accaccaccc | tgttctgcgc | cagcgatgcc | aagagctaca agaccgaggc | 180 |
| ccacaatatc | tggggccaccc | acgcctgcgt | gcctaccgat | cccaaccctc aggagatcga | 240 |
| gctggagaac | gtgaccgaga | acttcaacat | gtggaagaac | aacatggtgg agcagatgca | 300 |
| cgaggacatc | atcagcctgt | gggaccagag | cctgaagcct | tgcgtgaagc tgacccctct | 360 |
| gtgcgtgacc | ctgaactgca | ccgacggcat | gaggaacgac | accaacgata ccaacgtgac | 420 |
| catggaggag | ggcgagatga | agaactgcag | cttcaacatc | accaccgaag tgcgggacaa | 480 |
| gaagaagcag | gtgcacgccc | tgttctacaa | gctggacgtg | gtgcccatcg acgacaacaa | 540 |
| caccaacaac | agcaactacc | ggctgatcaa | ctgcaacacc | agcgccatca cccaggcctg | 600 |
| ccccaaagtg | accttcgagc | ccatccccat | ccactactgc | gcccctgccg gcttcgccat | 660 |
| cctgaagtgc | aaggataaga | agttcaacgg | caccggcccc | tgcaagaatg tgagcaccgt | 720 |
| gcagtgcacc | cacggcatca | gacccgtggt | gtccacccag | ctgctgctga acggcagcct | 780 |
| ggccgaggag | gagatcatca | tccggagcga | gaacctgacc | aacaacgcca gatcatcat | 840 |
| tgtgcagctg | aacgagagcg | tgaccatcaa | ttgcacccgg | ccctacaaca tacccggaa | 900 |
| gcgcatcccc | atcggcctgg | gccaggcctt | ctacaccacc | agaggcatca tcggcgacat | 960 |
| cagacaggcc | cactgcaata | tcagcggagc | cgagtggaat | aagaccctgc agcaggtggc | 1020 |
| caagaagctg | ggcgacctgc | tgaacaagac | caccatcatc | ttcaagccta gcagcggcgg | 1080 |
| cagacctaga | atcaccaccc | acagcttcaa | ttgtggcggc | gagttcttct actgcaatac | 1140 |
| cagccggctg | ttcaacagca | cctggagcaa | gaacagcacc | agcaactcca ccaaggagaa | 1200 |
| caacaccatc | accctgcccct | gccggatcaa | gcagatcatc | aatatgtggc agggagtggg | 1260 |
| caaggccatg | tacgcccctc | ccatcgaggg | cctgatcaag | tgcagcagca catcaccgg | 1320 |
| cctgctgctg | accagagatg | gcggagccaa | caactccac | aacgagacct tcagacctgg | 1380 |
| cggcggagac | atgagggaca | actggcggag | cgagctgtac | aagtacaaag tggtgaagat | 1440 |
| cgagccccctg | ggcgtggccc | ccaccagagc | caagagaaga | gtggtggagc gggagaagag | 1500 |
| agccatcgga | ctgggcgcca | tgttcctggg | cttcctggga | gccgccggaa gcaccatggg | 1560 |
| agccgccagc | ctgaccctga | ccgtgcaggc | cagacagctg | ctgagcggca tcgtgcagca | 1620 |
| gcagaacaac | ctgctgagag | ccattgaggc | ccagcagcac | ctgctgcagc tgacagtgtg | 1680 |
| gggcattaag | cagctgcagg | ccaggattct | ggccgtggag | cgctacctga aggatcagca | 1740 |
| gctgctggga | atctggggct | gcagcggcaa | gcacatctgc | accaccaccg tgccttggaa | 1800 |

```
tagcagctgg agcaacaaga gcctggacga gatctggaac aacatgacct ggatggagtg   1860
ggagagggag atcgacaact acaccggcct gatctacagc ctgatcgagg agagccagac   1920
ccagcaggag aagaacgagc aggagctgct ggagctggac aagtgggcca gcctgtggaa   1980
ctggttcagc atcacccagt ggctgtggta catcaagatc ttcatcatga ttgtgggcgg   2040
cctgatcggc ctgagaatcg tgttcgccgt gctgagcctg tgactcgag                2089
```

<210> SEQ ID NO 8
<211> LENGTH: 714
<212> TYPE: PRT
<213> ORGANISM: Artificial Sequence
<220> FEATURE:
<223> OTHER INFORMATION: Subtype D consensus Envelope protein sequence construct

<400> SEQUENCE: 8

```
Met Asp Trp Thr Trp Ile Leu Phe Leu Val Ala Ala Thr Arg Val
1               5                   10                  15

His Ser Arg Val Arg Gly Ile Lys Arg Asn Tyr Gln His Leu Trp Lys
            20                  25                  30

Trp Gly Thr Met Leu Leu Gly Met Leu Met Thr Cys Ser Val Ala Gl

```
Asn Glu Ser Val Thr Ile Asn Cys Thr Arg Pro Tyr Asn Asn Thr Arg
305                 310                 315                 320

Lys Arg Ile Pro Ile Gly Leu Gly Gln Ala Phe Tyr Thr Thr Arg Gly
                325                 330                 335

Ile Ile Gly Asp Ile Arg Gln Ala His Cys Asn Ile Ser Gly Ala Glu
            340                 345                 350

Trp Asn Lys Thr Leu Gln Gln Val Ala Lys Lys Leu Gly Asp Leu Leu
        355                 360                 365

Asn Lys Thr Thr Ile Ile Phe Lys Pro Ser Ser Gly Arg Pro Arg
    370                 375                 380

Ile Thr Thr His Ser Phe Asn Cys Gly Gly Glu Phe Phe Tyr Cys Asn
385                 390                 395                 400

Thr Ser Arg Leu Phe Asn Ser Thr Trp Ser Lys Asn Ser Thr Ser Asn
                405                 410                 415

Ser Thr Lys Glu Asn Asn Thr Ile Thr Leu Pro Cys Arg Ile Lys Gln
            420                 425                 430

Ile Ile Asn Met Trp Gln Gly Val Gly Lys Ala Met Tyr Ala Pro Pro
        435                 440                 445

Ile Glu Gly Leu Ile Lys Cys Ser Ser Asn Ile Thr Gly Leu Leu Leu
    450                 455                 460

Thr Arg Asp Gly Gly Ala Asn Asn Ser His Asn Glu Thr Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Val Ala Pro Thr Arg Ala Lys
            500                 505                 510

Arg Arg Val Val Glu Arg Glu Lys Arg Ala Ile Gly Leu Gly Ala Met
        515                 520                 525

Phe Leu Gly Phe Leu Gly Ala Ala Gly Ser Thr Met Gly Ala Ala Ser
530                 535                 540

Leu Thr Leu Thr Val Gln Ala Arg Gln Leu Leu Ser Gly Ile Val Gln
545                 550                 555                 560

Gln Gln Asn Asn Leu Leu Arg Ala Ile Glu Ala Gln Gln His Leu Leu
                565                 570                 575

Gln Leu Thr Val Trp Gly Ile Lys Gln Leu Gln Ala Arg Ile Leu Ala
            580                 585                 590

Val Glu Arg Tyr Leu Lys Asp Gln Gln Leu Leu Gly Ile Trp Gly Cys
        595                 600                 605

Ser Gly Lys His Ile Cys Thr Thr Thr Val Pro Trp Asn Ser Ser Trp
610                 615                 620

Ser Asn Lys Ser Leu Asp Glu Ile Trp Asn Asn Met Thr Trp Met Glu
625                 630                 635                 640

Trp Glu Arg Glu Ile Asp Asn Tyr Thr Gly Leu Ile Tyr Ser Leu Ile
                645                 650                 655

Glu Glu Ser Gln Thr Gln Gln Glu Lys Asn Glu Gln Glu Leu Leu Glu
            660                 665                 670

Leu Asp Lys Trp Ala Ser Leu Trp Asn Trp Phe Ser Ile Thr Gln Trp
        675                 680                 685

Leu Trp Tyr Ile Lys Ile Phe Ile Met Ile Val Gly Gly Leu Ile Gly
    690                 695                 700

Leu Arg Ile Val Phe Ala Val Leu Ser Leu
705                 710
```

<210> SEQ ID NO 9
<211> LENGTH: 1049
<212> TYPE: DNA
<213> ORGANISM: Artificial Sequence
<220> FEATURE:
<223> OTHER INFORMATION: Subtype B consensus Nef-Rev DNA sequence
      construct

<400> SEQUENCE: 9

```
ggatccgcca ccatggactg gacctggatt ctgttcctgg tggccgctgc caccagagtg      60
cacagcagca agagaagcgt ggtgggttgg cctacagtgc gggagaggat gagaagagcc     120
gagcctgccg ccgatggagt gggcgccgtg tctagagatc tggagaagca cggcgccatc     180
accagcagca ataccgccgc caacaatgcc gactgcgcct ggctggaggc ccaggaggag     240
gaggaagtgg gcttccctgt gagagcccag gtggccctga gccatgac ctacaaggcc      300
gccgtggatc tgagccactt cctgaaggag aagggcggcc tggagggcct gatctacagc     360
cagaagcggc aggacatcct ggatctgtgg gtgtaccaca cccagggcta cttccccgac     420
tggcagaatt acacccctgg ccctggcatc agataccctc tgaccttcgg ctggtgcttc     480
aagctggtgc ctgtggagcc tgagaaagtg gaggaggcca acgagggcga gaacaattct     540
gccgcccacc ctatgagcct gcacggcatg acgatcccg agaggaagt gctggtgtgg      600
aagttcgaca gcaggctggc cttccaccac atggccagag agctgcaccc cgagtactac     660
aaggactgcc ggggcaggaa gagaagaagc gccggcagaa cggcgacag cgacgaggag     720
ctgctgaaaa cagtgcggct gatcaagttc ctgtaccaga gcaaccctcc tcccagcccc     780
gagggcacca gacaggcccg gagaaaccgg aggaggcgt ggagagagag cagcggcag      840
atcagaagca tcagcgagtg gattctgagc acctacctgg gcagaccgc cgagcccgtg     900
cccctgcagc tgccccccct ggagagactg acctggact gcaacgagga ctgcggcacc     960
agcggcaccc agggagtggg cagccccag atcctggtgg agagccctgc cgtgctggag    1020
agcggcacca aggagtgatg agcggccgc                                     1049
```

<210> SEQ ID NO 10
<211> LENGTH: 341
<212> TYPE: PRT
<213> ORGANISM: Artificial Sequence
<220> FEATURE:
<223> OTHER INFORMATION: Subtype B consensus Nef-Rev protein sequence
      construct

<400> SEQUENCE: 10

Met Asp Trp Thr Trp Ile Leu Phe Leu Val Ala Ala Thr Arg Val
1               5                   10                  15

His Ser Ser Lys Arg Ser Val Val Gly Trp Pro Thr Val Arg Glu Arg
            20                  25                  30

Met Arg Arg Ala Glu Pro Ala Ala Asp Gly Val Gly Ala Val Ser Arg
        35                  40                  45

Asp Leu Glu Lys His Gly Ala Ile Thr Ser Ser Asn Thr Ala Ala Asn
    50                  55                  60

Asn Ala Asp Cys Ala Trp Leu Glu Ala Gln Glu Glu Glu Val Gly
65                  70                  75                  80

Phe Pro Val Arg Ala Gln Val Ala Leu Arg Ala Met Thr Tyr Lys Ala
                85                  90                  95

Ala Val Asp Leu Ser His Phe Leu Lys Glu Lys Gly Gly Leu Glu Gly
            100                 105                 110

Leu Ile Tyr Ser Gln Lys Arg Gln Asp Ile Leu Asp Leu Trp Val Tyr

| | | | | | | | | | | | | | |
|---|---|---|---|---|---|---|---|---|---|---|---|---|---|
| | | | | 115 | | | | | 120 | | | | 125 |
| His | Thr | Gln | Gly | Tyr | Phe | Pro | Asp | Trp | Gln | Asn | Tyr | Thr | Pro | Gly | Pro |
| 130 | | | | | 135 | | | | | 140 | | | |
| Gly | Ile | Arg | Tyr | Pro | Leu | Thr | Phe | Gly | Trp | Cys | Phe | Lys | Leu | Val | Pro |
| 145 | | | | | 150 | | | | | 155 | | | | | 160 |
| Val | Glu | Pro | Glu | Lys | Val | Glu | Glu | Ala | Asn | Gly | Glu | Asn | Asn | Ser |
| | | | | 165 | | | | | 170 | | | | | 175 |
| Ala | Ala | His | Pro | Met | Ser | Leu | His | Gly | Met | Asp | Asp | Pro | Glu | Arg | Glu |
| | | | 180 | | | | | 185 | | | | | 190 | | |
| Val | Leu | Val | Trp | Lys | Phe | Asp | Ser | Arg | Leu | Ala | Phe | His | His | Met | Ala |
| | | 195 | | | | | 200 | | | | | 205 | | | |
| Arg | Glu | Leu | His | Pro | Glu | Tyr | Tyr | Lys | Asp | Cys | Arg | Gly | Arg | Lys | Arg |
| | 210 | | | | | 215 | | | | | 220 | | | | |
| Arg | Ser | Ala | Gly | Arg | Ser | Gly | Asp | Ser | Asp | Glu | Glu | Leu | Leu | Lys | Thr |
| 225 | | | | | 230 | | | | | 235 | | | | | 240 |
| Val | Arg | Leu | Ile | Lys | Phe | Leu | Tyr | Gln | Ser | Asn | Pro | Pro | Ser | Pro |
| | | | | 245 | | | | | 250 | | | | | 255 |
| Glu | Gly | Thr | Arg | Gln | Ala | Arg | Arg | Asn | Arg | Arg | Arg | Arg | Trp | Arg | Glu |
| | | | 260 | | | | | 265 | | | | | 270 | | |
| Arg | Gln | Arg | Gln | Ile | Arg | Ser | Ile | Ser | Glu | Trp | Ile | Leu | Ser | Thr | Tyr |
| | 275 | | | | | 280 | | | | | 285 | | | | |
| Leu | Gly | Arg | Pro | Ala | Glu | Pro | Val | Pro | Leu | Gln | Leu | Pro | Pro | Leu | Glu |
| | 290 | | | | | 295 | | | | | 300 | | | | |
| Arg | Leu | Thr | Leu | Asp | Cys | Asn | Glu | Asp | Cys | Gly | Thr | Ser | Gly | Thr | Gln |
| 305 | | | | | 310 | | | | | 315 | | | | | 320 |
| Gly | Val | Gly | Ser | Pro | Gln | Ile | Leu | Val | Glu | Ser | Pro | Ala | Val | Leu | Glu |
| | | | | 325 | | | | | 330 | | | | | 335 |
| Ser | Gly | Thr | Lys | Glu |
| | | | 340 | |

<210> SEQ ID NO 11
<211> LENGTH: 1863
<212> TYPE: DNA
<213> ORGANISM: Artificial Sequence
<220> FEATURE:
<223> OTHER INFORMATION: Gag consensus DNA sequence of subtype A, B,
      C and D construct

<400> SEQUENCE: 11

```
ggatccgcca ccatggactg gacctggatt ctgtttctgg tcgccgccgc cacaagagtg      60
cacagcggcg ccagagccag cgtgctgtcc ggcggcaagc tggacgcctg ggagaagatc     120
agactgaggc ctggcggcaa gaagaagtac cggctgaagc accttgtgtg ggccagcaga     180
gagctggaga gattcgccct gaatcctggc tgctggaga ccagcgaggg ctgtaagcag     240
atcatcggcc agctgcagcc cgccctgcag accggcagcg aggagctgag aagcctgtac     300
aacaccgtgg ccaccctgta ctgcgtgcac gagaagatcg aggtgaagga caccaaggag     360
gccctggaca gatcgagga ggagcagaac aagagcaagc agaaggccca gcaggccgcc     420
gccgacaccg caacagcag ccaggtgtcc cagaactacc ccatcgtgca gaatctgcag     480
ggccagatgg tgcaccaggc catcagcccc agaaccctga tgcctgggt gaaggtgatc     540
gaggagaagg ccttcagccc tgaggtgatc cctatgttca gcgccctgag cgagggcgcc     600
acacctcagg acctgaacac catgctgaac acagtggggg ccaccaggc cgccatgcag     660
atgctgaagg ataccatcaa cgaggaggcc gccgagtggg acagactgca ccccgtgcac     720
```

```
gccggaccta tcgccctgg ccagatgaga gagcccagag gcagcgacat cgccggcacc      780
acctccaccc tgcaagagca gatcggctgg atgaccagca accccccat ccctgtgggc      840
gacatctaca gcggtggat catcctgggc ctgaacaaga ttgtgaggat gtacagcccc      900
gtgtccatcc tggatatcag gcagggcccc aaggagccct tcagagacta cgtggaccgg      960
ttcttcaaga ccctgagagc cgagcaggcc agccaggacg tgaagaactg gatgaccgag     1020
accctgctgg tgcagaacgc caaccccgac tgtaagacca tcctgagagc cctgggccct     1080
ggcgccaccc tggaggagat gatgaccgcc tgccaggag tgggcggacc cggccacaag     1140
gccagagtgc tggccgaggc catgagccag gccaccaaca gcaacatcat gatgcagcgg     1200
ggcaacttca gaggccccag gaggatcgtg aagtgcttca actgtggcaa ggagggccac     1260
atcgccagaa actgtagggc ccccaggaag aagggctgct ggaagtgtgg caaagagggg     1320
caccagatga aggactgtac cgagcggcag gccaatttcc tggggaagat ctggcccagc     1380
cacaagggca gacccggcaa tttcctgcag agcagacctg agcccaccgc ccctcccgcc     1440
gagagcttcg gcttcggcga ggagatcacc cccagcccca gcaggagcc aaggacaga      1500
gagctgtacc ctctggccag cctgaagagc ctgttcggca cgatcccct gagccagtac     1560
ccctacgacg tgcccgatta cgcctgagaa ttcgtaagta agtgtcatat gggagagctc     1620
gactagactg gacagccaat gacgggtaag agagtgacat ttctcactaa cctaagacag     1680
gagggccgtc aaagctactg cctaatccaa tgacgggtaa tagtgacaag aaatgtatca     1740
ctccaaccta agacaggcgc agcctccgag ggatgtgtct tttgtttttt ataattaaaa     1800
agggtgacat gtccggagcc gtgctgcccg gatgatgtct tggcctctgt ttgctgcggc     1860
cgc                                                                   1863
```

<210> SEQ ID NO 12
<211> LENGTH: 524
<212> TYPE: PRT
<213> ORGANISM: Artificial Sequence
<220> FEATURE:
<223> OTHER INFORMATION: Gag consensus protein sequence of subtype A,
      B, C and D construct

<400> SEQUENCE: 12

```
Met Asp Trp Thr Trp Ile Leu Phe Leu Val Ala Ala Ala Thr Arg Val
1               5                   10                  15

His Ser Gly Ala Arg Ala Ser Val Leu Ser Gly Gly Lys Leu Asp Ala
            20                  25                  30

Trp Glu Lys Ile Arg Leu Arg Pro Gly Gly Lys Lys Tyr Arg Leu
        35                  40                  45

Lys His Leu Val Trp Ala Ser Arg Glu Leu Glu Arg Phe Ala Leu Asn
    50                  55                  60

Pro Gly Leu Leu Glu Thr Ser Glu Gly Cys Lys Gln Ile Ile Gly Gln
65                  70                  75                  80

Leu Gln Pro Ala Leu Gln Thr Gly Ser Glu Gly Leu Arg Ser Leu Tyr
                85                  90                  95

Asn Thr Val Ala Thr Leu Tyr Cys Val His Glu Lys Ile Glu Val Lys
            100                 105                 110

Asp Thr Lys Glu Ala Leu Asp Lys Ile Glu Glu Glu Gln Asn Lys Ser
        115                 120                 125

Lys Gln Lys Ala Gln Gln Ala Ala Ala Asp Thr Gly Asn Ser Ser Gln
    130                 135                 140

Val Ser Gln Asn Tyr Pro Ile Val Gln Asn Leu Gln Gly Gln Met Val
```

```
            145                 150                 155                 160
        His Gln Ala Ile Ser Pro Arg Thr Leu Asn Ala Trp Val Lys Val Ile
                        165                 170                 175
        Glu Glu Lys Ala Phe Ser Pro Glu Val Ile Pro Met Phe Ser Ala Leu
                        180                 185                 190
        Ser Glu Gly Ala Thr Pro Gln Asp Leu Asn Thr Met Leu Asn Thr Val
                        195                 200                 205
        Gly Gly His Gln Ala Ala Met Gln Met Leu Lys Asp Thr Ile Asn Glu
                        210                 215                 220
        Glu Ala Ala Glu Trp Asp Arg Leu His Pro Val His Ala Gly Pro Ile
        225                 230                 235                 240
        Ala Pro Gly Gln Met Arg Glu Pro Arg Gly Ser Asp Ile Ala Gly Thr
                        245                 250                 255
        Thr Ser Thr Leu Gln Glu Gln Ile Gly Trp Met Thr Ser Asn Pro Pro
                        260                 265                 270
        Ile Pro Val Gly Asp Ile Tyr Lys Arg Trp Ile Ile Leu Gly Leu Asn
                        275                 280                 285
        Lys Ile Val Arg Met Tyr Ser Pro Val Ser Ile Leu Asp Ile Arg Gln
                        290                 295                 300
        Gly Pro Lys Glu Pro Phe Arg Asp Tyr Val Asp Arg Phe Phe Lys Thr
        305                 310                 315                 320
        Leu Arg Ala Glu Gln Ala Ser Gln Asp Val Lys Asn Trp Met Thr Glu
                        325                 330                 335
        Thr Leu Leu Val Gln Asn Ala Asn Pro Asp Cys Lys Thr Ile Leu Arg
                        340                 345                 350
        Ala Leu Gly Pro Gly Ala Thr Leu Glu Glu Met Met Thr Ala Cys Gln
                        355                 360                 365
        Gly Val Gly Gly Pro Gly His Lys Ala Arg Val Leu Ala Glu Ala Met
                        370                 375                 380
        Ser Gln Ala Thr Asn Ser Asn Ile Met Met Gln Arg Gly Asn Phe Arg
        385                 390                 395                 400
        Gly Pro Arg Arg Ile Val Lys Cys Phe Asn Cys Gly Lys Glu Gly His
                        405                 410                 415
        Ile Ala Arg Asn Cys Arg Ala Pro Arg Lys Lys Gly Cys Trp Lys Cys
                        420                 425                 430
        Gly Lys Glu Gly His Gln Met Lys Asp Cys Thr Glu Arg Gln Ala Asn
                        435                 440                 445
        Phe Leu Gly Lys Ile Trp Pro Ser His Lys Gly Arg Pro Gly Asn Phe
        450                 455                 460
        Leu Gln Ser Arg Pro Glu Pro Thr Ala Pro Ala Glu Ser Phe Gly
        465                 470                 475                 480
        Phe Gly Glu Glu Ile Thr Pro Ser Pro Lys Gln Glu Pro Lys Asp Arg
                        485                 490                 495
        Glu Leu Tyr Pro Leu Ala Ser Leu Lys Ser Leu Phe Gly Asn Asp Pro
                        500                 505                 510
        Leu Ser Gln Tyr Pro Tyr Asp Val Pro Asp Tyr Ala
                515                 520

<210> SEQ ID NO 13
<211> LENGTH: 43
<212> TYPE: DNA
<213> ORGANISM: Artificial Sequence
<220> FEATURE:
<223> OTHER INFORMATION: IgE Primer Sequence 1
```

-continued

<400> SEQUENCE: 13
gtcgctccgc tagcttgtgg gtcacagtct attatggggt acc 43

<210> SEQ ID NO 14
<211> LENGTH: 35
<212> TYPE: DNA
<213> ORGANISM: Artificial Sequence
<220> FEATURE:
<223> OTHER INFORMATION: IgE Primer Sequence 2

<400> SEQUENCE: 14
ggtcggatcc ttactccacc actctccttt ttgcc 35

<210> SEQ ID NO 15
<211> LENGTH: 17
<212> TYPE: PRT
<213> ORGANISM: Artificial Sequence
<220> FEATURE:
<223> OTHER INFORMATION: IgE leader sequence

<400> SEQUENCE: 15

```
Met Asp Trp Thr Trp Ile Leu Phe Leu Val Ala Ala Ala Thr Arg Val
1               5                   10                  15

His
```

<210> SEQ ID NO 16
<211> LENGTH: 692
<212> TYPE: PRT
<213> ORGANISM: Artificial Sequence
<220> FEATURE:
<223> OTHER INFORMATION: Subtype A consensus Envelope protein sequence

<400> SEQUENCE: 16

```
Ser Arg Val Met Gly Ile Gln Arg Asn Cys Gln His Leu Trp Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Asn Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asn Val Asn Val Thr Thr Asn Ile Met Lys Gly Glu Ile
    130                 135                 140

Lys Asn Cys Ser Phe Asn Met Thr Thr Glu Leu Arg Asp Lys Lys Gln
145                 150                 155                 160

Lys Val Tyr Ser Leu Phe Tyr Lys Leu Asp Val Val Gln Ile Asn Lys
                165                 170                 175

Ser Asn Ser Ser Ser Gln Tyr Arg Leu Ile Asn Cys Asn Thr Ser Ala
            180                 185                 190

Ile Thr Gln Ala Cys Pro Lys Val Ser Phe Glu Pro Ile Pro Ile His
        195                 200                 205
```

```
Tyr Cys Ala Pro Ala Gly Phe Ala Ile Leu Lys Cys Lys Asp Lys Glu
        210                 215                 220

Phe Asn Gly Thr Gly Pro Cys Lys Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Glu Glu Val Met Ile Arg Ser Glu Asn Ile Thr Asn Asn
                260                 265                 270

Ala Lys Asn Ile Ile Val Gln Leu Thr Lys Pro Val Lys Ile Asn Cys
        275                 280                 285

Thr Arg Pro Asn Asn Asn Thr Arg Lys Ser Ile Arg Ile Gly Pro Gly
        290                 295                 300

Gln Ala Phe Tyr Ala Thr Gly Asp Ile Ile Gly Asp Ile Arg Gln Ala
305                 310                 315                 320

His Cys Asn Val Ser Arg Thr Glu Trp Asn Glu Thr Leu Gln Lys Val
                325                 330                 335

Ala Lys Gln Leu Arg Lys Tyr Phe Asn Asn Lys Thr Ile Ile Phe Thr
                340                 345                 350

Asn Ser Ser Gly Gly Arg Leu Arg Ile Thr Thr His Ser Phe Asn Cys
        355                 360                 365

Gly Gly Glu Phe Phe Tyr Cys Asn Thr Ser Gly Leu Phe Asn Ser Thr
370                 375                 380

Trp Asn Gly Asn Gly Thr Lys Lys Lys Asn Ser Thr Glu Ser Asn Asp
385                 390                 395                 400

Thr Ile Thr Leu Pro Cys Arg Ile Lys Gln Ile Ile Asn Met Trp Gln
                405                 410                 415

Arg Val Gly Gln Ala Met Tyr Ala Pro Pro Ile Gln Gly Val Ile Arg
                420                 425                 430

Cys Glu Ser Asn Ile Thr Gly Leu Leu Leu Thr Arg Asp Gly Gly Asp
        435                 440                 445

Asn Asn Ser Lys Asn Glu Thr Phe Arg Pro Gly Gly Gly Asp Met Arg
450                 455                 460

Asp Asn Trp Arg Ser Glu Leu Tyr Lys Tyr Lys Val Val Lys Ile Glu
465                 470                 475                 480

Pro Leu Gly Val Ala Pro Thr Lys Ala Lys Arg Arg Val Val Glu Arg
                485                 490                 495

Glu Lys Arg Ala Val Gly Ile Gly Ala Val Phe Leu Gly Phe Leu Gly
        500                 505                 510

Ala Ala Gly Ser Thr Met Gly Ala Ala Ser Ile Thr Leu Thr Val Gln
        515                 520                 525

Ala Arg Gln Leu Leu Ser Gly Ile Val Gln Gln Ser Asn Leu Leu
530                 535                 540

Arg Ala Ile Glu Ala Gln Gln His Leu Leu Lys Leu Thr Val Trp Gly
545                 550                 555                 560

Ile Lys Gln Leu Gln Ala Arg Val Leu Ala Val Glu Arg Tyr Leu Lys
                565                 570                 575

Asp Gln Gln Leu Leu Gly Ile Trp Gly Cys Ser Gly Lys Leu Ile Cys
                580                 585                 590

Thr Thr Asn Val Pro Trp Asn Ser Ser Trp Ser Asn Lys Ser Gln Ser
        595                 600                 605

Glu Ile Trp Asp Asn Met Thr Trp Leu Gln Trp Asp Lys Glu Ile Ser
610                 615                 620
```

```
Asn Tyr Thr Asp Ile Ile Tyr Asn Leu Ile Glu Glu Ser Gln Asn Gln
625                 630                 635                 640

Gln Glu Lys Asn Glu Gln Asp Leu Leu Ala Leu Asp Lys Trp Ala Asn
                645                 650                 655

Leu Trp Asn Trp Phe Asp Ile Ser Asn Trp Leu Trp Tyr Ile Lys Ile
                660                 665                 670

Phe Ile Met Ile Val Gly Gly Leu Ile Gly Leu Arg Ile Val Phe Ala
            675                 680                 685

Val Leu Ser Val
    690

<210> SEQ ID NO 17
<211> LENGTH: 697
<212> TYPE: PRT
<213> ORGANISM: Artificial Sequence
<220> FEATURE:
<223> OTHER INFORMATION: Subtype B consensus Envelope protein sequence

<400> SEQUENCE: 17

Arg Val Lys Gly Ile Arg Lys Asn Tyr Gln His Leu Trp Arg Trp Gly
1               5                   10                  15

Thr Met Leu Leu Gly Met Leu Met Ile Cys Ser Ala Ala Glu Lys Leu
                20                  25                  30

Trp Val Thr Val Tyr Tyr Gly Val Pro Val Trp Lys Glu Ala Thr Thr
            35                  40                  45

Thr Leu Phe Cys Ala Ser Asp Ala Lys Ala Tyr Asp Thr Glu Val His
        50                  55                  60

Asn Val Trp Ala Thr His Ala Cys Val Pro Thr Asp Pro Asn Pro Gln
65                  70                  75                  80

Glu Val Val Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
                100                 105                 110

Ser Leu Lys Pro Cys Val Lys Leu Thr Pro Leu Cys Val Thr Leu Asn
            115                 120                 125

Cys Thr Asp Leu Ser Gly Glu Lys Met Glu Lys Gly Glu Ile Lys Asn
        130                 135                 140

Cys Ser Phe Asn Ile Thr Thr Ser Ile Arg Asp Lys Val Gln Lys Glu
145                 150                 155                 160

Tyr Ala Leu Phe Tyr Lys Leu Asp Val Val Pro Ile Asp Asn Asp Asn
                165                 170                 175

Thr Ser Tyr Arg Leu Ile Ser Cys Asn Thr Ser Val Ile Thr Gln Ala
                180                 185                 190

Cys Pro Lys Val Ser Phe Glu Pro Ile Pro Ile His Tyr Cys Ala Pro
            195                 200                 205

Ala Gly Phe Ala Ile Leu Lys Cys Asn Asp Lys Lys Phe Asn Gly Thr
        210                 215                 220

Gly Pro Cys Thr Asn Val Ser Thr Val Gln Cys Thr His Gly Ile Arg
225                 230                 235                 240

Pro Val Val Ser Thr Gln Leu Leu Leu Asn Gly Ser Leu Ala Glu Glu
                245                 250                 255

Glu Val Val Ile Arg Ser Glu Asn Phe Thr Asn Asn Ala Lys Thr Ile
                260                 265                 270

Ile Val Gln Leu Asn Glu Ser Val Glu Ile Asn Cys Thr Arg Pro Asn
            275                 280                 285
```

```
Asn Asn Thr Arg Lys Ser Ile His Ile Gly Pro Gly Gln Ala Phe Tyr
290                 295                 300
Thr Thr Gly Glu Ile Ile Gly Asp Ile Arg Gln Ala His Cys Asn Ile
305                 310                 315                 320
Ser Arg Ala Lys Trp Asn Asn Thr Leu Lys Gln Ile Val Lys Lys Leu
                325                 330                 335
Arg Glu Gln Phe Gly Asn Lys Thr Ile Val Phe Asn Gln Ser Ser Gly
                340                 345                 350
Gly Arg Pro Arg Ile Val Met His Ser Phe Asn Cys Gly Gly Glu Phe
            355                 360                 365
Phe Tyr Cys Asn Thr Thr Gln Leu Phe Asn Ser Thr Trp Asn Val Asn
370                 375                 380
Gly Thr Trp Asn Asn Thr Glu Gly Asn Asp Thr Ile Thr Leu Pro
385                 390                 395                 400
Cys Arg Ile Lys Gln Ile Ile Asn Met Trp Gln Glu Val Gly Lys Ala
                405                 410                 415
Met Tyr Ala Pro Pro Ile Arg Gly Gln Ile Arg Cys Ser Ser Asn Ile
                420                 425                 430
Thr Gly Leu Leu Leu Thr Arg Asp Gly Gly Asn Asn Asn Thr Asn Glu
            435                 440                 445
Thr Glu Ile Phe Arg Pro Gly Gly Gly Asp Met Arg Asp Asn Trp Arg
450                 455                 460
Ser Glu Leu Tyr Lys Tyr Lys Val Val Lys Ile Glu Pro Leu Gly Val
465                 470                 475                 480
Ala Pro Thr Lys Ala Lys Arg Arg Val Val Gln Arg Glu Lys Arg Ala
                485                 490                 495
Val Gly Ile Gly Ala Met Phe Leu Gly Phe Leu Gly Ala Ala Gly Ser
            500                 505                 510
Thr Met Gly Ala Ala Ser Met Thr Leu Thr Val Gln Ala Arg Gln Leu
            515                 520                 525
Leu Ser Gly Ile Val Gln Gln Gln Asn Asn Leu Leu Arg Ala Ile Glu
    530                 535                 540
Ala Gln Gln His Leu Leu Gln Leu Thr Val Trp Gly Ile Lys Gln Leu
545                 550                 555                 560
Gln Ala Arg Val Leu Ala Val Glu Arg Tyr Leu Lys Asp Gln Gln Leu
                565                 570                 575
Leu Gly Ile Trp Gly Cys Ser Gly Lys Leu Ile Cys Thr Thr Thr Val
            580                 585                 590
Pro Trp Asn Ala Ser Trp Ser Asn Lys Ser Leu Asp Glu Ile Trp Asp
            595                 600                 605
Asn Met Thr Trp Met Glu Trp Glu Arg Glu Ile Asp Asn Tyr Thr Ser
610                 615                 620
Leu Ile Tyr Thr Leu Ile Glu Glu Ser Gln Asn Gln Gln Glu Lys Asn
625                 630                 635                 640
Glu Gln Glu Leu Leu Glu Leu Asp Lys Trp Ala Ser Leu Trp Asn Trp
                645                 650                 655
Phe Asp Ile Thr Asn Trp Leu Trp Tyr Ile Lys Ile Phe Ile Met Ile
                660                 665                 670
Val Gly Gly Leu Ile Gly Leu Arg Ile Val Phe Ala Val Leu Ser Ile
            675                 680                 685
Tyr Pro Tyr Asp Val Pro Asp Tyr Ala
    690                 695
```

<210> SEQ ID NO 18
<211> LENGTH: 687
<212> TYPE: PRT
<213> ORGANISM: Artificial Sequence
<220> FEATURE:
<223> OTHER INFORMATION: Subtype C consensus Envelope protein sequence

<400> SEQUENCE: 18

```
Arg Val Arg Gly Ile Leu Arg Asn Cys Gln Gln Trp Trp Ile Trp Gly
1               5                   10                  15

Ile Leu Gly Phe Trp Met Leu Met Ile Cys Asn Val Met Gly Asn Leu
            20                  25                  30

Trp Val Thr Val Tyr Tyr Gly Val Pro Val Trp Lys Glu Ala Lys Thr
        35                  40                  45

Thr Leu Phe Cys Ala Ser Asp Ala Lys Ala Tyr Glu Thr Glu Val His
    50                  55                  60

Asn Val Trp Ala Thr His Ala Cys Val Pro Thr Asp Pro Asn Pro Gln
65                  70                  75                  80

Glu Met Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Arg Asn Asn Val Asn Asn Asn Thr Met Lys Glu Glu Ile Lys
    130                 135                 140

Asn Cys Ser Phe Asn Ile Thr Thr Glu Leu Arg Asp Lys Lys Gln Lys
145                 150                 155                 160

Val Tyr Ala Leu Phe Tyr Arg Leu Asp Ile Val Pro Leu Asn Glu Lys
                165                 170                 175

Asn Asn Ser Asn Asp Tyr Arg Leu Ile Asn Cys Asn Thr Ser Ala Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Thr Gly Pro Cys Asn Asn Val Ser Thr Val Gln Cys Thr His
225                 230                 235                 240

Gly Ile Lys Pro Val Val Ser Thr Gln Leu Leu Asn Gly Ser Leu
                245                 250                 255

Ala Glu Glu Glu Ile Ile Ile Arg Ser Glu Asn Leu Thr Asn Asn Ala
            260                 265                 270

Lys Thr Ile Ile Val His Leu Asn Glu Ser Val Glu Ile Val Cys Thr
        275                 280                 285

Arg Pro Asn Asn Asn Thr Arg Lys Ser Ile Arg Ile Gly Pro Gly Gln
    290                 295                 300

Thr Phe Tyr Ala Thr Gly Asp Ile Ile Gly Asp Ile Arg Gln Ala His
305                 310                 315                 320

Cys Asn Ile Ser Glu Glu Lys Trp Asn Lys Thr Leu Gln Arg Val Ser
                325                 330                 335

Glu Lys Leu Lys Glu His Phe Pro Asn Lys Thr Ile Lys Phe Ala Pro
            340                 345                 350

Ser Ser Gly Gly Arg Leu Glu Ile Thr Thr His Ser Phe Asn Cys Arg
        355                 360                 365

Gly Glu Phe Phe Tyr Cys Asn Thr Ser Lys Leu Phe Asn Ser Thr Tyr
```

```
    370                 375                 380

Met Pro Asn Ser Thr Asn Asn Thr Asn Thr Thr Ile Thr Leu Pro Cys
385                 390                 395                 400

Arg Ile Lys Gln Ile Ile Asn Met Trp Gln Glu Val Gly Arg Ala Met
                405                 410                 415

Tyr Ala Pro Pro Ile Glu Gly Asn Ile Thr Cys Lys Ser Asn Ile Thr
            420                 425                 430

Gly Leu Leu Leu Thr Arg Asp Gly Gly Lys Asn Asp Thr Asn Asp Thr
        435                 440                 445

Glu Thr Phe Arg Pro Gly Gly Gly Asp Met Arg Asp Asn Trp Arg Ser
    450                 455                 460

Glu Leu Tyr Lys Tyr Lys Val Val Glu Ile Lys Pro Leu Gly Val Ala
465                 470                 475                 480

Pro Thr Lys Ala Lys Arg Arg Val Val Glu Arg Glu Lys Arg Ala Val
                485                 490                 495

Gly Ile Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
        515                 520                 525

Ser Gly Ile Val Gln Gln Gln Ser Asn Leu Leu Arg Ala Ile Glu Ala
    530                 535                 540

Gln Gln His Met Leu Gln Leu Thr Val Trp Gly Ile Lys Gln Leu Gln
545                 550                 555                 560

Thr Arg Val Leu Ala Ile Glu Arg Tyr Leu Lys Asp Gln Gln Leu Leu
                565                 570                 575

Gly Ile Trp Gly Cys Ser Gly Lys Leu Ile Cys Thr Thr Ala Val Pro
            580                 585                 590

Trp Asn Ser Ser Trp Ser Asn Lys Ser Gln Glu Asp Ile Trp Asp Asn
        595                 600                 605

Met Thr Trp Met Gln Trp Asp Arg Glu Ile Ser Asn Tyr Thr Asp Thr
    610                 615                 620

Ile Tyr Arg Leu Leu Glu Asp Ser Gln Asn Gln Gln Glu Lys Asn Glu
625                 630                 635                 640

Lys Asp Leu Leu Ala Leu Asp Ser Trp Lys Asn Leu Trp Asn Trp Phe
                645                 650                 655

Asp Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Ile
        675                 680                 685

<210> SEQ ID NO 19
<211> LENGTH: 696
<212> TYPE: PRT
<213> ORGANISM: Artificial Sequence
<220> FEATURE:
<223> OTHER INFORMATION: Subtype D consensus Envelope protein sequence

<400> SEQUENCE: 19

Arg Val Arg Gly Ile Lys Arg Asn Tyr Gln His Leu Trp Lys Trp Gly
1               5                   10                  15

Thr Met Leu Leu Gly Met Leu Met Thr Cys Ser Val Ala Glu Asn Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ser Tyr Lys Thr Glu Ala His
```

```
                50                  55                  60
Asn Ile Trp Ala Thr His Ala Cys Val Pro Thr Asp Pro Asn Pro Gln
 65                  70                  75                  80

Glu Ile Glu Leu Glu Asn Val Thr Glu Asn Phe Asn Met Trp Lys Asn
                 85                  90                  95

Asn Met Val Glu Gln Met His Glu Asp Ile Ile Ser Leu Trp Asp Gln
                100                 105                 110

Ser Leu Lys Pro Cys Val Lys Leu Thr Pro Leu Cys Val Thr Leu Asn
                115                 120                 125

Cys Thr Asp Gly Met Arg Asn Asp Thr Asn Asp Thr Asn Val Thr Met
130                 135                 140

Glu Glu Gly Glu Met Lys Asn Cys Ser Phe Asn Ile Thr Thr Glu Val
145                 150                 155                 160

Arg Asp Lys Lys Lys Gln Val His Ala Leu Phe Tyr Lys Leu Asp Val
                165                 170                 175

Val Pro Ile Asp Asp Asn Asn Thr Asn Asn Ser Asn Tyr Arg Leu Ile
                180                 185                 190

Asn Cys Asn Thr Ser Ala Ile Thr Gln Ala Cys Pro Lys Val Thr Phe
                195                 200                 205

Glu Pro Ile Pro Ile His Tyr Cys Ala Pro Ala Gly Phe Ala Ile Leu
210                 215                 220

Lys Cys Lys Asp Lys Lys Phe Asn Gly Thr Gly Pro Cys Lys Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Ile Ile Ile Arg Ser
                260                 265                 270

Glu Asn Leu Thr Asn Asn Ala Lys Ile Ile Ile Val Gln Leu Asn Glu
                275                 280                 285

Ser Val Thr Ile Asn Cys Thr Arg Pro Tyr Asn Asn Thr Arg Lys Arg
                290                 295                 300

Ile Pro Ile Gly Leu Gly Gln Ala Phe Tyr Thr Thr Arg Gly Ile Ile
305                 310                 315                 320

Gly Asp Ile Arg Gln Ala His Cys Asn Ile Ser Gly Ala Glu Trp Asn
                325                 330                 335

Lys Thr Leu Gln Gln Val Ala Lys Lys Leu Gly Asp Leu Leu Asn Lys
                340                 345                 350

Thr Thr Ile Ile Phe Lys Pro Ser Ser Gly Gly Arg Pro Arg Ile Thr
                355                 360                 365

Thr His Ser Phe Asn Cys Gly Gly Glu Phe Phe Tyr Cys Asn Thr Ser
                370                 375                 380

Arg Leu Phe Asn Ser Thr Trp Ser Lys Asn Ser Thr Asn Ser Thr
385                 390                 395                 400

Lys Glu Asn Asn Thr Ile Thr Leu Pro Cys Arg Ile Lys Gln Ile Ile
                405                 410                 415

Asn Met Trp Gln Gly Val Gly Lys Ala Met Tyr Ala Pro Pro Ile Glu
                420                 425                 430

Gly Leu Ile Lys Cys Ser Ser Asn Ile Thr Gly Leu Leu Leu Thr Arg
                435                 440                 445

Asp Gly Gly Ala Asn Asn Ser His Asn Glu Thr Phe Arg Pro Gly Gly
                450                 455                 460

Gly Asp Met Arg Asp Asn Trp Arg Ser Glu Leu Tyr Lys Tyr Lys Val
465                 470                 475                 480
```

```
Val Lys Ile Glu Pro Leu Gly Val Ala Pro Thr Arg Ala Lys Arg Arg
            485                 490                 495

Val Val Glu Arg Glu Lys Arg Ala Ile Gly Leu Gly Ala Met Phe Leu
            500                 505                 510

Gly Phe Leu Gly Ala Ala Gly Ser Thr Met Gly Ala Ala Ser Leu Thr
            515                 520                 525

Leu Thr Val Gln Ala Arg Gln Leu Leu Ser Gly Ile Val Gln Gln Gln
            530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Ile Leu Ala Val Glu
            565                 570                 575

Arg Tyr Leu Lys Asp Gln Gln Leu Leu Gly Ile Trp Gly Cys Ser Gly
            580                 585                 590

Lys His Ile Cys Thr Thr Thr Val Pro Trp Asn Ser Ser Trp Ser Asn
            595                 600                 605

Lys Ser Leu Asp Glu Ile Trp Asn Asn Met Thr Trp Met Glu Trp Glu
            610                 615                 620

Arg Glu Ile Asp Asn Tyr Thr Gly Leu Ile Tyr Ser Leu Ile Glu Glu
625                 630                 635                 640

Ser Gln Thr Gln Gln Glu Lys Asn Glu Gln Glu Leu Leu Glu Leu Asp
            645                 650                 655

Lys Trp Ala Ser Leu Trp Asn Trp Phe Ser Ile Thr Gln Trp Leu Trp
            660                 665                 670

Tyr Ile Lys Ile Phe Ile Met Ile Val Gly Gly Leu Ile Gly Leu Arg
            675                 680                 685

Ile Val Phe Ala Val Leu Ser Leu
            690                 695

<210> SEQ ID NO 20
<211> LENGTH: 323
<212> TYPE: PRT
<213> ORGANISM: Artificial Sequence
<220> FEATURE:
<223> OTHER INFORMATION: Subtype B consensus Nef-Rev protein sequence

<400> SEQUENCE: 20

Ser Lys Arg Ser Val Val Gly Trp Pro Thr Val Arg Glu Arg Met Arg
1               5                   10                  15

Arg Ala Glu Pro Ala Ala Asp Gly Val Gly Ala Val Ser Arg Asp Leu
            20                  25                  30

Glu Lys His Gly Ala Ile Thr Ser Ser Asn Thr Ala Ala Asn Asn Ala
            35                  40                  45

Asp Cys Ala Trp Leu Glu Ala Gln Glu Glu Glu Val Gly Phe Pro
            50                  55                  60

Val Arg Ala Gln Val Ala Leu Arg Ala Met Thr Tyr Lys Ala Ala Val
65                  70                  75                  80

Asp Leu Ser His Phe Leu Lys Glu Lys Gly Gly Leu Glu Gly Leu Ile
            85                  90                  95

Tyr Ser Gln Lys Arg Gln Asp Ile Leu Asp Leu Trp Val Tyr His Thr
            100                 105                 110

Gln Gly Tyr Phe Pro Asp Trp Gln Asn Tyr Thr Pro Gly Pro Gly Ile
            115                 120                 125

Arg Tyr Pro Leu Thr Phe Gly Trp Cys Phe Lys Leu Val Pro Val Glu
            130                 135                 140
```

```
Pro Glu Lys Val Glu Glu Ala Asn Glu Gly Glu Asn Asn Ser Ala Ala
145                 150                 155                 160

His Pro Met Ser Leu His Gly Met Asp Asp Pro Glu Arg Glu Val Leu
                165                 170                 175

Val Trp Lys Phe Asp Ser Arg Leu Ala Phe His His Met Ala Arg Glu
            180                 185                 190

Leu His Pro Glu Tyr Tyr Lys Asp Cys Arg Gly Arg Lys Arg Arg Ser
        195                 200                 205

Ala Gly Arg Ser Gly Asp Ser Asp Glu Glu Leu Leu Lys Thr Val Arg
    210                 215                 220

Leu Ile Lys Phe Leu Tyr Gln Ser Asn Pro Pro Ser Pro Glu Gly
225                 230                 235                 240

Thr Arg Gln Ala Arg Arg Asn Arg Arg Arg Trp Arg Glu Arg Gln
                245                 250                 255

Arg Gln Ile Arg Ser Ile Ser Glu Trp Ile Leu Ser Thr Tyr Leu Gly
                260                 265                 270

Arg Pro Ala Glu Pro Val Pro Leu Gln Leu Pro Pro Leu Glu Arg Leu
            275                 280                 285

Thr Leu Asp Cys Asn Glu Asp Cys Gly Thr Ser Gly Thr Gln Gly Val
        290                 295                 300

Gly Ser Pro Gln Ile Leu Val Glu Ser Pro Ala Val Leu Glu Ser Gly
305                 310                 315                 320

Thr Lys Glu

<210> SEQ ID NO 21
<211> LENGTH: 506
<212> TYPE: PRT
<213> ORGANISM: Artificial Sequence
<220> FEATURE:
<223> OTHER INFORMATION: Gag consensus protein sequence of subtype A,
      B, C and D

<400> SEQUENCE: 21

Gly Ala Arg Ala Ser Val Leu Ser Gly Gly Lys Leu Asp Ala Trp Glu
1               5                   10                  15

Lys Ile Arg Leu Arg Pro Gly Gly Lys Lys Tyr Arg Leu Lys His
            20                  25                  30

Leu Val Trp Ala Ser Arg Glu Leu Glu Arg Phe Ala Leu Asn Pro Gly
        35                  40                  45

Leu Leu Glu Thr Ser Glu Gly Cys Lys Gln Ile Ile Gly Gln Leu Gln
    50                  55                  60

Pro Ala Leu Gln Thr Gly Ser Glu Glu Leu Arg Ser Leu Tyr Asn Thr
65                  70                  75                  80

Val Ala Thr Leu Tyr Cys Val His Glu Lys Ile Glu Val Lys Asp Thr
                85                  90                  95

Lys Glu Ala Leu Asp Lys Ile Glu Glu Glu Gln Asn Lys Ser Lys Gln
            100                 105                 110

Lys Ala Gln Gln Ala Ala Ala Asp Thr Gly Asn Ser Ser Gln Val Ser
        115                 120                 125

Gln Asn Tyr Pro Ile Val Gln Asn Leu Gln Gly Gln Met Val His Gln
    130                 135                 140

Ala Ile Ser Pro Arg Thr Leu Asn Ala Trp Val Lys Val Ile Glu Glu
145                 150                 155                 160

Lys Ala Phe Ser Pro Glu Val Ile Pro Met Phe Ser Ala Leu Ser Glu
                165                 170                 175
```

Gly Ala Thr Pro Gln Asp Leu Asn Thr Met Leu Asn Thr Val Gly Gly
            180                 185                 190

His Gln Ala Ala Met Gln Met Leu Lys Asp Thr Ile Asn Glu Glu Ala
        195                 200                 205

Ala Glu Trp Asp Arg Leu His Pro Val His Ala Gly Pro Ile Ala Pro
    210                 215                 220

Gly Gln Met Arg Glu Pro Arg Gly Ser Asp Ile Ala Gly Thr Thr Ser
225                 230                 235                 240

Thr Leu Gln Glu Gln Ile Gly Trp Met Thr Ser Asn Pro Pro Ile Pro
                245                 250                 255

Val Gly Asp Ile Tyr Lys Arg Trp Ile Ile Leu Gly Leu Asn Lys Ile
            260                 265                 270

Val Arg Met Tyr Ser Pro Val Ser Ile Leu Asp Ile Arg Gln Gly Pro
        275                 280                 285

Lys Glu Pro Phe Arg Asp Tyr Val Asp Arg Phe Phe Lys Thr Leu Arg
    290                 295                 300

Ala Glu Gln Ala Ser Gln Asp Val Lys Asn Trp Met Thr Glu Thr Leu
305                 310                 315                 320

Leu Val Gln Asn Ala Asn Pro Asp Cys Lys Thr Ile Leu Arg Ala Leu
                325                 330                 335

Gly Pro Gly Ala Thr Leu Glu Glu Met Met Thr Ala Cys Gln Gly Val
            340                 345                 350

Gly Gly Pro Gly His Lys Ala Arg Val Leu Ala Glu Ala Met Ser Gln
        355                 360                 365

Ala Thr Asn Ser Asn Ile Met Met Gln Arg Gly Asn Phe Arg Gly Pro
    370                 375                 380

Arg Arg Ile Val Lys Cys Phe Asn Cys Gly Lys Glu Gly His Ile Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser His Lys Gly Arg Pro Gly Asn Phe Leu Gln
        435                 440                 445

Ser Arg Pro Glu Pro Thr Ala Pro Pro Ala Glu Ser Phe Gly Phe Gly
    450                 455                 460

Glu Glu Ile Thr Pro Ser Pro Lys Gln Glu Pro Lys Asp Arg Glu Leu
465                 470                 475                 480

Tyr Pro Leu Ala Ser Leu Lys Ser Leu Phe Gly Asn Asp Pro Leu Ser
                485                 490                 495

Gln Tyr Pro Tyr Asp Val Pro Asp Tyr Ala
            500                 505

<210> SEQ ID NO 22
<211> LENGTH: 818
<212> TYPE: DNA
<213> ORGANISM: Artificial Sequence
<220> FEATURE:
<223> OTHER INFORMATION: HPV genotype 16 E6-E7 DNA sequence

<400> SEQUENCE: 22
gaattcgcca ccatggactg gacctggatc ctgttcctgg tggccgccgc cacacgggtg      60
cacagcttcc aggaccccca ggagagcggc agaaagctgc ctcagctgtg taccgagctg     120
cagaccacca tccacgacat catcctggag tgtgtgtact gtaagcagca gctgctgagg     180

```
agagaggtgt acgaccggga cctgtgtatc gtgtacaggg acggcaatcc ctacgccgtg    240
tgtgacaagt gcctgaagtt ctacagcaag atcagcgagt accggcacta ctgctacagc    300
ctgtacggca ccaccctgga gcagcagtac aacaagcccc tgtgtgacct gctgatccgg    360
tgtatcaact gccagaagcc cctgcagaga cacctggaca gaagcagcg gttccacaac    420 atcaggggca gatggaccgg cagatgtatg agctgctgcc ggagcagcag aaccagaagg    480
gagacccagc tgagaggccg aagagaaga gccacggcg ataccccac cctgcacgag    540 tacatgctgg acctgcagcc tgagaccacc gatctgtacg ctacggcca gctgaatgac    600 agcagcgagg aggaggatga gatcgacggc cctgccggcc aggccgagcc cgacagagcc    660
cactacaaca tcgtgacctt ttgctgtaag tgtgacagca ccctgagact gtgcgtgcag    720
agcacccacg tggacatcag aaccctggag gatctgctga tgggcaccct gggcatcgtg    780
tgtcccatct gctcccagaa acctgatga gcggccgc                             818
```

<210> SEQ ID NO 23
<211> LENGTH: 264
<212> TYPE: PRT
<213> ORGANISM: Artificial sequence
<220> FEATURE:
<223> OTHER INFORMATION: HPV genotype 16 E6-E7 protein sequence

<400> SEQUENCE: 23

```
Met Asp Trp Thr Trp Ile Leu Phe Leu Val Ala Ala Thr Arg Val
1               5                   10                  15

His Ser Phe Gln Asp Pro Gln Glu Ser Gly Arg Lys Leu Pro Gln Leu
            20                  25                  30

Cys Thr Glu Leu Gln Thr Thr Ile His Asp Ile Ile Leu Glu Cys Val
        35                  40                  45

Tyr Cys Lys Gln Gln Leu Leu Arg Arg Glu Val Tyr Asp Arg Asp Leu
    50                  55                  60

Cys Ile Val Tyr Arg Asp Gly Asn Pro Tyr Ala Val Cys Asp Lys Cys
65                  70                  75                  80

Leu Lys Phe Tyr Ser Lys Ile Ser Glu Tyr Arg His Tyr Cys Tyr Ser
                85                  90                  95

Leu Tyr Gly Thr Thr Leu Glu Gln Gln Tyr Asn Lys Pro Leu Cys Asp
            100                 105                 110

Leu Leu Ile Arg Cys Ile Asn Cys Gln Lys Pro Leu Gln Arg His Leu
        115                 120                 125

Asp Lys Lys Gln Arg Phe His Asn Ile Arg Gly Arg Trp Thr Gly Arg
    130                 135                 140

Cys Met Ser Cys Cys Arg Ser Ser Arg Thr Arg Arg Glu Thr Gln Leu
145                 150                 155                 160

Arg Gly Arg Lys Arg Arg Ser His Gly Asp Thr Pro Thr Leu His Glu
                165                 170                 175

Tyr Met Leu Asp Leu Gln Pro Glu Thr Thr Asp Leu Tyr Gly Tyr Gly
            180                 185                 190

Gln Leu Asn Asp Ser Ser Glu Glu Glu Asp Glu Ile Asp Gly Pro Ala
        195                 200                 205

Gly Gln Ala Glu Pro Asp Arg Ala His Tyr Asn Ile Val Thr Phe Cys
    210                 215                 220

Cys Lys Cys Asp Ser Thr Leu Arg Leu Cys Val Gln Ser Thr His Val
225                 230                 235                 240

Asp Ile Arg Thr Leu Glu Asp Leu Leu Met Gly Thr Leu Gly Ile Val
```

```
                245                 250                 255
Cys Pro Ile Cys Ser Gln Lys Pro
            260

<210> SEQ ID NO 24
<211> LENGTH: 15
<212> TYPE: PRT
<213> ORGANISM: Artificial Sequence
<220> FEATURE:
<223> OTHER INFORMATION: HPV E6 immunodominant epitope

<400> SEQUENCE: 24

Leu Cys Ile Val Tyr Arg Asp Gly Asn Pro Tyr Ala Val Cys Asp
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: HPV E7 immunodominant epitope

<400> SEQUENCE: 25

Ala Glu Pro Asp Arg Ala His Tyr Asn Ile Val Thr Phe Cys Cys
1               5                   10                  15

<210> SEQ ID NO 26
<211> LENGTH: 142
<212> TYPE: PRT
<213> ORGANISM: Artificial Sequence
<220> FEATURE:
<223> OTHER INFORMATION: HPV E6 consensus sequence

<400> SEQUENCE: 26

Phe Gln Asp Pro Gln Glu Ser Gly Arg Lys Leu Pro Gln Leu Cys Thr
1               5                   10                  15

Glu Leu Gln Thr Thr Ile His Asp Ile Ile Leu Glu Cys Val Tyr Cys
            20                  25                  30

Lys Gln Gln Leu Leu Arg Arg Glu Val Tyr Asp Arg Asp Leu Cys Ile
        35                  40                  45

Val Tyr Arg Asp Gly Asn Pro Tyr Ala Val Cys Asp Lys Cys Leu Lys
    50                  55                  60

Phe Tyr Ser Lys Ile Ser Glu Tyr Arg His Tyr Cys Tyr Ser Leu Tyr
65                  70                  75                  80

Gly Thr Thr Leu Glu Gln Gln Tyr Asn Lys Pro Leu Cys Asp Leu Leu
                85                  90                  95

Ile Arg Cys Ile Asn Cys Gln Lys Pro Leu Gln Arg His Leu Asp Lys
            100                 105                 110

Lys Gln Arg Phe His Asn Ile Arg Gly Arg Trp Thr Gly Arg Cys Met
        115                 120                 125

Ser Cys Cys Arg Ser Ser Arg Thr Arg Arg Glu Thr Gln Leu
    130                 135                 140

<210> SEQ ID NO 27
<211> LENGTH: 97
<212> TYPE: PRT
<213> ORGANISM: Artificial Sequence
<220> FEATURE:
<223> OTHER INFORMATION: HPV E7 consensus sequence

<400> SEQUENCE: 27

His Gly Asp Thr Pro Thr Leu His Glu Tyr Met Leu Asp Leu Gln Pro
```

```
                1               5              10              15

Glu Thr Thr Asp Leu Tyr Gly Tyr Gly Gln Leu Asn Asp Ser Ser Glu
                                20                  25                  30

Glu Glu Asp Glu Ile Asp Gly Pro Ala Gly Gln Ala Glu Pro Asp Arg
                         35                  40                  45

Ala His Tyr Asn Ile Val Thr Phe Cys Cys Lys Cys Asp Ser Thr Leu
                     50                  55                  60

Arg Leu Cys Val Gln Ser Thr His Val Asp Ile Arg Thr Leu Glu Asp
             65                  70                  75                  80

Leu Leu Met Gly Thr Leu Gly Ile Val Cys Pro Ile Cys Ser Gln Lys
                                85                  90                  95

Pro

<210> SEQ ID NO 28
<211> LENGTH: 18
<212> TYPE: PRT
<213> ORGANISM: Artificial Sequence
<220> FEATURE:
<223> OTHER INFORMATION: IgE Leader Sequence

<400> SEQUENCE: 28

Met Asp Trp Thr Trp Ile Leu Phe Leu Val Ala Ala Thr Arg Val
1               5                  10                  15

His Ser

<210> SEQ ID NO 29
<211> LENGTH: 7
<212> TYPE: PRT
<213> ORGANISM: Artificial Sequence
<220> FEATURE:
<223> OTHER INFORMATION: Proteolytic Cleavage Sequence

<400> SEQUENCE: 29

Arg Gly Arg Lys Arg Arg Ser
1               5

<210> SEQ ID NO 30
<211> LENGTH: 1766
<212> TYPE: DNA
<213> ORGANISM: Artificial Sequence
<220> FEATURE:
<223> OTHER INFORMATION: HCV genotype 1a and 1b consensus E1-E2 DNA
      sequence

<400> SEQUENCE: 30
gaattcgcca ccatggactg gacctggatc ctgttcctgg tggccgctgc aacacgggtg      60
cacagctacc aagtgaggaa tagcagcggc ctgtaccacg tgaccaacga ctgctccaac     120
agcagcatcg tgtacgaggc cgccgacatg atcatgcaca cccccggctg tgtgccctgt     180
gtgagagagg caacagctc cagatgctgg gtggccctga cccctaccgt ggccgccaga     240
gatggcagcc tgcccaccac caccctgagg agacacgtgg acctgcttgt gggcagcgcc     300
accctgtgta gcgccatgta tgtgggcgat ctgtgtggca gcgtgtttct tgtgggccag     360
ctgttcacct tcagccccag aaggcactgg accgtgcagg actgtaactg ctccatctac     420
cccggccaca tcaccggcca cagaatggcc tgggacatga tgatgaactg gagccctacc     480
accgccctgg tggtgtccca gctgctgaga atccctcagg ccatcgtgga catggtggcc     540
ggagcccact ggggcgtgct ggccggcatc gcctacttca gcatggtggg caactgggcc     600
aaggtgctcg tggtgctgct gctgttcgcc ggcgtggacg gcagaggcag gaagagaagg     660
```

```
agcgagaccc acgtgaccgg cggcaccgcc ggcagaacca cagccggc

```
Val Ser Gln Leu Leu Arg Ile Pro Gln Ala Ile Val Asp Met Val Ala
            165                 170                 175

Gly Ala His Trp Gly Val Leu Ala Gly Ile Ala Tyr Phe Ser Met Val
            180                 185                 190

Gly Asn Trp Ala Lys Val Leu Val Val Leu Leu Leu Phe Ala Gly Val
            195                 200                 205

Asp Gly Arg Gly Arg Lys Arg Arg Ser Glu Thr His Val Thr Gly Gly
            210                 215                 220

Thr Ala Gly Arg Thr Thr Ala Gly Leu Val Gly Leu Phe Thr Pro Gly
225                 230                 235                 240

Ala Lys Gln Asn Ile Gln Leu Ile Asn Thr Asn Gly Ser Trp His Ile
            245                 250                 255

Asn Ser Thr Ala Leu Asn Cys Asn Asp Ser Leu Asn Thr Gly Trp Leu
            260                 265                 270

Ala Gly Leu Phe Tyr Gln His Lys Phe Asn Ser Ser Gly Cys Pro Glu
            275                 280                 285

Arg Met Ala Ser Cys Arg Pro Leu Asp Glu Phe Ala Gln Gly Trp Gly
            290                 295                 300

Pro Ile Thr Tyr Ala Asn Gly Ser Gly Pro Asp Gln Arg Pro Tyr Cys
305                 310                 315                 320

Trp His Tyr Ala Pro Arg Pro Cys Gly Ile Val Pro Ala Lys Ser Val
            325                 330                 335

Cys Gly Pro Val Tyr Cys Phe Thr Pro Ser Pro Val Val Val Gly Thr
            340                 345                 350

Thr Asp Arg Ser Gly Ala Pro Thr Tyr Ser Trp Gly Glu Asn Glu Thr
            355                 360                 365

Asp Val Leu Val Leu Asn Asn Thr Arg Pro Pro Leu Gly Asn Trp Phe
            370                 375                 380

Gly Cys Thr Trp Met Asn Ser Thr Gly Phe Thr Lys Val Cys Gly Ala
385                 390                 395                 400

Pro Pro Cys Val Ile Gly Gly Val Gly Asn Asn Thr Leu Thr Cys Pro
            405                 410                 415

Thr Asp Cys Phe Arg Lys His Pro Glu Ala Thr Tyr Ser Arg Cys Gly
            420                 425                 430

Ser Gly Pro Trp Leu Thr Pro Arg Cys Met Val Asp Tyr Pro Tyr Arg
            435                 440                 445

Leu Trp His Tyr Pro Cys Thr Val Asn Phe Thr Ile Phe Lys Val Arg
            450                 455                 460

Met Tyr Val Gly Gly Val Glu His Arg Leu Glu Ala Ala Cys Asn Trp
465                 470                 475                 480

Thr Arg Gly Glu Arg Cys Asp Leu Glu Asp Arg Asp Arg Ser Glu Leu
            485                 490                 495

Ser Pro Leu Leu Leu Ser Thr Thr Glu Trp Gln Val Leu Pro Cys Ser
            500                 505                 510

Phe Thr Thr Leu Pro Ala Leu Ser Thr Gly Leu Ile His Leu His Gln
            515                 520                 525

Asn Ile Val Asp Val Gln Tyr Leu Tyr Gly Val Gly Ser Ser Ile Val
            530                 535                 540

Ser Trp Ala Ile Lys Trp Glu Tyr Val Val Leu Leu Phe Leu Leu Leu
545                 550                 555                 560

Ala Asp Ala Arg Val Cys Ser Cys Leu Trp Met Met Leu Leu Ile Ser
            565                 570                 575
```

-continued

Gln Ala Glu Ala
        580

<210> SEQ ID NO 32
<211> LENGTH: 192
<212> TYPE: PRT
<213> ORGANISM: Artificial Sequence
<220> FEATURE:
<223> OTHER INFORMATION: HCV E1 consensus sequence

<400> SEQUENCE: 32

Tyr Gln Val Arg Asn Ser Ser Gly Leu Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Gly Asn Ser Ser Arg Cys Trp
        35                  40                  45

Val Ala Leu Thr Pro Thr Val Ala Ala Arg Asp Gly Ser Leu Pro Thr
    50                  55                  60

Thr Thr Leu Arg Arg His Val Asp Leu Leu Val Gly Ser Ala Thr Leu
65                  70                  75                  80

Cys Ser Ala Met Tyr Val Gly Asp Leu Cys Gly Ser Val Phe Leu Val
                85                  90                  95

Gly Gln Leu Phe Thr Phe Ser Pro Arg Arg His Trp Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Ile Val Asp Met Val Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Gly
            180                 185                 190

<210> SEQ ID NO 33
<211> LENGTH: 363
<212> TYPE: PRT
<213> ORGANISM: Artificial Sequence
<220> FEATURE:
<223> OTHER INFORMATION: HCV E2 consensus sequence

<400> SEQUENCE: 33

Glu Thr His Val Thr Gly Gly Thr Ala Gly Arg Thr Thr Ala Gly Leu
1               5                   10                  15

Val Gly Leu Phe Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Asp
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Met Ala Ser Cys Arg Pro Leu Asp
65                  70                  75                  80

Glu Phe Ala Gln Gly Trp Gly Pro Ile Thr Tyr Ala Asn Gly Ser Gly
                85                  90                  95

Pro Asp Gln Arg Pro Tyr Cys Trp His Tyr Ala Pro Arg Pro Cys Gly
            100                 105                 110

```
Ile Val Pro Ala Lys Ser Val Cys Gly Pro Val Tyr Cys Phe Thr Pro
        115                 120                 125
Ser Pro Val Val Val Gly Thr Thr Asp Arg Ser Gly Ala Pro Thr Tyr
    130                 135                 140
Ser Trp Gly Glu Asn Glu Thr Asp Val Leu Val Leu Asn Asn Thr Arg
145                 150                 155                 160
Pro Pro Leu Gly Asn Trp Phe Gly Cys Thr Trp Met Asn Ser Thr Gly
                165                 170                 175
Phe Thr Lys Val Cys Gly Ala Pro Pro Cys Val Ile Gly Gly Val Gly
            180                 185                 190
Asn Asn Thr Leu Thr Cys Pro Thr Asp Cys Phe Arg Lys His Pro Glu
        195                 200                 205
Ala Thr Tyr Ser Arg Cys Gly Ser Gly Pro Trp Leu Thr Pro Arg Cys
    210                 215                 220
Met Val Asp Tyr Pro Tyr Arg Leu Trp His Tyr Pro Cys Thr Val Asn
225                 230                 235                 240
Phe Thr Ile Phe Lys Val Arg Met Tyr Val Gly Gly Val Glu His Arg
                245                 250                 255
Leu Glu Ala Ala Cys Asn Trp Thr Arg Gly Glu Arg Cys Asp Leu Glu
            260                 265                 270
Asp Arg Asp Arg Ser Glu Leu Ser Pro Leu Leu Leu Ser Thr Thr Glu
        275                 280                 285
Trp Gln Val Leu Pro Cys Ser Phe Thr Thr Leu Pro Ala Leu Ser Thr
    290                 295                 300
Gly Leu Ile His Leu His Gln Asn Ile Val Asp Val Gln Tyr Leu Tyr
305                 310                 315                 320
Gly Val Gly Ser Ser Ile Val Ser Trp Ala Ile Lys Trp Glu Tyr Val
                325                 330                 335
Val Leu Leu Phe Leu Leu Leu Ala Asp Ala Arg Val Cys Ser Cys Leu
            340                 345                 350
Trp Met Met Leu Leu Ile Ser Gln Ala Glu Ala
        355                 360

<210> SEQ ID NO 34
<211> LENGTH: 3512
<212> TYPE: DNA
<213> ORGANISM: Homo sapiens

<400> SEQUENCE: 34
ggtaccgaat cgccaccat ggactggacc tggatcctgt tcctggtggc cgctgccaca      60
agagtgcaca gccccagggc ccccaggtgc agagccgtgc ggagcctgct gcggagccac     120
taccgggagg tgctgccct ggccaccttc gtgcggaggc tgggccctca ggggtggcgg     180
ctggtgcaga gaggcgaccc tgccgccttc agagccctgg tgcccagtg cctggtgtgc     240 gtgccctggg acgccagacc tcccctgcc gccctagct ccggcaggt gtcctgcctg     300 aaagaactgg tggcccgggt gctgcagcgg ctgtgcgaga ggggcgccaa gaacgtgctg     360
gccttcggct cgccctgct ggacggcgcc agaggcggcc ctcccgaggc cttcaccacc     420
tccgtgagaa gctacctgcc aacaccgtg accgacgccc tgagaggcag cggcgcttgg     480
ggcctgctgc tgcgcagagt gggcgacgac gtgctggtgc acctgctggc cagatgcgcc     540
ctgttcgtgc tggtcgcccc cagctgcgcc taccaggtgt gcgggccacc cctgtaccag     600
ctgggagccg ccacccaggc cagacccct cctcacgcct ccggcccag gcggagactg     660
```

```
ggctgcgagc gggcctggaa ccacagcgtg cgggaggccg gcgtgcccct gggcctgcca    720
gccccctggcg ccagaagaag gggcggcagc gccagcagaa gcctgcccct gcccaagcgg    780
cccagacgcg gagccgcccc tgagcccgag agaaccccccg tgggccaggg ctcttgggcc    840
caccctggcc ggaccagagg ccccagcgac cggggcttct gcgtggtgtc cccgccaga    900
cccgccgagg aagccaccte cctggaaggc gccctgagcg gcaccaggca cagccacccc    960
agcgtgggcc gccagcacca cgccggaccc cccagcacct caggccccc caggccctgg    1020
gacacccctt gcccccctgt gtacgccgag accaagcact tcctgtacag cagcggcgac    1080
aaagagcagc tgcggcccag cttcctgctg tccagcctga ggccctccct gaccggcgct    1140
aggcgcctgg tggagaccat ctttctgggc agccggccct ggatgccgg cacccccagg    1200
cggctgccca ggctgcccca gcggtactgg cagatgaggc ctctgttcct ggaactgctg    1260
ggcaaccacg cccagtgccc ctacggcgtg ctgctgaaaa cccactgccc cctgagagcc    1320
gccgtgaccc cagccgccgg agtgtgcgcc agagagaagc tcagggcag cgtggccgct    1380
cccgaggaag aggacaccga ccccagacgc ctggtgcagc tgctgcggca gcacagcagc    1440
ccttggcagg tgtacggctt cgtgcgggcc tgcctgagaa ggctggtgcc ccctggcctg    1500
tggggcagca gcacaacga gcggcggttt ctgcggaaca ccaagaagtt catcagcctg    1560
gggaagcacg ccaagctgtc cctgcaggaa ctgacctgga agatgagcgt gcggggctgc    1620
gcctggctga agatccccc tggcgtgggc tgcgtgcctg ccgccgagca ccggctgcgg    1680
gaggaaatcc tggccaagtt cctgcactgg ctgatgagcg tgtacgtggt ggagctgctg    1740
agatccttct tctacgtgac cgagaccacc ttccagaaga actacctgtt cttctaccgg    1800
aagagcgtgt ggagcaagct gcagagcatc ggcatccggc agcacctgaa gcgggtgcag    1860
ctgagagagc tgtccgaggc cgaagtgagg cagcaccggg aggccagacc tgccctgctg    1920
accagccggc tgcggttcat ccccaagccc gacggcctgc ggcccatcgt gaacatggac    1980
tacgtggtgg gcgccaggac cttccggcgg gagaagcggg ccgagcggct gacctcgagg    2040
gtgaaggccc tgttcagcgt gctgaactac gagcgggcca ggcggccagg cctgctgggc    2100
gccagcgtgc tgggcctgga cgacatccac cgggcctggc ggaccttcgt gctgagagtg    2160
cgggcccagg acccccctcc cgagctgtac ttcgtgaagg tggacgtgac aggcgcctac    2220
gacaccatcc cccaggaccg gctgaccgag gtgatcgcca gcatcatcaa gccccagaac    2280
acctactgcg tgcggagata cgccgtggtg cagaaggccg cccacggcca cgtgcggaag    2340
gccttcaaga gccacgtgag caccctgacc gacctgcagc cctacatgcg gcagttcgtg    2400
gcccacctgc aggaaaccag ccccctgcgg gatgccgtgg tgatcgagca gagcagcagc    2460
ctgaacgagg ccagcagcgg cctgttcgac gtgttcctga gattcatgtg ccaccacgcc    2520
gtgcggatcc ggggcaagag ctacgtgcag tgccagggca tcccacaggg cagcatcctg    2580
tccaccctgc tgtgctccct gtgctacggc gacatggaaa acaagctgtt cgccggcatc    2640
aggcgggacg gactgctgct gagactggtg gacgacttcc tgctggtgac ccccacctg    2700
acccacgcca gacctttct gcggaccctg gtgcgcggcg tgcccgagta cggctgcgtg    2760
gtgaacctga gaaagaccgt ggtgaacttc cccgtggagg acgaggccct gggcggcaca    2820
gccttcgtgc agatgcctgc ccatggactg ttcccttggt gcgggctgct gctggacacc    2880
cggaccctgg aagtgcagag cgactacagc agctacgccc ggaccagcat ccgggcctcc    2940
ctgaccttca cagggggctt caaggccggc aggaacatgc ggcggaagct gtttggcgtg    3000
ctgcggctga agtgccacag cctgtttctg tacctgcagg tgaacagcct gcagaccgtg    3060
```

```
tgcaccaaca tctacaagat cctgctgctg caggcctacc ggttccacgc ctgcgtgctg    3120
cagctgccct ttcaccagca ggtgtggaag aaccctacct tcttcctgcg ggtgatcagc    3180
gacaccgcca gcctgtgcta cagcatcctg aaggccaaga cgccggcat gagcctgggc     3240 gccaagggag ccgccggacc tctgcccagc gaggccgtgc agtggctgtg ccaccaggcc    3300
tttctgctga agctgacccg gcaccgggtg acctacgtgc ccctgctggg cagcctgcgg    3360
accgcccaga cccagctgtc ccggaagctg cctggcacca ccctgacagc cctggaagcc    3420
gccgccaacc ccgccctgcc ctccgacttc aagaccatcc tggactaccc ctacgacgtg    3480
cccgactacg cctgatgagc ggccgcgagc tc                                  3512
```

<210> SEQ ID NO 35
<211> LENGTH: 1158
<212> TYPE: PRT
<213> ORGANISM: Homo sapiens

<400> SEQUENCE: 35

```
Met Asp Trp Thr Trp Ile Leu Phe Leu Val Ala Ala Thr Arg Val
 1               5                   10                  15

His Ser Pro Arg Ala Pro Arg Cys Arg Ala Val Arg Ser Leu Leu Arg
                20                  25                  30

Ser His Tyr Arg Glu Val Leu Pro Leu Ala Thr Phe Val Arg Arg Leu
            35                  40                  45

Gly Pro Gln Gly Trp Arg Leu Val Gln Arg Gly Asp Pro Ala Ala Phe
        50                  55                  60

Arg Ala Leu Val Ala Gln Cys Leu Val Cys Val Pro Trp Asp Ala Arg
65                  70                  75                  80

Pro Pro Pro Ala Ala Pro Ser Phe Arg Gln Val Ser Cys Leu Lys Glu
                85                  90                  95

Leu Val Ala Arg Val Leu Gln Arg Leu Cys Glu Arg Gly Ala Lys Asn
            100                 105                 110

Val Leu Ala Phe Gly Phe Ala Leu Leu Asp Gly Ala Arg Gly Gly Pro
        115                 120                 125

Pro Glu Ala Phe Thr Thr Ser Val Arg Ser Tyr Leu Pro Asn Thr Val
    130                 135                 140

Thr Asp Ala Leu Arg Gly Ser Gly Ala Trp Gly Leu Leu Leu Arg Arg
145                 150                 155                 160

Val Gly Asp Asp Val Leu Val His Leu Leu Ala Arg Cys Ala Leu Phe
                165                 170                 175

Val Leu Val Ala Pro Ser Cys Ala Tyr Gln Val Cys Gly Pro Pro Leu
            180                 185                 190

Tyr Gln Leu Gly Ala Ala Thr Gln Ala Arg Pro Pro His Ala Ser
        195                 200                 205

Gly Pro Arg Arg Arg Leu Gly Cys Glu Arg Ala Trp Asn His Ser Val
    210                 215                 220

Arg Glu Ala Gly Val Pro Leu Gly Leu Pro Ala Pro Gly Ala Arg Arg
225                 230                 235                 240

Arg Gly Gly Ser Ala Ser Arg Ser Leu Pro Leu Pro Lys Arg Pro Arg
                245                 250                 255

Arg Gly Ala Ala Pro Glu Pro Glu Arg Thr Pro Val Gly Gln Gly Ser
            260                 265                 270

Trp Ala His Pro Gly Arg Thr Arg Gly Pro Ser Asp Arg Gly Phe Cys
        275                 280                 285
```

-continued

Val Val Ser Pro Ala Arg Pro Ala Glu Glu Ala Thr Ser Leu Glu Gly
    290                 295                 300

Ala Leu Ser Gly Thr Arg His Ser His Pro Ser Val Gly Arg Gln His
305                 310                 315                 320

His Ala Gly Pro Pro Ser Thr Ser Arg Pro Pro Arg Pro Trp Asp Thr
                    325                 330                 335

Pro Cys Pro Pro Val Tyr Ala Glu Thr Lys His Phe Leu Tyr Ser Ser
                340                 345                 350

Gly Asp Lys Glu Gln Leu Arg Pro Ser Phe Leu Leu Ser Ser Leu Arg
            355                 360                 365

Pro Ser Leu Thr Gly Ala Arg Arg Leu Val Glu Thr Ile Phe Leu Gly
370                 375                 380

Ser Arg Pro Trp Met Pro Gly Thr Pro Arg Arg Leu Pro Arg Leu Pro
385                 390                 395                 400

Gln Arg Tyr Trp Gln Met Arg Pro Leu Phe Leu Glu Leu Leu Gly Asn
                405                 410                 415

His Ala Gln Cys Pro Tyr Gly Val Leu Leu Lys Thr His Cys Pro Leu
                420                 425                 430

Arg Ala Ala Val Thr Pro Ala Ala Gly Val Cys Ala Arg Glu Lys Pro
435                 440                 445

Gln Gly Ser Val Ala Ala Pro Glu Glu Glu Asp Thr Asp Pro Arg Arg
    450                 455                 460

Leu Val Gln Leu Leu Arg Gln His Ser Ser Pro Trp Gln Val Tyr Gly
465                 470                 475                 480

Phe Val Arg Ala Cys Leu Arg Arg Leu Val Pro Pro Gly Leu Trp Gly
                485                 490                 495

Ser Arg His Asn Glu Arg Arg Phe Leu Arg Asn Thr Lys Lys Phe Ile
                500                 505                 510

Ser Leu Gly Lys His Ala Lys Leu Ser Leu Gln Glu Leu Thr Trp Lys
            515                 520                 525

Met Ser Val Arg Gly Cys Ala Trp Leu Arg Arg Ser Pro Gly Val Gly
530                 535                 540

Cys Val Pro Ala Ala Glu His Arg Leu Arg Glu Glu Ile Leu Ala Lys
545                 550                 555                 560

Phe Leu His Trp Leu Met Ser Val Tyr Val Val Glu Leu Leu Arg Ser
                565                 570                 575

Phe Phe Tyr Val Thr Glu Thr Thr Phe Gln Lys Asn Tyr Leu Phe Phe
                580                 585                 590

Tyr Arg Lys Ser Val Trp Ser Lys Leu Gln Ser Ile Gly Ile Arg Gln
            595                 600                 605

His Leu Lys Arg Val Gln Leu Arg Glu Leu Ser Glu Ala Glu Val Arg
610                 615                 620

Gln His Arg Glu Ala Arg Pro Ala Leu Leu Thr Ser Arg Leu Arg Phe
625                 630                 635                 640

Ile Pro Lys Pro Asp Gly Leu Arg Pro Ile Val Asn Met Asp Tyr Val
                645                 650                 655

Val Gly Ala Arg Thr Phe Arg Arg Glu Lys Arg Ala Glu Arg Leu Thr
                660                 665                 670

Ser Arg Val Lys Ala Leu Phe Ser Val Leu Asn Tyr Glu Arg Ala Arg
            675                 680                 685

Arg Pro Gly Leu Leu Gly Ala Ser Val Leu Gly Leu Asp Asp Ile His
690                 695                 700

Arg Ala Trp Arg Thr Phe Val Leu Arg Val Arg Ala Gln Asp Pro Pro

```
        705                 710                 715                 720
    Pro Glu Leu Tyr Phe Val Lys Val Asp Val Thr Gly Ala Tyr Asp Thr
                        725                 730                 735
    Ile Pro Gln Asp Arg Leu Thr Glu Val Ile Ala Ser Ile Ile Lys Pro
                740                 745                 750
    Gln Asn Thr Tyr Cys Val Arg Arg Tyr Ala Val Val Gln Lys Ala Ala
                755                 760                 765
    His Gly His Val Arg Lys Ala Phe Lys Ser His Val Ser Thr Leu Thr
                770                 775                 780
    Asp Leu Gln Pro Tyr Met Arg Gln Phe Val Ala His Leu Gln Glu Thr
    785                 790                 795                 800
    Ser Pro Leu Arg Asp Ala Val Val Ile Glu Gln Ser Ser Leu Asn
                    805                 810                 815
    Glu Ala Ser Ser Gly Leu Phe Asp Val Phe Leu Arg Phe Met Cys His
                820                 825                 830
    His Ala Val Arg Ile Arg Gly Lys Ser Tyr Val Gln Cys Gln Gly Ile
                835                 840                 845
    Pro Gln Gly Ser Ile Leu Ser Thr Leu Leu Cys Ser Leu Cys Tyr Gly
    850                 855                 860
    Asp Met Glu Asn Lys Leu Phe Ala Gly Ile Arg Arg Asp Gly Leu Leu
    865                 870                 875                 880
    Leu Arg Leu Val Asp Asp Phe Leu Leu Val Thr Pro His Leu Thr His
                        885                 890                 895
    Ala Lys Thr Phe Leu Arg Thr Leu Val Arg Gly Val Pro Glu Tyr Gly
                    900                 905                 910
    Cys Val Val Asn Leu Arg Lys Thr Val Val Asn Phe Pro Val Glu Asp
                915                 920                 925
    Glu Ala Leu Gly Gly Thr Ala Phe Val Gln Met Pro Ala His Gly Leu
                930                 935                 940
    Phe Pro Trp Cys Gly Leu Leu Leu Asp Thr Arg Thr Leu Glu Val Gln
    945                 950                 955                 960
    Ser Asp Tyr Ser Ser Tyr Ala Arg Thr Ser Ile Arg Ala Ser Leu Thr
                    965                 970                 975
    Phe Asn Arg Gly Phe Lys Ala Gly Arg Asn Met Arg Arg Lys Leu Phe
                980                 985                 990
    Gly Val Leu Arg Leu Lys Cys His Ser Leu Phe Leu Tyr Leu Gln Val
                    995                 1000                1005
    Asn Ser Leu Gln Thr Val Cys Thr Asn Ile Tyr Lys Ile Leu Leu
        1010                1015                1020
    Leu Gln Ala Tyr Arg Phe His Ala Cys Val Leu Gln Leu Pro Phe
        1025                1030                1035
    His Gln Gln Val Trp Lys Asn Pro Thr Phe Phe Leu Arg Val Ile
        1040                1045                1050
    Ser Asp Thr Ala Ser Leu Cys Tyr Ser Ile Leu Lys Ala Lys Asn
        1055                1060                1065
    Ala Gly Met Ser Leu Gly Ala Lys Gly Ala Ala Gly Pro Leu Pro
        1070                1075                1080
    Ser Glu Ala Val Gln Trp Leu Cys His Gln Ala Phe Leu Leu Lys
        1085                1090                1095
    Leu Thr Arg His Arg Val Thr Val Pro Leu Leu Gly Ser Leu
        1100                1105                1110
    Arg Thr Ala Gln Thr Gln Leu Ser Arg Lys Leu Pro Gly Thr Thr
        1115                1120                1125
```

```
Leu Thr Ala Leu Glu Ala Ala Ala Asn Pro Ala Leu Pro Ser Asp
    1130            1135                1140

Phe Lys Thr Ile Leu Asp Tyr Pro Tyr Asp Val Pro Asp Tyr Ala
    1145                1150                1155

<210> SEQ ID NO 36
<211> LENGTH: 1707
<212> TYPE: DNA
<213> ORGANISM: Artificial Sequence
<220> FEATURE:
<223> OTHER INFORMATION: Influenza H5N1 HA consensus sequence

<400> SEQUENCE: 36
atggaaaaga tcgtgctgct gttcgccatc gtgagcctgg tgaagagcga ccagatctgc     60
atcggctacc acgccaacaa cagcaccgag caggtggaca ccatcatgga aaaaaacgtg    120
accgtgaccc acgcccagga catcctggaa aagacccaca cggcaagct gtgcgacctg     180 gacggcgtga gcccctgat cctgcggac tgcagcgtgg ccggctggct gctgggcaac      240
cccatgtgcg acgagttcat caacgtgccc gagtggagct acatcgtgga aggccaac     300 cccgtgaacg acctgtgcta ccccggcgac ttcaacgact acgaggaact gaagcacctg    360
ctgtcccgga tcaaccactt cgagaagatc cagatcatcc caagagcag ctggtccagc     420 cacgaggcca gctgggcgt gagcagcgcc tgcccatacc agggcaagtc cagcttcttc    480
cggaacgtgg tgtggctgat caagaagaac agcacctacc ccaccatcaa gcggagctac    540
aacaacacca ccaggaaga tctgctggtc ctgtggggca tccaccaccc caacgacgcc     600
gccgagcaga ccaagctgta ccagaacccc accacctaca tcagcgtggg caccagcacc    660
ctgaaccagc ggctggtgcc ccggatcgcc acccggtcca aggtgaacgg ccagagcggc    720
cggatggaat tcttctggac catcctgaag cccaacgatg ccatcaactt cgagagcaac    780
ggcaacttca tcgcccccga gtacgcctac aagatcgtga agaagggcga cagcaccatc    840
atgaagagcg agctggaata cggcaactgc aacaccaagt gccagacccc catgggcgcc    900
atcaacagca gcatgccctt ccacaacatc cacccctga ccatcggcga gtgccccaag     960
tacgtgaaga gcaacaggct ggtgctggcc accggcctgc ggaacagccc ccagcgggag   1020
cggcgggccg ccgcccgggg cctgttcggc gccatcgccg gcttcatcga gggcggctgg   1080
cagggcatgg tggacgggtg gtacggctac accacagca atgagcaggg cagcggctac   1140
gccgccgaca agagagcac ccagaaggcc atcgacggcg tcaccaacaa ggtgaacagc    1200
atcatcgaca gatgaacac ccagttcgag gccgtgggcc gggagttcaa caacctggaa    1260
cggcggatcg agaacctgaa caagaaaatg gaagatggct tcctggacgt gtggacctac    1320
aacgccgagc tgctggtgct gatggaaaac gagcggaccc tggacttcca cgacagcaac    1380
gtgaagaacc tgtacgacaa agtgcggctg cagctgcggg acaacgccaa agagctgggc    1440
aacggctgct tcgagttcta ccacaagtgc gacaacgagt gcatggaaag cgtgcggaac    1500
ggcacctacg actacccca gtacagcgag gaagcccggc tgaagcggga ggaaatcagc    1560
ggcgtgaaac tggaaagcat cggcatctac cagatcctga gcatctacag caccgtggcc    1620
agcagcctgg ccctggccat catggtggcc ggcctgagcc tgtggatgtg cagcaacggc    1680
agcctgcagt gccggatctg catctag                                       1707

<210> SEQ ID NO 37
<211> LENGTH: 568
<212> TYPE: PRT
```

<213> ORGANISM: Artificial Sequence
<220> FEATURE:
<223> OTHER INFORMATION: Influenza H5N1 HA consensus sequence

<400> SEQUENCE: 37

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
            85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
            165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Arg Arg Ala Ala Ala Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
```

```
                385                 390                 395                 400
Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 38
<211> LENGTH: 1466
<212> TYPE: DNA
<213> ORGANISM: Artificial Sequence
<220> FEATURE:
<223> OTHER INFORMATION: Influenza H1N1&H5N1 NA consensus Sequence

<400> SEQUENCE: 38
ggtaccgaat tcgccaccat ggactggacc tggatcctgt tcctggtggc cgctgccacc      60
cgggtgcaca gcatgaaccc caaccagaag atcatcacca tcggcagcat ctgcatggtg     120
atcggcatcg tgagcctgat gctgcagatc ggcaacatga tcagcatctg ggtgtcccac     180
agcatccaga ccggcaacca gcaccaggcc gagcccatca gcaacaccaa ctttctgacc     240
gagaaggccg tggccagcgt gaccctggcc ggcaacagca gcctgtgccc catcagcggc     300
tgggccgtgt acagcaagga caacagcatc cggatcggca gcaagggcga cgtgttcgtg     360
atccgggagc ccttcatcag ctgcagccac ctggaatgcc ggaccttctt cctgacccag     420
ggggccctgc tgaacgacaa gcacagcaac ggcaccgtga aggacagaag ccccctaccgg     480 accctgatga gctgccccgt gggcgaggcc cccagcccct acaacagccg gttcgagagc     540
gtggcctggt ccgccagcgc ctgccacgac ggcaccagct ggctgaccat cggcatcagc     600
ggccctgaca cggcgccgt ggccgtgctg aagtacaacg gcatcatcac cgacaccatc     660
aagagctggc ggaacaacat cctgcggacc caggaaagcg agtgcgcctg cgtgaacggc     720
agctgcttca ccgtgatgac cgacggcccc agcaacggcc aggccagcta caagatcttc     780
aagatggaaa agggcaaggt ggtgaagagc gtggagctgg acgcccccaa ctaccactac     840
gaggaatgca gctgctaccc cgacgccggc gagatcacct gcgtgtgccg ggacaactgg     900
cacggcagca accggccctg ggtgtccttc aaccagaacc tggaatacca gatcggctac     960
atctgcagcg gcgtgttcgg cgacaacccc aggcccaacg atggcaccgg cagctgcggc    1020
```

```
cctgtgagcg ccaacggcgc ctacggcgtg aagggcttca gcttcaagta cggcaacggc    1080
gtgtggatcg ccggaccaa gagcaccaac agcagatccg gcttcgagat gatctgggac     1140
cccaacggct ggaccgagac cgacagcagc ttcagcgtga agcaggacat cgtggccatc    1200
accgactggt ccggctacag cggcagcttc gtgcagcacc ccgagctgac cggcctggac    1260
tgcatccggc cctgcttttg ggtggagctg atcagaggca ggcccaaaga gagcaccatc    1320
tggaccagcg gcagcagcat cagcttttgc ggcgtgaaca cgacaccgt gagctggtcc    1380 tggcccgacg gcgccgagct gcccttcacc atcgacaagt accctacga cgtgcccgac    1440 tacgcctgat gagcggccgc gagctc                                         1466
```

<210> SEQ ID NO 39
<211> LENGTH: 476
<212> TYPE: PRT
<213> ORGANISM: Artificial Sequence
<220> FEATURE:
<223> OTHER INFORMATION: Influenza H1N1&H5N1 NA consensus sequence

<400> SEQUENCE: 39

```
Met Asp Trp Thr Trp Ile Leu Phe Leu Val Ala Ala Thr Arg Val
1               5                   10                  15

His Ser Met Asn Pro Asn Gln Lys Ile Ile Thr Ile Gly Ser Ile Cys
                20                  25                  30

Met Val Ile Gly Ile Val Ser Leu Met Leu Gln Ile Gly Asn Met Ile
            35                  40                  45

Ser Ile Trp Val Ser His Ser Ile Gln Thr Gly Asn Gln His Gln Ala
    50                  55                  60

Glu Pro Ile Ser Asn Thr Asn Phe Leu Thr Glu Lys Ala Val Ala Ser
65                  70                  75                  80

Val Thr Leu Ala Gly Asn Ser Ser Leu Cys Pro Ile Ser Gly Trp Ala
                85                  90                  95

Val Tyr Ser Lys Asp Asn Ser Ile Arg Ile Gly Ser Lys Gly Asp Val
            100                 105                 110

Phe Val Ile Arg Glu Pro Phe Ile Ser Cys Ser His Leu Glu Cys Arg
        115                 120                 125

Thr Phe Phe Leu Thr Gln Gly Ala Leu Leu Asn Asp Lys His Ser Asn
    130                 135                 140

Gly Thr Val Lys Asp Arg Ser Pro Tyr Arg Thr Leu Met Ser Cys Pro
145                 150                 155                 160

Val Gly Glu Ala Pro Ser Pro Tyr Asn Ser Arg Phe Glu Ser Val Ala
                165                 170                 175

Trp Ser Ala Ser Ala Cys His Asp Gly Thr Ser Trp Leu Thr Ile Gly
            180                 185                 190

Ile Ser Gly Pro Asp Asn Gly Ala Val Ala Val Leu Lys Tyr Asn Gly
        195                 200                 205

Ile Ile Thr Asp Thr Ile Lys Ser Trp Arg Asn Asn Ile Leu Arg Thr
    210                 215                 220

Gln Glu Ser Glu Cys Ala Cys Val Asn Gly Ser Cys Phe Thr Val Met
225                 230                 235                 240

Thr Asp Gly Pro Ser Asn Gly Gln Ala Ser Tyr Lys Ile Phe Lys Met
                245                 250                 255

Glu Lys Gly Lys Val Val Lys Ser Val Glu Leu Asp Ala Pro Asn Tyr
            260                 265                 270

His Tyr Glu Glu Cys Ser Cys Tyr Pro Asp Ala Gly Glu Ile Thr Cys
        275                 280                 285
```

```
Val Cys Arg Asp Asn Trp His Gly Ser Asn Arg Pro Trp Val Ser Phe
    290                 295                 300
Asn Gln Asn Leu Glu Tyr Gln Ile Gly Tyr Ile Cys Ser Gly Val Phe
305                 310                 315                 320
Gly Asp Asn Pro Arg Pro Asn Asp Gly Thr Gly Ser Cys Gly Pro Val
                325                 330                 335
Ser Ala Asn Gly Ala Tyr Gly Val Lys Gly Phe Ser Phe Lys Tyr Gly
            340                 345                 350
Asn Gly Val Trp Ile Gly Arg Thr Lys Ser Thr Asn Ser Arg Ser Gly
        355                 360                 365
Phe Glu Met Ile Trp Asp Pro Asn Gly Trp Thr Glu Thr Asp Ser Ser
    370                 375                 380
Phe Ser Val Lys Gln Asp Ile Val Ala Ile Thr Asp Trp Ser Gly Tyr
385                 390                 395                 400
Ser Gly Ser Phe Val Gln His Pro Glu Leu Thr Gly Leu Asp Cys Ile
                405                 410                 415
Arg Pro Cys Phe Trp Val Glu Leu Ile Arg Gly Arg Pro Lys Glu Ser
            420                 425                 430
Thr Ile Trp Thr Ser Gly Ser Ser Ile Ser Phe Cys Gly Val Asn Ser
        435                 440                 445
Asp Thr Val Ser Trp Ser Trp Pro Asp Gly Ala Glu Leu Pro Phe Thr
    450                 455                 460
Ile Asp Lys Tyr Pro Tyr Asp Val Pro Asp Tyr Ala
465                 470                 475

<210> SEQ ID NO 40
<211> LENGTH: 875
<212> TYPE: DNA
<213> ORGANISM: Artificial Sequence
<220> FEATURE:
<223> OTHER INFORMATION: Influenza H1N1&H5N1 M1 consensus sequence

<400> SEQUENCE: 40
ggtaccggat ccgccaccat ggactggacc tggattctgt tcctggtggc cgctgccacc      60
cgggtgcaca gcatgagcct gctgaccgag gtggagacct acgtgctgtc catcatccc     120
agcggccctc tgaaggccga gatcgcccag cggctggaag atgtgttcgc cggcaagaac    180
accgacctgg aagccctgat ggaatggctg aaaacccggc ccatcctgag ccccctgacc    240
aagggcatcc tgggcttcgt gttcaccctg accgtgccca gcgagcgggg cctgcagcgg    300
cggagattcg tgcagaacgc cctgaacggc acggcgacc ccaacaacat ggaccgggcc    360
gtgaagctgt acaagaagct gaagcgggag atcaccttcc acggcgccaa gaggtggcc    420
ctgagctaca gcacaggcgc cctggccagc tgcatgggcc tgatctacaa ccggatgggc    480
accgtgacca ccgaggtggc cttcggcctg gtgtgcgcca cctgcgagca gatcgccgac    540
agccagcaca tcccaccg gcagatggcc accaccacca cccctgat ccggacgag        600
aaccggatgg tcctggcctc caccaccgcc aaggccatgg aacagatggc cggcagcagc    660
gagcaggccg ccgaagccat ggaagtggcc agccaggcca ggcagatggt gcaggccatg    720
cggaccatcg gcacccaccc cagcagcagc gccggactgc gggacgacct gctggaaaac    780
ctgcaggcct accagaaacg gatgggcgtg cagatgcagc ggttcaagta ccctacgac    840
gtgcccgact acgcctgatg agcggccgcg agctc                              875

<210> SEQ ID NO 41
```

<211> LENGTH: 279
<212> TYPE: PRT
<213> ORGANISM: Artificial Sequence
<220> FEATURE:
<223> OTHER INFORMATION: Influenza H1N1&H5N1 M1 consensus sequence

<400> SEQUENCE: 41

```
Met Asp Trp Thr Trp Ile Leu Phe Leu Val Ala Ala Thr Arg Val
1               5                   10                  15

His Ser Met Ser Leu Leu Thr Glu Val Glu Thr Tyr Val Leu Ser Ile
            20                  25                  30

Ile Pro Ser Gly Pro Leu Lys Ala Glu Ile Ala Gln Arg Leu Glu Asp
        35                  40                  45

Val Phe Ala Gly Lys Asn Thr Asp Leu Glu Ala Leu Met Glu Trp Leu
    50                  55                  60

Lys Thr Arg Pro Ile Leu Ser Pro Leu Thr Lys Gly Ile Leu Gly Phe
65                  70                  75                  80

Val Phe Thr Leu Thr Val Pro Ser Glu Arg Gly Leu Gln Arg Arg
                85                  90                  95

Phe Val Gln Asn Ala Leu Asn Gly Asn Gly Asp Pro Asn Asn Met Asp
                100                 105                 110

Arg Ala Val Lys Leu Tyr Lys Lys Leu Lys Arg Glu Ile Thr Phe His
            115                 120                 125

Gly Ala Lys Glu Val Ala Leu Ser Tyr Ser Thr Gly Ala Leu Ala Ser
130                 135                 140

Cys Met Gly Leu Ile Tyr Asn Arg Met Gly Thr Val Thr Thr Glu Val
145                 150                 155                 160

Ala Phe Gly Leu Val Cys Ala Thr Cys Glu Gln Ile Ala Asp Ser Gln
                165                 170                 175

His Arg Ser His Arg Gln Met Ala Thr Thr Thr Asn Pro Leu Ile Arg
            180                 185                 190

His Glu Asn Arg Met Val Leu Ala Ser Thr Thr Ala Lys Ala Met Glu
        195                 200                 205

Gln Met Ala Gly Ser Ser Glu Gln Ala Ala Glu Ala Met Glu Val Ala
    210                 215                 220

Ser Gln Ala Arg Gln Met Val Gln Ala Met Arg Thr Ile Gly Thr His
225                 230                 235                 240

Pro Ser Ser Ser Ala Gly Leu Arg Asp Asp Leu Leu Glu Asn Leu Gln
                245                 250                 255

Ala Tyr Gln Lys Arg Met Gly Val Gln Met Gln Arg Phe Lys Tyr Pro
            260                 265                 270

Tyr Asp Val Pro Asp Tyr Ala
        275
```

<210> SEQ ID NO 42
<211> LENGTH: 1700
<212> TYPE: DNA
<213> ORGANISM: Artificial Sequence
<220> FEATURE:
<223> OTHER INFORMATION: Influenza H5N1 M2E-NP consensus sequence

<400> SEQUENCE: 42

```
ggtaccgaat cgccaccatg gactggacc tggatcctgt tcctggtcgc tgccgccacc        60
agggtgcaca gcagcctgct gaccgaggtg gagaccccca cccggaacga gtggggctgc      120
cggtgcagcg acagcagcga ccggggcagg aagcggagaa cgccagcca gggcaccaag      180 cggagctacg agcagatgga aacaggcggc gagcggcaga acgccaccga gatccgggcc     240
```

```
agcgtgggca gaatggtcgg cggcatcggc cggttctaca tccagatgtg caccgagctg    300
aagctgtccg actacgaggg ccggctgatc cagaacagca tcaccatcga gcggatggtg    360
ctgtccgcct cgacgagcg gcggaacaga tacctggaag agcaccccag cgccggcaag    420
gaccccaaga aaccggcgg acccatctac cggcggaggg acggcaagtg ggtgcgggag    480
ctgatcctgt acgacaaaga ggaaatccgg cggatctggc ggcaggccaa caacggcgag    540
gacgccacag ccggcctgac ccacctgatg atctggcaca gcaacctgaa cgacgccacc    600
taccagcgga caagggctct ggtccggacc ggcatggacc cccggatgtg cagcctgatg    660
cagggcagca cactgcccag aagaagcgga gccgctggcg cagccgtgaa gggcgtgggc    720
accatggtga tggaactgat ccggatgatc aagcggggca tcaacgaccg gaatttttgg    780
aggggcgaga acggcaggcg gacccggatc gcctacgagc ggatgtgcaa catcctgaag    840
ggcaagttcc agacagccgc ccagcgggcc atgatggacc aggtccggga gagccggaac    900
cccggcaacg ccgagatcga ggacctgatc ttcctggcca gaagcgccct gatcctgcgg    960
ggcagcgtgg cccacaagag ctgcctgccc gcctgcgtgt acggactggc cgtggccagc   1020
ggctacgact cgagcgggga gggctacagc ctggtcggca tcgacccctt ccggctgctg   1080
cagaactccc aggtgttcag cctgatccgg cccaacgaga ccccgcca caagtcccag    1140 ctggtctgga tggcctgcca cagcgccgcc ttcgaggatc tgagagtgag cagcttcatc   1200
cggggcacca gagtggtgcc caggggccag ctgtccacca ggggcgtgca gatcgccagc   1260
aacgagaaca tggaagccat ggacagcaac accctggaac tgcggagccg gtactgggcc   1320
atccggacca gaagcggcgg caacaccaac cagcagcggg ccagcgccgg acagatcagc   1380
gtgcagccca ccttctccgt gcagcggaac ctgccttcg agagggccac catcatggcc   1440
gccttcaccg gcaacaccga gggccggacc agcgacatgc ggaccgagat catcaggatg   1500
atggaaagcg ccaggcccga ggacgtgagc ttccagggca ggggcgtgtt cgagctgtcc   1560
gatgagaagg ccaccaaccc catcgtgccc agcttcgaca tgaacaacga gggcagctac   1620
ttcttcggcg acaacgccga ggaatacgac aactacccct acgacgtgcc cgactacgcc   1680
tgatgagcgg ccgcgagctc                                              1700
```

<210> SEQ ID NO 43
<211> LENGTH: 554
<212> TYPE: PRT
<213> ORGANISM: Artificial Sequence
<220> FEATURE:
<223> OTHER INFORMATION: Influenza H5N1 M2E-NP consensus sequence

<400> SEQUENCE: 43

Met Asp Trp Thr Trp Ile Leu Phe Leu Val Ala Ala Thr Arg Val
1               5                   10                  15

His Ser Ser Leu Leu Thr Glu Val Glu Thr Pro Thr Arg Asn Glu Trp
            20                  25                  30

Gly Cys Arg Cys Ser Asp Ser Ser Asp Arg Gly Arg Lys Arg Ser
            35                  40                  45

Ala Ser Gln Gly Thr Lys Arg Ser Tyr Glu Gln Met Glu Thr Gly Gly
        50                  55                  60

Glu Arg Gln Asn Ala Thr Glu Ile Arg Ala Ser Val Gly Arg Met Val
65                  70                  75                  80

Gly Gly Ile Gly Arg Phe Tyr Ile Gln Met Cys Thr Glu Leu Lys Leu
                85                  90                  95

Ser Asp Tyr Glu Gly Arg Leu Ile Gln Asn Ser Ile Thr Ile Glu Arg
            100                 105                 110

Met Val Leu Ser Ala Phe Asp Glu Arg Asn Arg Tyr Leu Glu Glu
            115                 120                 125

His Pro Ser Ala Gly Lys Asp Pro Lys Lys Thr Gly Gly Pro Ile Tyr
            130                 135                 140

Arg Arg Arg Asp Gly Lys Trp Val Arg Glu Leu Ile Leu Tyr Asp Lys
145                 150                 155                 160

Glu Glu Ile Arg Arg Ile Trp Arg Gln Ala Asn Asn Gly Glu Asp Ala
                165                 170                 175

Thr Ala Gly Leu Thr His Leu Met Ile Trp His Ser Asn Leu Asn Asp
            180                 185                 190

Ala Thr Tyr Gln Arg Thr Arg Ala Leu Val Arg Thr Gly Met Asp Pro
            195                 200                 205

Arg Met Cys Ser Leu Met Gln Gly Ser Thr Leu Pro Arg Arg Ser Gly
            210                 215                 220

Ala Ala Gly Ala Ala Val Lys Gly Val Gly Thr Met Val Met Glu Leu
225                 230                 235                 240

Ile Arg Met Ile Lys Arg Gly Ile Asn Asp Arg Asn Phe Trp Arg Gly
                245                 250                 255

Glu Asn Gly Arg Arg Thr Arg Ile Ala Tyr Glu Arg Met Cys Asn Ile
            260                 265                 270

Leu Lys Gly Lys Phe Gln Thr Ala Ala Gln Arg Ala Met Met Asp Gln
            275                 280                 285

Val Arg Glu Ser Arg Asn Pro Gly Asn Ala Glu Ile Glu Asp Leu Ile
            290                 295                 300

Phe Leu Ala Arg Ser Ala Leu Ile Leu Arg Gly Ser Val Ala His Lys
305                 310                 315                 320

Ser Cys Leu Pro Ala Cys Val Tyr Gly Leu Ala Val Ala Ser Gly Tyr
                325                 330                 335

Asp Phe Glu Arg Glu Gly Tyr Ser Leu Val Gly Ile Asp Pro Phe Arg
            340                 345                 350

Leu Leu Gln Asn Ser Gln Val Phe Ser Leu Ile Arg Pro Asn Glu Asn
            355                 360                 365

Pro Ala His Lys Ser Gln Leu Val Trp Met Ala Cys His Ser Ala Ala
            370                 375                 380

Phe Glu Asp Leu Arg Val Ser Ser Phe Ile Arg Gly Thr Arg Val Val
385                 390                 395                 400

Pro Arg Gly Gln Leu Ser Thr Arg Gly Val Gln Ile Ala Ser Asn Glu
                405                 410                 415

Asn Met Glu Ala Met Asp Ser Asn Thr Leu Glu Leu Arg Ser Arg Tyr
            420                 425                 430

Trp Ala Ile Arg Thr Arg Ser Gly Gly Asn Thr Asn Gln Gln Arg Ala
            435                 440                 445

Ser Ala Gly Gln Ile Ser Val Gln Pro Thr Phe Ser Val Gln Arg Asn
450                 455                 460

Leu Pro Phe Glu Arg Ala Thr Ile Met Ala Ala Phe Thr Gly Asn Thr
465                 470                 475                 480

Glu Gly Arg Thr Ser Asp Met Arg Thr Glu Ile Ile Arg Met Met Glu
                485                 490                 495

Ser Ala Arg Pro Glu Asp Val Ser Phe Gln Gly Arg Gly Val Phe Glu
            500                 505                 510

Leu Ser Asp Glu Lys Ala Thr Asn Pro Ile Val Pro Ser Phe Asp Met

-continued

```
                515                 520                 525
Asn Asn Glu Gly Ser Tyr Phe Phe Gly Asp Asn Ala Glu Glu Tyr Asp
    530                 535                 540

Asn Tyr Pro Tyr Asp Val Pro Asp Tyr Ala
545                 550

<210> SEQ ID NO 44
<211> LENGTH: 701
<212> TYPE: PRT
<213> ORGANISM: Human immunodeficiency virus type 1

<400> SEQUENCE: 44

Met Asp Trp Thr Trp Ile Leu Phe Leu Val Ala Ala Thr Arg Val
1               5                   10                  15

His Ser Glu Glu Lys Leu Trp Val Thr Val Tyr Tyr Gly Val Pro Val
                20                  25                  30

Trp Lys Glu Ala Thr Thr Thr Leu Phe Cys Ala Ser Asp Ala Lys Ala
            35                  40                  45

His His Ala Glu Ala His Asn Val Trp Ala Thr His Ala Cys Val Pro
        50                  55                  60

Thr Asp Pro Asn Pro Gln Glu Val Ile Leu Glu Asn Val Thr Glu Lys
65                  70                  75                  80

Tyr Asn Met Trp Lys Asn Asn Met Val Asp Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Ala Thr Tyr Thr Asn Ser Asp
        115                 120                 125

Ser Lys Asn Ser Thr Ser Asn Ser Ser Leu Glu Asp Ser Gly Lys Gly
    130                 135                 140

Asp Met Asn Cys Ser Phe Asp Val Thr Thr Ser Ile Asp Lys Lys Lys
145                 150                 155                 160

Lys Thr Glu Tyr Ala Ile Phe Asp Lys Leu Asp Val Met Asn Ile Gly
                165                 170                 175

Asn Gly Arg Tyr Thr Leu Leu Asn Cys Asn Thr Ser Val Ile Thr Gln
            180                 185                 190

Ala Cys Pro Lys Met Ser Phe Glu Pro Ile Pro Ile His Tyr Cys Thr
        195                 200                 205

Pro Ala Gly Tyr Ala Ile Leu Lys Cys Asn Asp Asn Lys Phe Asn Gly
    210                 215                 220

Thr Gly Pro Cys Thr Asn Val Ser Thr Ile Gln Cys Thr His Gly Ile
225                 230                 235                 240

Lys Pro Val Val Ser Thr Gln Leu Leu Leu Asn Gly Ser Leu Ala Glu
                245                 250                 255

Gly Gly Glu Val Ile Ile Arg Ser Glu Asn Leu Thr Asp Asn Ala Lys
            260                 265                 270

Thr Ile Ile Val Gln Leu Lys Glu Pro Val Glu Ile Asn Cys Thr Arg
        275                 280                 285

Pro Asn Asn Asn Thr Arg Lys Ser Ile His Met Gly Pro Gly Ala Ala
    290                 295                 300

Phe Tyr Ala Arg Gly Glu Val Ile Gly Asp Ile Arg Gln Ala His Cys
305                 310                 315                 320

Asn Ile Ser Arg Gly Arg Trp Asn Asp Thr Leu Lys Gln Ile Ala Lys
                325                 330                 335
```

-continued

```
Lys Leu Arg Glu Gln Phe Asn Lys Thr Ile Ser Leu Asn Gln Ser Ser
                340                 345                 350

Gly Gly Asp Leu Glu Ile Val Met His Thr Phe Asn Cys Gly Gly Glu
            355                 360                 365

Phe Phe Tyr Cys Asn Thr Thr Gln Leu Phe Asn Ser Thr Trp Asn Glu
        370                 375                 380

Asn Asp Thr Thr Trp Asn Asn Thr Ala Gly Ser Asn Asn Asn Glu Thr
385                 390                 395                 400

Ile Thr Leu Pro Cys Arg Ile Lys Gln Ile Ile Asn Arg Trp Gln Glu
                405                 410                 415

Val Gly Lys Ala Met Tyr Ala Pro Pro Ile Ser Gly Pro Ile Asn Cys
            420                 425                 430

Leu Ser Asn Ile Thr Gly Leu Leu Leu Thr Arg Asp Gly Gly Asp Asn
        435                 440                 445

Asn Asn Thr Ile Glu Thr Phe Arg Pro Gly Gly Gly Asp Met Arg Asp
    450                 455                 460

Asn Trp Arg Ser Glu Leu Tyr Lys Tyr Lys Val Val Arg Ile Glu Pro
465                 470                 475                 480

Leu Gly Ile Ala Pro Thr Lys Ala Lys Arg Arg Val Val Gln Arg Glu
                485                 490                 495

Lys Arg Ala Val Gly Ile Gly Ala Met Phe Leu Gly Phe Leu Gly Ala
            500                 505                 510

Ala Gly Ser Thr Met Gly Ala Ala Ser Val Thr Leu Thr Val Gln Ala
        515                 520                 525

Arg Leu Leu Leu Ser Gly Ile Val Gln Gln Gln Asn Asn Leu Leu Arg
    530                 535                 540

Ala Ile Glu Ala Gln Gln His Leu Leu Gln Leu Thr Val Trp Gly Ile
545                 550                 555                 560

Lys Gln Leu Gln Ala Arg Val Leu Ala Met Glu Arg Tyr Leu Lys Asp
                565                 570                 575

Gln Gln Leu Leu Gly Ile Trp Gly Cys Ser Gly Lys Leu Ile Cys Thr
            580                 585                 590

Thr Asn Val Pro Trp Asn Ala Ser Trp Ser Asn Lys Ser Leu Asp Lys
        595                 600                 605

Ile Trp His Asn Met Thr Trp Met Glu Trp Asp Arg Glu Ile Asp Asn
    610                 615                 620

Tyr Thr Lys Leu Ile Tyr Thr Leu Ile Glu Ala Ser Gln Ile Gln Gln
625                 630                 635                 640

Glu Lys Asn Glu Gln Glu Leu Leu Glu Leu Asp Ser Trp Ala Ser Leu
                645                 650                 655

Trp Ser Trp Phe Asp Ile Ser Lys Trp Leu Trp Tyr Ile Gly Val Phe
            660                 665                 670

Ile Ile Val Ile Gly Gly Leu Val Gly Leu Lys Ile Val Phe Ala Val
        675                 680                 685

Leu Ser Ile Val Asn Arg Val Arg Gln Val Thr Arg Val
    690                 695                 700
```

HTERT SEQUENCES AND METHODS FOR USING THE SAME

CROSS-REFERENCE TO RELATED APPLICATIONS

This application is a divisional of U.S. patent application Ser. No. 13/458,013, filed on Apr. 27, 2012, now issued as U.S. Pat. No. 8,697,084 on Apr. 15, 2014, which is a divisional of 12/375,518, filed on Oct. 27, 2009, now issued as U.S. Pat. No. 8,168,769 on May 1, 2012, which claims priority to and is a national stage application under 35 U.S.C. §371 of PCT International Application Serial Number PCT/US2007/074769, filed Jul. 30, 2007, which claims priority to U.S. Provisional Patent Application Ser. Nos. 60/890,352, filed Feb. 16,2007; 60/833,856, filed Jul. 28, 2006; and 60/833,861, filed Jul. 28,2006, each of which is incorporated herein by reference in its entirety.

FIELD OF THE INVENTION

The present invention relates to improved HIV, HPV, HCV, Influenza and cancer vaccines, improved methods for inducing immune responses, and for prophylactically and/or therapeutically immunizing individuals against HIV, HPV, HCV, Influenza and cancer.

BACKGROUND OF THE INVENTION

The HIV genome is highly plastic due to a high mutation rate and functional compensation. This high mutation rate is driven by at least two mechanisms: the low fidelity of the viral reverse transcriptase (RT) resulting in at least one mutation per replication cycle, and the dual effects of the anti-retroviral cellular factor APOBEC3G gene and viral infectivity factor Vif accessory gene. Genomes with every possible mutation and many double mutations are generated during every replication cycle, resulting in tremendous antigenic diversity. Accordingly, it has been argued that a candidate vaccine derived from an individual isolate may not elicit sufficient cross reactivity to protect against diverse circulating HIV viruses. Recent studies have suggested that consensus immunogens (Gao, F., et al. 2005. Antigenicity and immunogenicity of a synthetic human immunodeficiency virus type 1 group m consensus envelope glycoprotein. J Virol 79:1154-63.; Scriba, T. J., et al. 2005. Functionally-inactive and immunogenic Tat, Rev and Nef DNA vaccines derived from sub-Saharan subtype C human immunodeficiency virus type 1 consensus sequences. Vaccine 23:1158-69) or ancestral immunogens (Doria-Rose, N. A., et al. 2005. Human Immunodeficiency Virus Type I subtype B Ancestral Envelope Protein Is Functional and Elicits Neutralizing Antibodies in Rabbits Similar to Those Elicited by a Circulating Subtype B Envelope. J. Virol. 79:11214-11224; Gao, F., et al. 2004. Centralized immunogens as a vaccine strategy to overcome HIV-1 diversity. Expert Rev. Vaccines 3:S161-S168; Mullins, J. I., et al. 2004. Immunogen sequence: the fourth tier of AIDS vaccine design. Expert Rev. Vaccines 3:S151-S159; Nickle, D. C., et al. 2003. Consensus and ancestral state HIV vaccines. Science 299:1515-1517) may be useful in this regard. However, the initial studies of these approaches showed relatively modest cellular immune enhancement induced by these immunogens.

Recently Derdeyn et al. analyzed HIV-1 subtype C envelope glycoprotein sequences in eight African heterosexual transmission pairs and found that shorter V1, V2 and V4 length and fewer glycans are the common features shared by the sequences obtained from early transmitters (Derdeyn, C. A., et al. 2004. Envelope-constrained neutralization-sensitive HIV-1 after heterosexual transmission. Science 303:2019-2022.). This data suggests that antigens that mimic such viruses might have relevance for the early-transmitted viruses. However, such early transmitter structures have not been observed for all subtypes (Chohan, B., et al. 2005. Selection for Human Immunodeficiency Virus Type 1 envelope glycosylation variants with shorter V1-V2 loop sequences occurs during transmission of certain genetic subtypes and may impact viral RNA levels. J. Virol. 79:6528-6531). However, incorporation of shorter V loops in an envelope immunogen may have other benefits, such as enhancement of sensitivity to soluble CD4 (Pickora, C., et al. 2005. Identification of two N-linked glycosylation sites within the core of the Simian Immunodeficiency virus glycoprotein whose removal enhances sensitivity to soluble CD4. J. Virol. 79:12575-12583), and should be considered.

Studies have shown the importance of HIV-1 specific CTL responses in controlling viral load during acute and asymptomatic infection and the development of AIDS. However, it is unclear if current envelope based DNA vaccines are as potent as needed. Several methods have been used to increase the expression levels of HIV-1 immunogens, such as codon optimization (Andre, S., et al. 1998. Increased immune response elicited by DNA vaccination with a synthetic gp120 sequence with optimized codon usage. J Virol 72:1497-503; Deml, L., et al. A. 2001. Multiple effects of codon usage optimization on expression and immunogenicity of DNA candidate vaccines encoding the human immunodeficiency virus type 1 gag protein. J. Virol. 75:10991-11001), RNA optimization (Muthumani, K., et al. 2003. Novel engineered HIV-1 East African Clade-A gp160 plasmid construct induces strong humoral and cell-mediated immune responses in vivo. Virology 314:134-46; Schneider, R., M. et al. 1997. Inactivation of the human immunodeficiency virus type 1 inhibitory elements allows Rev-independent expression of Gag and Gag/protease and particle formation. J. Virol. 71:4892-4903) and the addition of immunoglobin leader sequences that have weak RNA secondary structure (Yang, J. S., et al., 2001. Induction of potent Th1-Type immune responses from a novel DNA vaccine for West Nile Virus New York Isolate (WNV-NY1999). J. Infect Diseases 184:809-816).

Human Papillomavirus (HPV) has a circular dsDNA genome (7,000-8,000 base pairs). There are up to 200 different genotypes. Phylogenetically, HPV is highly conserved. Mucosal HPV are Classified as "High Risk" or "Low Risk". The Low Risk group includes types 6, 11, 42, and others. Associated Diseases include: Genital Warts; Low grade cervical, anal, vulvar, vaginal dysplasia; and Recurrent Respiratory Papillomatosis. The High Risk group includes types 16, 18, 31, 33, 45, 52, 58, and others. Associated Diseases include: Essential cause of Cervical cancer, pre-cancerous dysplasia; major cause of Anal, vulvar, vaginal, tonsillar cancer; and co-factor for other aerodigestive cancer. Every Day, 800 women die of cervical cancer.

HPV E6 and E7 proteins are tumor-specific antigens, required for tumorigenesis and maintenance of the tumor state. E7-specific immune responses are deleted in cervical cancer patients. Both E6 and E7 proteins interact specifically with the products of cellular human tumor suppressor genes, E6 with p53 and E7 with Rb (retinoblastoma tumor suppressor gene). E6 and E7 are ideal immunotherapeutic targets.

hTERT is a human telomerase reverse transcriptase that synthesizes a TTAGGG tag on the end of telomeres to prevent cell death due to chromosomal shortening. Embryonic cells and some germ line cells normally express hTERT to regulate homeostasis of cell populations. Cancer cells, however, exploit this mechanism of regulation to disrupt homeostasis of cell populations. For instance, hTERT over-expression occurs in more than 85% of human cancer cells. Therefore, hTERT is an ideal immunotherapeutic target.

hTERT may also enhance immunotherapeutics against hyperproliferating cells expressing hTERT due to HCV or HPV infection. The E6 oncoprotein from high-risk HPV types activates human telomerase reverse transcriptase (hTERT) transcription in human keratinocytes. Dysplastic legions and early neoplastic legions within the liver also express hTERT at abnormally high levels. Thus, immunotherapy against HPV and HCV may be enhanced by targeting cells that express hTERT at abnormal levels. Combination immunotherapy using both hTERT and HPV or HCV proteins or nucleic acids encoding such proteins is an attractive immunotherapy.

Influenza Hemagglutinin (HA) is expressed on the surface of Influenza viral particles and is responsible for initial contact between the virus and its host cell. HA is a well-known immunogen. Influenza A strain H1N5, an avian influenza strain, particularly threatens the human population because of its HA protein which, if slightly genetically reasserted by natural mutation, has greatly increased infectivity of human cells as compared to other strains of the virus. Infection of infants and older or immunocompromised adults humans with the viral H1N5 strain is often correlated to poor clinical outcome. Therefore, HA and other influenza molecules of the H1N5 strain of Influenza arc ideal immunotherapeutic targets.

SUMMARY OF THE INVENTION

The present invention relates to nucleic acid constructs and proteins encoded thereby which provide improved immunogenic targets against which an anti-HIV immune response can be generated.

The present invention provides consensus sequences for HIV Subtype A Envelope protein, consensus sequences for HIV Subtype B Envelope protein, consensus sequences for HIV Subtype C Envelope protein, consensus sequences for HIV Subtype D Envelope protein, consensus sequences for HIV Subtype B consensus Nef-Rev protein, and consensus sequences form HIV Gag protein subtypes A, B, C and D.

The present invention provides constructs which encode such proteins sequences, vaccines which comprise such proteins and/or nucleic acid molecules that encode such proteins, and methods of inducing anti-HIV immune responses.

The present invention relates to nucleic acid molecules comprising a nucleotide sequence selected from the group consisting of SEQ ID NO:1; fragments of SEQ ID NO:1; sequences having at least 90% homology to SEQ ID NO:1; fragments of sequences having at least 90% homology to SEQ ID NO:1; SEQ ID NO:3; fragments of SEQ ID NO:3; sequences having at least 90% homology to SEQ ID NO:3; fragments of sequences having at least 90% homology to SEQ ID NO:3; SEQ ID NO:5; fragments of SEQ ID NO:5; sequences having at least 90% homology to SEQ ID NO:5; fragments of sequences having at least 90% homology to SEQ ID NO:5; SEQ ID NO:7; fragments of SEQ ID NO:7; sequences having at least 90% homology to SEQ ID NO:7; fragments of sequences having at least 90% homology to SEQ ID NO:7; SEQ ID NO:9; fragments of SEQ ID NO:9; sequences having at least 90% homology to SEQ ID NO:9; fragments of sequences having at least 90% homology to SEQ ID NO:9; SEQ ID NO:11; fragments of SEQ ID NO:11; sequences having at least 90% homology to SEQ ID NO:11; fragments of sequences having at least 90% homology to SEQ ID NO: 11.

The present invention relates to nucleic acid molecule that encode a protein selected from the group consisting of SEQ ID NO:16; SEQ ID NO:17; SEQ ID NO:18; SEQ ID NO:19; SEQ ID NO:20 and SEQ ID NO:21.

The present invention relates to nucleic acid molecules comprising a nucleotide sequence selected from the group consisting of: nucleotide sequences that encode SEQ ID NO:2; nucleotide sequences that encode an amino acid sequences having at least 90% homology to SEQ ID NO:2; fragments of nucleotide sequences that encode SEQ ID NO:2; fragments of a nucleotide sequence that encode an amino acid sequence having at least 90% homology to SEQ ID NO:2; nucleotide sequences that encode SEQ ID NO:4; nucleotide sequences that encodes an amino acid sequences having at least 90% homology to SEQ ID NO:4; fragments of nucleotide sequences that encodes SEQ ID NO:4; fragments of nucleotide sequences that encodes an amino acid sequence having at least 90% homology to SEQ ID NO:4; nucleotide sequences that encode SEQ ID NO:6; nucleotide sequences that encode an ammo acid sequences having at least 90% homology to SEQ ID NO:6; fragments of nucleotide sequences that encode SEQ ID NO:6; fragments of a nucleotide sequence that encode an amino acid sequence having at least 90% homology to SEQ ID NO:6; nucleotide sequences that encode SEQ ID NO:8; nucleotide sequences that encodes an amino acid sequences having at least 90% homology to SEQ ID NO:8; fragments of nucleotide sequences that encodes SEQ ID NO:8; fragments of nucleotide sequences that encodes an amino acid sequence having at least 90% homology to SEQ ID NO:8; nucleotide sequences that encode SEQ ID NO:10; nucleotide sequences that encode an amino acid sequences having at least 90% homology to SEQ ID NO:10; fragments of nucleotide sequences that encode SEQ ID NO:10; fragments of a nucleotide sequence that encode an amino acid sequence having at least 90% homology to SEQ ID NO:10; nucleotide sequences that encode SEQ ID NO:12; nucleotide sequences that encodes an amino acid sequences having at least 90% homology to SEQ ID NO:12; fragments of nucleotide sequences that encodes SEQ ID NO:12; fragments of nucleotide sequences that encodes an amino acid sequence having at least 90% homology to SEQ ID NO:12.

The present invention further provides pharmaceutical compositions comprising such nucleic acid molecules and their use in methods of inducing an immune response in an individual against HIV that comprise administering to an individual a composition comprising such nucleic acid molecules.

The present invention further provides recombinant vaccine comprising such nucleic acid molecules and their use in methods of inducing an immune response in an individual against HIV that comprise administering to an individual such a recombinant vaccine.

The present invention further provides live attenuated pathogens comprising such nucleic acid molecules and their use in methods of inducing an immune response in an individual against HIV that comprise administering to an individual such live attenuated pathogens. live attenuated pathogen The present invention further provides proteins comprising amino acid sequences selected from the group consisting of: SEQ ID NO:2, sequences having at least 90% homology to SEQ ID NO:2; fragments of SEQ ID NO:2; fragments of sequences having at least 90% homology to SEQ ID NO:2;

SEQ ID NO:4, sequences having at least 90% homology to SEQ ID NO:4; fragments of SEQ ID NO:; fragments of sequences having at least 90% homology to SEQ ID NO:4; SEQ ID NO:6, sequences having at least 90% homology to SEQ ID NO:6; fragments of SEQ ID NO:6; fragments of sequences having at least 90% homology to SEQ ID NO:6; SEQ ID NO:8, sequences having at least 90% homology to SEQ ID NO:8; fragments of SEQ ID NO:8; fragments of sequences having at least 90% homology to SEQ ID NO:8; SEQ ID NO:10, sequences having at least 90% homology to SEQ ID NO:10; fragments of SEQ TD NO:10; fragments of sequences having at least 90% homology to SEQ ID NO:10; SEQ ID NO:12, sequences having at least 90% homology to SEQ ID NO:12; fragments of SEQ ID NO:12; and fragments of sequences having at least 90% homology to SEQ ID NO:12.

The present invention further provides proteins comprising amino acid sequences selected from the group consisting of SEQ ID NO:16; SEQ ID NO:17; SEQ ID NO:18; SEQ ID NO:19; SEQ ID NO:20 and SEQ ID NO:21.

The present invention further provides pharmaceutical compositions comprising such proteins and their use in methods of inducing an immune response in an individual against HIV that comprise administering to an individual a composition comprising such proteins.

The present invention further provides recombinant vaccine comprising such proteins and their use in methods of inducing an immune response in an individual against HIV that comprise administering to an individual such a recombinant vaccine.

The present invention further provides live attenuated pathogens comprising such proteins and their use in methods of inducing an immune response in an individual against HIV that comprise administering to an individual such live attenuated pathogens.

Proteins comprising consensus HPV genotype 16 E6-E7 amino acid sequences and nucleic acid molecules that comprising a nucleotide sequence encoding such proteins are provided.

The present invention relates to nucleic acid molecules that comprising a nucleotide sequence selected from the group consisting of SEQ ID NO:22; fragments thereof; nucleotide sequences having at least 90% homology to SEQ ID NO:22; and fragments thereof.

The present invention also relates to nucleic acid molecules that comprising a nucleotide sequence selected from the group consisting of: a nucleic acid sequence that encodes SEQ ID NO:23; a nucleic acid sequence that encodes SEQ ID NO:24; a nucleic acid sequence that encodes SEQ ID NO:25; a nucleic acid sequence that encodes SEQ ID NO:26; and a nucleic acid sequence that encodes SEQ ID NO:27.

The present invention also relates to pharmaceutical composition such nucleic acid molecules and to methods of inducing an immune response in an individual against HPV comprising administering to said individual a composition comprising such nucleic acid molecules.

The present invention further relates to recombinant vaccines comprising such nucleic acid molecules and methods of inducing an immune response in an individual against HPV comprising administering to said individual such a recombinant vaccine.

The present invention further relates to live attenuated pathogen comprising such nucleic acid molecules and methods of inducing an immune response in an individual against HPV comprising administering to said individual such live attenuated pathogens.

The present invention also relates to nucleic acid molecules that comprising a nucleotide sequence selected from the group consisting of proteins comprising an amino acid sequence selected from the group consisting of: SEQ ID NO:23, fragments thereof; nucleotide sequences having at least 90% homology to SEQ ID NO:23; and fragments thereof.

The present invention also relates to proteins comprising an amino acid sequence selected from the group consisting of SEQ ID NO:23; SEQ ID NO:24; SEQ ID NO:25; SEQ ID NO:26; and SEQ ID NO:27.

The present invention also relates to pharmaceutical compositions comprising such proteins and to methods of inducing an immune response in an individual against HPV comprising administering to said individual a composition comprising such proteins.

The present invention also relates to recombinant vaccines comprising such proteins and to method of inducing an immune response in an individual against HPV comprising administering to said individual such recombinant vaccines.

The present invention also relates to live attenuated pathogens comprising such protein and to methods of inducing an immune response in an individual against HPV comprising administering to said individual such live attenuated pathogens.

Proteins comprising consensus HCV genotype 1a and 1b E1-E2 amino acid sequences and nucleic acid molecules that comprising a nucleotide sequence encoding such proteins are provided.

The present invention relates to nucleic acid molecules that comprising a nucleotide sequence selected from the group consisting of: SEQ ID NO:30; fragments thereof; nucleotide sequences having at least 90% homology to SEQ ID NO:30; and fragments thereof.

The present invention also relates to nucleic acid molecules that comprising a nucleotide sequence selected from the group consisting of a nucleic acid sequence that encodes SEQ ID NO:31.

The present invention also relates to pharmaceutical composition such nucleic acid molecules and to methods of inducing an immune response in an individual against HCV comprising administering to said individual a composition comprising such nucleic acid molecules.

The present invention further relates to recombinant vaccines comprising such nucleic acid molecules and methods of inducing an immune response in an individual against HCV comprising administering to said individual such a recombinant vaccine.

The present invention further relates to live attenuated pathogen comprising such nucleic acid molecules and methods of inducing an immune response in an individual against HCV comprising administering to said individual such live attenuated pathogens.

The present invention also relates to nucleic acid molecules that comprising a nucleotide sequence selected from the group consisting of: proteins comprising an amino acid sequence selected from the group consisting of SEQ ID NO:31; fragments thereof; nucleotide sequences having at least 90% homology to SEQ ID NO:31; and fragments thereof.

The present invention also relates to pharmaceutical compositions comprising such proteins and to methods of inducing an immune response in an individual against HCV comprising administering to said individual a composition comprising such proteins.

The present invention also relates to recombinant vaccines comprising such proteins and to method of inducing an immune response in an individual against HCV comprising administering to said individual such recombinant vaccines.

The present invention also relates to live attenuated pathogens comprising such protein and to methods of inducing an immune response in an individual against HCV comprising administering to said individual such live attenuated pathogens.

Proteins comprising consensus hTERT amino acid sequences and nucleic acid molecules that comprising a nucleotide sequence encoding such proteins are provided.

The present invention further relates to nucleic acid molecules comprising a nucleotide sequence selected from the group consisting of: SEQ ID NO: 34; fragments thereof; nucleotide sequences having at least 90% homology to SEQ ID NO: 34; and fragments thereof.

The present invention also relates to pharmaceutical composition such nucleic acid molecules and to methods of inducing an immune response in an individual against hyperproliferative cells expressing hTERT comprising administering to said individual a composition comprising such nucleic acid molecules.

The present invention further relates to recombinant vaccines comprising such nucleic acid molecules and methods of inducing an immune response in an individual against hyperproliferative cells expressing hTERT comprising administering to said individual such a recombinant vaccine.

The present invention further relates to live attenuated pathogen comprising such nucleic acid molecules and methods of inducing an immune response in an individual against hyperproliferative cells expressing hTERT comprising administering to said individual such live attenuated pathogens.

The present invention also relates to nucleic acid molecules that comprising a nucleotide sequence selected from the group consisting of proteins comprising an amino acid sequence selected from the group consisting of: SEQ ID NO:35; fragments thereof; nucleotide sequences having at least 90% homology to SEQ ID NO:35; and fragments thereof.

The present invention also relates to pharmaceutical compositions comprising such proteins and to methods of inducing an immune response in an individual against hyperproliferative cells expressing hTERT comprising administering to said individual a composition comprising such proteins.

The present invention also relates to recombinant vaccines comprising such proteins and to method of inducing an immune response in an individual against hyperproliferative cells expressing hTERT comprising administering to said individual such recombinant vaccines.

The present invention also relates to live attenuated pathogens comprising such protein and to methods of inducing an immune response in an individual against hyperproliferative cells expressing hTERT comprising administering to said individual such live attenuated pathogens.

Proteins comprising Influenza H5N1 consensus HA amino acid sequences, Influenza H1N1 and H5N1 consensus NA amino acid sequences, Influenza H1N1 and H5N1 consensus M1 amino acid sequences, and influenza H5N1 consensus M2E-NP amino acid sequences and nucleic acid molecules that comprising a nucleotide sequence encoding such proteins are provided.

The present invention further relates to nucleic acid molecules comprising a nucleotide sequence selected from the group consisting of SEQ ID NO:36; fragments thereof; nucleotide sequences having at least 90% homology to SEQ ID NO:36; and fragments thereof.

The present invention further relates to nucleic acid molecules comprising a nucleotide sequence selected from the group consisting of: SEQ ID NO:38; fragments thereof; nucleotide sequences having at least 90% homology to SEQ ID NO:38; and fragments thereof.

The present invention further relates to nucleic acid molecules comprising a nucleotide sequence selected from the group consisting of: SEQ ID NO:40; fragments thereof; nucleotide sequences having at least 90% homology to SEQ ID NO:40; and fragments thereof.

The present invention further relates to nucleic acid molecules comprising a nucleotide sequence selected from the group consisting of: SEQ ID NO:42; fragments thereof; nucleotide sequences having at least 90% homology to SEQ ID NO:42; and fragments thereof.

The present invention also relates to pharmaceutical compositions comprising such nucleic acid molecules and to methods of inducing an immune response in an individual against HPV, HCV, and Influenza virus comprising administering to said individual a composition comprising such nucleic acid molecules.

The present invention further relates to recombinant vaccines comprising such nucleic acid molecules and methods of inducing an immune response in an individual against HPV, HCV, and Influenza virus comprising administering to said individual such a recombinant vaccine.

The present invention further relates to live attenuated pathogens comprising such nucleic acid molecules and methods of inducing an immune response in an individual against HPV, HCV, and Influenza virus comprising administering to said individual such live attenuated pathogens.

The present invention also relates to pharmaceutical compositions comprising such nucleic acid molecules and to methods of inducing an immune response in an individual against HPV, HCV, and Influenza virus comprising administering to said individual a composition comprising such nucleic acid molecules.

The present invention further relates to recombinant vaccines comprising such nucleic acid molecules and methods of inducing an immune response in an individual against HPV, HCV, and Influenza virus comprising administering to said individual such a recombinant vaccine.

The present invention further relates to live attenuated pathogens comprising such nucleic acid molecules and methods of inducing an immune response in an individual against HPV, HCV, and Influenza virus comprising administering to said individual such live attenuated pathogens.

The present invention further relates to protein molecules comprising an amino acid sequence selected from the group consisting of: SEQ ID NO:37; fragments thereof; nucleotide sequences having at least 90% homology to SEQ ID NO:37; and fragments thereof.

The present invention further relates to protein molecules comprising an amino acid sequence selected from the group consisting of: SEQ ID NO:39; fragments thereof; nucleotide sequences having at least 90% homology to SEQ ID NO:39; and fragments thereof.

The present invention further relates to protein molecules comprising an amino acid sequence selected from the group consisting of: SEQ ID NO:41; fragments thereof; nucleotide sequences having at least 90% homology to SEQ ID NO:41; and fragments thereof.

The present invention further relates to protein molecules comprising an amino acid sequence selected from the group consisting of SEQ ID NO:43; fragments thereof; nucleotide sequences having at least 90% homology to SEQ ID NO:43; and fragments thereof.

The present invention also relates to pharmaceutical compositions comprising such protein molecules and to methods of inducing an immune response in an individual against Influenza virus comprising administering to said individual a composition comprising such protein molecules.

The present invention further relates to recombinant vaccines comprising such protein molecules and methods of inducing an immune response in an individual against Influenza virus comprising administering to said individual such a recombinant vaccine.

The present invention further relates to live attenuated pathogens comprising such protein molecules and methods of inducing an immune response in an individual against Influenza virus comprising administering to said individual such live attenuated pathogens.

The present invention also relates to pharmaceutical compositions comprising such protein molecules and to methods of inducing an immune response in an individual against Influenza virus comprising administering to said individual a composition comprising such protein molecules.

The present invention further relates to recombinant vaccines comprising such protein molecules and methods of inducing an immune response in an individual against Influenza virus comprising administering to said individual such a recombinant vaccine.

The present invention further relates to live attenuated pathogens comprising such protein molecules and methods of inducing an immune response in an individual against Influenza virus comprising administering to said individual such live attenuated pathogens.

BRIEF DESCRIPTION OF THE FIGURES

FIG. 1 shows a comparison of the amino acid sequences of EY2E1-B and EK2P-B. The IgE leader sequence is underlined. The boxed regions show variable regions. The * denotes six important residues involved in CCR5 utilization. The cleavage site is indicated by an arrow. The transmembrane domain is shown by the dotted line.

FIG. 3 shows expression of envelope immunogens.

FIG. 4. shows total IgG antibody titers in the sera of the immunized mice.

Figure 18A:
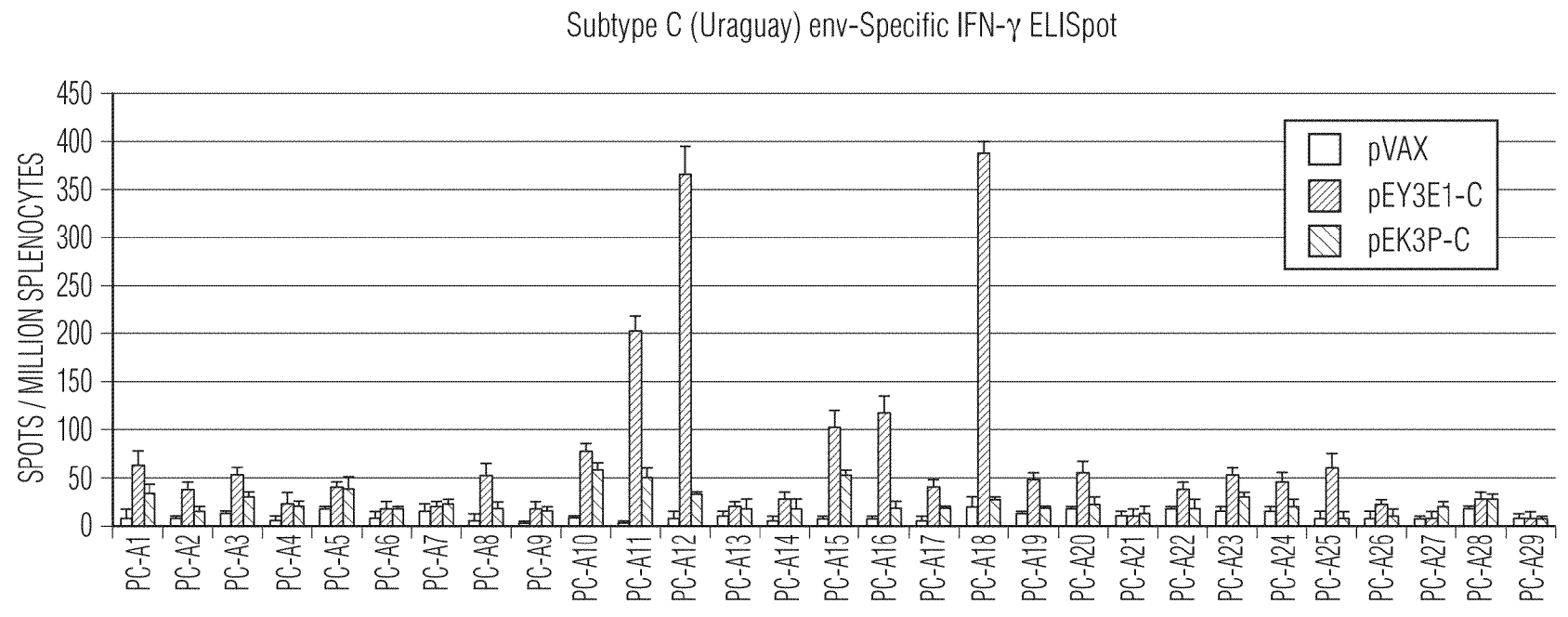

FIG. 18 (FIG. 18A and FIG. 18B) show data from studies of cross-reactive cellular responses elicited by pEY3E1-C. FIG.18A shows data from subtype C (Uruguay) env-Specific IFN-γ ELISpot.

DETAILED DESCRIPTION OF PREFERRED EMBODIMENTS

Definitions

As used herein, the phrase "stringent hybridization conditions" or "stringent conditions" refers to conditions under which a nucleic acid molecule will hybridize another a nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

Figure 14:
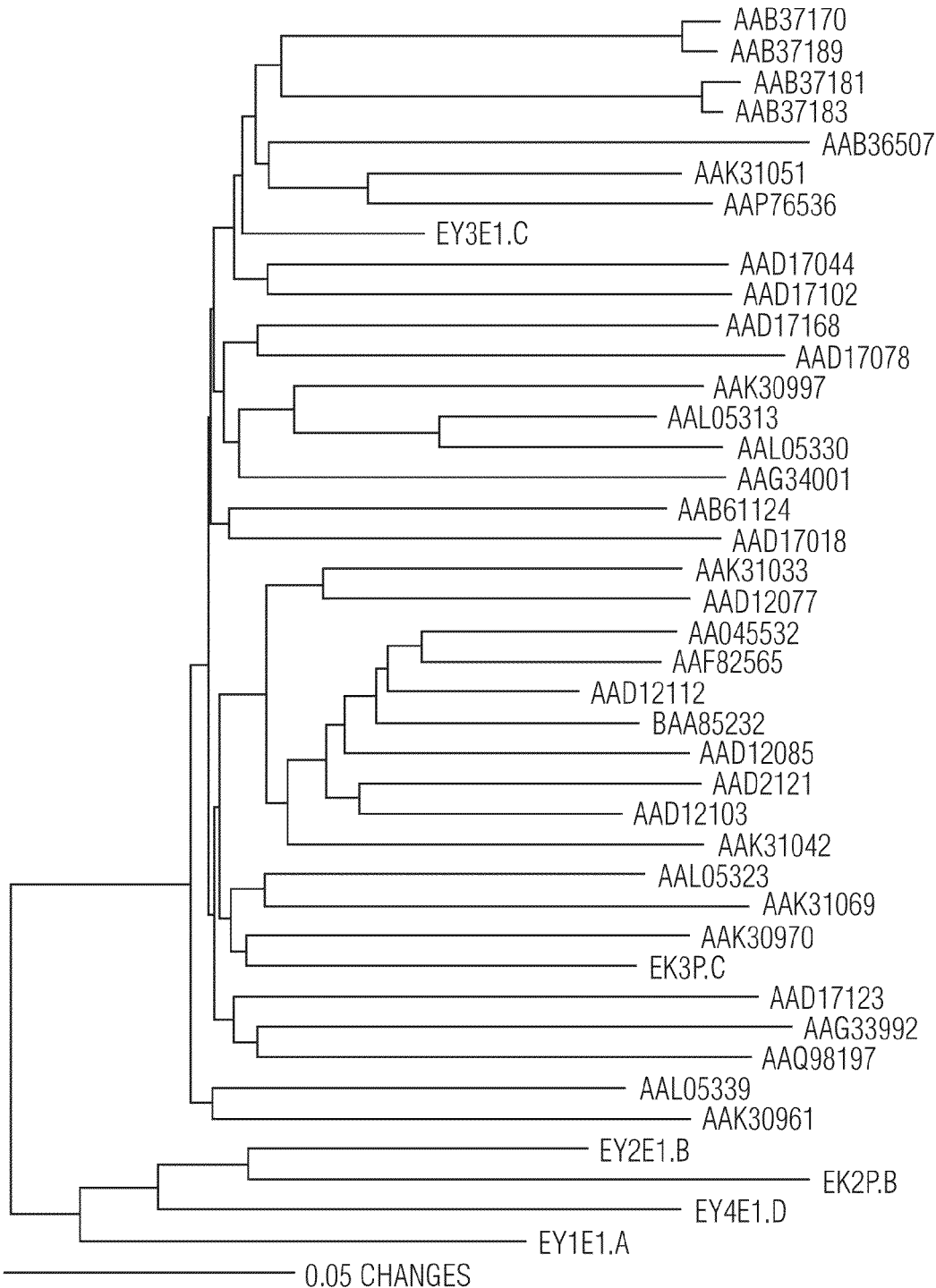
FIG. 14 shows phylogenetic relationships: Thirty-Six HIV-1 subtype C envelope sequences, EY3E1-C, EK3P-C, two subtype B, one subtype A and one subtype D sequences (outgroup) were included in the phylogenetic analysis. The subtype C envelope sequences representing a broad sample of diversity were from 12 countries.
Figure 15A:
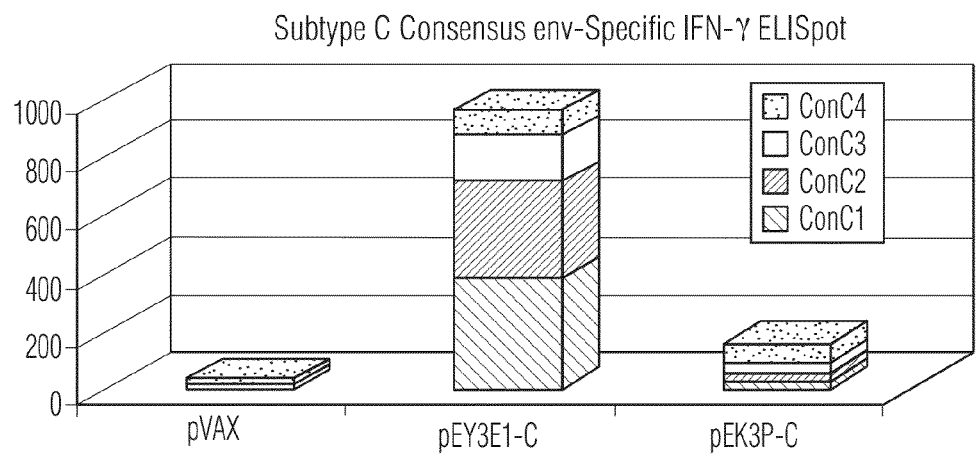
FIG. 15 (FIG. 15A and FIG. 15B) show data from studies of cellular response elicited by pEY3E1-C.
Figure 15B:
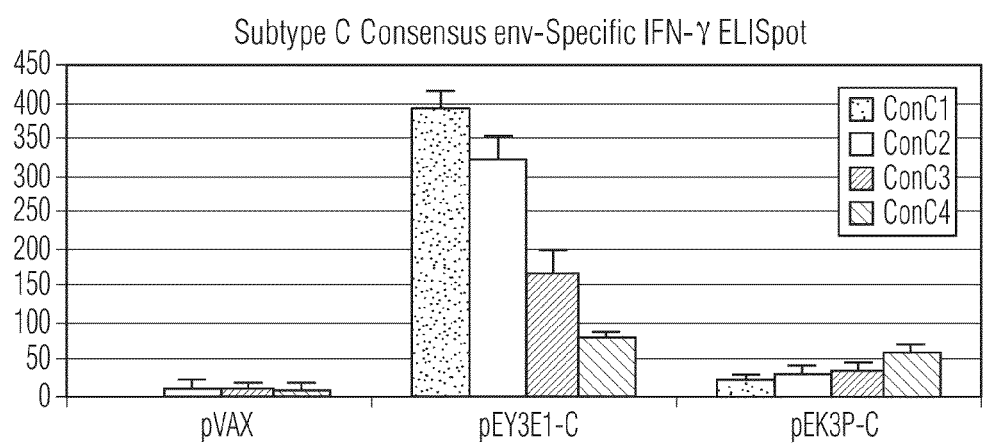
Figure 16:
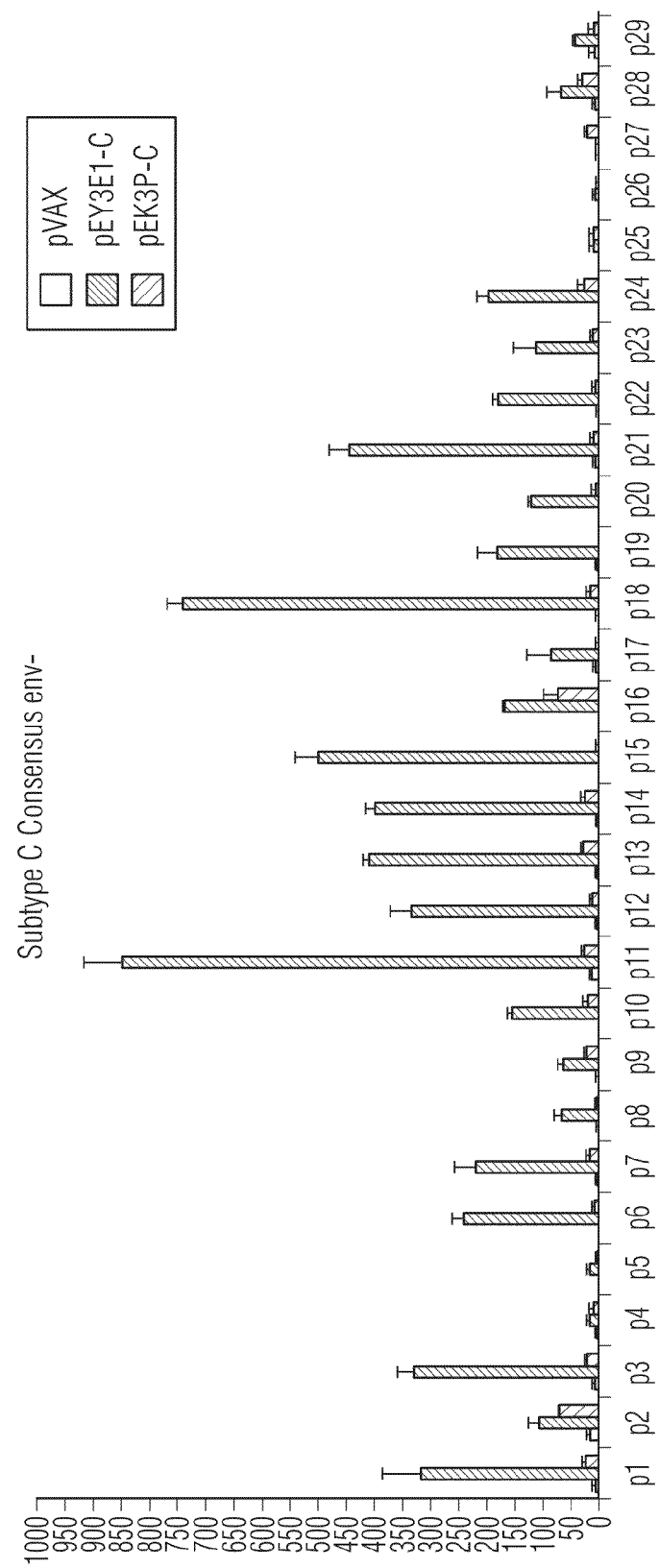
FIG. 16 shows data from studies of cellular responses elicited by pEY3E1-C.
Figure 17A:
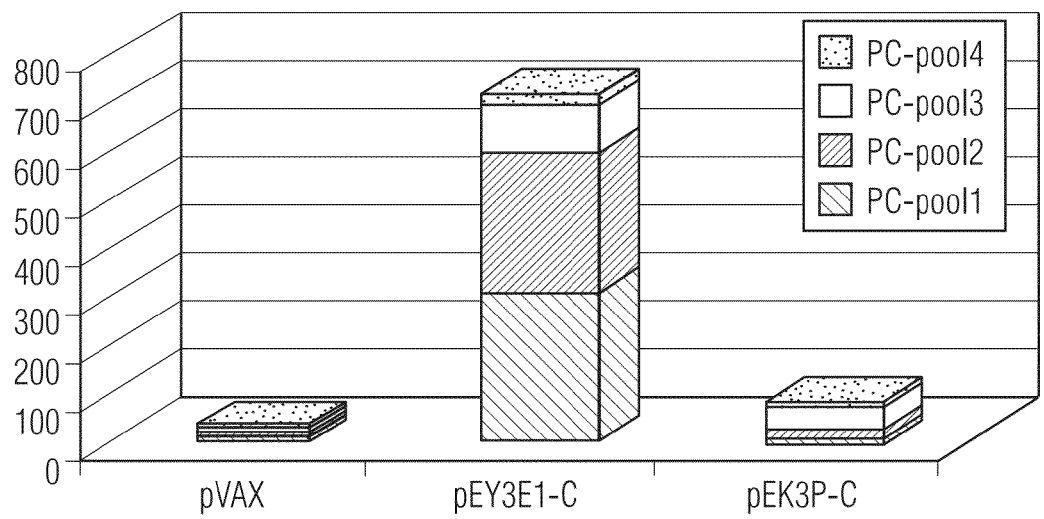
FIG. 17 (FIG. 17A through FIG. 17D) show data from studies of cross-reactive cellular responses elicited by pEY3E1-C within the same clade.
Figure 17B:
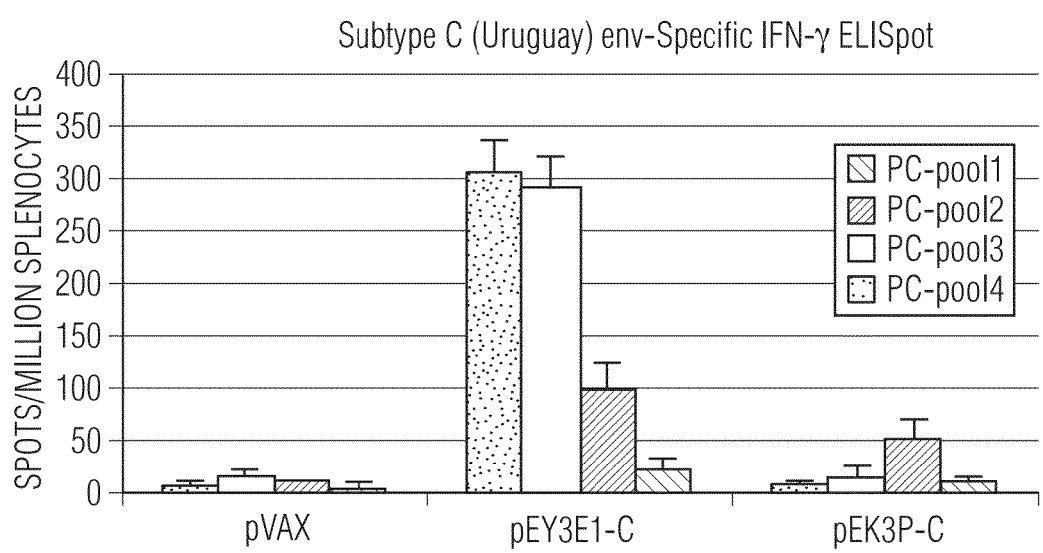
Figure 17C:
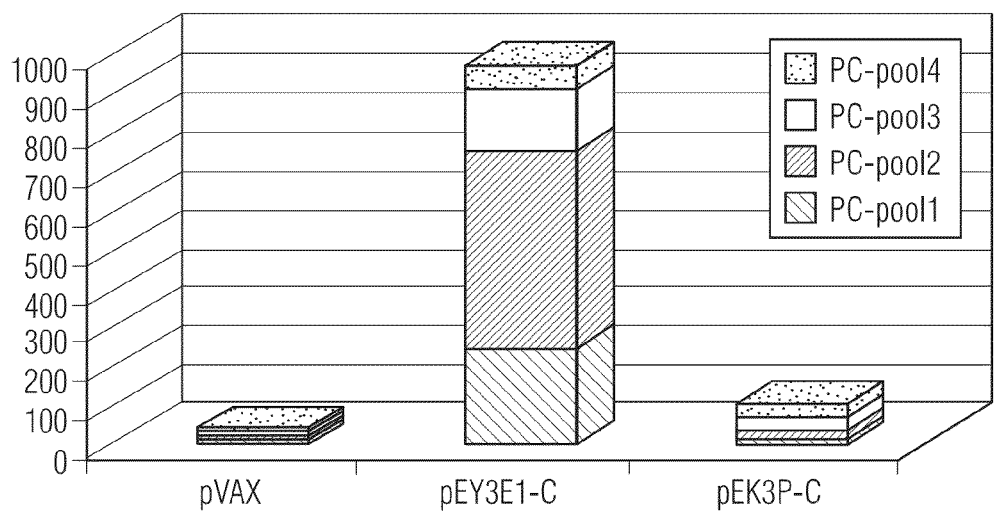
Figure 17D:
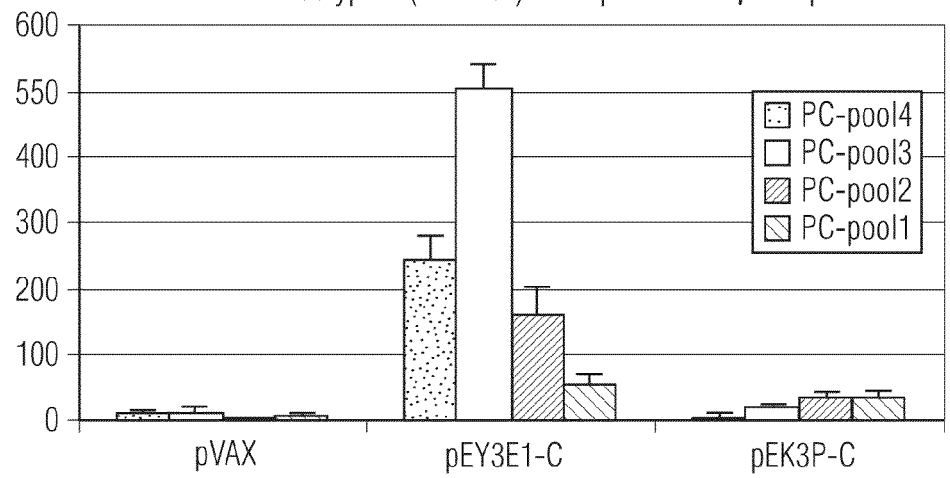
Figure 18B:
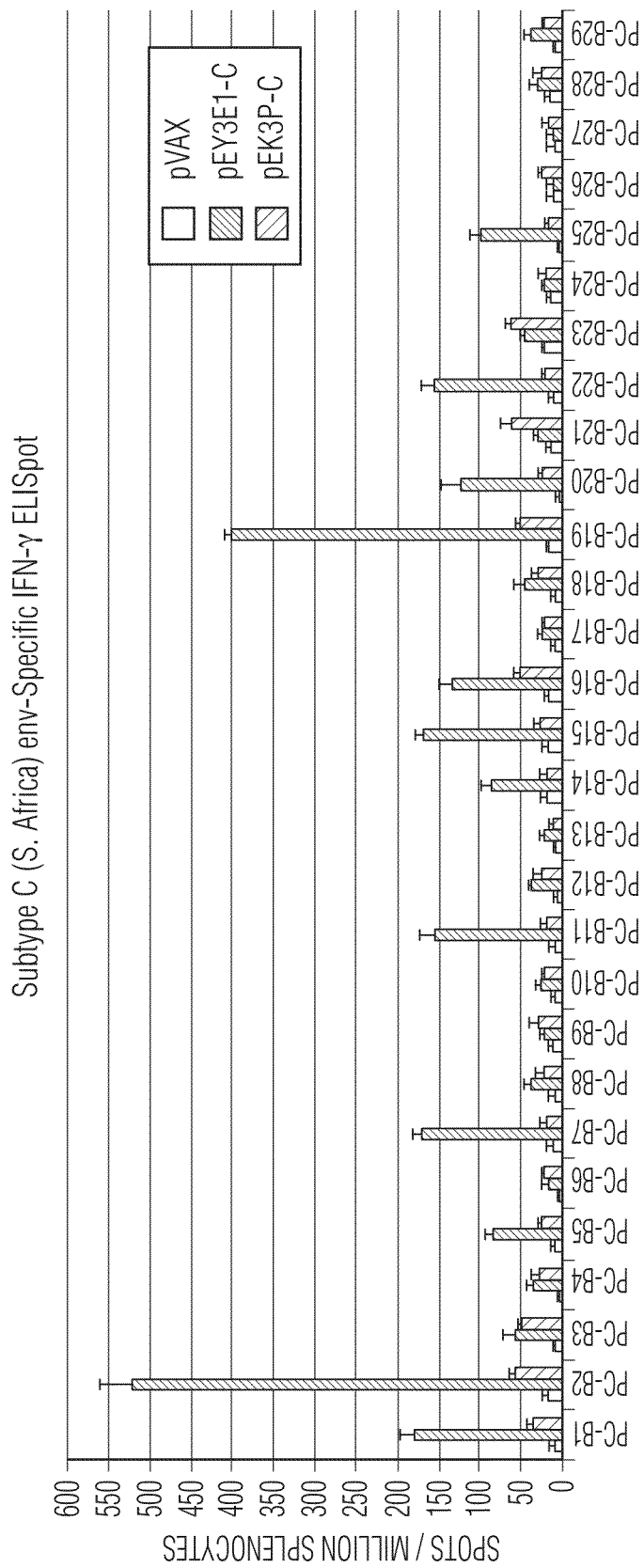
FIG. 18B shows data from Subtype C(S. Africa) env-Specific IFN-γ ELISpot.
Figure 19A:
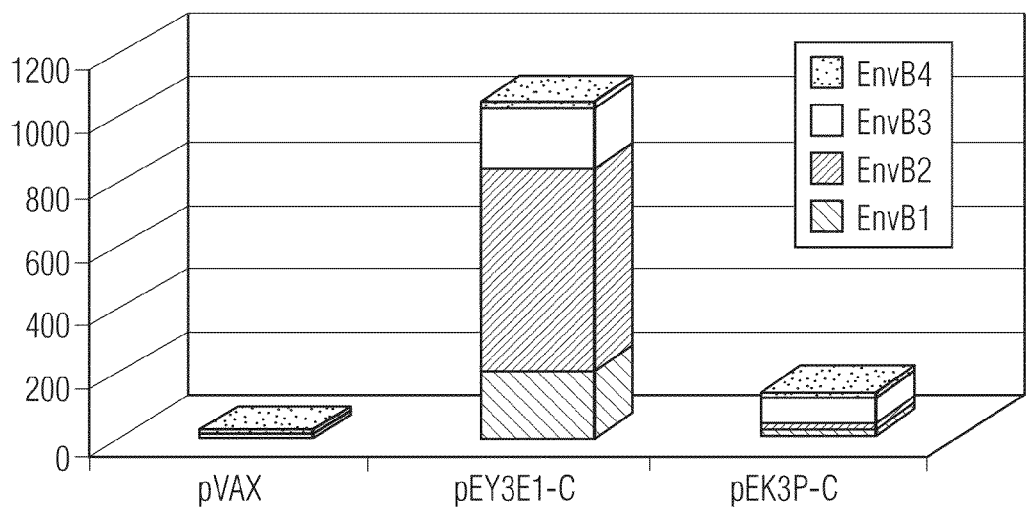
FIG. 19 (FIG. 19A through FIG.19F) show data from studies of cross-reactive cellular responses elicited by pEY3E1-C between clades.
Figure 19B:
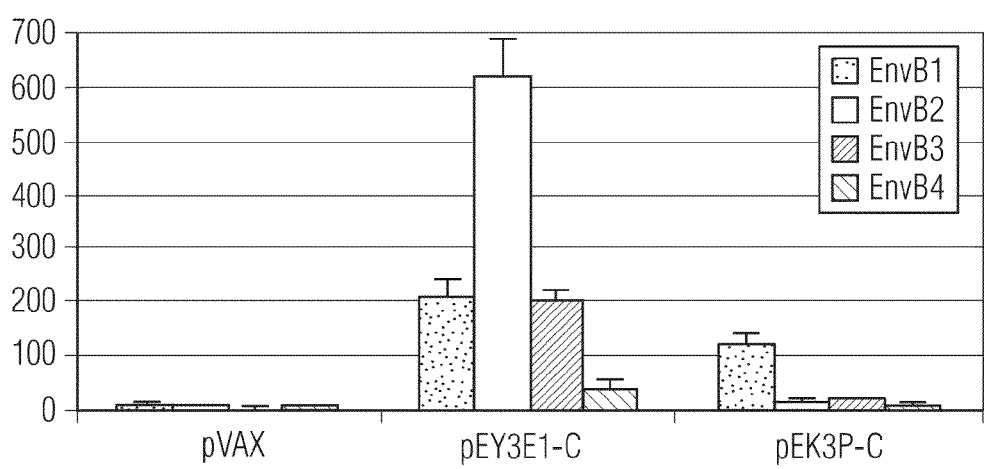
Figure 19C:
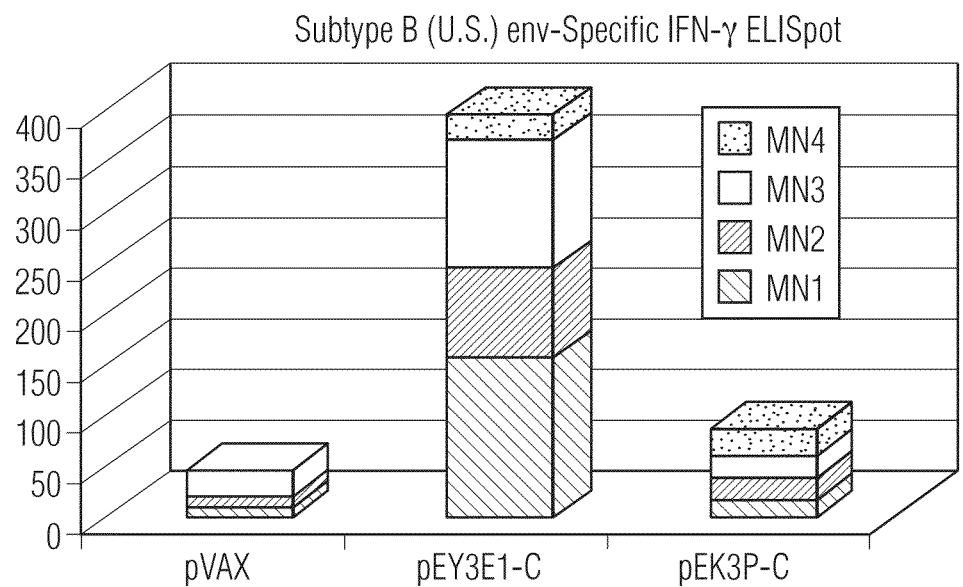
Figure 19D:
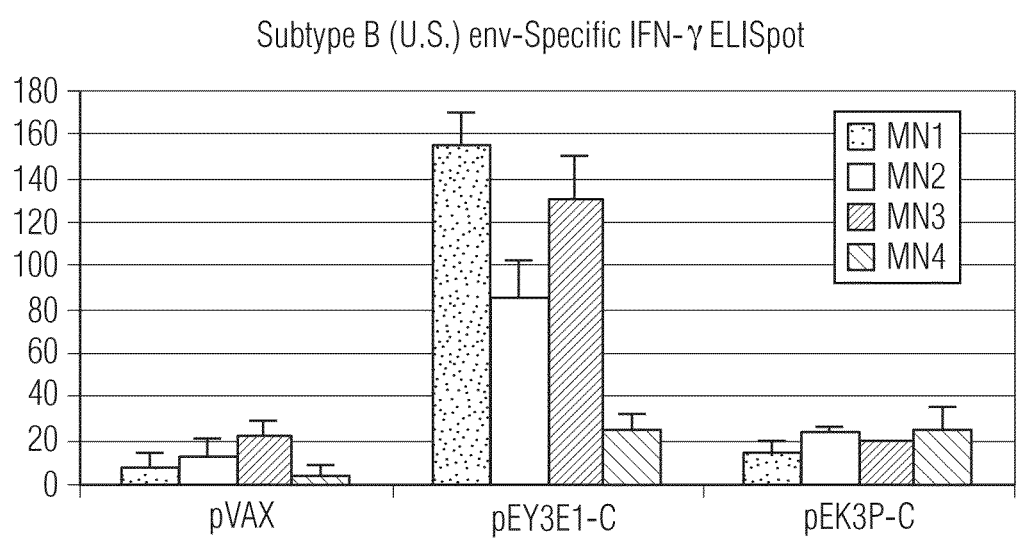
Figure 19E:
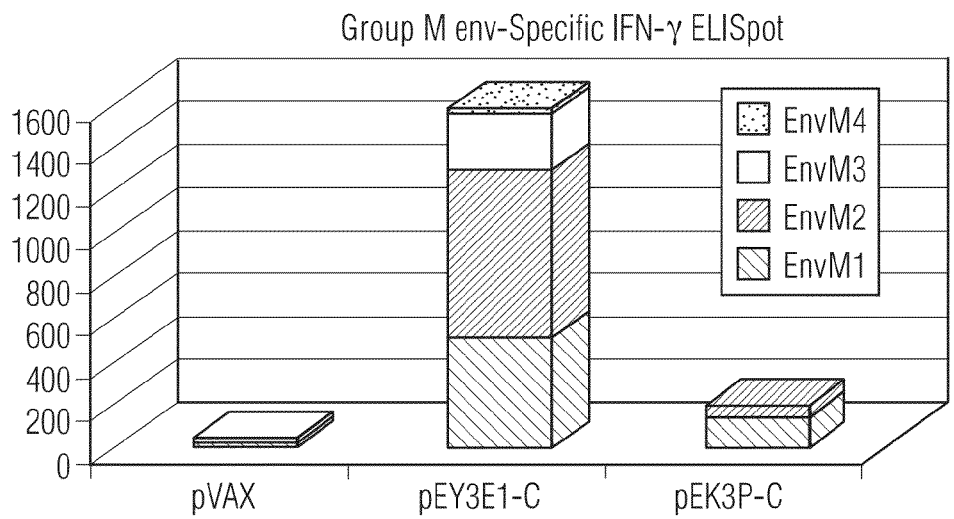
Figure 19F:
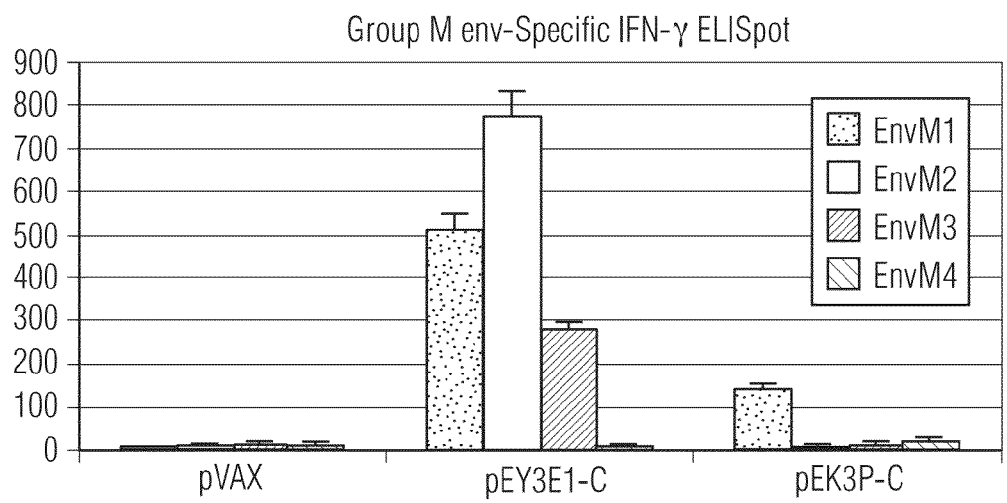
Figure 20A:
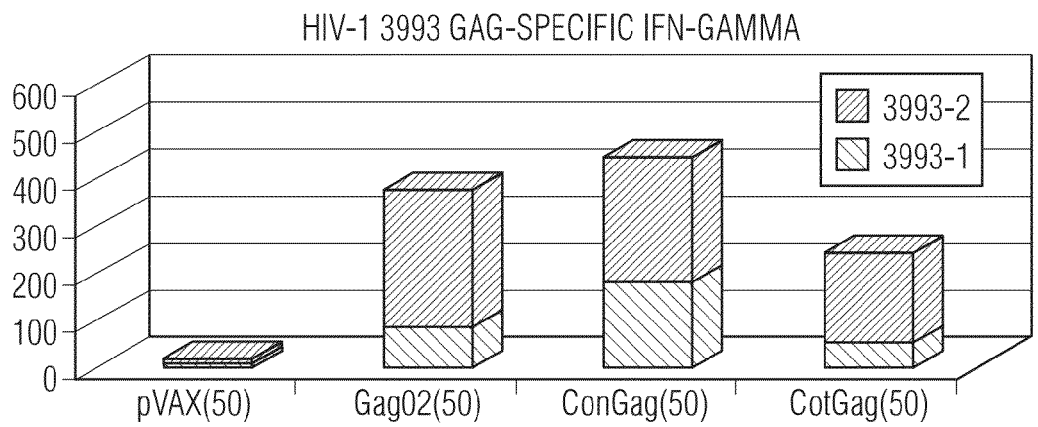
FIG. 20 (FIG. 20A through FIG 20X) show data from studies of immune responses elicited by HIV-1 gag consensus constructs.
Figure 20B:
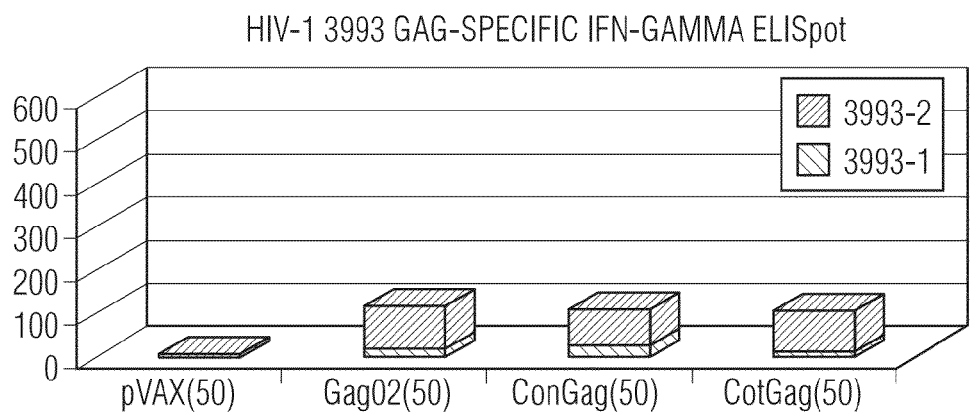
Figure 20C:
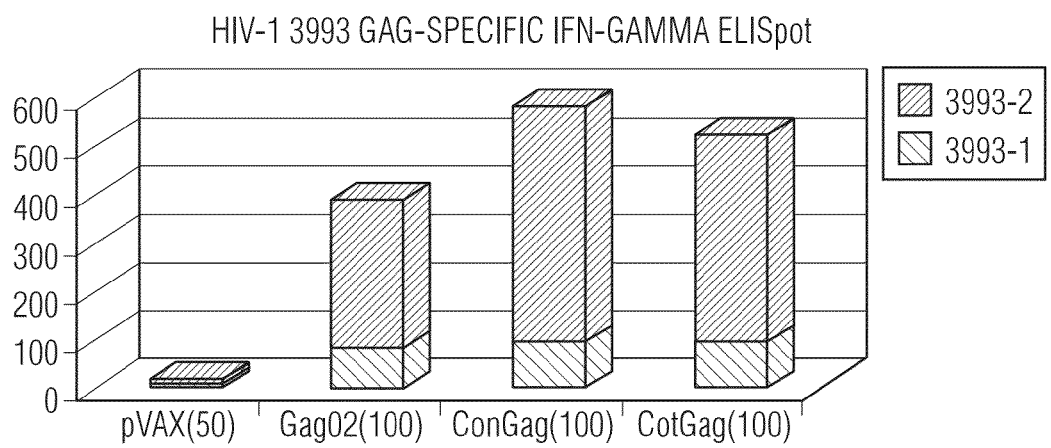
Figure 20D:
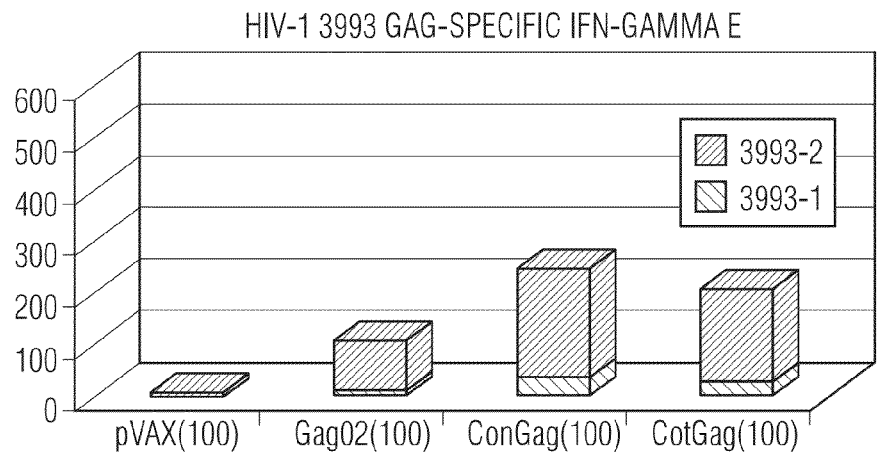
Figure 20E:
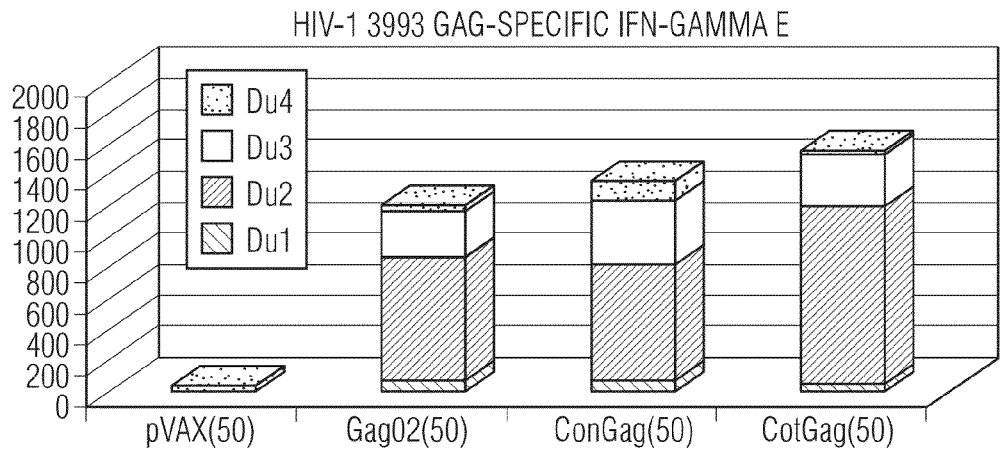
Figure 20F:
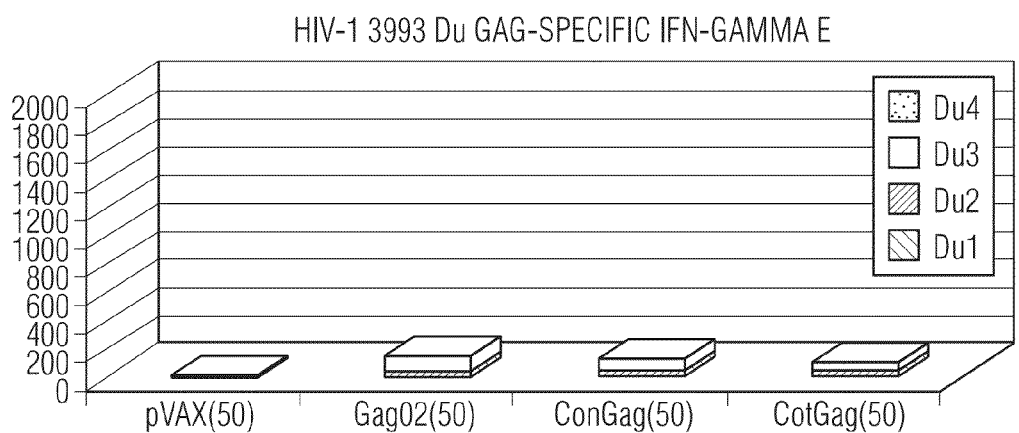
Figure 20G:
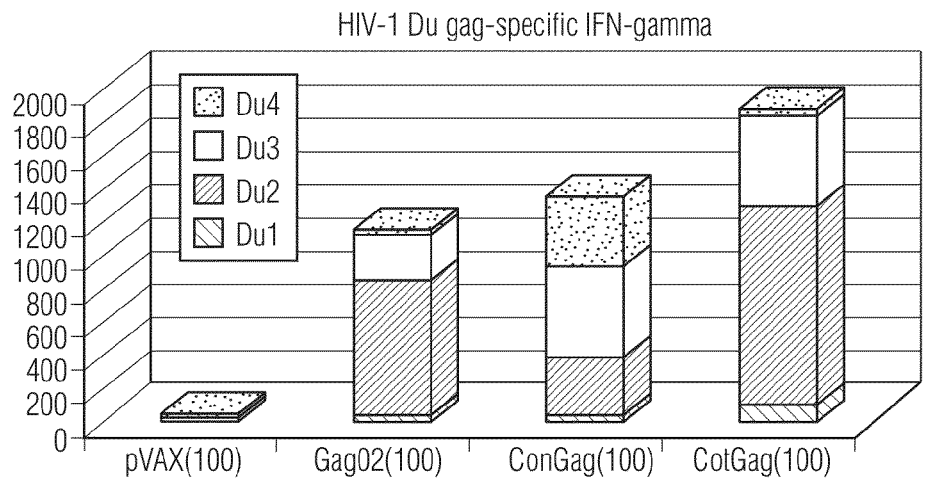
Figure 20H:
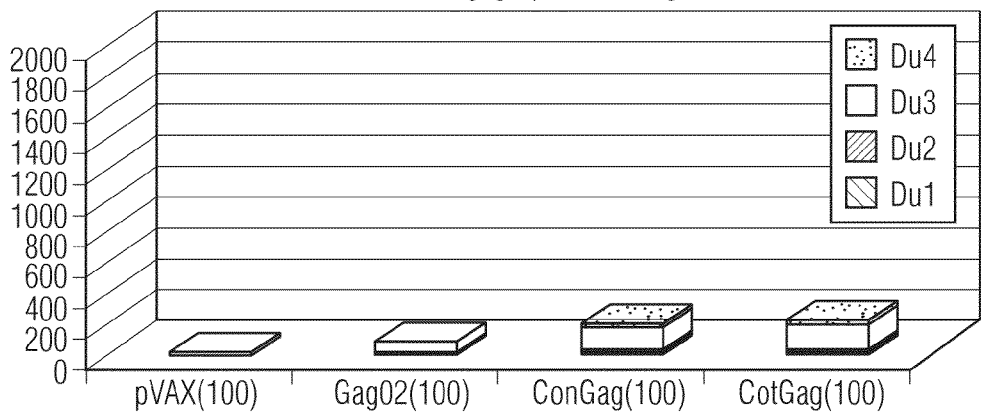
Figure 20I:
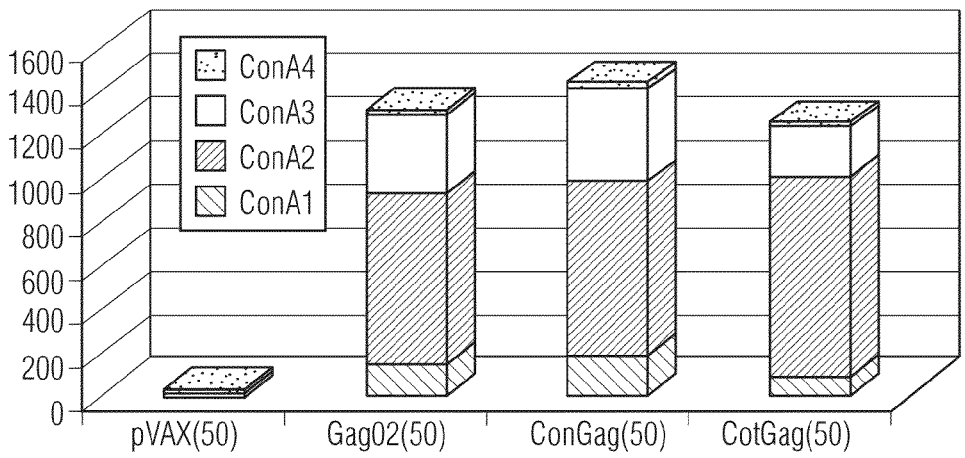
Figure 20J:
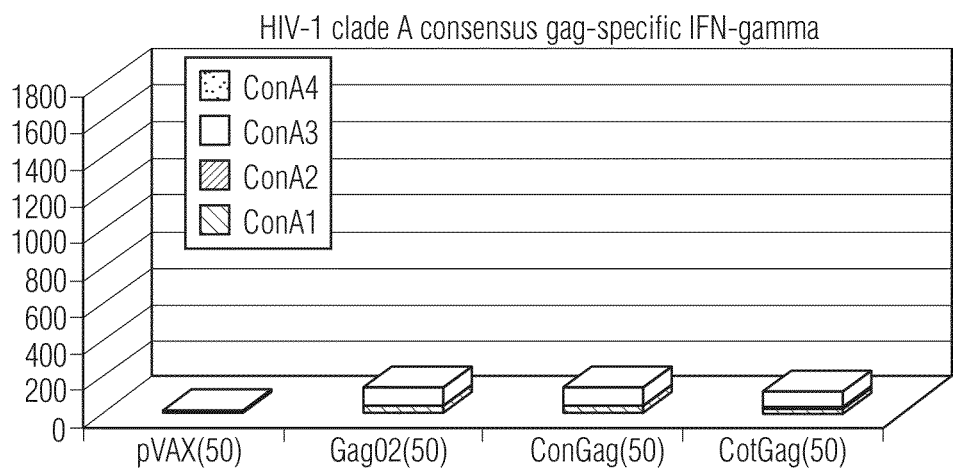
Figure 20K:
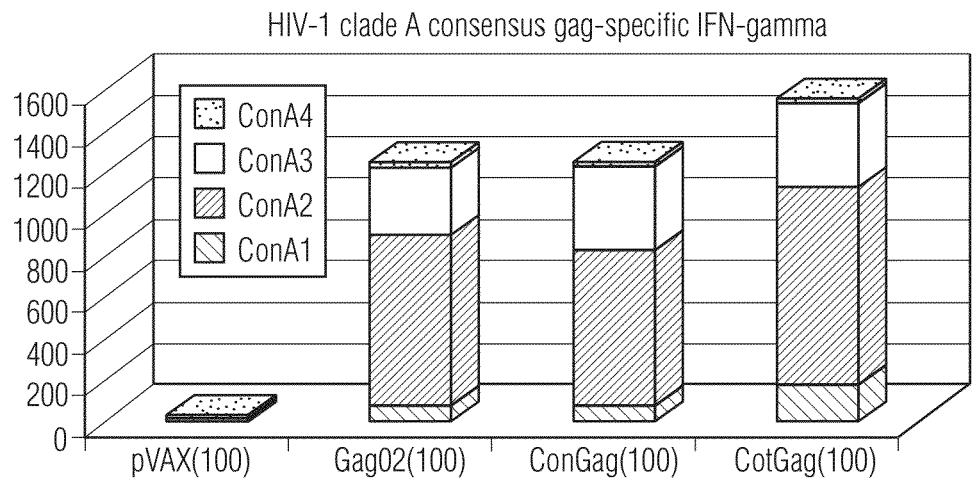
Figure 20L:
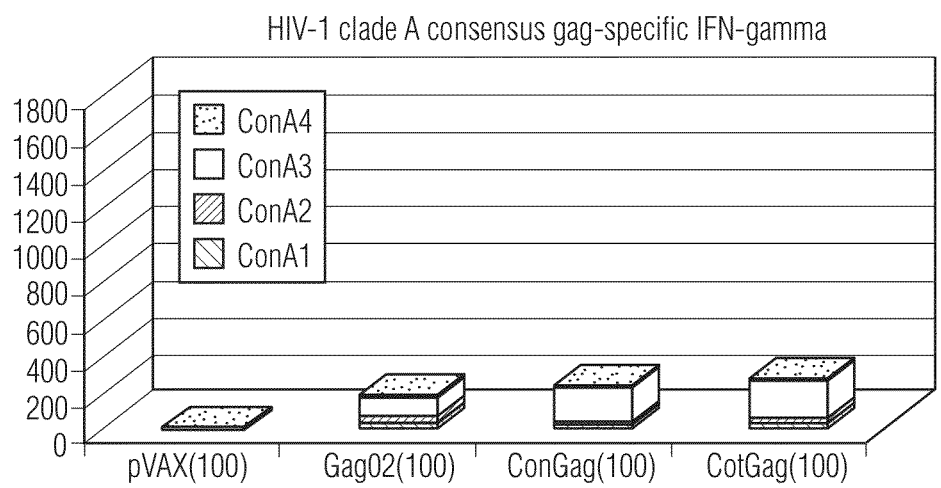
Figure 20M:
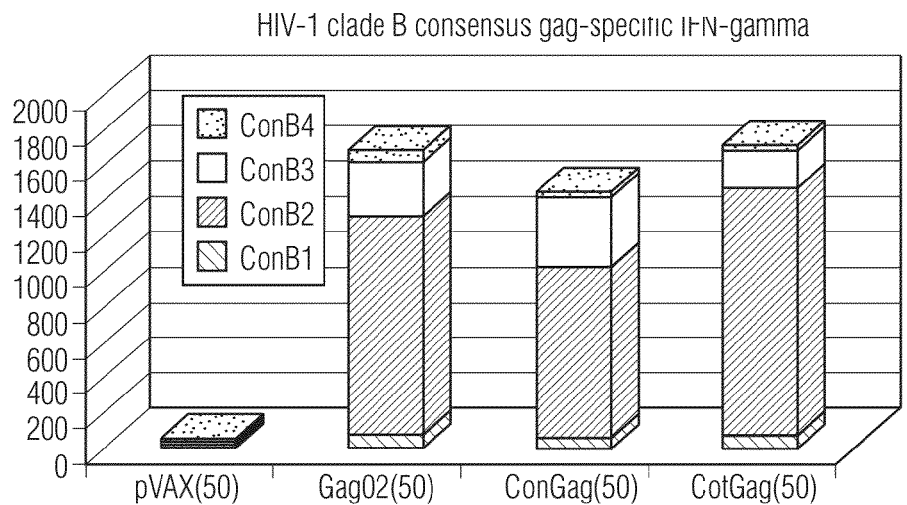
Figure 20N:
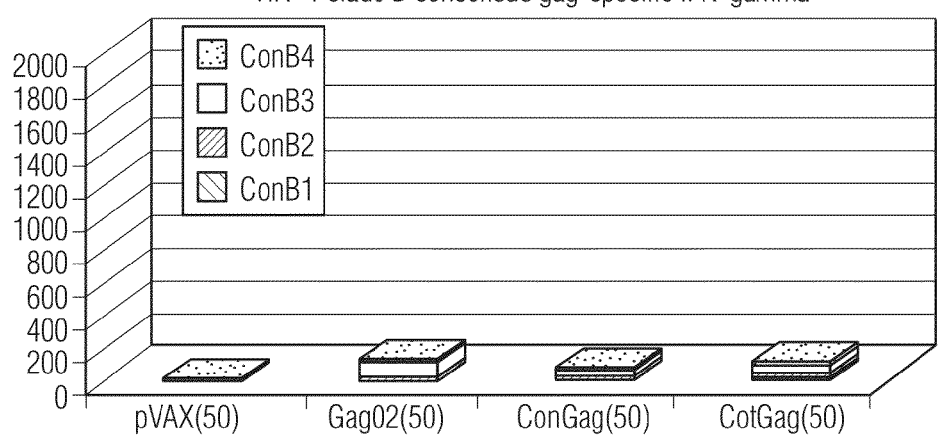
Figure 20O:
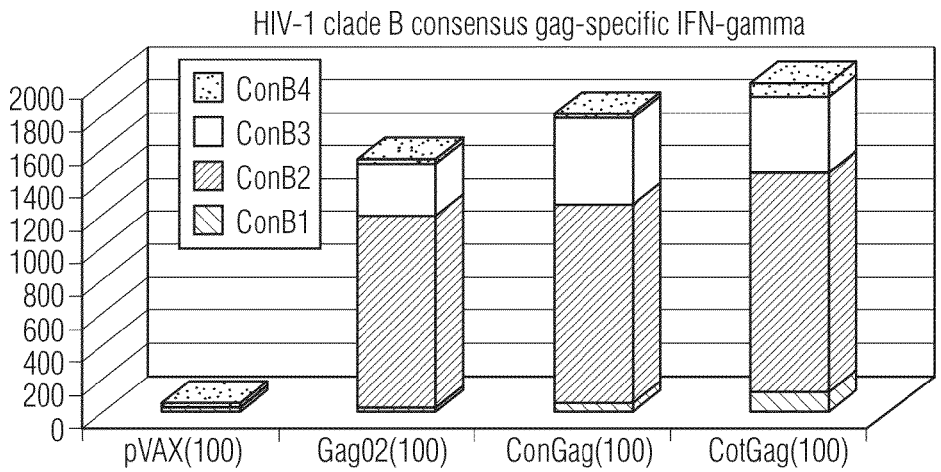
Figure 20P:
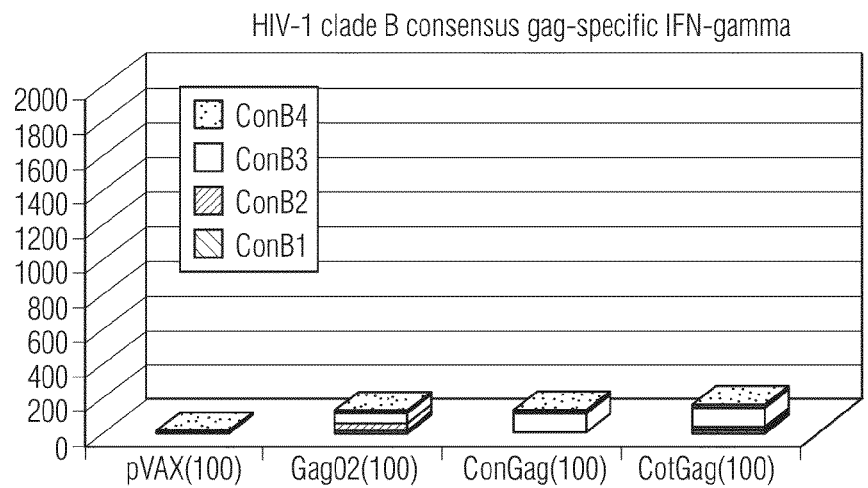
Figure 20Q:
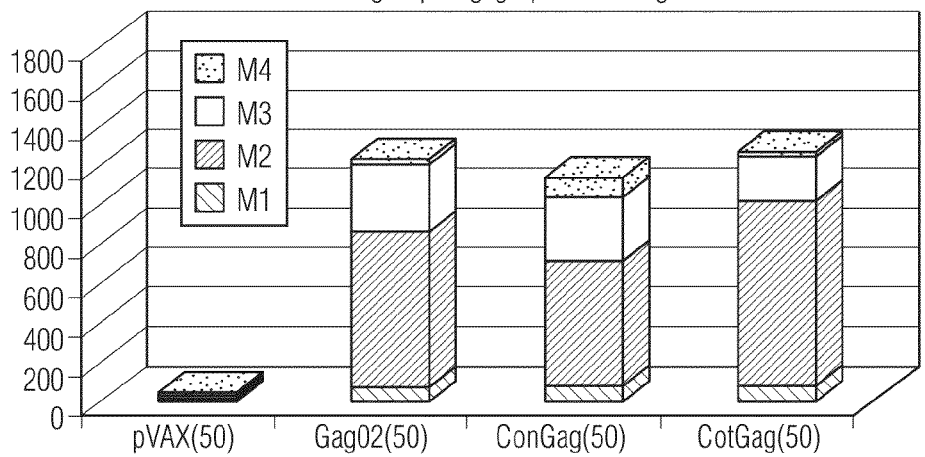
Figure 20R:
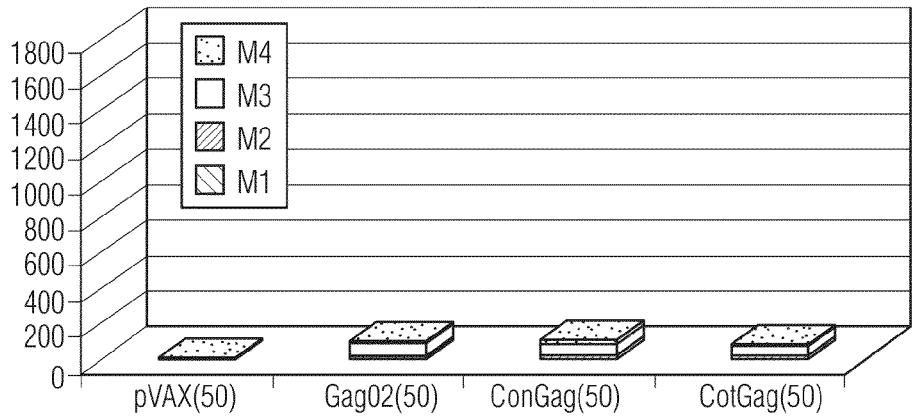
Figure 20S:
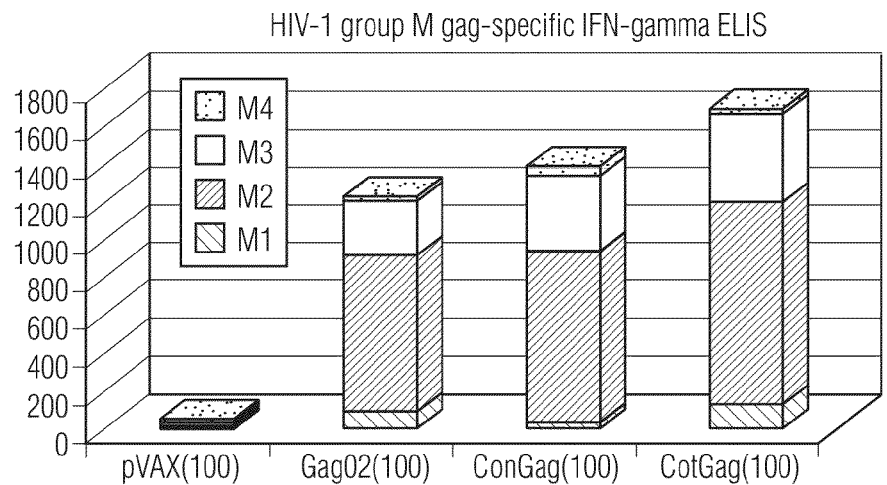
Figure 20T:
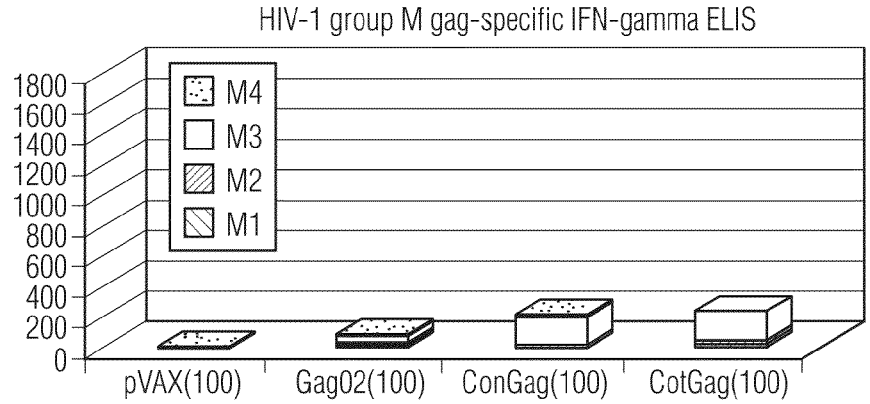
Figure 20U:
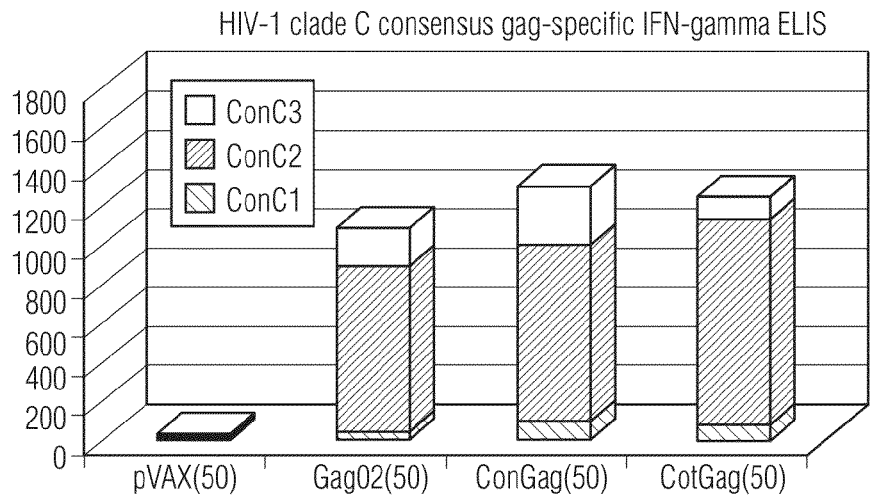
Figure 20V:
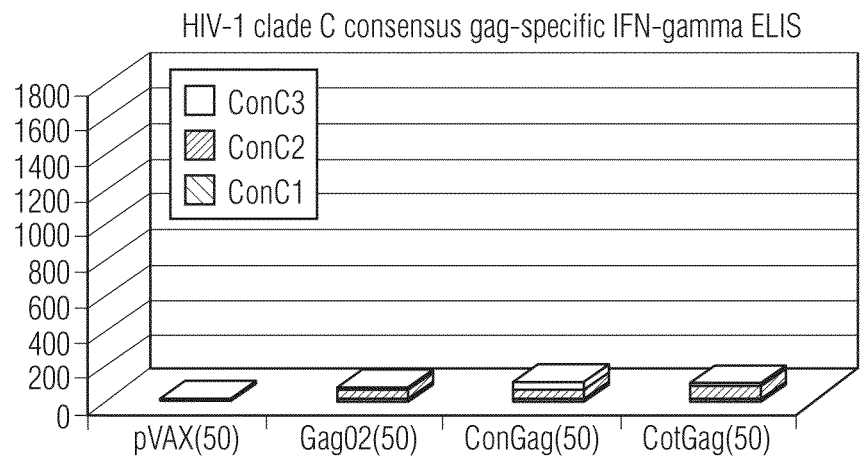
Figure 20W:
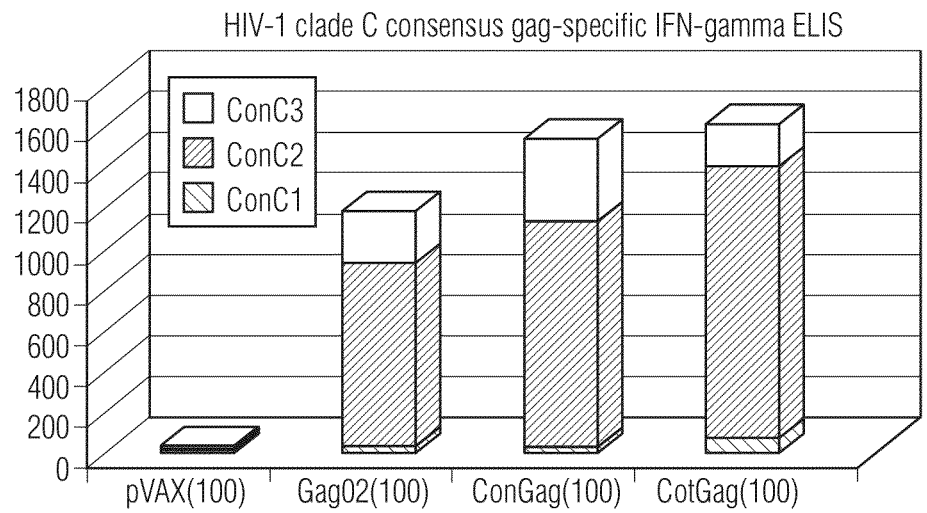
Figure 20X:
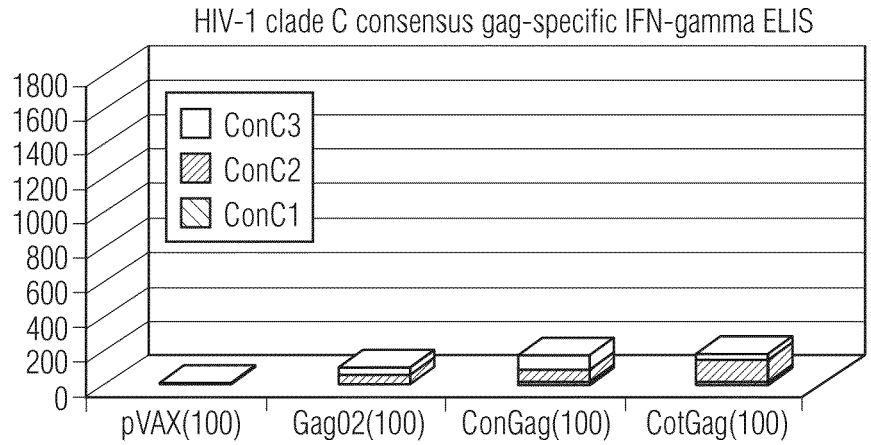
Figure 21:
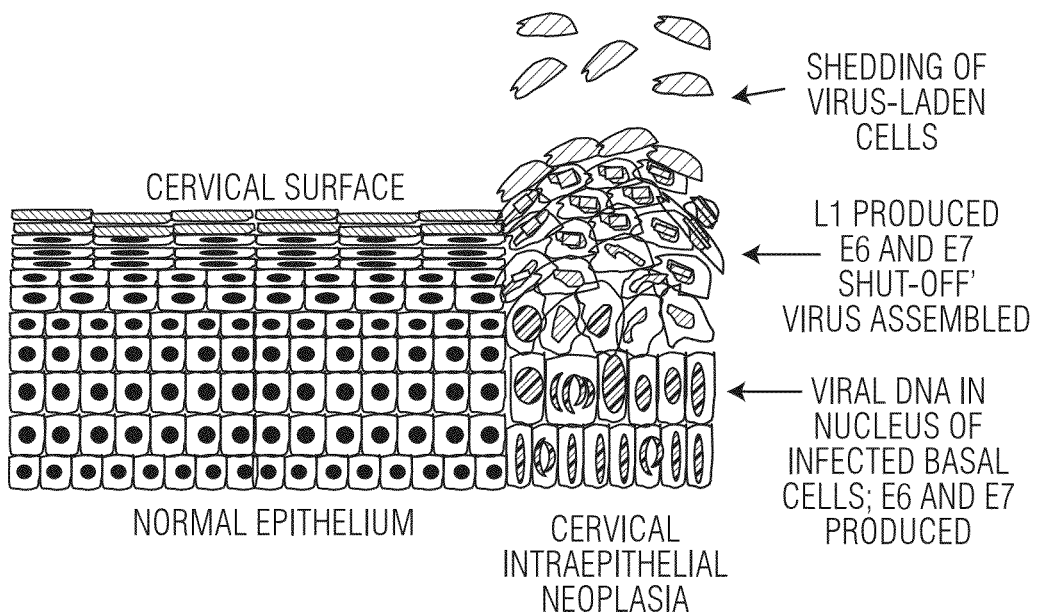
FIG. 21 illustrates the HPV life cycle in the genital tract epithelium.
Figure 22:
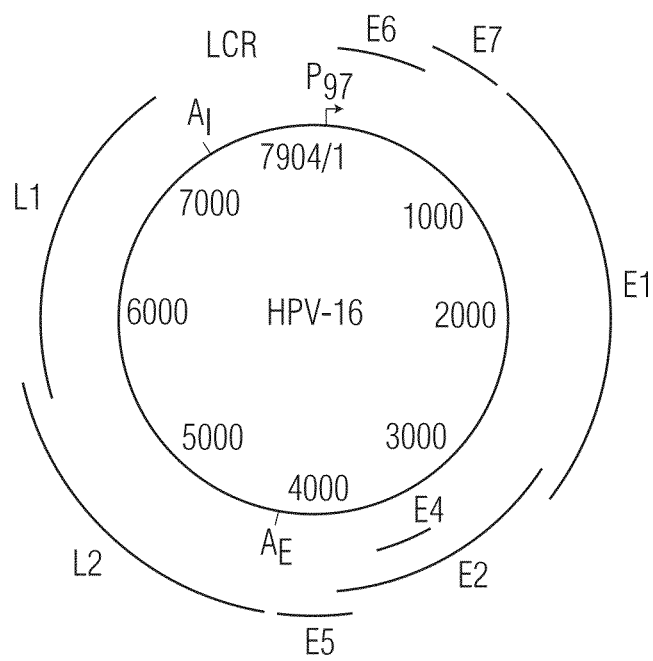
FIG. 22 shows a map of HPV-16 genome organization.
Figure 23:
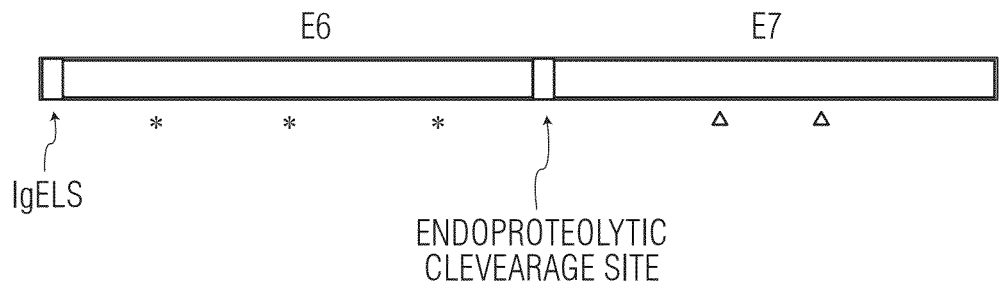
FIG. 23 illustrates immunogen design: * refers to deletions or mutations important for p53 binding and degradation; Δ refers to mutations in Rb binding site.
Figure 24:
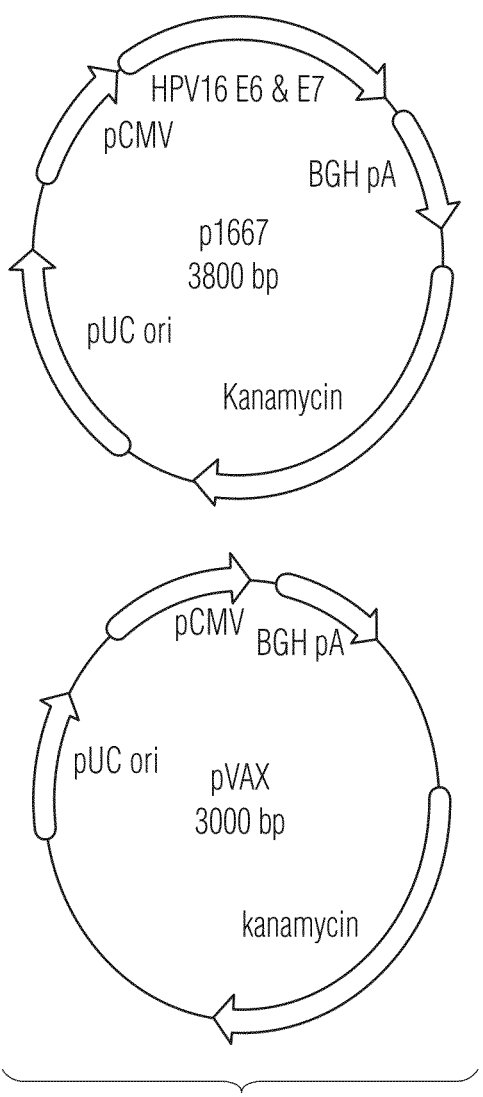
FIG. 24 includes an illustration of the genetic construct p1667 which includes coding sequences for HPV E6 and E7 proteins, and pVAX, the backbone plasmid which lacks the HPV insert and is used a negative control.
Figure 25A:
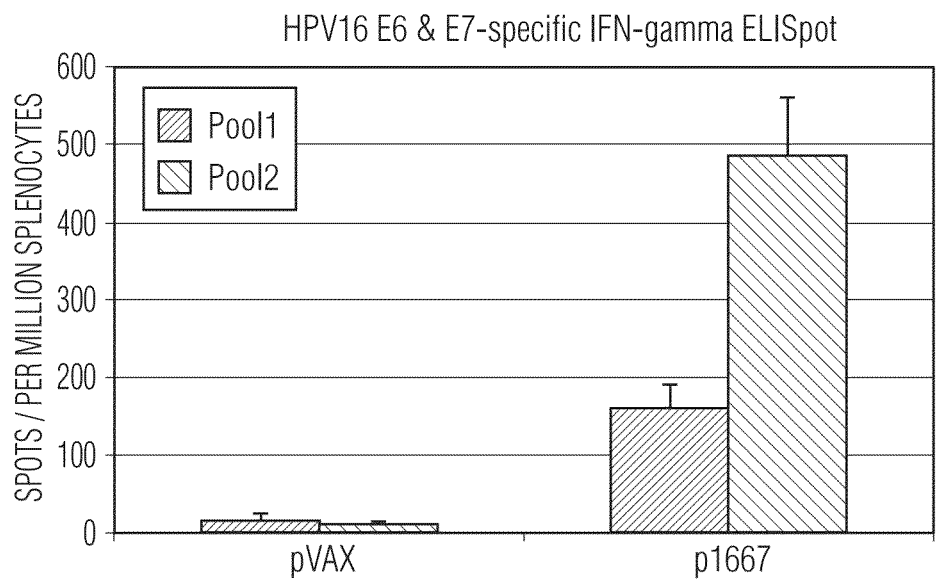
FIG. 25 (FIG. 25A through FIG. 25D) show cellular immune responses induced by the DNA immunogen p1667.
Figure 25B:
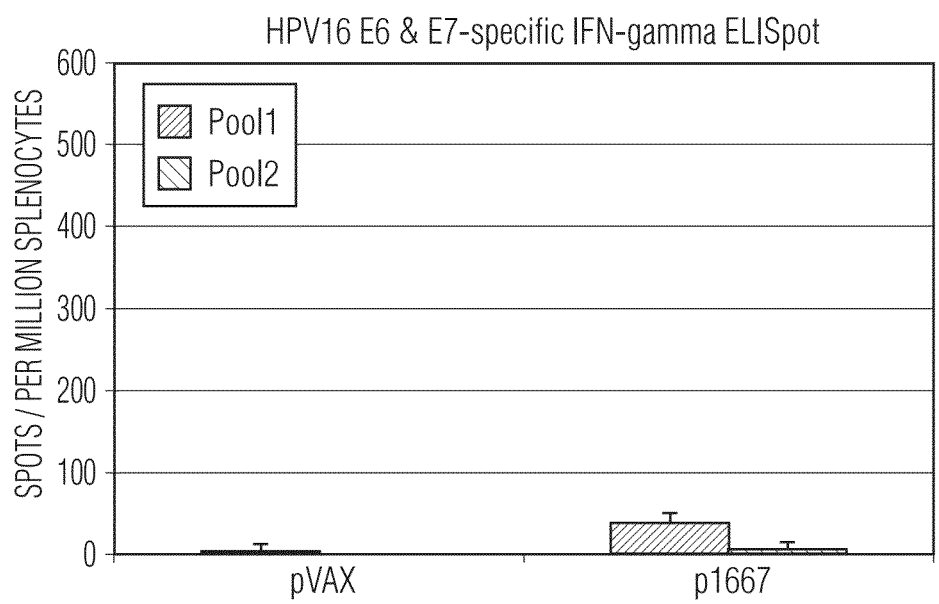
Figure 25C:
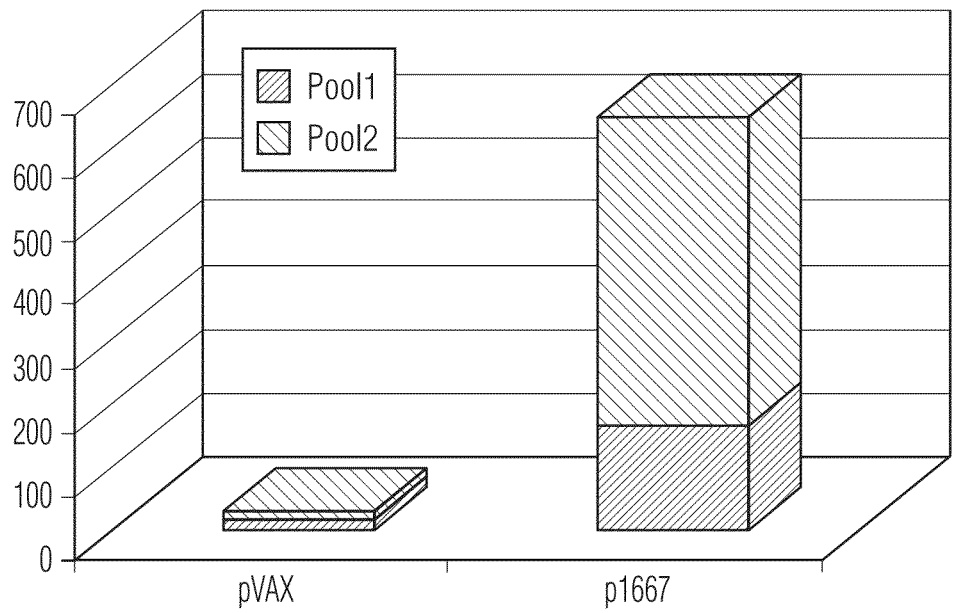
Figure 25D:
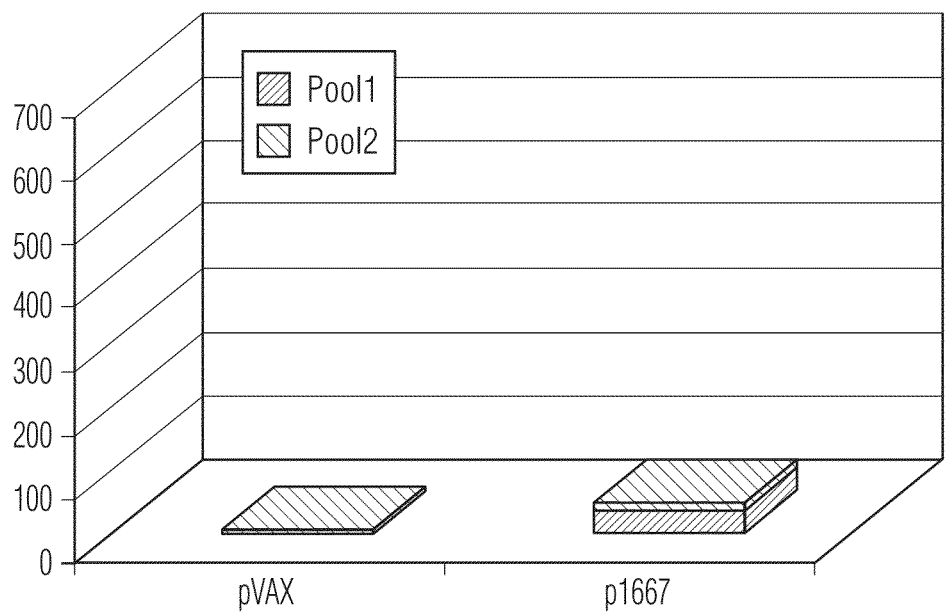

Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP*4.0b10 software (D. L. Swofford, Sinauer Associates, Massachusetts). "Percentage of similarity" is calculated using PAUP*4.0b10 software (D. L, Swofford, Sinauer Associates, Massachusetts). The average similarity of the consensus sequence is calculated compared to all sequences in the phylogenic tree (see FIGS. 2 and 14).

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about I, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

Overview

The present invention provides improved vaccines by utilizing a multi-phase strategy to enhance cellular immune responses induced by immunogens. Modified consensus sequences for immunogens were generated. Genetic modifications including codon optimization, RNA optimization, and the addition of a high efficient immunoglobin leader sequence to increase the immunogenicity of constructs are also disclosed. The novel immunogens have been designed to elicit stronger and broader cellular immune responses than a corresponding codon optimized immunogens.

The invention provides improved HIV, HPV, HCV, Influenza and cancer vaccines by providing proteins and genetic constructs that encode proteins with epitopes that make them particularly effective as immunogens against which anti-HIV, anti-HPV, anti-HCV, anti-influenze and anti-hTert immune responses, respectively, can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments of the invention, a vaccine according to the invention is delivered to an individual to modulate the activity of the individual's immune system and thereby enhance the immune response against HIV, HPV, HCV, Influenza or hTERT. When a nucleic acid molecules that encodes the protein is taken up by cells of the individual the nucleotide sequence is expressed in the cells and the protein are thereby delivered to the individual. Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual against HIV, HIV, HPV, HCV, Influenza and cancer.

The present invention relates to compositions for delivering nucleic acid molecules that comprise a nucleotide sequence that encodes a protein of the invention operably linked to regulatory elements. Aspects of the present invention relate to compositions a recombinant vaccine comprising a nucleotide sequence that encodes that encodes a protein of the invention; a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

HIV

The present invention provides improved anti-HIV vaccines by utilizing a multi-phase strategy to enhance cellular immune responses induced by HIV immunogens. Modified consensus sequences for immunogens were generated Genetic modifications including codon optimization, RNA optimization, and the addition of a high efficient immunoglobin leader sequence to increase the immunogenicity of constructs are also disclosed. The novel immunogens have been designed to elicit stronger and broader cellular immune responses than a corresponding codon optimized immunogens.

SEQ ID NO:1 is a subtype A consensus envelope DNA sequence construct. SEQ ID NO:1 comprises coding sequence for HIV vaccine sequence that comprises an IgE leader sequence linked to a consensus sequence for Subtype A envelope protein. SEQ ID NO:2 comprises the amino acid sequence for HIV vaccine sequence construct that comprises an IgE leader sequence linked to a consensus sequence for Subtype A envelope protein. The IgE leader sequence is SEQ ID NO:15. SEQ ID NO:16 is the Subtype A consensus Envelope protein sequence.

In some embodiments, vaccines of the invention preferably include SEQ ID NO:16, fragment thereof, a nucleic acid molecule that encodes SEQ ID NO:16, or fragments thereof. In some embodiments, vaccines of the invention preferably include SEQ ID NO:2 or a nucleic acid molecule that encodes it. In some embodiments, vaccines of the invention preferably include SEQ ID NO: 11. Vaccines of the present invention preferably include the IgE leader sequence SEQ ID NO:15 or nucleic acid sequence which encodes the same.

Fragments of SEQ ID NO:1 may comprise 90 or more nucleotides. In some embodiments, fragments of SEQ ID NO:1 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, 1890 or more nucleotides; in some embodiments, 1980 or more nucleotides; and in some embodiments, 2070 or more nucleotides. In some embodiments, fragments of SEQ ID NO:1 may comprise coding sequences for the IgE leader sequences. In some embodiments, fragments of SEQ ID NO:1 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, in some embodiments fewer than 990 nucleotides, in some embodiments fewer than 1080 nucleotides, in some embodiments fewer than 1170 nucleotides, in some embodiments fewer than 1260 nucleotides, in some embodiments fewer than 1350 nucleotides, in some embodiments fewer than 1440 nucleotides, in some embodiments fewer than 1530 nucleotides, in some embodiments fewer than 1620 nucleotides, in some embodiments fewer than 1710 nucleotides, in some embodiments fewer than 1800 nucleotides, in some embodiments fewer than 1890 nucleotides, in some embodiments fewer than 1980 nucleotides, in some embodiments fewer than 1020 nucleotides, and in some embodiments fewer than 2070 nucleotides.

Fragments of SEQ ID NO:2 may comprise 30 or more amino acids. In some embodiments, fragments of SEQ ID NO:2 may comprise 60 or more amino acids; in some embodiments, 90 or more amino acids; in same embodiments, 120 or more amino acids; in some embodiments; 150 or more amino acids, in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; in some embodiments, 600 or more amino acids; in some embodiments, 630 or more amino acids; in some embodiments, 660 or more amino acid; and in some embodiments, 690 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in some embodiments fewer than 450 amino acids, in some embodiments fewer than 480 amino acids, in some embodiments fewer than 540 amino acids, in some embodiments fewer than 600 amino acids, in some embodiments fewer than 660 amino acids, and in some embodiments fewer than 690 amino acids.

SEQ ID NO:3 is a subtype B consensus envelope DNA sequence construct. SEQ ID NO:3 comprises coding sequence for HIV vaccine sequence that comprises an IgE leader sequence linked to a consensus sequence for Subtype B envelope protein. SEQ ID NO:4 comprises the amino acid sequence for HIV vaccine sequence construct that comprises an IgE leader sequence linked to a consensus sequence for Subtype B envelope protein. The IgE leader sequence is SEQ ID NO:15. SEQ ID NO:17 is the Subtype B consensus Envelope protein sequence.

In some embodiments, vaccines of the invention preferably include SEQ ID NO:17, fragment thereof, a nucleic acid molecule that encodes SEQ ID NO:17, or fragments thereof. In some embodiments, vaccines of the invention preferably include SEQ ID NO:4 or a nucleic acid molecule that encodes it. In some embodiments, vaccines of the invention preferably include SEQ ID NO:3. Vaccines of the present invention preferably include the IgE leader sequence SEQ ID NO:15 or nucleic acid sequence which encodes the same.

Fragments of SEQ ID NO:3 may comprise 90 or more nucleotides. In some embodiments, fragments of SEQ ID NO:3 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, 1890 or more nucleotides; in some embodiments, 1980 or more nucleotides; in some embodiments, 2070 or more nucleotides; in some embodiments, 2160 or more nucleotides; in some embodiments, 2250 or more nucleotides; in some embodiments, 2340 or more nucleotides; in some embodiments, 2430 or more nucleotides; in some embodiments, 2520 or more nucleotides; in some embodiments, 2620 or more nucleotides; and in some embodiments, 2700 or more nucleotides. In some embodiments, fragments of SEQ ID NO:3 may comprise coding sequences for the IgE leader sequences. In some embodiments, fragments of SEQ ID NO:3 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, in some embodiments fewer than 990 nucleotides, in some embodiments fewer than 1080 nucleotides, in some embodiments fewer than 1170 nucleotides, in some embodiments fewer than 1260 nucleotides, in some embodiments fewer than 1350 nucleotides, in some embodiments fewer than 1440 nucleotides, in some embodiments fewer than 1530 nucleotides, in some embodiments fewer than 1620 nucleotides, in some embodiments fewer than 1710 nucleotides, in some embodiments fewer than 1800 nucleotides, in some embodiments fewer than 1890 nucleotides, in some embodiments fewer than 1980 nucleotides, in some embodiments fewer than 1020 nucleotides, in some embodiments fewer than 2070 nucleotides, in some embodiments fewer than 2160 nucleotides, in some embodiments fewer than 2250 nucleotides, in some embodiments fewer than 2340 nucleotides, in some embodiments fewer than 2430 nucleotides, in some embodiments fewer than 2520 nucleotides, in some embodiments fewer than 2610 nucleotides, and in some embodiments fewer than 2700 nucleotides.

Fragments of SEQ ID NO:4 may comprise 30 or more amino acids. In some embodiments, fragments of SEQ ID NO:4 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments. 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; in some embodiments, 600 or more amino acids; in some embodiments, 630 or more amino acids; in some embodiments, 660 or more amino acid; and in some embodiments, 690 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in some embodiments fewer than 450 amino acids, in some embodiments fewer than 480 amino acids, in some embodiments fewer than 540 amino acids, in some embodiments fewer than 600 amino acids, in some embodiments fewer than 660 amino acids, and in some embodiments fewer than 690 amino acids.

SEQ ID NO:5 is a subtype C consensus envelope DNA sequence construct. SEQ ID NO:5 comprises coding sequence for HIV vaccine sequence that comprises an IgE leader sequence linked to a consensus sequence for Subtype C envelope protein. SEQ ID NO:6 comprises the amino acid sequence for HIV vaccine sequence construct that comprises an IgE leader sequence linked to a consensus sequence for Subtype C envelope protein. The IgE leader sequence is SEQ ID NO:15. SEQ ID NO:18 is the Subtype C consensus Envelope protein sequence.

In some embodiments, vaccines of the invention preferably include SEQ ID NO:18, fragment thereof, a nucleic acid molecule that encodes SEQ ID NO:18, or fragments thereof. In some embodiments, vaccines of the invention preferably include SEQ 10 NO:6 or a nucleic acid molecule that encodes it. In some embodiments, vaccines of the invention preferably include SEQ ID NO:5. Vaccines of the present invention preferably include the IgE leader sequence SEQ ID NO:15 or nucleic acid sequence which encodes the same.

Fragments of SEQ ID NO:5 may comprise 90 or more nucleotides. In some embodiments, fragments of SEQ ID NO:5 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, 1890 or more nucleotides; in some embodiments, 1980 or more nucleotides; and in some embodiments, 2070 or more nucleotides. In some embodiments, fragments of SEQ ID NO:5 may comprise coding sequences for the IgE leader sequences. In some embodiments, fragments of SEQ ID NO:5 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, in some embodiments fewer than 990 nucleotides, in some embodiments fewer than 1080 nucleotides, in some embodiments fewer than 1170 nucleotides, in some embodiments fewer than 1260 nucleotides, in some embodiments fewer than 1350 nucleotides, in some embodiments fewer than 1440 nucleotides, in some embodiments fewer than 1530 nucleotides, in some embodiments fewer than 1620 nucleotides, in some embodiments fewer than 1710 nucleotides, in some embodiments fewer than 1800 nucleotides, in some embodiments fewer than 1890 nucleotides, in some embodiments fewer than 1980 nucleotides, in some embodiments fewer than 1020 nucleotides, and in some embodiments fewer than 2070 nucleotides.

Fragments of SEQ ID NO:6 may comprise 30 or more amino acids. In some embodiments, fragments of SEQ ID NO:6 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; in some embodiments, 600 or more amino acids; in some embodiments, 630 or more amino acids; in some embodiments, 660 or more amino acid; and in some embodiments, 690 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in some embodiments fewer than 450 amino acids, in some embodiments fewer than 480 amino acids, in some embodiments fewer than 540 amino acids, in some embodiments fewer than 600 amino acids, in some embodiments fewer than 660 amino acids, and in some embodiments fewer than 690 amino acids.

SEQ ID NO:7 is a subtype D consensus envelope DNA sequence construct. SEQ NO:7 comprises coding sequence for HIV vaccine sequence that comprises an IgE leader sequence linked to a consensus sequence for Subtype D envelope protein. SEQ ID NO:8 comprises the amino acid sequence for HIV vaccine sequence construct that comprises an IgE leader sequence linked to a consensus sequence for Subtype D envelope protein. The IgE leader sequence is SEQ ID NO:15. SEQ ID NO:19 is the Subtype D consensus Envelope protein sequence.

In some embodiments, vaccines of the invention preferably include SEQ ID NO:19, fragment thereof, a nucleic acid molecule that encodes SEQ ID NO:19, or fragments thereof. In some embodiments, vaccines of the invention preferably include SEQ ID NO:8 or a nucleic acid molecule that encodes it. In some embodiments, vaccines of the invention preferably include SEQ ID NO:7. Vaccines of the present invention preferably include the IgE leader sequence SEQ ID NO:15 or nucleic acid sequence which encodes the same.

Fragments of SEQ ID NO:7 may comprise 90 or more nucleotides. In some embodiments, fragments of SEQ ID NO:7 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, 1890 or more nucleotides; in some embodiments, 1980 or more nucleotides; and in some embodiments, 2070 or more nucleotides; and in some embodiments, 2140 or more nucleotides. In some embodiments, fragments of SEQ ID NO:7 may comprise coding sequences for the IgE leader sequences. In some embodiments, fragments of SEQ ID NO:7 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, in some embodiments fewer than 990 nucleotides, in some embodiments fewer than 1080 nucleotides, in some embodiments fewer than 1170 nucleotides, in some embodiments fewer than 1260 nucleotides, in some embodiments fewer than 1350 nucleotides, in some embodiments fewer than 1440 nucleotides, in some embodiments fewer than 1530 nucleotides, in some embodiments fewer than 1620 nucleotides, in some embodiments fewer than 1710 nucleotides, in some embodiments fewer than 1800 nucleotides, in some embodiments fewer than 1890 nucleotides, in some embodiments fewer than 1980 nucleotides, in some embodiments fewer than 1020 nucleotides, in some embodiments fewer than 2070 nucleotides and in some embodiments fewer than 2140 nucleotides.

Fragments of SEQ ID NO:8 may comprise 30 or more amino acids. In some embodiments, fragments of SEQ ID NO:8 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; in some embodiments, 600 or more amino acids; in some embodiments, 630 or more amino acids; in some embodiments, 660 or more amino acid; and in some embodiments, 690 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in seine embodiments fewer than 450 amino acids, in some embodiments fewer than 480 amino acids, in some embodiments fewer than 540 amino acids, in some embodiments fewer than 600 amino acids, in some embodiments fewer than 660 amino acids, and in some embodiments fewer than 690 amino acids.

SEQ ID NO:9 is a subtype B Nef-Rev consensus envelope DNA sequence construct. SEQ ID NO:9 comprises coding sequence for HIV vaccine sequence that comprises an IgE leader sequence linked to a consensus sequence for Subtype B Nef-Rev protein. SEQ ID NO:10 comprises the amino acid sequence for HIV vaccine sequence construct that comprises an IgE leader sequence linked to a consensus sequence for Subtype B Nef-Rev protein. The IgE leader sequence is SEQ ID NO:15. SEQ ID NO:20 is the Subtype B Nef-Rev consensus protein sequence.

In some embodiments, vaccines of the invention preferably include SEQ ID NO:20 fragment thereof, a nucleic acid molecule that encodes SEQ ID NO:20, or fragments thereof. In some embodiments, vaccines of the invention preferably include SEQ ID NO:10 or a nucleic acid molecule that encodes it. In some embodiments, vaccines of the invention preferably include SEQ ID NO:9. Vaccines of the present invention preferably include the IgE leader sequence SEQ ID NO:15 or nucleic acid sequence which encodes the same.

Fragments of SEQ ID NO:9 may comprise 90 or more nucleotides. In some embodiments, fragments of SEQ ID NO:9 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; and in some embodiments, 990 or more nucleotides; in some embodiments. In some embodiments, fragments of SEQ ID NO:9 may comprise coding sequences for the IgE leader sequences. In some embodiments, fragments of SEQ ID NO:9 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, and in some embodiments fewer than 990 nucleotides.

Fragments of SEQ ID NO:2 may comprise 30 or more amino acids. In some embodiments, fragments of SEQ ID NO:2 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; and in some embodiments, 330 or more amino acids.

SEQ ID NO:11 is a Gag consensus DNA sequence of subtype A, B, C and D DNA sequence construct. SEQ ID NO:11 comprises coding sequence for HIV vaccine sequence that comprises an IgE leader sequence linked to a consensus sequence for Gag consensus subtype A, B, C and D protein. SEQ ID NO:12 comprises the amino acid sequence for HIV vaccine sequence construct that comprises an IgE leader sequence linked to a consensus sequence for Gag subtype A, B, C and D protein. The IgE leader sequence is SEQ ID NO:15. SEQ ID NO:21 is the consensus Gag subtype A, B, C and D protein sequence.

In some embodiments, vaccines of the invention preferably include SEQ ID NO:21, fragment thereof, a nucleic acid molecule that encodes SEQ ID NO:21, or fragments thereof. In some embodiments, vaccines of the invention preferably include SEQ ID NO:12 or a nucleic acid molecule that encodes it. In some embodiments, vaccines of the invention preferably include SEQ ID NO:11. Vaccines of the present invention preferably include the IgE leader sequence SEQ ID NO:15 or nucleic acid sequence which encodes the same.

Fragments of SEQ ID NO:11 may comprise 90 or more nucleotides. In some embodiments, fragments of SEQ ID NO:11 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments. 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; and in some embodiments, 1800 or more nucleotides. In some embodiments, fragments of SEQ ID NO:11 may comprise coding sequences for the IgE leader sequences. In some embodiments, fragments of SEQ ID NO:11 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 720 nucleotides, in some embodiments fewer than 810 nucleotides, in some embodiments fewer than 900 nucleotides, in some embodiments fewer than 990 nucleotides, in some embodiments fewer than 1080 nucleotides, in some embodiments fewer than 1170 nucleotides, in some embodiments fewer than 1260 nucleotides, in some embodiments fewer than 1350 nucleotides, in some embodiments fewer than 1440 nucleotides, in some embodiments fewer than 1530 nucleotides, in some embodiments fewer than 1620 nucleotides, in some embodiments fewer than 1710 nucleotides, and in some embodiments fewer than 1800 nucleotides.

Fragments of SEQ ID NO:12 may comprise 30 or more amino acids. In some embodiments, fragments of SEQ ID NO:12 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; and in some embodiments, 510 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in some embodiments fewer than 450 amino acids, in some embodiments fewer than 480 amino acids, and in some embodiments fewer than 510 amino acids.

HPV

SEQ ID NO:22 comprises coding sequence for HPV vaccine sequence that comprises and IgE leader sequence, a consensus sequence for HPV E6, linked to a consensus sequence for HPV E7 by a proteolytic cleavage sequence. The consensus sequence for HPV E6 includes the immunodominant epitope set forth in SEQ ID NO:24. The consensus sequence for HPV E7 includes the immunodominant epitope set forth in SEQ ID NO:25. The consensus sequence for HPV E6 is SEQ ID NO:26. The consensus sequence for HPV E6 is SEQ ID NO:27. The IgE leader sequence is SEQ ID NO:28. A proteolytic cleavage sequence useful to link the two consensus sequences is SEQ ID NO:29.

In some embodiments, vaccines of the invention preferably include SEQ ID NO:24 and/or SEQ ID NO:25, or nucleic acid sequence which encode one of both of them. Vaccines of the invention preferably include SEQ ID NO:27 and/or the SEQ ID NO:28, or nucleic acid sequences which encode one or both of them. Vaccines of the invention preferably include SEQ ID NO:27 linked to SEQ ID NO:28 by a proteolytic cleavage sequence such as SEQ ID NO:29, or nucleic acid sequence which encodes the fusion protein. Vaccines of the present invention preferably include the IgE leader sequence SEQ ID NO:28 or nucleic acid sequence which encodes the same. Vaccines of the invention preferably include SEQ ID NO:23 or the nucleic acid sequence in SEQ ID NO:22.

In some embodiments, proteins comprises fragments of SEQ ID NO:23. In some embodiments, proteins consist of fragments of SEQ ID NO:23. In some embodiments, nucleic acids comprises fragment of SEQ ID NO:22. In some embodiments, nucleic acids consist of a fragment of SEQ ID NO:22.

Fragments of SEQ ID NO:22 may comprise 30 or more nucleotides, including preferably sequences that encode an immunodominant epitope. In some embodiments, fragments of SEQ ID NO:22 may comprise 45 or more nucleotides, including preferably sequences that encode an immunodominant epitope. In some embodiments, fragments of SEQ ID NO:22 may comprise 60 or more nucleotides, including preferably sequences that encode an immunodominant epitope. In some embodiments, fragments of SEQ ID NO:22 may comprise 75 or more nucleotides, including preferably sequences that encode an immunodominant epitope. In some embodiments, fragments of SEQ ID NO:22 may comprise 90 or more nucleotides, including preferably sequences that encode an immunodominant epitope. In some embodiments, fragments of SEQ ID NO:22 may comprise 120 or more nucleotides, including preferably sequences that encode an immunodominant epitope. In some embodiments, fragments of SEQ ID NO:22 may comprise 150 or more nucleotides, including preferably sequences that encode an immunodominant epitope. In some embodiments, fragments of SEQ ID NO:22 may comprise 180 or more nucleotides, including preferably sequences that encode an immunodominant epitope. In some embodiments, fragments of SEQ ID NO:22 may comprise 210 or more nucleotides, including preferably sequences that encode an immunodominant epitope. In some embodiments, fragments of SEQ ID NO:22 may comprise 240 or more nucleotides, including preferably sequences that encode an immunodominant epitope. In some embodiments, fragments of SEQ ID NO:22 may comprise 270 or more nucleotides, including preferably sequences that encode an immunodominant epitope. In some embodiments, fragments of SEQ ID NO:22 may comprise 300 or more nucleotides, including preferably sequences that encode an immunodominant epitope. In some embodiments, fragments of SEQ ID NO:22 may comprise 360 or more nucleotides, including preferably sequences that encode an immunodominant epitope. In some embodiments, fragments of SEQ ID NO:22 may comprise 420 or more nucleotides, including preferably sequences that encode an immunodominant epitope. In some embodiments, fragments of SEQ ID NO:22 may comprise 480 or more nucleotides, including preferably sequences that encode an immunodominant epitope. In some embodiments, fragments of SEQ ID NO:22 may comprise 540 or more nucleotides, including preferably sequences that encode an immunodominant epitope. In some embodiments, fragments of SEQ ID NO:22 may comprise 600 or more nucleotides, including preferably sequences that encode an immunodominant epitope. In some embodiments, fragments of SEQ ID NO:22 may comprise 300 or more nucleotides, including preferably sequences that encode an immunodominant epitope. In some embodiments, fragments of SEQ ID NO:22 may comprise 660 or more nucleotides, including preferably sequences that encode an immunodominant epitope. In some embodiments, fragments of SEQ ID NO:22 may comprise 720 or more nucleotides, including preferably sequences that encode an immunodominant epitope. In some embodiments, fragments of SEQ ID NO:22 may comprise 780 or more nucleotides, including preferably sequences that encode an immunodominant epitope. In some embodiments, fragments of SEQ ID NO:22 may comprise coding sequences for the IgE leader sequences. In some embodiments, fragments of SEQ ID NO:22 do not comprise coding sequences for the IgE leader sequences. Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, and in some embodiments fewer than 780 nucleotides.

Fragments of SEQ ID NO:23 may comprise 15 or more amino acids, including preferably sequences that encode an immunodominant epitope. In some embodiments, fragments of SEQ ID NO:23 may comprise 18 or more amino acids, including preferably sequences that encode an immunodominant epitope. In some embodiments, fragments of SEQ ID NO:23 may comprise 21 or more amino acids, including preferably sequences that encode an immunodominant epitope. In some embodiments, fragments of SEQ ID NO:23 may comprise 24 or more amino acids, including preferably sequences that encode an immunodominant epitope. In some embodiments, fragments of SEQ ID NO:23 may comprise 30 or more amino acids, including preferably sequences that encode an immunodominant epitope. In some embodiments, fragments of SEQ ID NO:23 may comprise 36 or more amino acids, including preferably sequences that encode an immunodominant epitope. In some embodiments, fragments of SEQ ID NO:23 may comprise 42 or more amino acids, including preferably sequences that encode an immunodominant epitope. In some embodiments, fragments of SEQ ID NO:23 may comprise 48 or more amino acids, including preferably sequences that encode an immunodominant epitope. In some embodiments, fragments of SEQ ID NO:23 may comprise 54 or more amino acids, including preferably sequences that encode an immunodominant epitope. In some embodiments, fragments of SEQ ID NO:23 may comprise 60 or more amino acids, including preferably sequences that encode an immunodominant epitope. In some embodiments, fragments of SEQ ID NO:23 may comprise 18 or more amino acids, including preferably sequences that encode an immunodominant epitope. In some embodiments, fragments of SEQ ID NO:23 may comprise 72 or more amino acids, including preferably sequences that encode an immunodominant epitope. In some embodiments, fragments of SEQ ID NO:23 may comprise 90 or more amino acids, including preferably sequences that encode an immunodominant epitope. In some embodiments, fragments of SEQ ID NO:23 may comprise 120 or more amino acids, including preferably sequences that encode an immunodominant epitope. In some embodiments, fragments of SEQ ID NO:23 may comprise 150 or more amino acids, including preferably sequences that encode an immunodominant epitope. In some embodiments, fragments of SEQ ID NO:23 may comprise 180 or more amino acids, including preferably sequences that encode an immunodominant epitope. In some embodiments, fragments of SEQ ID NO:23 may comprise 210 or more amino acids, including preferably sequences that encode an immunodominant epitope. In some embodiments, fragments of SEQ ID NO:23 may comprise 240 or more amino acids, including preferably sequences that encode an immunodominant epitope. In some embodiments, fragments of SEQ ID NO:23 may comprise 260 or more amino acids, including preferably sequences that encode an immunodominant epitope. In some embodiments, fragments of SEQ ID NO:23 may comprise coding sequences for the IgE leader sequences. In some embodiments, fragments of SEQ ID NO:23 do not comprise coding sequences for the IgE leader sequences. Fragments may comprise fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, and in some embodiments fewer than 260 amino acids.

HCV

SEQ ID NO:30 comprises coding sequence for HCV vaccine sequence that comprises and IgE leader sequence, a consensus sequence for HCV E1, linked to a consensus sequence for HCV E2 by a proteolytic cleavage sequence. The consensus sequence for HCV E1 is SEQ ID NO:32. The consensus sequence for HCV E2 is SEQ ID NO:33.

In some embodiments, vaccines of the invention preferably include SEQ ID NO:32 and/or SEQ ID NO:33, or nucleic acid sequence which encode one of both of them. Vaccines of the invention preferably include SEQ ID NO:32 linked to SEQ ID NO:33 by a proteolytic cleavage sequence such as SEQ ID NO:29, or nucleic acid sequence which encodes the fusion protein. Vaccines of the present invention preferably include the IgE leader sequence SEQ ID NO:28 or nucleic acid sequence which encodes the same. Vaccines of the invention preferably include SEQ ID NO:31 or the nucleic acid sequence in SEQ ID NO:30.

In some embodiments of the invention, the vaccines of the invention include the SEQ ID NO:30 and a nucleic acid sequence or amino acid sequence encoded by the nucleic acid sequences thereof selected from the following group: SEQ ID NO:34, SEQ ID NO:35, and any combination thereof.

Fragments of SEQ ID NO:30 may comprise 30 or more nucleotides. In some embodiments, fragments of SEQ ID NO:30 may comprise 45 or more nucleotides. In some embodiments, fragments of SEQ ID NO:30 may comprise 60 or more nucleotides. In some embodiments, fragments of SEQ ID NO:30 may comprise 75 or more nucleotides. In some embodiments, fragments of SEQ ID NO:30 may comprise 90 or more nucleotides. In some embodiments, fragments of SEQ ID NO:30 may comprise 120 or more nucleotides. In some embodiments, fragments of SEQ ID NO:30 may comprise 150 or more nucleotides. In some embodiments, fragments of SEQ ID NO:30 may comprise 180 or more nucleotides. In some embodiments, fragments of SEQ ID NO:30 may comprise 210 or more nucleotides. In some embodiments, fragments of SEQ ID NO:30 may comprise 240 or more nucleotides. In some embodiments, fragments of SEQ ID NO:30 may comprise 270 or more nucleotides. In some embodiments, fragments of SEQ ID NO:30 may comprise 300 or more nucleotides. In some embodiments, fragments of SEQ ID NO:30 may comprise 360 or more nucleotides. In some embodiments, fragments of SEQ ID NO:30 may comprise 420 or more nucleotides. In some embodiments, fragments of SEQ ID NO:30 may comprise 480 or more nucleotides. In some embodiments, fragments of SEQ ID NO:30 may comprise 540 or more nucleotides. In some embodiments, fragments of SEQ ID NO:30 may comprise 600 or more nucleotides. In some embodiments, fragments of SEQ ID NO:30 may comprise 660 or more nucleotides. In some embodiments, fragments of SEQ ID NO:30 may comprise 720 or more nucleotides. In some embodiments, fragments of SEQ ID NO:30 may comprise 780 or more nucleotides. In some embodiments, fragments of SEQ ID NO:30 may comprise 840 or more nucleotides. In some embodiments, fragments of SEQ ID NO:30 may comprise 900 or more nucleotides. In some embodiments, fragments of SEQ ID NO:30 may comprise 960 or more nucleotides. In some embodiments, fragments of SEQ ID NO:30 may comprise 1020 or more nucleotides. In some embodiments, fragments of SEQ ID NO:30 may comprise 1080 or more nucleotides. In some embodiments, fragments of SEQ ID NO:30 may comprise 1140 or more nucleotides. In some embodiments, fragments of SEQ ID NO:30 may comprise 1200 or more nucleotides. In some embodiments, fragments of SEQ ID NO:30 may comprise 1260 or more nucleotides. In some embodiments, fragments of SEQ ID NO:30 may comprise 1320 or more nucleotides. In some embodiments, fragments of SEQ ID NO:30 may comprise 1380 or more nucleotides. In some embodiments, fragments of SEQ CD NO:30 may comprise 1440 or more nucleotides. In some embodiments, fragments of SEQ ED NO:30 may comprise 1500 or more nucleotides. In some embodiments, fragments of SEQ ID NO:30 may comprise 1560 or more nucleotides. In some embodiments, fragments of SEQ ID NO:30 may comprise 1620 or more nucleotides. In some embodiments, fragments of SEQ ID NO:30 may comprise 1680 or more nucleotides. In some embodiments, fragments of SEQ ID NO:30 may comprise 1740 or more nucleotides. In some embodiments, fragments of SEQ ID NO:30 may comprise coding sequences for the IgE leader sequences. En some embodiments, fragments of SEQ ID NO:30 do not comprise coding sequences for the IgE leader sequences. Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, and in some embodiments fewer than 1740 nucleotides.

Fragments of SEQ ID NO:31 may comprise 15 or more amino acids. In some embodiments, fragments of SEQ ID NO:31 may comprise 30 or more amino acids. In some embodiments, fragments of SEQ ID NO:31 may comprise 45 or more amino acids. In some embodiments, fragments of SEQ ID NO:31 may comprise 60 or more amino acids. In some embodiments, fragments of SEQ ID NO:31 may comprise 75 or more amino acids. In some embodiments, fragments of SEQ ID NO:31 may comprise 90 or more amino acids. In some embodiments, fragments of SEQ ID NO:31 may comprise 105 or more amino acids. In some embodiments, fragments of SEQ ID NO:31 may comprise 120 or more amino acids. In some embodiments, fragments of SEQ ID NO:31 may comprise 150 or more amino acids. In some embodiments, fragments of SEQ ID NO:31 may comprise 180 or more amino acids. In some embodiments, fragments of SEQ ID NO:31 may comprise 210 or more amino acids. In some embodiments, fragments of SEQ ID NO:31 may comprise 240 or more amino acids. In some embodiments, fragments of SEQ ID NO:31 may comprise 270 or more amino acids. In some embodiments, fragments of SEQ ID NO:31 may comprise 300 or more amino acids. In some embodiments, fragments of SEQ ID NO:31 may comprise 360 or more amino acids. In some embodiments, fragments of SEQ ID NO:31 may comprise 420 or more amino acids. In some embodiments, fragments of SEQ ID NO:31 may comprise 480 or more amino acids. In some embodiments, fragments of SEQ ID NO:31 may comprise 540 or more amino acids. In some embodiments, fragments of SEQ ID NO:31 may comprise 575 or more amino acids. Fragments may comprise fewer than 30 amino acids, in some embodiments fewer than 45 amino acids, in some embodiments fewer than 60 amino acids, in some embodiments fewer than 75 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 360 amino acids, in some embodiments fewer than 420 amino acids, in some embodiments fewer than 480 amino acids, in some embodiments fewer than 540 amino acids, and in some embodiments fewer than 575 amino acids.

hTERT hTERT is a human telomerase reverse transcriptase that synthesizes a TTAGGG tag on the end of telomeres to prevent cell death due to chromosomal shortening. Hyperproliferative cells with abnormally high expression of hTERT may be targeted by immunotherapy. Recent studies also support the abnormal expression of hTERT on hyperproliferative cells infected with HCV and HPV. Thus, immunotherapy for both HPV and HCV may be enhanced by targeting cells that express hTERT at abnormal levels.

Recent studies demonstrate that hTERT expression in dendritic cells transfected with hTERT genes can induce CD8+ cytotoxic T cells and elicit a CD4+ T cells in an antigen-specific fashion. Therefore, use of hTERT expression within antigen presenting cells (APCs) to delay senescence and sustain their capacity to present the antigen of choice is attractive in developing new methods of immunotherapy.

According to some embodiments of the invention, methods of inducing an immune response in individuals against an immunogen comprise administering to the individual the hTERT protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine.

In some embodiments of the invention, the vaccines of the invention include the SEQ ID NO:30 and a nucleic acid sequence or amino acid sequence encoded by the nucleic acid sequences thereof selected from the following group: SEQ ID NO:34, SEQ ID NO:35, and any combination thereof. In some embodiments of the invention, the vaccines of the invention comprise SEQ ID NO:34 or SEQ ID NO:35. SEQ ID NO:34 comprises the nucleic acid sequence that encodes hTERT. SEQ ID NO:35 comprises the amino acid sequence for hTERT.

In some embodiments of the invention, the vaccines of the invention comprise SEQ ID NO:22 and SEQ ID NO:34 or SEQ ID NO: 35. Using nucleic acid sequences that encode hTERT and/or protein of hTERT in combination with the HPV immunogens enhance the cell-mediated immune response against HPV-infected cells.

Fragments of SEQ ID NO:34 may comprise 30 or more nucleotides, including preferably sequences that encode an immunodominant epitope. In some embodiments, fragments of SEQ ID NO:34 may comprise 45 or more nucleotides, including preferably sequences that encode an immunodominant epitope. In some embodiments, fragments of SEQ ID NO:34 may comprise 60 or more nucleotides, including preferably sequences that encode an immunodominant epitope. In some embodiments, fragments of SEQ ID NO:1 may comprise 75 or more nucleotides, including preferably sequences that encode an immunodominant epitope. In some embodiments, fragments of SEQ ID NO:34 may comprise 90 or more nucleotides, including preferably sequences that encode an immunodominant epitope. In some embodiments, fragments of SEQ ID NO:34 may comprise 120 or more nucleotides, including preferably sequences that encode an immunodominant epitope. In some embodiments, fragments of SEQ ID NO:34 may comprise 150 or more nucleotides, including preferably sequences that encode an immunodominant epitope. In some embodiments, fragments of SEQ ID NO:34 may comprise 180 or more nucleotides, including preferably sequences that encode an immunodominant epitope. In some embodiments, fragments of SEQ ID NO:34 may comprise 210 or more nucleotides, including preferably sequences that encode an immunodominant epitope. In some embodiments, fragments of SEQ ID NO:34 may comprise 240 or more nucleotides, including preferably sequences that encode an immunodominant epitope. In some embodiments, fragments of SEQ ID NO:34 may comprise 270 or more nucleotides, including preferably sequences that encode an immunodominant epitope. In some embodiments, fragments of SEQ ID NO:34 may comprise 300 or more nucleotides, including preferably sequences that encode an immunodominant epitope. In some embodiments, fragments of SEQ ID NO:34 may comprise 360 or more nucleotides, including preferably sequences that encode an immunodominant epitope. In some embodiments, fragments of SEQ ID NO:34 may comprise 420 or more nucleotides, including preferably sequences that encode an immunodominant epitope. In some embodiments, fragments of SEQ ID NO:34 may comprise 480 or more nucleotides, including preferably sequences that encode an immunodominant epitope. In some embodiments, fragments of SEQ ID NO:34 may comprise 540 or more nucleotides, including preferably sequences that encode an immunodominant epitope. In some embodiments, fragments of SEQ ID NO:34 may comprise 600 or more nucleotides, including preferably sequences that encode an immunodominant epitope. In some embodiments, fragments of SEQ ID NO:34 may comprise 300 or more nucleotides, including preferably sequences that encode an immunodominant epitope. In some embodiments, fragments of SEQ ID NO:34 may comprise 660 or more nucleotides, including preferably sequences that encode an immunodominant epitope. In some embodiments, fragments of SEQ ID NO:34 may comprise 720 or more nucleotides, including preferably sequences that encode an immunodominant epitope. In some embodiments, fragments of SEQ ID NO:34 may comprise 780 or more nucleotides, including preferably sequences that encode an immunodominant epitope. In some embodiments, fragments of SEQ ID NO:34 may comprise 840 or more nucleotides, including preferably sequences that encode an immunodominant epitope. In some embodiments, fragments of SEQ ID NO:34 may comprise 900 or more nucleotides, including preferably sequences that encode an immunodominant epitope. In some embodiments, fragments of SEQ ID NO:34 may comprise 960 or more nucleotides, including preferably sequences that encode an immunodominant epitope. In some embodiments, fragments of SEQ ID NO:34 may comprise 1020 or more nucleotides, including preferably sequences that encode an immunodominant epitope. In some embodiments, fragments of SEQ ID NO:34 may comprise 1080 or more nucleotides, including preferably sequences that encode an immunodominant epitope. In some embodiments, fragments of SEQ ID NO:34 may comprise 1140 or more nucleotides, including preferably sequences that encode an immunodominant epitope. In some embodiments, fragments of SEQ ID NO:34 may comprise 1200 or more nucleotides, including preferably sequences that encode an immunodominant epitope. In some embodiments, fragments of SEQ ID NO:34 may comprise 1260 or more nucleotides, including preferably sequences that encode an immunodominant epitope. In some embodiments, fragments of SEQ ID NO:34 may comprise 1320 or more nucleotides, including preferably sequences that encode an immunodominant epitope. In some embodiments, fragments of SEQ ID NO:34 may comprise 1380 or more nucleotides, including preferably sequences that encode an immunodominant epitope. In some embodiments, fragments of SEQ ID NO:34 may comprise 1440 or more nucleotides, including preferably sequences that encode an immunodominant epitope. In some embodiments, fragments of SEQ ID NO:34 may comprise 1500 or more nucleotides, including preferably sequences that encode an immunodominant epitope. In some embodiments, fragments of SEQ ID NO:34 may comprise 1560 or more nucleotides, including preferably sequences that encode an immunodominant epitope. In some embodiments, fragments of SEQ ID NO:34 may comprise 1620 or more nucleotides, including preferably sequences that encode an immunodominant epitope. In some embodiments, fragments of SEQ ID NO:34 may comprise 1680 or more nucleotides, including preferably sequences that encode an immunodominant epitope. In some embodiments, fragments of SEQ ID NO:34 may comprise 1740 or more nucleotides, including preferably sequences that encode an immunodominant epitope. In some embodiments, fragments of SEQ ID NO:34 may comprise 1800 or more nucleotides, including preferably sequences that encode an immunodominant epitope. In some embodiments, fragments of SEQ ID NO:34 may comprise 1860 or more nucleotides, including preferably sequences that encode an immunodominant epitope. In some embodiments, fragments of SEQ ID NO:34 may comprise 1920 or more nucleotides, including preferably sequences that encode an immunodominant epitope. In some embodiments, fragments of SEQ ID NO:34 may comprise 1980 or more nucleotides, including preferably sequences that encode an immunodominant epitope. In some embodiments, fragments of SEQ ID NO:34 may comprise 2040 or more nucleotides, including preferably sequences that encode an immunodominant epitope. In some embodiments, fragments of SEQ ID NO:34 may comprise 2100 or more nucleotides, including preferably sequences that encode an immunodominant epitope. In some embodiments, fragments of SEQ ID NO:34 may comprise 2160 or more nucleotides, including preferably sequences that encode an immunodominant epitope. In some embodiments, fragments of SEQ ID NO:34 may comprise 2220 or more nucleotides, including preferably sequences that encode an immunodominant epitope. In some embodiments, fragments of SEQ ID NO:34 may comprise 2280 or more nucleotides, including preferably sequences that encode an immunodominant epitope. In some embodiments, fragments of SEQ ID NO:34 may comprise 2340 or more nucleotides, including preferably sequences that encode an immunodominant epitope. In some embodiments, fragments of SEQ ID NO:34 may comprise 2400 or more nucleotides, including preferably sequences that encode an immunodominant epitope. In some embodiments, fragments of SEQ ID NO:34 may comprise 2460 or more nucleotides, including preferably sequences that encode an immunodominant epitope. In some embodiments, fragments of SEQ ID NO:34 may comprise 2520 or more nucleotides, including preferably sequences that encode an immunodominant epitope. In some embodiments, fragments of SEQ ID NO:34 may comprise 2580 or more nucleotides, including preferably sequences that encode an immunodominant epitope. In some embodiments, fragments of SEQ ID NO:34 may comprise 2640 or more nucleotides, including preferably sequences that encode an immunodominant epitope. In some embodiments, fragments of SEQ ID NO:34 may comprise 2700 or more nucleotides, including preferably sequences that encode an immunodominant epitope. In some embodiments, fragments of SEQ ID NO:34 may comprise 2760 or more nucleotides, including preferably sequences that encode an immunodominant epitope. In some embodiments, fragments of SEQ ID NO:34 may comprise 2820 or more nucleotides, including preferably sequences that encode an immunodominant epitope. In some embodiments, fragments of SEQ ID NO:34 may comprise 2880 or more nucleotides, including preferably sequences that encode an immunodominant epitope. In some embodiments, fragments of SEQ ID NO:34 may comprise 2940 or more nucleotides, including preferably sequences that encode an immunodominant epitope. In some embodiments, fragments of SEQ ID NO:34 may comprise 3000 or more nucleotides, including preferably sequences that encode an immunodominant epitope. In some embodiments, fragments of SEQ ID NO:34 may comprise 3060 or more nucleotides, including preferably sequences that encode an immunodominant epitope. In some embodiments, fragments of SEQ ID NO:34 may comprise 3120 or more nucleotides, including preferably sequences that encode an immunodominant epitope. In some embodiments, fragments of SEQ ID NO:34 may comprise 3180 or more nucleotides, including preferably sequences that encode an immunodominant epitope. In some embodiments, fragments of SEQ ID NO:34 may comprise 3240 or more nucleotides, including preferably sequences that encode an immunodominant epitope. In some embodiments, fragments of SEQ ID NO:34 may comprise 3300 or more nucleotides, including preferably sequences that encode an immunodominant epitope. In some embodiments, fragments of SEQ ID NO:34 may comprise 3360 or more nucleotides, including preferably sequences that encode an immunodominant epitope. In some embodiments, fragments of SEQ ID NO:34 may comprise 3420 or more nucleotides, including preferably sequences that encode an immunodominant epitope. In some embodiments, fragments of SEQ ID NO:34 may comprise 3480 or more nucleotides, including preferably sequences that encode an immunodominant epitope. In some embodiments, fragments of SEQ ID NO:34 may comprise coding sequences for the IgE leader sequences. In some embodiments, fragments of SEQ ID NO:34 do not comprise coding sequences for the IgE leader sequences. Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, in some embodiments fewer than 1740 nucleotides, in some embodiments fewer than 1800 nucleotides, in some embodiments fewer than 1860 nucleotides, in some embodiments fewer than 1920 nucleotides, in some embodiments fewer than 1980 nucleotides, in some embodiments fewer than 2040 nucleotides, in some embodiments fewer than 2100 nucleotides, in some embodiments fewer than 2160 nucleotides, in some embodiments fewer than 2220 nucleotides, in some embodiments fewer than 2280 nucleotides, in some embodiments fewer than 2340 nucleotides, in some embodiments fewer than 2400 nucleotides, in some embodiments fewer than 2460 nucleotides, in some embodiments fewer than 2520 nucleotides, in some embodiments fewer than 2580 nucleotides, in some embodiments fewer than 2640 nucleotides, in some embodiments fewer than 2700 nucleotides, in some embodiments fewer than 2760 nucleotides, in some embodiments fewer than 2820 nucleotides, in some embodiments fewer than 2860 nucleotides, in some embodiments fewer than 2940 nucleotides, in some embodiments fewer than 3000 nucleotides, in some embodiments fewer than 3060 nucleotides, in some embodiments fewer than 3120 nucleotides, in some embodiments fewer than 3180 nucleotides, in some embodiments fewer than 3240 nucleotides, in some embodiments fewer than 3300 nucleotides, in some embodiments fewer than 3360 nucleotides, in some embodiments fewer than 3420 nucleotides, in some embodiments fewer than 3480 nucleotides, and in some embodiments fewer than 3510 nucleotides.

Fragments of SEQ ID NO:35 may comprise 15 or more amino acids, including preferably sequences that encode an immunodominant epitope. In some embodiments, fragments of SEQ ID NO:35 may comprise 18 or more amino acids, including preferably sequences that encode an immunodominant epitope. In some embodiments, fragments of SEQ ID NO:35 may comprise 21 or more amino acids, including preferably sequences that encode an immunodominant epitope. In some embodiments, fragments of SEQ ID NO:35 may comprise 24 or more amino acids, including preferably sequences that encode an immunodominant epitope. In some embodiments, fragments of SEQ ID NO:35 may comprise 30 or more amino acids, including preferably sequences that encode an immunodominant epitope. In some embodiments, fragments of SEQ ID NO:35 may comprise 36 or more amino acids, including preferably sequences that encode an immunodominant epitope. In some embodiments, fragments of SEQ ID NO:35 may comprise 42 or more amino acids, including preferably sequences that encode an immunodominant epitope. In some embodiments, fragments of SEQ ID NO:35 may comprise 48 or more amino acids, including preferably sequences that encode an immunodominant epitope. In some embodiments, fragments of SEQ ID NO:35 may comprise 54 or more amino acids, including preferably sequences that encode an immunodominant epitope. In some embodiments, fragments of SEQ ID NO:35 may comprise 60 or more amino acids, including preferably sequences that encode an immunodominant epitope. In some embodiments, fragments of SEQ ID NO:35 may comprise 66 or more amino acids, including preferably sequences that encode an immunodominant epitope. In some embodiments, fragments of SEQ ID NO:35 may comprise 72 or more amino acids, including preferably sequences that encode an immunodominant epitope. In some embodiments, fragments of SEQ ID NO:35 may comprise 90 or more amino acids, including preferably sequences that encode an immunodominant epitope. In some embodiments, fragments of SEQ ID NO:35 may comprise 120 or more amino acids, including preferably sequences that encode an immunodominant epitope. In some embodiments, fragments of SEQ ID NO:35 may comprise 150 or more amino acids, including preferably sequences that encode an immunodominant epitope. In some embodiments, fragments of SEQ ID NO:35 may comprise 180 or more amino acids, including preferably sequences that encode an immunodominant epitope. In some embodiments, fragments of SEQ ID NO:35 may comprise 210 or more amino acids, including preferably sequences that encode an immunodominant epitope. In some embodiments, fragments of SEQ ID NO:35 may comprise 240 or more amino acids, including preferably sequences that encode an immunodominant epitope. In some embodiments, fragments of SEQ ID NO:35 may comprise 270 or more amino acids, including preferably sequences that encode an immunodominant epitope. In some embodiments, fragments of SEQ ID NO:35 may comprise 300 or more amino acids, including preferably sequences that encode an immunodominant epitope. In some embodiments, fragments of SEQ ID NO:35 may comprise 330 or more amino acids, including preferably sequences that encode an immunodominant epitope. In some embodiments, fragments of SEQ ID NO:35 may comprise 360 or more amino acids, including preferably sequences that encode an immunodominant epitope. In some embodiments, fragments of SEQ ID NO:35 may comprise 390 or more amino acids, including preferably sequences that encode an immunodominant epitope. In some embodiments, fragments of SEQ ID NO:35 may comprise 420 or more amino acids, including preferably sequences that encode an immunodominant epitope. In some embodiments, fragments of SEQ ID NO:35 may comprise 450 or more amino acids, including preferably sequences that encode an immunodominant epitope. In some embodiments, fragments of SEQ ID NO:35 may comprise 480 or more amino acids, including preferably sequences that encode an immunodominant epitope. In some embodiments, fragments of SEQ ID NO:35 may comprise 510 or more amino acids, including preferably sequences that encode an immunodominant epitope. In some embodiments, fragments of SEQ ID NO:35 may comprise 540 or more amino acids, including preferably sequences that encode an immunodominant epitope. In some embodiments, fragments of SEQ ID NO:35 may comprise 570 or more amino acids, including preferably sequences that encode an immunodominant epitope. In some embodiments, fragments of SEQ ID NO:35 may comprise 600 or more amino acids, including preferably sequences that encode an immunodominant epitope. In some embodiments, fragments of SEQ ID NO:35 may comprise 630 or more amino acids, including preferably sequences that encode an immunodominant epitope. In some embodiments, fragments of SEQ ID NO:35 may comprise 660 or more amino acids, including preferably sequences that encode an immunodominant epitope. In some embodiments, fragments of SEQ ID NO:35 may comprise 690 or more amino acids, including preferably sequences that encode an immunodominant epitope. In some embodiments, fragments of SEQ ID NO:35 may comprise 720 or more amino acids, including preferably sequences that encode an immunodominant epitope. In some embodiments, fragments of SEQ ID NO:35 may comprise 750 or more amino acids, including preferably sequences that encode an immunodominant epitope. In some embodiments, fragments of SEQ ID NO:35 may comprise 780 or more amino acids, including preferably sequences that encode an immunodominant epitope. In some embodiments, fragments of SEQ ID NO:35 may comprise 810 or more amino acids, including preferably sequences that encode an immunodominant epitope. In some embodiments, fragments of SEQ ID NO:35 may comprise 840 or more amino acids, including preferably sequences that encode an immunodominant epitope. In some embodiments, fragments of SEQ ID NO:35 may comprise 870 or more amino acids, including preferably sequences that encode an immunodominant epitope. In some embodiments, fragments of SEQ ID NO:35 may comprise 900 or more amino acids, including preferably sequences that encode an immunodominant epitope. In some embodiments, fragments of SEQ ID NO:35 may comprise 930 or more amino acids, including preferably sequences that encode an immunodominant epitope. In some embodiments, fragments of SEQ ID NO:35 may comprise 960 or more amino acids, including preferably sequences that encode an immunodominant epitope. In some embodiments, fragments of SEQ ID NO:35 may comprise 990 or more amino acids, including preferably sequences that encode an immunodominant epitope. In some embodiments, fragments of SEQ ID NO:35 may comprise 1020 or more amino acids, including preferably sequences that encode an immunodominant epitope. In some embodiments, fragments of SEQ ID NO:35 may comprise 1050 or more amino acids, including preferably sequences that encode an immunodominant epitope. In some embodiments, fragments of SEQ ID NO:35 may comprise 1080 or more amino acids, including preferably sequences that encode an immunodominant epitope. In some embodiments, fragments of SEQ ID NO:35 may comprise 1110 or more amino acids, including preferably sequences that encode an immunodominant epitope. In some embodiments, fragments of SEQ ID NO:35 may comprise 1140 or more amino acids, including preferably sequences that encode an immunodominant epitope. In some embodiments, fragments of SEQ ID NO:35 may comprise 1170 or more amino acids, including preferably sequences that encode an immunodominant epitope. In some embodiments, fragments of SEQ ID NO:35 may comprise 1200 or more amino acids, including preferably sequences that encode an immunodominant epitope. In some embodiments, fragments of SEQ ID NO:35 may comprise 1230 or more amino acids, including preferably sequences that encode an immunodominant epitope. In some embodiments, fragments of SEQ ID NO:35 may comprise 1260 or more amino acids, including preferably sequences that encode an immunodominant epitope. In some embodiments, fragments of SEQ ID NO:35 may comprise 1290 or more amino acids, including preferably sequences that encode an immunodominant epitope. In some embodiments, fragments of SEQ ID NO:35 may comprise 1320 or more amino acids, including preferably sequences that encode an immunodominant epitope. In some embodiments, fragments of SEQ ID NO:35 may comprise 1350 or more amino acids, including preferably sequences that encode an immunodominant epitope. In some embodiments, fragments of SEQ ID NO:35 may comprise 1380 or more amino acids, including preferably sequences that encode an immunodominant epitope. In some embodiments, fragments of SEQ ID NO:35 may comprise 1410 or more amino acids, including preferably sequences that encode an immunodominant epitope. In some embodiments, fragments of SEQ ID NO:35 may comprise 1440 or more amino acids, including preferably sequences that encode an immunodominant epitope. In some embodiments, fragments of SEQ ID NO:35 may comprise 1470 or more amino acids, including preferably sequences that encode an immunodominant epitope. In some embodiments, fragments of SEQ ID NO:35 may comprise 1500 or more amino acids, including preferably sequences that encode an immunodominant epitope. In some embodiments, fragments of SEQ ID NO:35 may comprise coding sequences for the IgE leader sequences. In some embodiments, fragments of SEQ ID NO:35 do not comprise coding sequences for the IgE leader sequences. Fragments may comprise fewer than 24 amino acids, in some embodiments fewer than 30 amino acids, in some embodiments fewer than 36 amino adds, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino adds, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 350 amino acids, in some embodiments fewer than 380 amino acids, in some embodiments fewer than 410 amino acids in some embodiments fewer than 440 amino acids, in some embodiments fewer than 470 amino acids in some embodiments fewer than 500 amino acids, in some embodiments fewer than 530 amino acids in some embodiments fewer than 560 amino acids, in some embodiments fewer than 590 amino acids, in some embodiments fewer than 620 amino acids, in some embodiments fewer than 650 amino acids, in some embodiments fewer than 680 amino acids, in some embodiments fewer than 710 amino acids, in some embodiments fewer than 740 amino acids, in some embodiments fewer than 770 amino acids, in some embodiments fewer than 800 amino acids, in some embodiments fewer than 830 amino acids, in some embodiments fewer than 860 amino acids, in some embodiments fewer than 890 amino acids, in some embodiments fewer than 920 amino acids, in some embodiments fewer than 950 amino acids, in some embodiments fewer than 980 amino acids, in some embodiments fewer than 1010 amino acids, in some embodiments fewer than 1040 amino acids, in some embodiments fewer than 1070 amino acids, in some embodiments fewer than 1200 amino acids, in some embodiments fewer than 1230 amino acids, in some embodiments fewer than 1260 amino acids, in some embodiments fewer than 1290 amino acids, in some embodiments fewer than 1320 amino acids, in some embodiments fewer than 1350 amino acids, in some embodiments fewer than 1380 amino acids, in some embodiments fewer than 1410 amino acids, in some embodiments fewer than 1440 amino acids, in some embodiments fewer than 1470 amino acids, and in some embodiments fewer than 1500 amino acids.

Influenza

According to some embodiments of the invention, methods of inducing an immune response in individuals against an immunogen comprise administering to the individual the Influenza strain H5N1 hemagglutinin (HA) protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. In some embodiments, the influenza vaccine compositions and methods comprise the use of a nucleic acid sequence that encodes HA protein from Influenza virus species. In some embodiments, the Influenza vaccine compositions and method comprise the use of nucleic acid sequences that encode HA from Influenza viral strain H1N5 and nucleic acid sequences encoding Influenza proteins selected from the group consisting of: SEQ ID NO:38, SEQ ID NO:40, and SEQ ID NO:42. In some embodiments of the invention, the vaccines of the invention comprise SEQ ID NO:36 or SEQ ID NO:37. SEQ ID NO:36 comprises the nucleic acid sequence that encodes H1N5 HA of Influenza virus. SEQ ID NO:37 comprises the amino acid sequence for H1N5 HA of Influenza virus. In some embodiments of the invention, the vaccines of the invention comprise SEQ ID NO:38 or SEQ ID NO:39. SEQ ID NO:38 comprises the nucleic acid sequence that encodes Influenza H1N1 and H5N1 NA consensus sequences. SEQ ID NO:39 comprises the amino acid sequence for Influenza H1N1 and H5N1 NA consensus sequences. In some embodiments of the invention, the vaccines of the invention comprise SEQ ID NO:40 or SEQ ID NO:41. SEQ ID NO:40 comprises the nucleic acid sequence that encodes Influenza H1N1 and H5N1 M1 consensus sequences. SEQ ID NO:41 comprises the amino acid sequence for Influenza H1N1 and H5N1 M1 consensus sequences. In some embodiments of the invention, the vaccines of the invention comprise SEQ ID NO:42 or SEQ ID NO:43. SEQ ID NO:42 comprises the nucleic acid sequence that encodes Influenza H5N1 M2E-NP consensus sequence. SEQ ID NO:43 comprises the amino acid sequence for Influenza H5N1 M2E-NP consensus sequence. In some embodiments of the invention, the vaccines of the invention include the SEQ ID NO:36 and a sequence selected from the following group: SEQ ID NO:37, SEQ ID NO:38, SEQ ID NO:39, SEQ ID NO:40, SEQ ID NO:41, SEQ ID NO:42, SEQ ID NO:43, and any combination thereof. The consensus sequence for Influenza virus strain H5N1 HA includes the immunodominant epitope set forth in SEQ ID NO:36. The Influenza virus H5N1 HA amino acid sequence encoded by SEQ ID NO:36 is SEQ ID NO:37. The consensus sequence for Influenza virus H1N1/H5N1 NA includes the immunodominant epitope set forth in SEQ ID NO:38. The Influenza virus strains H1N1/H5N1 NA amino acid sequence encoded by SEQ ID NO:38 is SEQ ID NO:39. The consensus sequence for Influenza virus strains H1N1/H5N1 M1 includes the immunodominant epitope set forth in SEQ ID NO:40. The Influenza virus H1N1/H5N1 M1 amino acid sequence encoded by SEQ ID NO:40 is SEQ ID NO:41. The consensus sequence for Influenza virus H5N1 M2E-NP includes the immunodominant epitope set forth in SEQ ID NO:42. The Influenza virus H5N1 M2E-NP amino acid sequence encoded by SEQ ID NO:42 is SEQ ID NO:43. Vaccines of the present invention may include protein products encoded by the nucleic acid molecules defined above or any fragments of proteins.

Fragments of SEQ ID NO:36 may comprise 30 or more nucleotides. In some embodiments, fragments of SEQ ID NO:36 may comprise 45 or more nucleotides. In some embodiments, fragments of SEQ ID NO:36 may comprise 60 or more nucleotides. In some embodiments, fragments of SEQ ID NO:36 may comprise 75 or more nucleotides. In some embodiments, fragments of SEQ ID NO:36 may comprise 90 or more nucleotides. In some embodiments, fragments of SEQ ID NO:36 may comprise 120 or more nucleotides. In some embodiments, fragments of SEQ ID NO:36 may comprise 150 or more nucleotides. In some embodiments, fragments of SEQ ID NO:36 may comprise 180 or more nucleotides. In some embodiments, fragments of SEQ ID NO:36 may comprise 210 or more nucleotides. In some embodiments, fragments of SEQ ID NO:36 may comprise 240 or more nucleotides. In some embodiments, fragments of SEQ ID NO:36 may comprise 270 or more nucleotides. In some embodiments, fragments of SEQ ID NO:36 may comprise 300 or more nucleotides. In some embodiments, fragments of SEQ ID NO:36 may comprise 360 or more nucleotides. In some embodiments, fragments of SEQ ID NO:36 may comprise 420 or more nucleotides. In some embodiments, fragments of SEQ ID NO:36 may comprise 480 or more nucleotides. In some embodiments, fragments of SEQ ID NO:36 may comprise 540 or more nucleotides. In some embodiments, fragments of SEQ ID NO:36 may comprise 600 or more nucleotides. In some embodiments, fragments of SEQ ID NO:36 may comprise 660 or more nucleotides. In some embodiments, fragments of SEQ ID NO:36 may comprise 720 or more nucleotides. In some embodiments, fragments of SEQ ID NO:36 may comprise 780 or more nucleotides. In some embodiments, fragments of SEQ ID NO:36 may comprise 840 or more nucleotides. In some embodiments, fragments of SEQ ID NO:36 may comprise 900 or more nucleotides. In some embodiments, fragments of SEQ ID NO:36 may comprise 960 or more nucleotides. In some embodiments, fragments of SEQ ID NO:36 may comprise 1020 or more nucleotides. In some embodiments, fragments of SEQ ID NO:36 may comprise 1080 or more nucleotides. In some embodiments, fragments of SEQ ID NO:36 may comprise 1140 or more nucleotides. In some embodiments, fragments of SEQ ID NO:36 may comprise 1200 or more nucleotides. In some embodiments, fragments of SEQ ID NO:36 may comprise 1260 or more nucleotides. In some embodiments, fragments of SEQ ID NO:36 may comprise 1320 or more nucleotides. In some embodiments, fragments of SEQ ID NO:36 may comprise 1380 or more nucleotides. In some embodiments, fragments of SEQ ID NO:36 may comprise 1440 or more nucleotides. In some embodiments, fragments of SEQ ID NO:36 may comprise 1500 or more nucleotides. In some embodiments, fragments of SEQ ID NO:36 may comprise 1560 or more nucleotides. In some embodiments, fragments of SEQ ID NO:36 may comprise 1620 or more nucleotides. In some embodiments, fragments of SEQ ID NO:36 may comprise 1680 or more nucleotides. In some embodiments, fragments of SEQ ID NO:36 may comprise 1740 or more nucleotides. In some embodiments, fragments of SEQ ID NO:36 may comprise coding sequences for the IgE leader sequences. In some embodiments, fragments of SEQ ID NO:36 do not comprise coding sequences for the IgE leader sequences. Fragments of SEQ ID NO:36 may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, and in some embodiments fewer than 1740 nucleotides.

Fragments of SEQ ID NO:37 may comprise 15 or more amino acids. In some embodiments, fragments of SEQ ID NO:37 may comprise 30 or more amino acids. In some embodiments, fragments of SEQ ID NO:37 may comprise 45 or more amino acids. In some embodiments, fragments of SEQ ID NO:37 may comprise 60 or more amino acids. In some embodiments, fragments of SEQ ID NO:37 may comprise 75 or more amino acids. In some embodiments, fragments of SEQ ID NO:37 may comprise 90 or more amino acids. In some embodiments, fragments of SEQ ID NO:37 may comprise 105 or more amino acids. In some embodiments, fragments of SEQ ID NO:37 may comprise 120 or more amino acids. In some embodiments, fragments of SEQ ID NO:37 may comprise 150 or more amino acids. In some embodiments, fragments of SEQ ID NO:37 may comprise 180 or more amino acids. In some embodiments, fragments of SEQ ID NO:37 may comprise 210 or more amino acids. In some embodiments, fragments of SEQ ID NO:37 may comprise 240 or more amino acids. In some embodiments, fragments of SEQ ID NO:37 may comprise 270 or more amino acids. In some embodiments, fragments of SEQ ID NO:37 may comprise 300 or more amino acids. In some embodiments, fragments of SEQ ID NO:37 may comprise 360 or more amino acids. In some embodiments, fragments of SEQ ID NO:37 may comprise 420 or more amino acids. In some embodiments, fragments of SEQ ID NO:37 may comprise 480 or more amino acids. In some embodiments, fragments of SEQ ID NO:37 may comprise 540 or more amino acids. In some embodiments, fragments of SEQ ID NO:37 may comprise 565 or more amino acids. Fragments of SEQ ID NO:37 may comprise fewer than 30 amino acids, in some embodiments fewer than 45 amino acids, in some embodiments fewer than 60 amino acids, in some embodiments fewer than 75 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 360 amino acids, in some embodiments fewer than 420 amino acids, in some embodiments fewer than 480 amino acids, in some embodiments fewer than 540 amino acids, and in some embodiments fewer than 565 amino acids.

According to some embodiments of the invention, methods of inducing an immune response in individuals against an immunogen comprise administering to the individual the Influenza strain H1N1 and Influenza strain H5N1 NA protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine.

According to some embodiments of the invention, methods of inducing an immune response in individuals against an immunogen comprise administering to the individual the Influenza strain H1N1 and Influenza strain H5N1 M1 protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine.

According to some embodiments of the invention, methods of inducing an immune response in individuals against an immunogen comprise administering to the individual the Influenza strain H5N1 M2E-NP protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine.

Vaccines

The invention provides improved vaccines by providing proteins and genetic constructs that encode proteins with epitopes that make them particularly effective as immunogens against which immune responses can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments of the invention, a vaccine according to the invention is delivered to an individual to modulate the activity of the individual's immune system and thereby enhance the immune response. When a nucleic acid molecules that encodes the protein is taken up by cells of the individual the nucleotide sequence is expressed in the cells and the protein are thereby delivered to the individual. Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual DNA vaccines are described in U.S. Pat. Nos. 5,593,972, 5,739,118, 5,817,637, 5,830,876, 5,962.428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothinein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen. San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA 1 or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, or "microprojectile bombardment gone guns".

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in US. Serial Number 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of CTACK, TECK, MEC and functional fragments thereof is administered to the individual.

EXAMPLES

Example 1

Materials and Methods

HIV-1 subtype B envelope sequences. To generate HIV-1 subtype B consensus envelope sequence, forty-two subtype B envelope gene sequences collected from eleven countries were selected from GenBank to avoid sampling bias. Each sequence represents a different patient. All sequences used are non-recombinant.

Multiple alignment. The alignment procedure applied in the phylogenetic study included the application of Clustal X (version 1.81) (Thompson, J. D., et al. 1997. The ClustalX windows interface: flexible strategies for multiple sequence alignment aided by quality analysis tools. Nucleic Acids Research 25:4876-4882). Pairwise alignment parameters were set to the dynamic "slow-accurate" programming, using 10 as the gap opening penalty and 0.1 as the gap extension penalty. Multiple alignment parameters included a gap extension penalty equal to 0.2.

Construction of HIV-1 subtype B envelope consensus sequence. The HIV-1 subtype B envelope consensus nucleotide sequence was obtained after performing multiple alignment and minor final manual adjustment. Deduced amino acid sequences were used to guide the introduction of alignment gaps so that they were inserted between codons. The consensus amino acid sequence was obtained by translating the consensus nucleotide sequence.

Phylogenetic tree. The neighbor-joining (NJ) method was employed for amino acid phylogenetic tree-building using the program PAUP*4.0b10 (Swofford, D. L. 1999. PAUP*4.0: phylogenetic analysis using parsimony (* and other methods), version 4.0b2a. Sinauer Associates, Inc., Sunderland, Mass.). Two additional sequences from subtype D (K03454 and AAA44873) and two sequences from subtype C (AAD12103 and AAD12112) were used as an outgroup for rooting (Kuiken, C., B. T. Korber, and R. W. Shafer. 2003. HIV sequence databases. AIDS Rev. 5:52-61).

Modifications of HIV-1 subtype B envelope consensus sequence. Several modifications were performed after obtaining HIV-1 subtype B consensus envelope sequence: highly variable V1 and V2 regions were shortened, V3 loop was designed for CCR5 utilization, the cytoplasmic tail region was removed from the C-terminal, a leader sequence and an upstream Kozak sequence were added to the N-terminal, codon optimization and RNA optimization was performed by using GeneOptimizer™ (GENEART, Germany).

Envelope Immunogens. The gene encoding modified HIV-1 subtype B early transmitter consensus envelope glycoprotein (EY2E1-B) was synthesized and sequence verified by GENEART. The synthesized EY2E1-B was digested with BamHI and NotI, cloned into the expression vector pVAX (Invitrogen) under the control of the cytomegalovirus immediate-early promoter and this construct was named as pEY2E1-B.

The primary subtype B immunogen (EK2P-B) was generated from a human codon biased, primary subtype B isolate 6101 gp140 envelope gene that was a gift of M. Sidhm (Wyeth). Basically, the optimized 6101 envelope gene was mutated by removing the native leader sequence and cytoplasmic tail. Then the IgE-leader sequence and Kozak sequence were introduced by designing forward and reverse specific-primers: Env-F: GTCGCTCCGCTAGCT-TGTGGGTCACAGTCTATTATGGGGTACC-3' (SEQ ID NO:13) Env-R: 5'-GGTCGGATCCTTACTCCAC- CACTCTCCTTTTTGCC-3' (SEQ ID NO:14). The purified PCR product was cloned into pVAX plasmid vector, which was also linearized with EcoR1 and XbaI. This construct was named as pEK2P-B.

In vivo Expression and Reactivity of EY2E1-B with Monoclonal Antibodies. Human rhabdomyosarcoma (RD) cells (2×106) were transfected in 60 mm dishes with 3 □g of pEY2E1-B and pEK2P-B plasmids using EUGENE 6 Transfection Reagent (Roche, Germany), respectively. Forty-eight hours after transfection, cells were washed three times with 1×PBS and lysed in 150 µl of lysis buffer (Cell Signaling Technology). The total protein lysates (50 µg) were fractioned on a SDS-PAGE gel, transferred to a PVDF membrane (Amersham). Immunoblot analyses were performed with an envelope-specific monoclonal antibody 2G12 (NIH AIDS Research and Reference Reagent Program, Rockville, Md., USA) and a monoclonal anti-actin antibody (Sigma-Aldrich) and visualized with HRP-conjugated goat anti-human IgG (Sigma-Aldrich) using an ECLTM Western blot analysis system (Amersham). Actin was used as a loading control for Western Blot, To detect the reactivity of EY2E1-B with monoclonal antibodies, the total protein lysates from transfection (100 µg) were immunoprecipitated with 5 µg envelope-specific monoclonal antibodies including 2G12, 4G10 and ID6 (NIH AIDS Research and Reference Reagent Program, Rockville, Md. USA). The same amount of total protein lysates from cells transfected with empty vector pVAX was used as a negative control. The immunoprecipitated proteins were Tractioned on a SDS-PAGE get and detected by Western Blotting described as above.

Indirect Immunofluorescent Assay. An indirect immunofluorescent assay for confirming the expression of EY2E1-B and EK2P-B genes was performed. Human rhabdomyosarcoma (RD) cells were plated in tissue culture chambered slides (BD Biosciences), at a density to obtain 60-70% confluency the next day in complete DIEM medium with 10% FBS (GIBCO) and allow to adhere overnight. The next day cells were transfected with pEY2E1-B, pEK2P-B and the control plasmid pVAX (1 µg/well) using FuGENE 6 Transfection Reagent (Roche) according to the manufacturer's instructions. Forty-eight hours after transfection, the cells were washed twice with cold 1×PBS and fixed on slides using methanol for 15 min. Upon removal of the residual solvents from the slides, the cells were incubated with anti-mouse HIV-1 env monoclonal F105 (NIH AIDS Research and Reference Reagent Program, Rockville, Md., USA) for 90 min. The slides were then incubated with TRITC-conjugated secondary antibody (Sigma-Aldrich) for 45 min. 4', 6-Diamido-2-phenylindole hydrochloride (Sigma-Aldrich) was added to the solution of secondary antibody to counter stain nuclei to show the nuclei of the total number of cells available in the given field. The slides were mounted with mounting medium containing antifading reagent (Molecular Probes). The images were analyzed using the Phase 3 Pro program for fluorescent microscopy (Media Cybernetics).

Envelope-specific Antibody determination The measurement of IgG antibodies specific for Envelope was performed by ELISA (enzyme linked immunosorbent assay) in both immunized and control mice. Nunc-Immuno™ Plates (Nalge Nunc International, Rochester, N.Y.) were coated with 1 µg/ml of clade B recombinant HIV-1 IIIB glycoprotein soluble gp160 (Immuno Diagnostics, MA), clade A/E primary envelope protein HIV-1 93TH975 gp120 and clade C primary envelope protein HIV-1 96ZM651 gp120 (NIH AIDS Research and Reference Reagent Program, Rockville, Md., USA), respectively, and incubated overnight at mom temperature. After washing, plates were blocked with 3% BSA in PBST (1×PBS+0.05% Tween-20) for 1 h at 37° C. Then plates were washed again and incubated with the specific mouse sera, diluted with 3% BSA in PBST overnight at 4° C., followed by incubation with a 1/10,000 dilution of HRP-conjugated goat anti-mouse IgG (Jackson ImmunoResearch, West Grove, Pa.) for 1 h at 37° C. The reaction was developed with the substrate TMB (3, 3□, 5, 5□-tetramethylbenzidine) (Sigma-Aldrich). Reaction was stopped with 100 µl of 2.5M sulfuric acid per well and the plates were read on the EL808 plate reader (Biotech Instrument Inc.) at OD of 450 nm.

Immunization of Mice Female 4-6-week-old BALB/c mice were purchased from The Jackson Laboratory, Bar Harbor, Me. The breeding pairs of transgenic B6.Cg-Tg (HLA-A/H2-D)2Enge/J mice were purchased from the Jackson Laboratory and bred by Dr. Michelle Kutzler in our lab. These transgenic mice express an interspecies hybrid class I MHC gene, AAD, which contains the alpha-1 and alpha-2 domains of the human HLA-A2.1 gene and the alpha-3 transmembrane and cytoplasmic domains of the mouse H-2Dd gene, under the direction of the human HLA-A2.1 promoter. The mouse alpha-3 domain expression enhances the immune response in this system. Compared to unmodified HLA-A2.1, the chimeric HLA-A2.1/H2-Dd MHC Class I molecule mediated efficient positive selection of mouse T cells to provide a more complete T cell repertoire capable of recognizing peptides presented by HLA-A2.1 Class I molecules. The peptide epitopes presented and recognized by mouse T cells in the context of the HLA-A2.1 Class I molecule are the same as those presented in HLA-A2.1+ humans. The female 4-6-week-old transgenic mice were used for further study described below. Their care was in accordance with the guidelines of the National Institutes of Health and the University of Pennsylvania Institutional Care and Use Committee (IACUC). Each mouse was immunized intramuscularly with three times, each of 100 µg of DNA at biweekly intervals. There are three mice in each group and the control group was vaccinated with pVAX DNA. Mice were sacrificed one week after the third immunization and the spleens were removed aseptically. The spleen cells were collected and resuspended in RBC lysis buffer to remove erythrocytes. After lysis, the splenocytes from the same group were pooled and resuspended in RPMI 1640 medium with 10% FBS. Cells were counted and prepared for analysis, IFN-γ ELISpot Assay. High-Protein Binding IP 96 well Multiscreen™ plates (Millipore, Bedford, Mass., USA) were used. Plates were coated with mAb to mouse IFN-γ (R&D Systems, Minneapolis, Minn.) diluted in 1×PBS, overnight at 4° C. Plates were washed three times with PBS and then blocked for 2 h at room temperature with 1×PBS supplemented with 1% BSA and 5% sucrose. Mice Splenocytes were added in triplicates at an input cell number of $2 \times 10^5$ cells per well resuspended in complete culture medium (RPMI 1640 supplemented with 10% FBS and antibiotics). Six sets of peptides each containing 15 amino acid residues overlapping by 11 amino acids representing the entire protein consensus sequences of HIV-1 subtype B, subtype C, group M and the entire protein sequences of HIV-1 MN (a subtype B isolate), HIV-1 C.UY.01.TRA3011 and C.ZA.01.J54Ma (two subtype C isolates) envelope were obtained from NIH AIDS Research and Reference Reagent Program. Each set of env peptides were pooled at a concentration of 2 µg/ml/peptide into 4 pools as antigens for specific stimulation of the IFN-γ release. Concavalin A (Sigma-Aldrich, St. Louis, Mo.), at 5 g/ml, and complete culture medium were used as positive and negative control, respectively. Plates were washed four times after a 24 h incubation at 37° C., in a 5% $CO_2$ atmosphere incubator. Then, a biotinilated anti-mouse IFN-γ detection antibody was added, and plates were incubated overnight at 4° C. The plates were washed, and color development was followed according to the manufacturer's instructions (ELISPOT Blue Color Module, R&D Systems, Minneapolis, Minn.). Plates were air-dried and the spots were counted using an automated ELISPOT reader system (CTL Analyzers, Cleveland, Ohio) with the ImmunoSpot® software. The average number of spot forming cells (SFC) was adjusted to $1 \times 10^6$ splenocytes for data display. The ELISpot assay was repeated three times in three separate experiments.

CD8+ T-cell depletion study. CD8 lymphocytes were depleted from splenocytes by using immune-magnetic beads coated with antibody to CD8 (Dynal Biotech Inc., Lake Success, N.Y.) following manufacturer's instructions. After depletion of CD8+ T-cells, IFN-γ ELiSpot assay was performed as described above.

Epitope mapping study. In order to map the reactive epitopes, two sets of peptides containing 15 amino acid residues overlapping by 11 amino acids representing the entire envelope proteins of HIV-1 consensus subtype B and HIV-1 MN were pooled into 29 pools of 14-15 peptides/per pool, respectively, and IFN-γ ELISpot assay was performed as described above. These different sets of 29 pooled stimulators were used in a matrix assay which facilitates epitope mapping.

Statistical Analysis. Student paired t-test was used for comparison of the cellular immune response between mice immunized with pEY2E1-B and pEK2P-B. In this study, $p<0.05$ has been considered statistically significant.

Results

Figure 1:
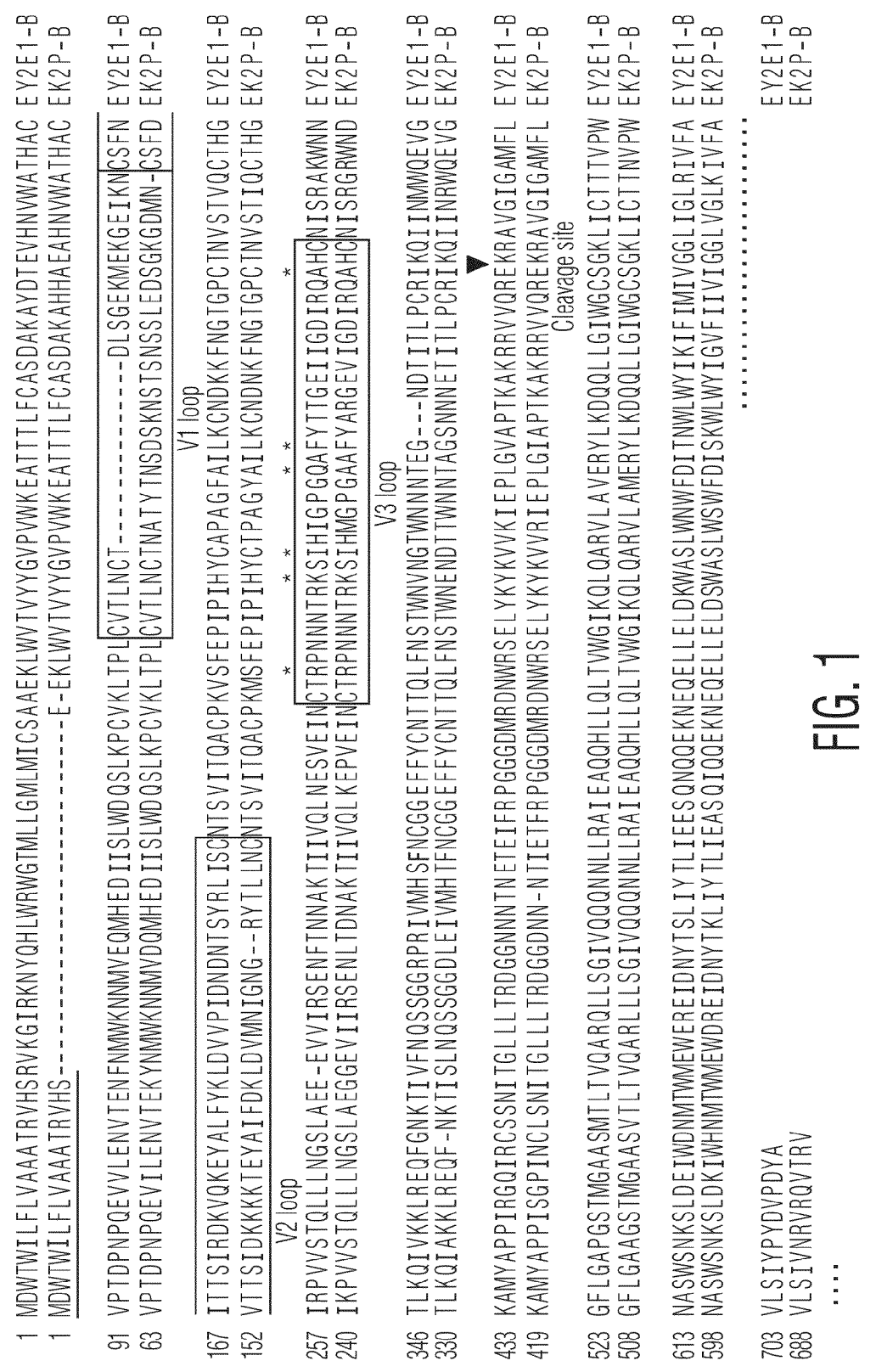

Construction and design of a novel subtype B early transmitter consensus-based envelope gene. The consensus sequence of HIV-1 subtype B was generated from 42 subtype B sequences retrieved from GenBank. As summarized in FIG. 1, several modifications were carried out after generating the consensus sequence. Briefly, to produce a CCR5-tropic version of HIV-1 envelope that mimicked mucosally transmitted viruses, six important amino acids in the V3 loop were designed according to the sequences of early transmitter isolates. Further, ten amino acids in V1 loop and one amino acid in V2 loop was also deleted from the consensus sequence. A highly efficient leader sequence was fused in frame upstream of the start codon to facilitate the expression. The transmembrane domain was kept intact to facilitate surface expression and the cleavage site was kept intact to obtain proper folding and host proteinase cleavage of the envelope protein. The cytoplasmic tail was removed to prevent envelope recycling and to promote more stable and higher surface expression (Berlioz-Torrent, C., et al, 1999. Interactions of the cytoplasmic domains of human and simian retroviral transmembrane proteins with components of the clathrin adaptor complexes modulate intracellular and cell surface expression of envelope glycoproteins. J. Virol. 73:1350-1359; Bultmann, A., et al. 2001. Identification of two sequences in the cytoplasmic tail of the human immunodeficiency virus type 1 envelope glycoprotein that inhibit cell surface expression. J. Virol. 75:5263-5276). Furthermore, in order to have a higher level of expression, the codon usage of this gene was adapted to the codon bias of *Homo Sapiens* genes (Andre, S., et al. B. 1998. Increased immune response elicited by DNA vaccination with a synthetic gp120 sequence with optimized codon usage. J Virol 72:1497-503; Deml, L., et al. 2001. Multiple effects of codon usage optimization on expression and immunogenicity of DNA candidate vaccines encoding the human immunodeficiency virus type 1 gag protein. J. Virol. 75:10991-11001). In addition, RNA optimization (Schneider, R., et al. 1997. Inactivation of the human immunodeficiency virus type 1 inhibitory elements allows Rev-independent expression of Gag and Gag/protease and particle formation. J. Virol. 71:4892-4903) was also performed: regions of very high (>80%) or very low (<30%) GC content and the cis-acting sequence motifs such as internal TATA boxes, chi-sites and ribosomal entry sites were avoided. The synthetic engineered EY2E1-B gene was constructed and was 2734 bp in length. The EY2E1-B gene was subcloned into pVAX at the BamHI and NotI sites for further study.

Figure 2:
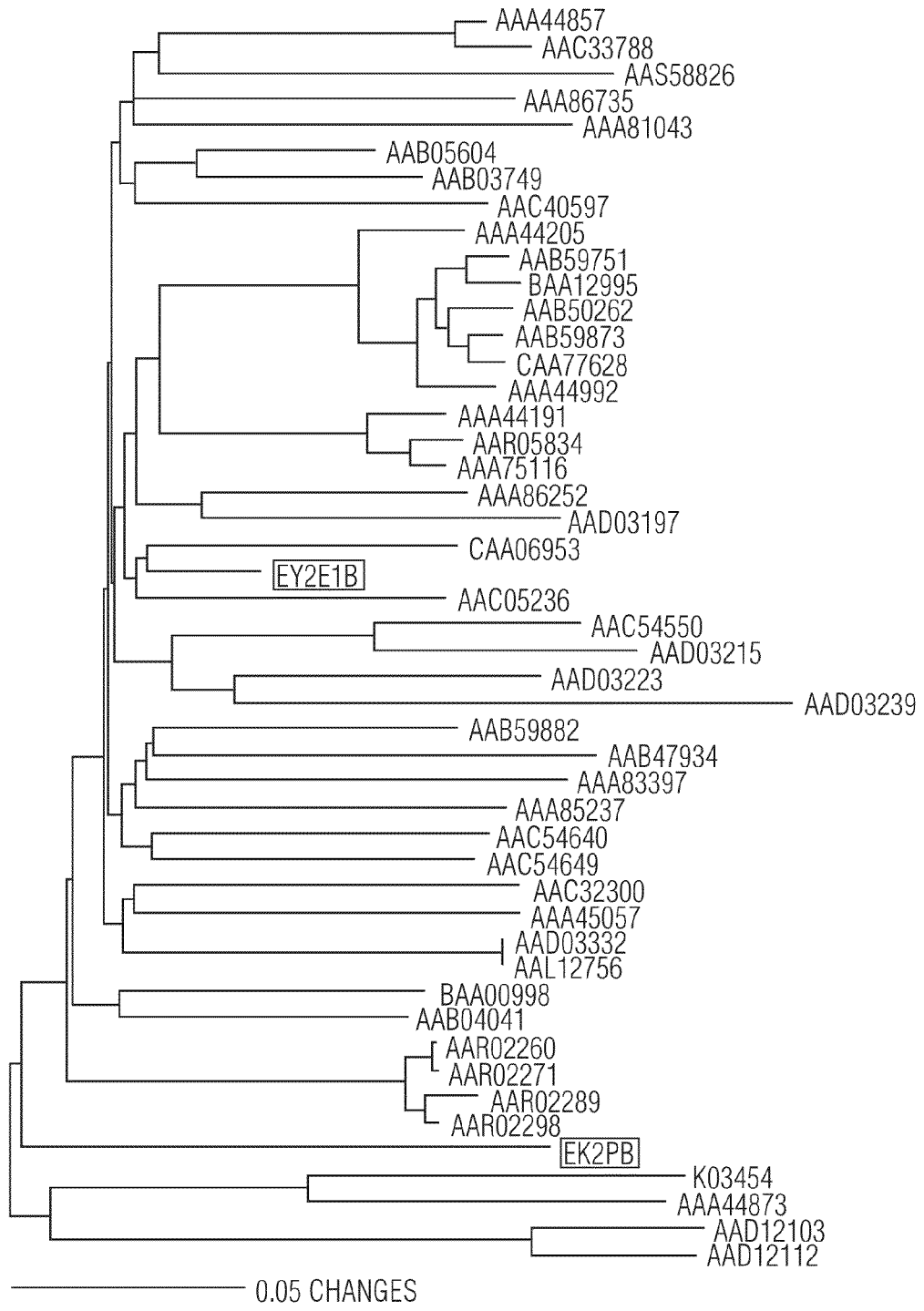
FIG. 2 shows phylogenetic relationships of two HIV-1 subtype B envelope sequences. Forty-two HIV-1 subtype B envelope sequences, EY2E1-B, EK2P-B, two subtype D and two subtype C sequences (outgroup) were included in the phylogenetic analysis. The subtype B envelope sequences representing a broad sample of diversity were from the following 11 countries: Argentina (1); Australia (6); China (1); France (4); Germany (1); Great Britain (2); Italy (1); Japan (1); The Netherlands (4); Spain (1); United States (20). The EY2E1-B and EK2P-B sequences are shown in black boxes.

Phylogenetic analysis. To assess the distribution of the distance from a randomly sampled envelope subtype B sequence to the EY2E1-B sequence, a phylogenetic analysis was performed. As shown in FIG. 2, there was an observed relative closeness of the EY2E1-B sequence to all sampled sequences. The EY2E1-B sequence, when compared with the primary isolate EK2P-B sequence, has comparable distributions of similarity scores (Table 1). The average percent similarity score for EY2E1-B was 85.7%, while it was 79.4% for EK2P-B.

TABLE 1

Table 1. The average and range of percent similarity scores between potential envelope vaccine candidates and an alignment of subtype B envelope sequences.

|  | Average percent similarity scores | Range of percent similarity scores |
|---|---|---|
| EY2E1-B | 85.7 | 92.1-79.6 |
| EK2P-B | 79.4 | 86.3-73.9 |

Figure 3A:
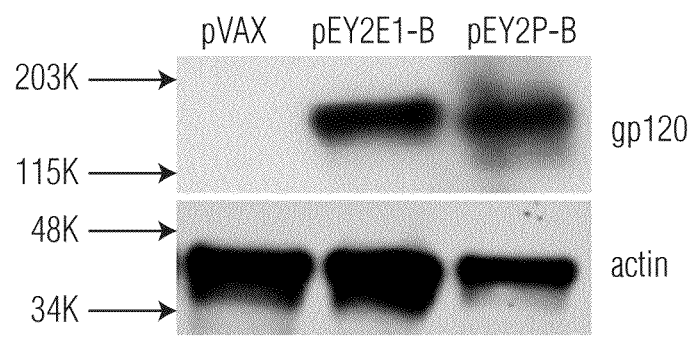
FIG. 3A shows results from Western blotting analysis of EY2E1-B and EK2P-B genes. RD cells were transfected with different plasmids. 48 hours later, cell lysates were collected. Samples were analyzed by Western blotting and probed with HIV-1 gp120 monoclonal (2G 12). As for loading control, the blot was stripped and reprobed with a monoclonal anti-actin antibody.

In Vivo Expression and Antigenic Determination of EY2E1-B. In order to test the in vivo expression of pEY2E1-B and pEK2P-B, RD cells were transfected with these plasmids as described in Materials and Methods section. Total proteins were extracted from cell lysates after transfection and immunoblotted with the envelope-specific monoclonal antibody 2G12 mentioned in Materials and Methods section to detect the expression of pEY2E1-B. Western blot results indicated that these two constructs expressed envelope protein (FIG. 3A). The envelope protein detected was about 120 KD. Table 2 shows a comparison of pEY2E1-B and pEK2P-B.

TABLE 2

|  | Consensus/ Primary | Early transmitter | Codon-optimized | RNA-optimized | IgELS | Cytoplasmic tail |
|---|---|---|---|---|---|---|
| EY2E1-B | Consensus | Yes | Yes | Yes | Yes | No |
| EK2P-B | Primary | No | Yes | Yes | Yes | No |

To determine the antigenic epitopes, the expressed envelope proteins from the RD cell lysates were immunoprecipitated with three different gp120-specific antibodies 2G12, 4G10 and ID6. Following the immunoprecipitation, Western Blotting was performed to detect the immunoprecipitated proteins. Our results showed that the synthetic immunogen could bind to antibodies 2G12 and ID6, but not 4G10. Since antibody 2G12 neutralizes a broad variety of primary isolates and reacts with a conformational and carbohydrate-dependent gp120 epitope, and antibody ID6 binds to gp120 and gp160 and is directed against the first 204 aa of gp120, our results suggested that the synthetic engineered immunogen EY2E1-B might be able to fold into a relatively native conformation and preserve some native antigenic epitopes. Furthermore, since the antibody 4G 10 is a HIV-1 LAI/BRU V3 monoclonal antibody that recognizes LAI gp160, a T-cell line adapted strain, our data also suggested that this synthetic envelope would not utilize the coreceptor CXCR4.

Figure 3B:
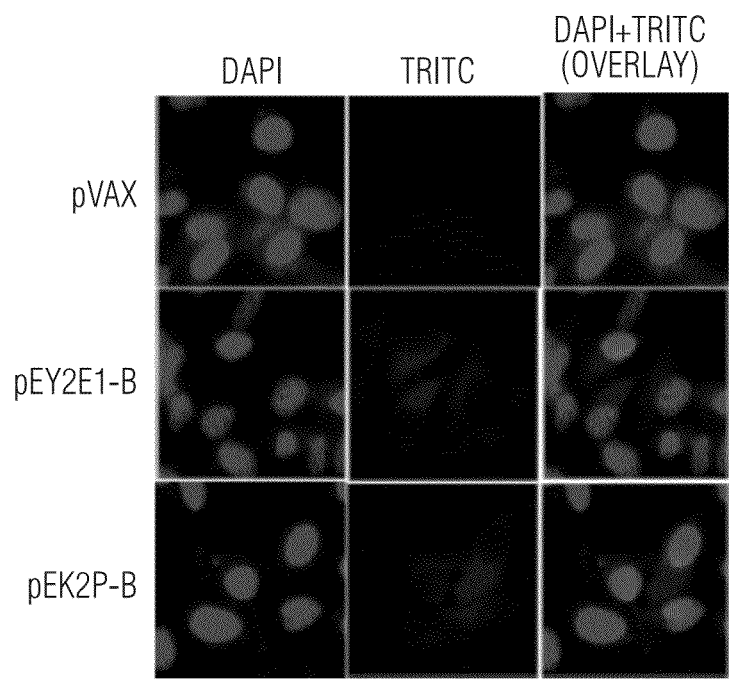
FIG. 3B shows results from immunofluorescence assay of EY2E1-B and EK2P-B genes. The transfected RD cells expressing envelope proteins showed typical red fluorescence. HIV-1 envelope-specific monoclonal antibody F105 served as the source of primary antibody.

To further confirm the expression and determine the antigenic epitopes, an indirect immunofluorescent assay was performed using transfected RD cells. High specific expression was observed under fluorescent microscope in the pEY2E1-B and pEK2P-B transfected cells. The HIV-1 env monoclonal F105 that reacts with a discontinuous, or conformational, gp120 epitope was used in the assay. As indicated in FIG. 3B, the transfected cells expressing Env proteins showed the typical rhodamine fluorescence, again suggesting the synthetic protein expressed and had a relatively native conformation. As a control, the expression was not detected in pVAX transfected RD cells.

Figure 4A:
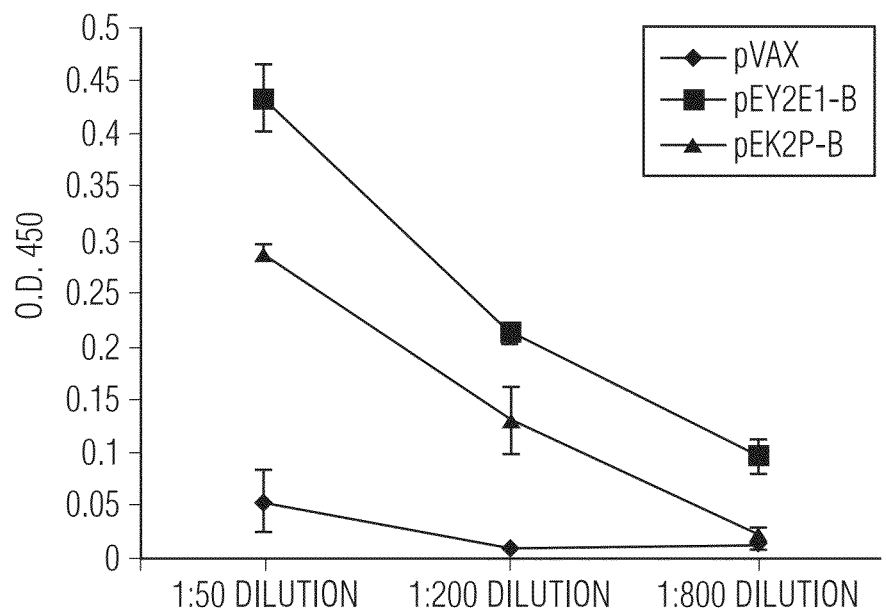
FIG. 4A shows the measurement of subtype B envelope-specific antibody responses.
Figure 4B:
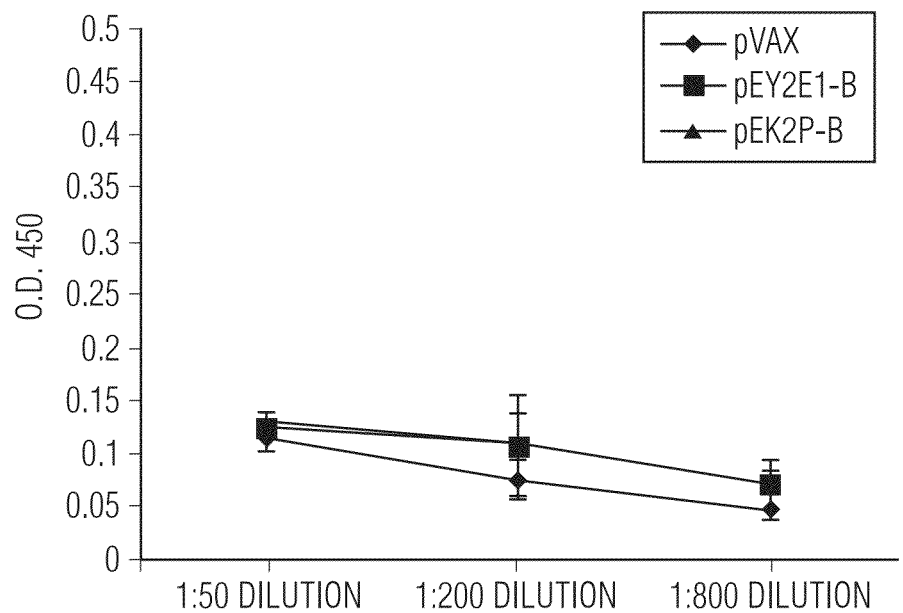
FIG. 4B shows the measurement of subtype A/E envelope-specific antibody responses.
Figure 4C:
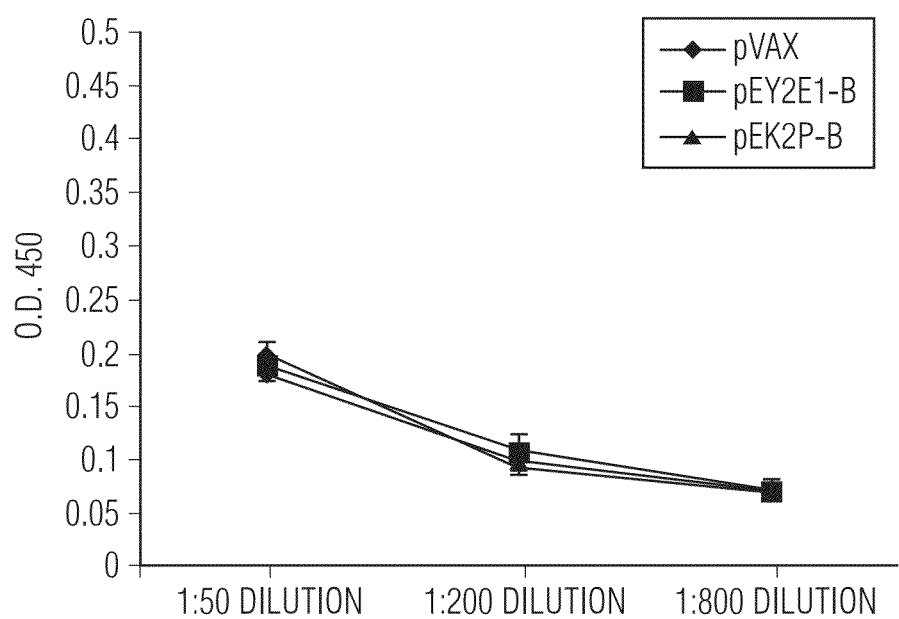
FIG. 4C shows the measurement of subtype C envelope-specific antibody responses. Humoral immune responses after immunization with DNA constructs pEY2E1-B and pEK2P-B were detected by enzyme-linked immunosorbent assay (ELISA). Each mouse was immunized intramuscularly with three times, each of 100 μg of DNA at bi-weekly intervals. Mice from each group (n=3) were bled one week after the third immunization and equally pooled sera were diluted in blocking buffer and analyzed as described in Materials and Methods. Pooled sera collected from mice immunized with pVAX were used as a control. Absorbance (OD) was measured at 450 nm. Each data point represents averaged three OD values from three mice sera per group and values represent the mean of ELISA obtained in three separate assays.

Induction of humoral response. To determine whether the synthetic immunogen could elicit higher-titer envelope-specific antibody response, sera were collected from BalB/C mice immunized pVAX, pEY2E1-B and pEK2P-B and ELISA was performed. As shown in FIG. 4A, we observed the relatively higher level of clade B envelope-specific antibody responses with sera collected from pEY2E1-B immunized mice compared to these in pEK2P-B immunized mice. In contract, the vector alone mice didn't develop specific antibody responses. However, there were not any detectable antibody responses against clade A/E and clade C proteins in both pEY2E1-B and pEK2P-B injected mice (FIGS. 4B and 4C), indicating that although the synthetic consensus-based immunogen has a relatively native conformation and preserve native antigenic epitopes, it may not be able to induce broad cross-clade antibody immune responses.

Figure 5A:
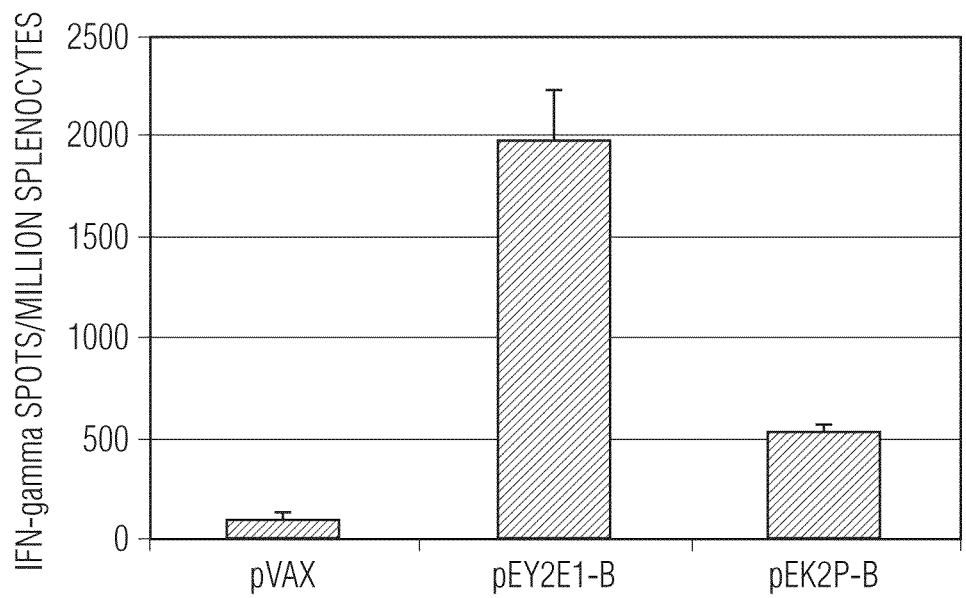
FIG. 5 shows induction of cell-mediated immune responses by pEY2E1-B in both BalB/C mice and HLA-A2 transgenic mice. Frequencies of subtype B consensus envelope-specific IFN-γ spot forming cells (SEC) per million splenocytes after DNA vaccination with pEY2E1-B and pEK2P-B were determined by ELISpot assay in both BalB/C mice FIG. 5A) and transgenic mice (FIG. 5C). Frequencies of CD8 depleted, subtype B consensus envelope-specific IFN-γ spot forming cells per million splenocytes after DNA vaccination with pEY2E1-B and pEK2P-B were also determined in both BalB/C mice (FIG. 5B) and transgenic mice (FIG. 5D). The slenocytes were isolated from individual immunized mice (three mice per group) and stimulated in vitro with overlapping consensus subtype B envelope peptides pools. Backbone pVAX immunized mice were included as a negative control. The values are the means+standard deviations of the means of IFN-γ SFCs.
(FIG. 5E) Characterization of subtype B consensus envelope-specific dominant epitopes. The splenocytes collected from pEY2E1-B and pEK2P-B vaccinated BalB/C mice, respectively, were cultured with 29 HIV-1 subtype B consensus envelope peptide pools for 24 hours. IFN-γ secreting cells were determined by ELISpot assay as described above.
Figure 5B:
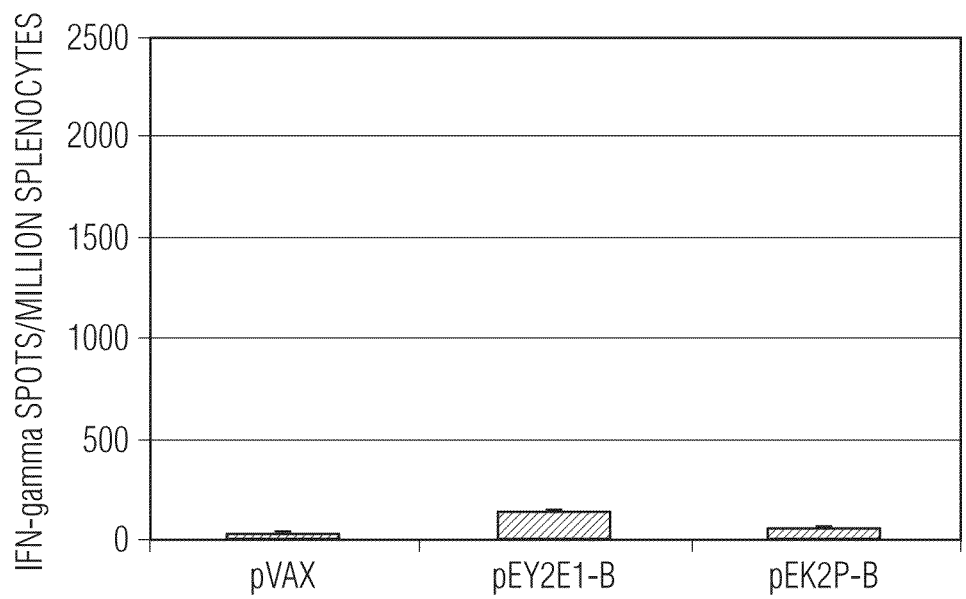

Strong and broad cellular immune responses measured by ELISpot. The BalB/C mice were immunized with pEY2E1-B and pEK2P-B and ELISpot analysis was performed to determine the number of antigen-specific IFN-γ secreting cells in response to four pools of peptides from HIV-1 consensus subtype B protein (FIG. 5A). The magnitude of the response as measured by the number of spot forming units (SFU) per million cells ranged from 27.5 to 520 in pEY2E1-B vaccinated mice. In comparison, splenocytes from pEK2P-B vaccinated mice only showed the range of spots from 2 to 237.5 ($p<0.05$). The additive frequency of SFU/per million splenocytes for all four pools in pEY2E1-B immunized mice was 1976.25+260, while the number of SFU/per million cells in pEK2P-B immunized mice was 519+45. Cells from mice immunized with pVAX vector were used as a negative control, showing only 60+5 SFU/per million splenocytes for consensus envelope B peptides pools ($p<0.05$). We observed similar results in three separate studies. Therefore, the pEY2E1-B construct is up to four times more potent in driving cell-mediated immune responses. We also determined whether CD8+ lymphocytes were responsible for the IFN-γ secretion detected in BalB/C mice immunized with pEY2E1-B. As shown in FIG. 5B, the number of SFU/per million cells was reduced to 127.5+11 after CD8+ depletion, indicating that there was about 90% of decrease in the frequencies of IFN-γ producing cells observed by CD8+ T-cell depleted ELISpot. The IFN-γ production induced by pEY2E1-B is mediated mainly by CD8+ T-cells.

Figure 5C:
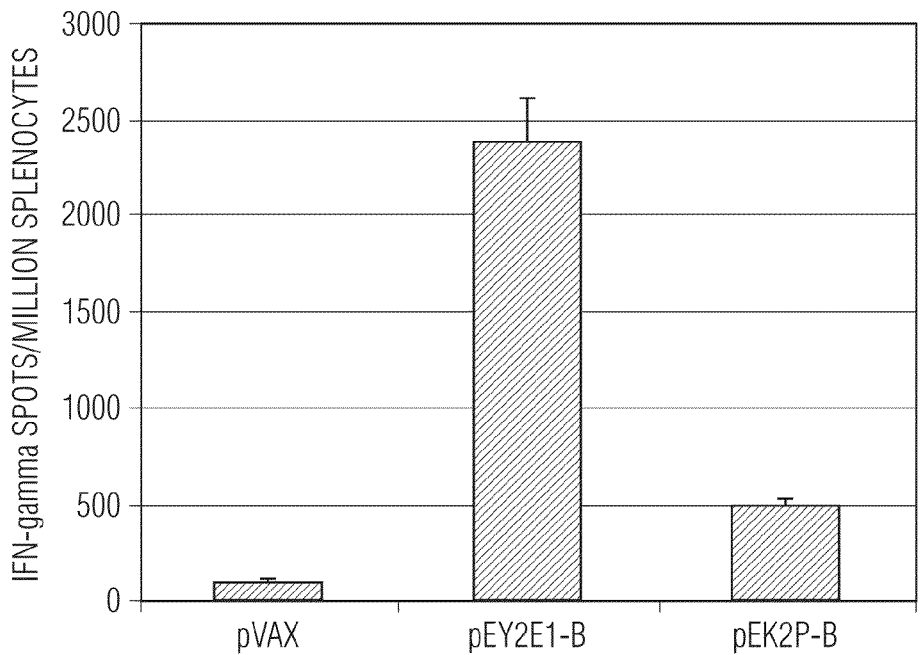
Figure 5D:
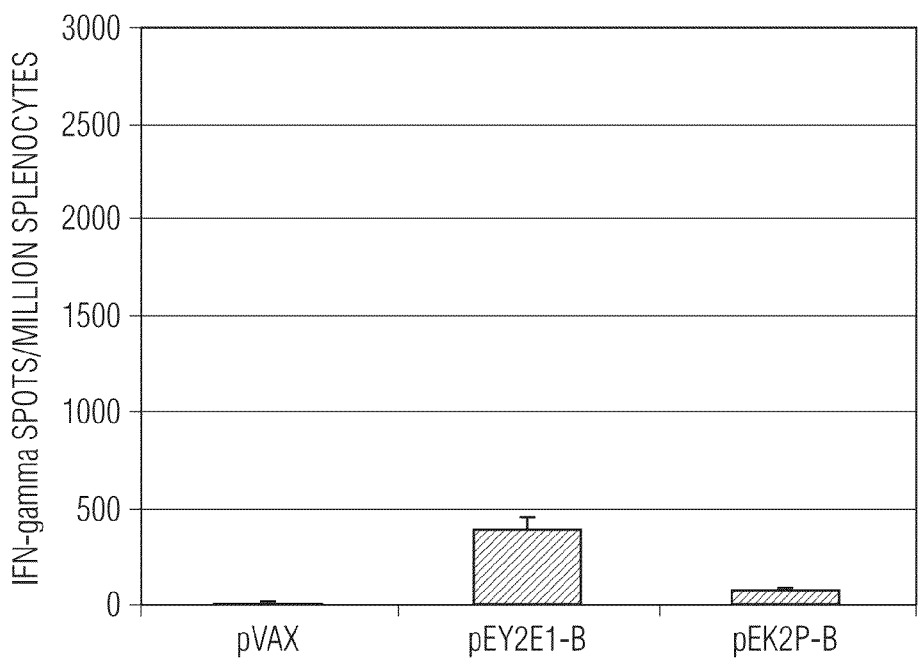

In addition, in order to model human T cell immune responses to HLA-A2 presented antigens and identify those antigens, we performed the same ELISpot assay mentioned above using transgenic HLA-A2.1/H2-Dd mice. As shown in FIG. 5C, the additive frequency of SFU/per million splenocytes for all four pools in pEY2E1-B immunized transgenic mice was 2362+257, while the number of SFU/per million cells in pEK2P-B immunized transgenic mice was only 493+57. These results indicated that the pEY2E1-B construct is up to four times more potent in driving cell-mediated immune responses in the transgenic mice. The ELISpot data after CD8 depletion suggested that the IFN-γ production induced by pEY2E1-B is primarily mediated by CD8+ T-cells (FIG. 5D).

Figure 5E:
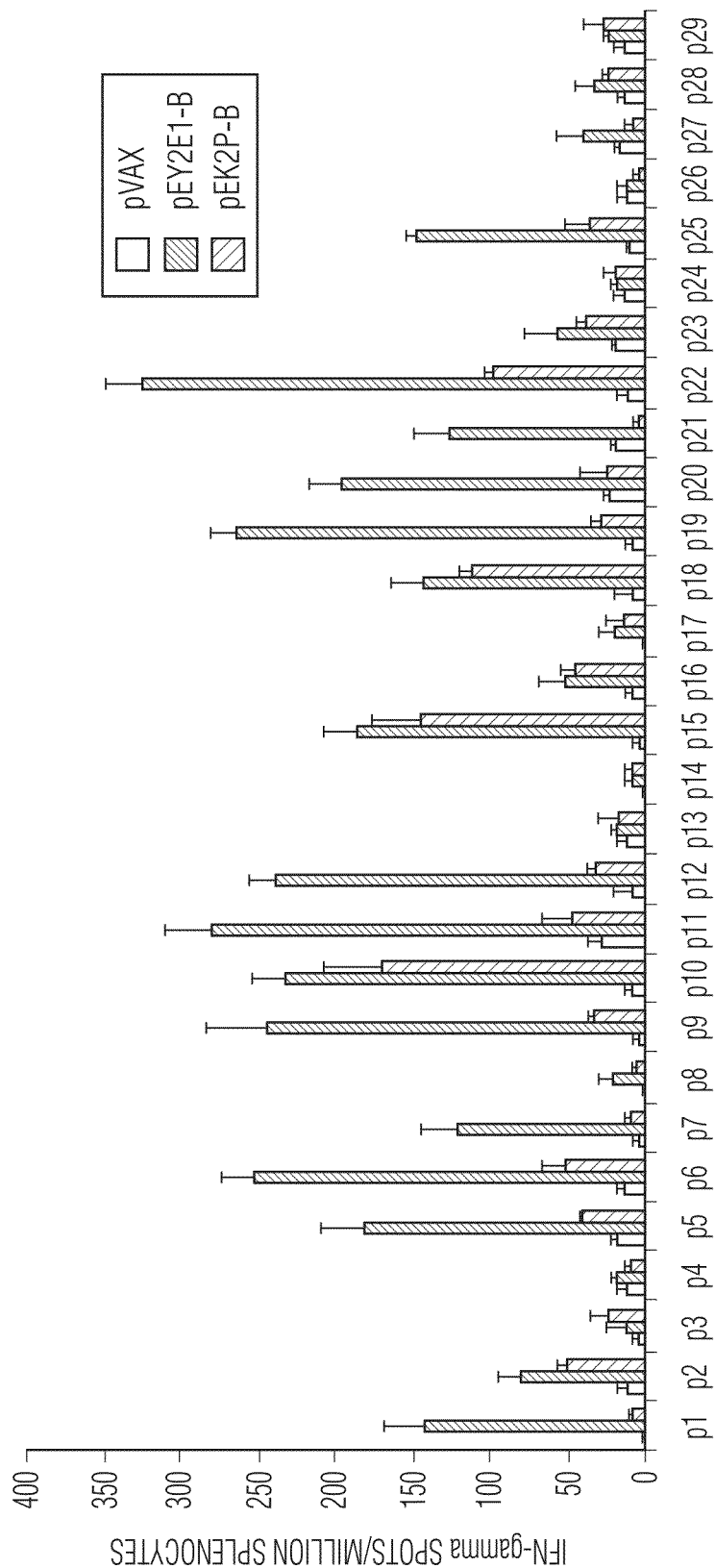

Moreover, we were interested in further detailing the cellular immune responses that were observed in the ELISpot assay. Accordingly, an additional set of ELISpot assay was performed against libraries of peptides spanning the consensus subtype B envelope protein. A complete set of 15-mer peptides overlapped by 11 amino acids, which comprise the subtype B consensus envelope protein, was used to perform this mapping study. The study illustrated that there was no clear dominant epitope induced by the synthetic envelope. However, IFN-γ ELISpot analysis of splenocytes derived from the pEY2E1-B-vaccinated BalB/C mice revealed that there were 18 pools out of 29 pools showing more than 50 spots, while there were only 6 pools in pEK2P-B vaccinated BalB/C mice (FIG. 5E). These results illustrated that there is a significant increase in the breadth and magnitude of cellular immune responses induced by the EY2E1-B immunogen.

Figure 6A:
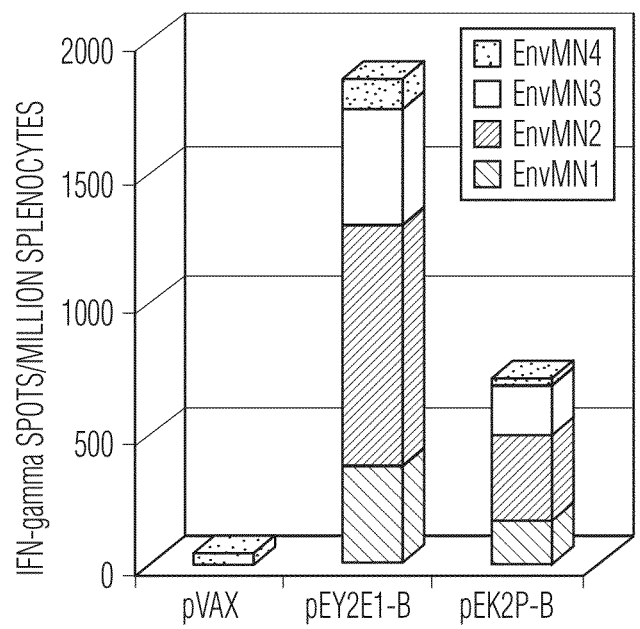
FIG. 6 shows cross reactivity induced by pEY2E1-B in both BalB/C mice and HLA-A2 transgenic mice. The additive T-cell immune responses in BalB/C mice induced by vaccination with pEY2E1-B and pEK2P-B against four individual peptide pools of HIV-1 MN envelope peptides (FIG. 6A), HIV-1 group M (FIG. 6B), subtype C consensus envelope peptides (FIG. 6C) and two subtype C isolate envelope peptides (FIG. 6D and FIG. 6E) were measured by IFN-γ ELISpot assay. The additive T-cell immune responses in HLA-A2 transgenic mice induced by vaccination with pEY2E1-B and pEK2P-B against four individual peptide pools of HIV-1 MN envelope peptides (FIG. 6F), HIV-1 group M (FIG. 6G), subtype C consensus envelope peptides (FIG. 6H) and two subtype C isolate envelope peptides (FIG. 6I and FIG. 6J) were also measured. Backbone pVAX immunized mice were included as a negative control.
Figure 6B:
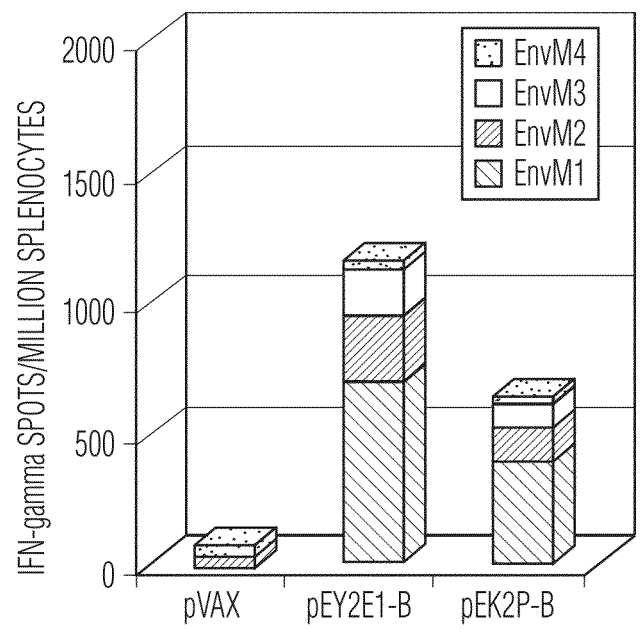
Figure 6C:
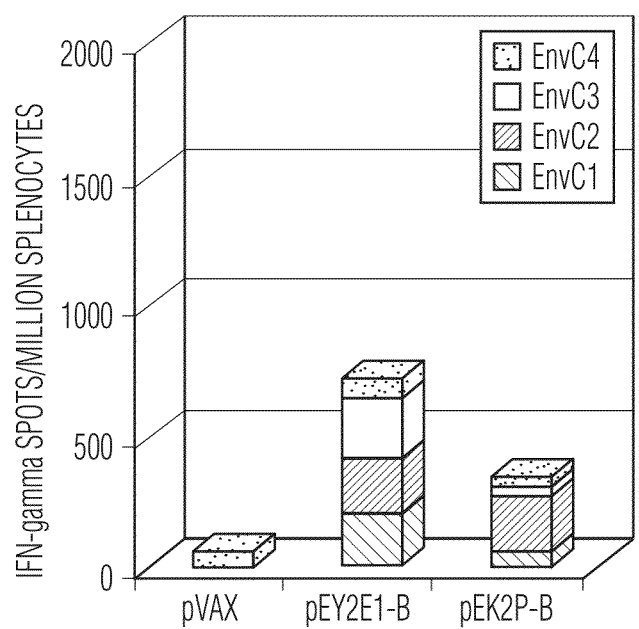

Strong cross-reactive cellular immune responses induced by pEY2E1-B. To determine whether the EY2E1-B immunogen could induce broad and cross-reactive cellular immune responses, IFN-γ ELISpot was performed both in BalB/C and HLA-A2 transgenic mice using HIV-1 group M, consensus subtype C, HIV-1 MN (subtype B isolate), HIV-1 C.UY.01.TRA3011 and C.ZA.01.J54Ma (two subtype C isolates) envelope peptides. These assays will further determine if the results observed in FIGS. 5A, C and E alone are related to the peptide targets or actually due to the increase in immune breadth. As shown in FIG. 6A, the additive number of SFU/per million splenocytes against four pools of HIV-1 MN envelope peptides in pEY2E 1-B vaccinated BalB/C mice was 1855+215.8, which was about two times more than those in pEK2P-B immunized BalB/C mice (SFU/per million splenocytes was 700+168.2), indicating that pEY2E1-B had stronger cross reactivity than pEK2P-B within subtype B. The numbers of IFN-γ spots in response to stimulation with four HIV group M (FIG. 6B) and subtype C (FIG. 6C) consensus envelope peptides pools in pEY2E1-B immunized BalB/C mice were 1150+191.3 and 715+116.1, respectively. Compared to the numbers of spots against group M and subtype C peptides which were 635+152.3 and 345+82.3 in pE.K2P-B vaccinated BalB/C mice, these data illustrate that the cross-clade immune responses elicited by pEY2E1-B is approximately 45% stronger than those induced by pEK2P-B in BalB/C mice.

Figure 6D:
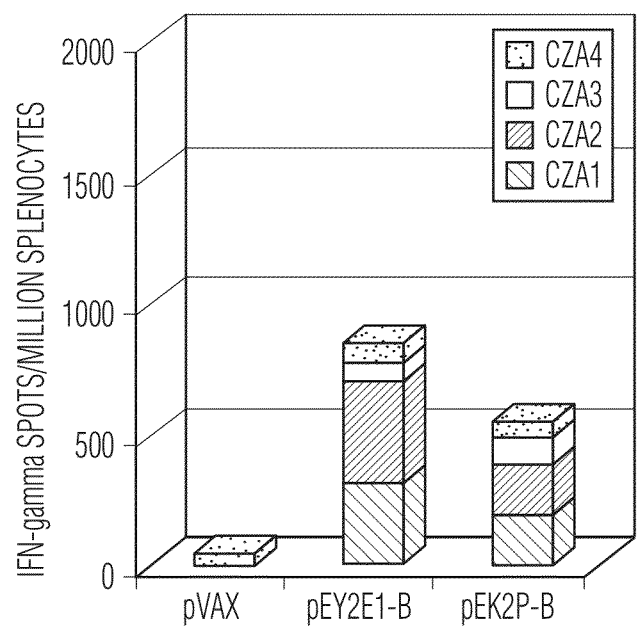
Figure 6E:
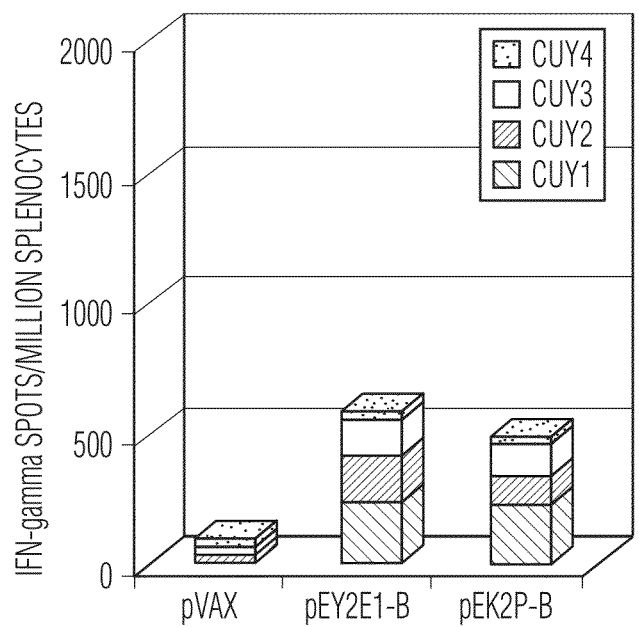
Figure 6F:
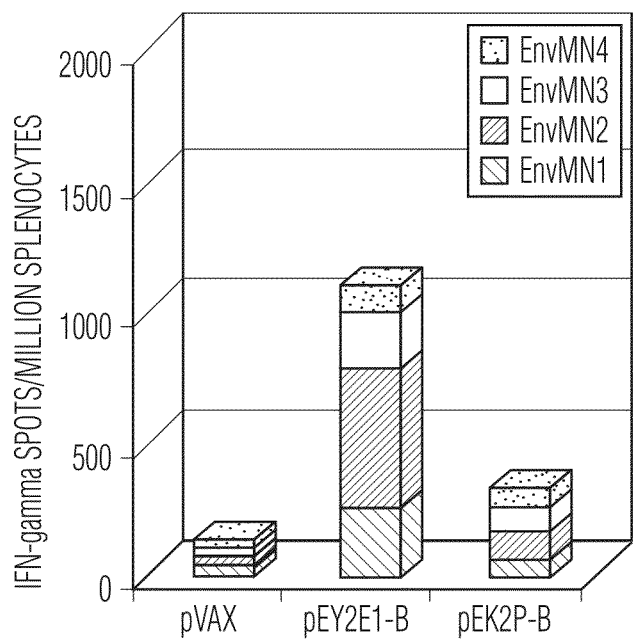
Figure 6G:
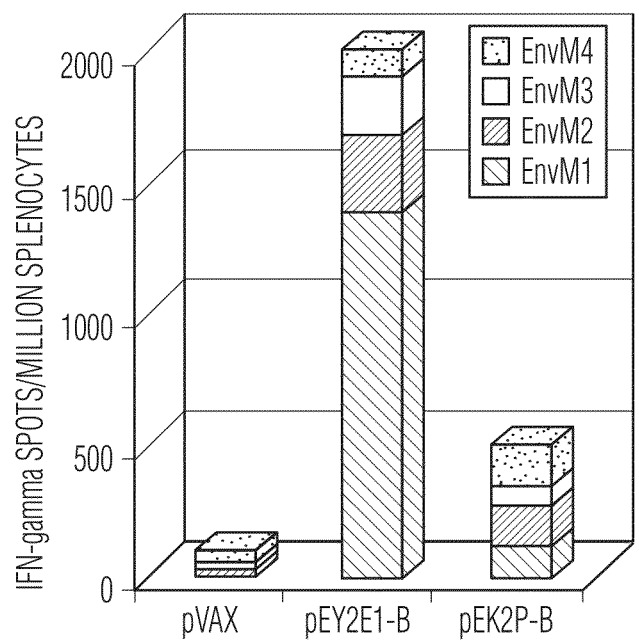
Figure 6H:
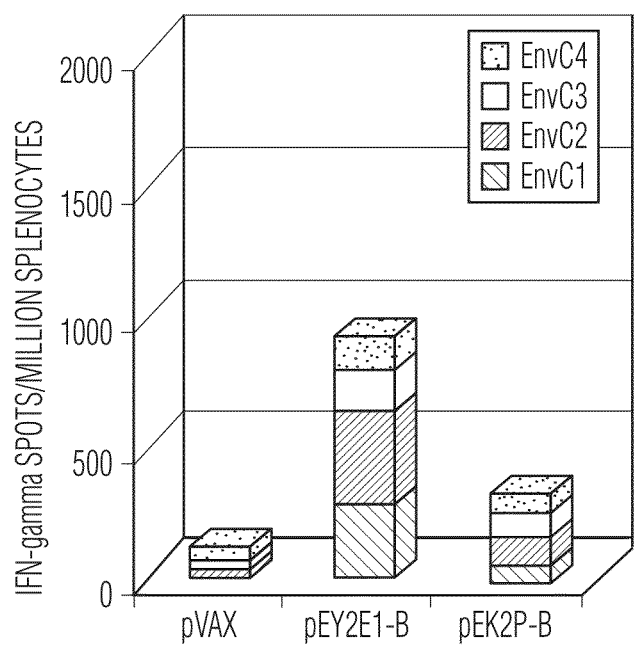
Figure 6I:
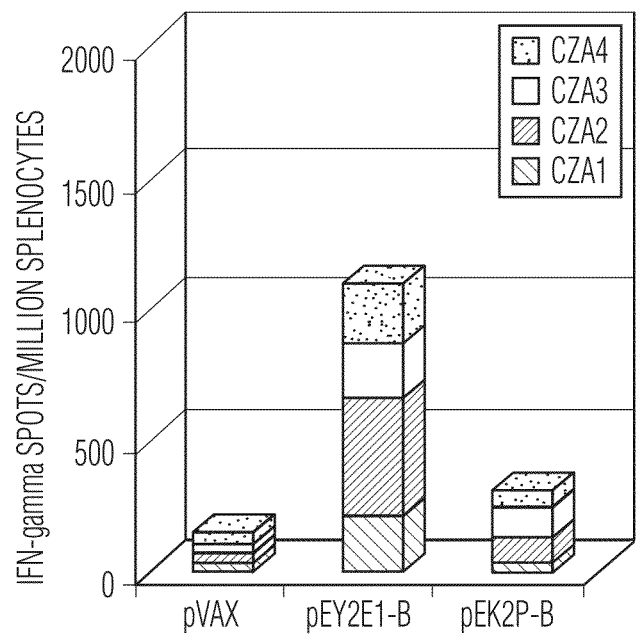
Figure 6J:
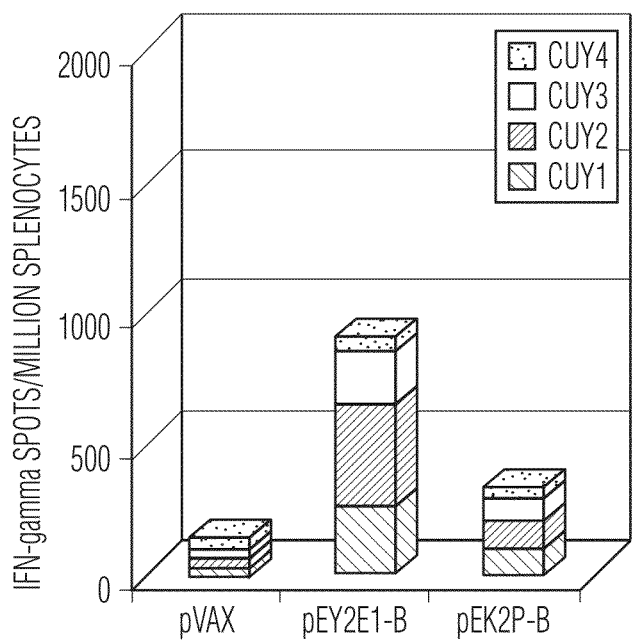

Importantly, we observed much stronger cross reactive cellular immune responses induced by pEY2E1-B in transgenic mice (FIG. 6F-J). The additive number of SFU/per million splenocytes against four pools of HIV-1 MN envelope peptides in pEY2E1-B vaccinated transgenic mice was 1087+153, which was about three times more than those in pEK2P-B immunized HLA-A2 mice (SFU/per million splenocytes was 316+63) (FIG. 6F), indicating that pEY2E1-B could also elicit stronger cross reactivity than pEK2P-B within subtype B in transgenic mice. The numbers of IFN-γ spots in response to stimulation with four HIV group M (FIG. 6G) and subtype C (FIG. 6H) consensus envelope peptides pools in pEY2E1-B immunized transgenic mice were 2116+216 and 893+154, respectively. Compared to the numbers of spots against group M and subtype C peptides which were 473+50 and 266+55 in pEK2P-B vaccinated transgenic mice, these data indicated that the cross-clade immune responses elicited by pEY2E1-B is about three to four times stronger than those induced by pEK2P-B in transgenic mice. Moreover, two subtype C isolate peptide sets that should serve as a stringent control for evaluating breadth and cross-reactivity achieved by other peptide sets were used to further determine the cross-clade C immune responses. Although there were not too many differences of cross reactivity against these two subtype C isolate sets elicited by pEY2E1-B and pEK2P-B in BalB/C mice (FIGS. 6D and E), the cross-clade reactivity against these two subtype C isolate sets induced by pEY2E1-B is about three times stronger than those induced by pEK2P-B (FIGS. 6I and J). The numbers of spots against C.ZA.01.J54Ma and C.UY.01.TRA3011 peptides were 1080+206 and 890+150 in pEY2E1-B vaccinated transgenic mice, while the numbers were only 305+38 and 310+62 in pEK2P-B vaccinated transgenic mice.

Figure 7A:
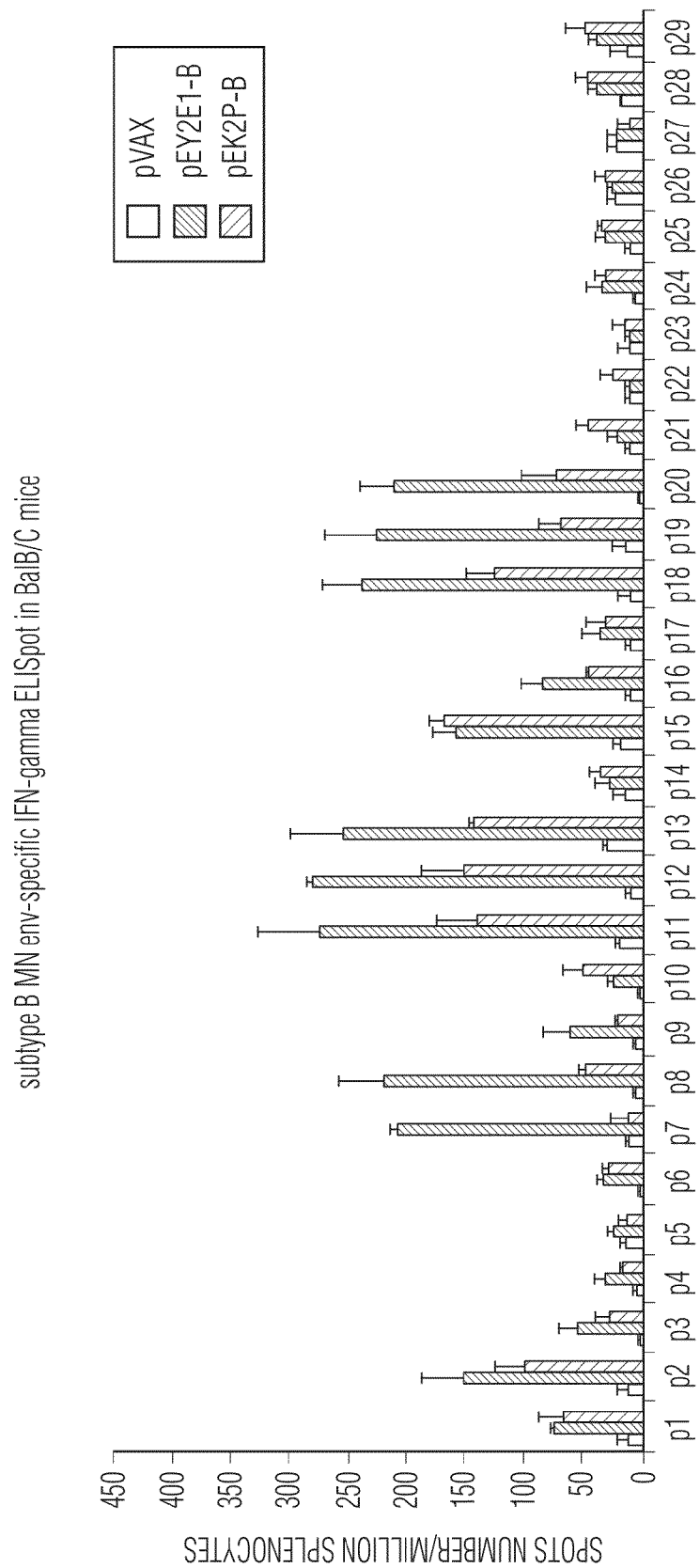
FIG. 7 show characterization of subtype B MN envelope-specific dominant epitopes in both BalB/C mice (FIG. 7A) and HLA-A2 transgenic mice (FIG. 7B) immunized with pEY2E1-B and pEK2P-B. The splenocytes collected from pEY2E1-B and pEK2P-B vaccinated BalB/C mice and transgenic mice, respectively, were cultured with 29 HIV-1 subtype B MN envelope peptide pools for 24 hours. IFN-γ secreting cells were determined by ELISpot assay as described above.
Figure 7B:
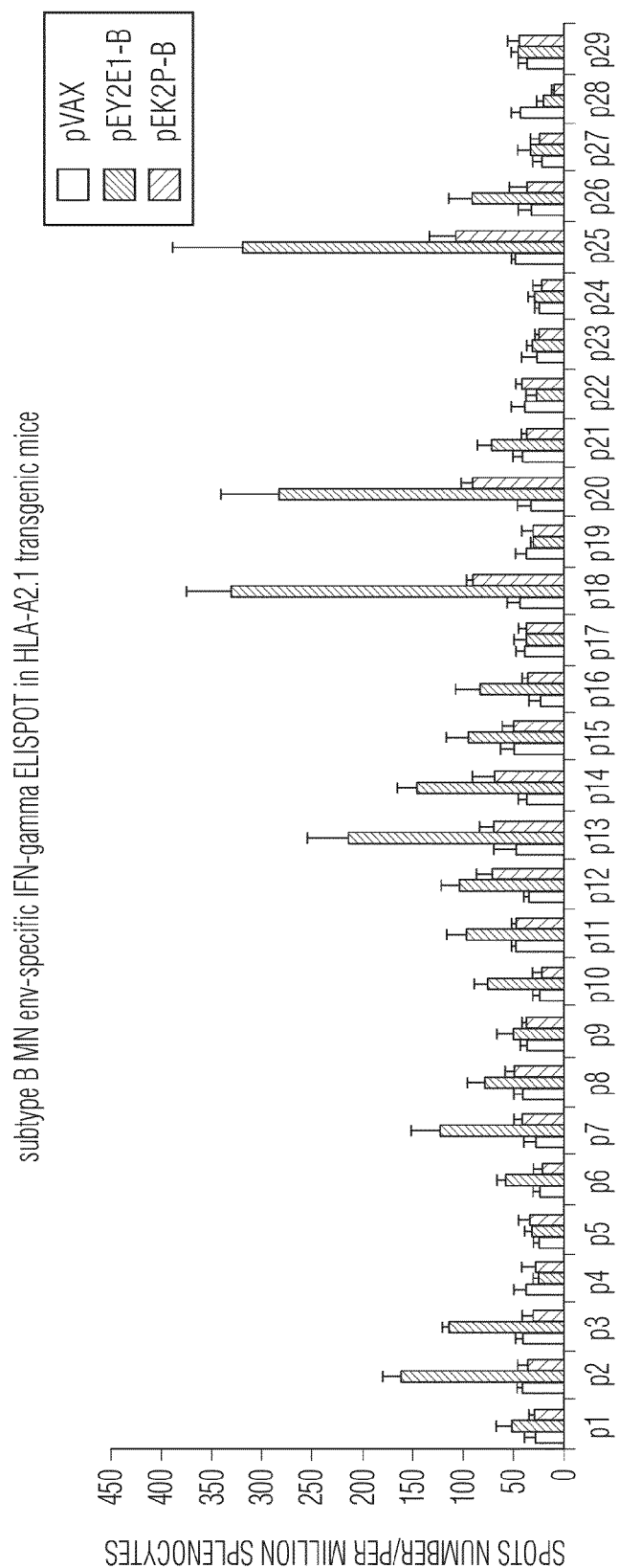
Figure 8:
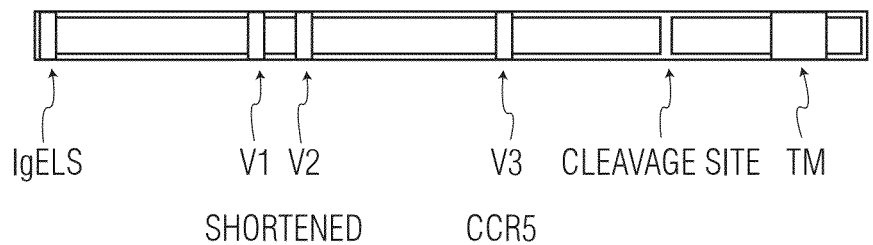
FIG. 8 shows a schematic representation of functional domains of E72E1-B (about 700+ amino acids).
Figure 9:
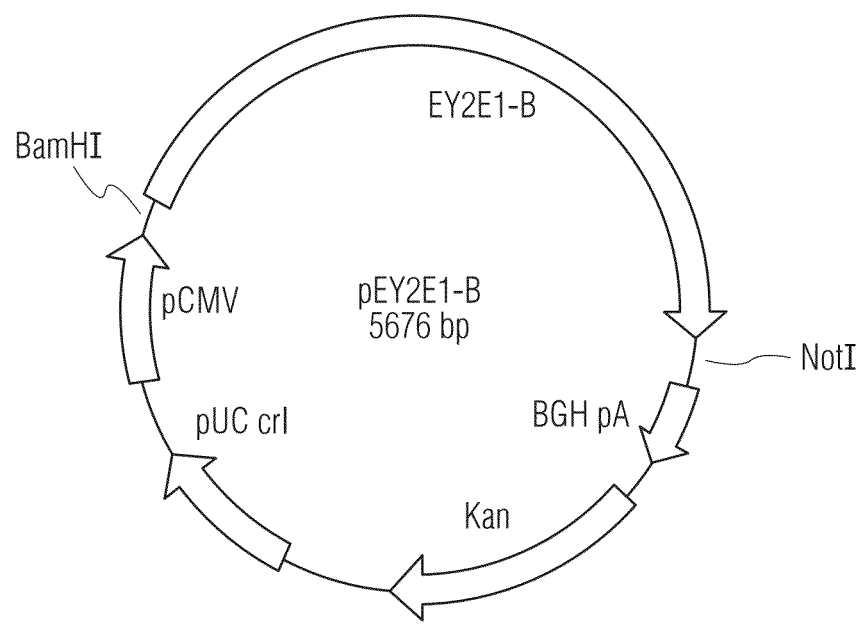
FIG. 9 shows a map of E72E1-B construct.
Figure 10A:
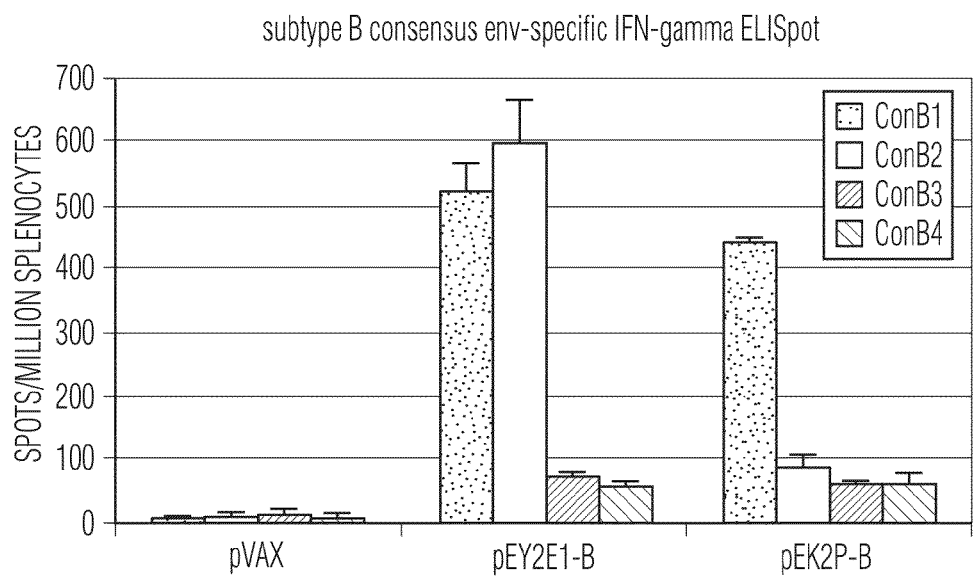
FIG. 10 (FIG. 10A and FIG. 10B), show that a strong cellular immune response is induced E72E1-B.
Figure 10B:
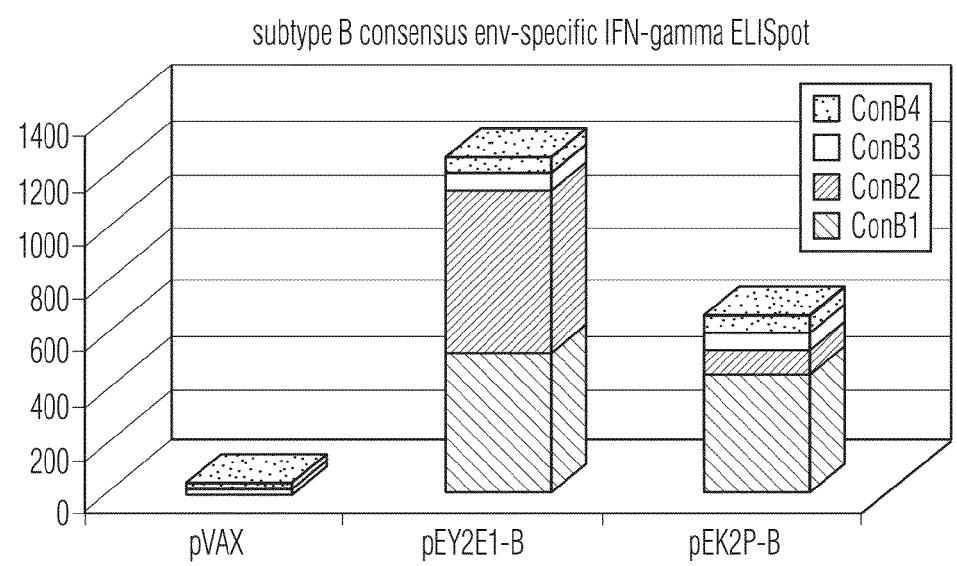
Figure 11A:
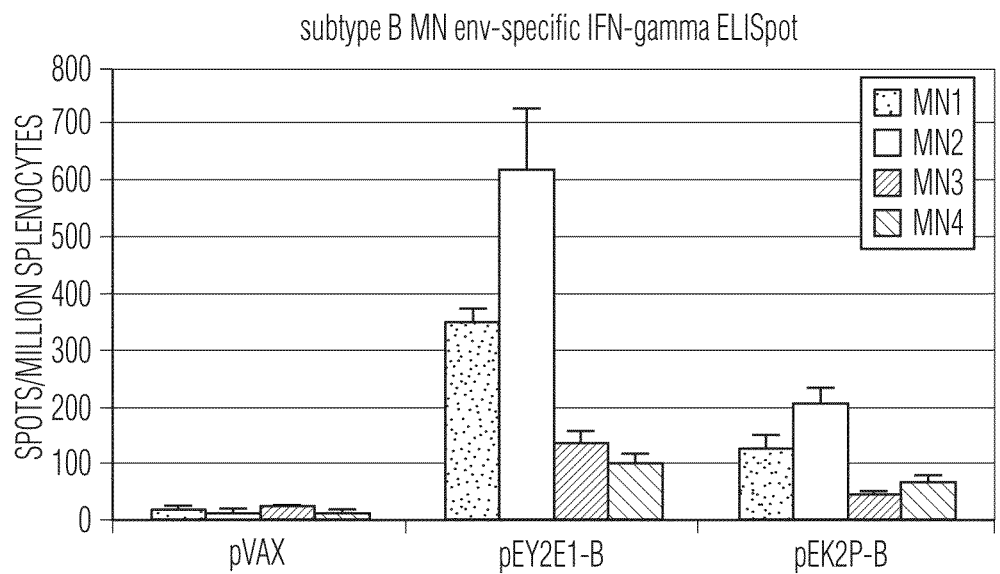
FIG. 11 (FIG.11A and FIG. 11B), show that strong and broad cross-reactive cellular immune responses are induced E72E1-B.
Figure 11B:
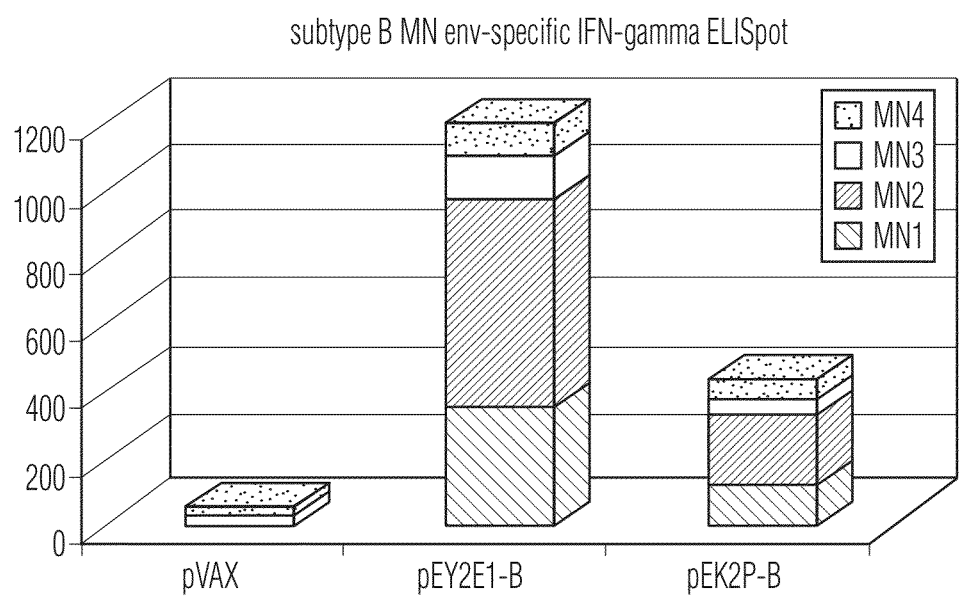
Figure 12A:
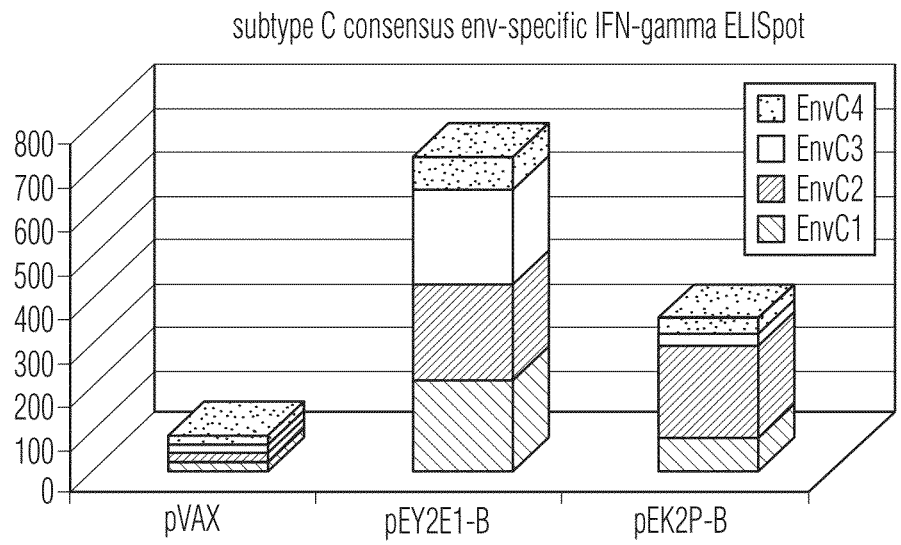
FIG. 12 (FIG.12A through FIG. 12D) show that strong cross-clade-cellular immune responses are induced E72E1-B.
Figure 12B:
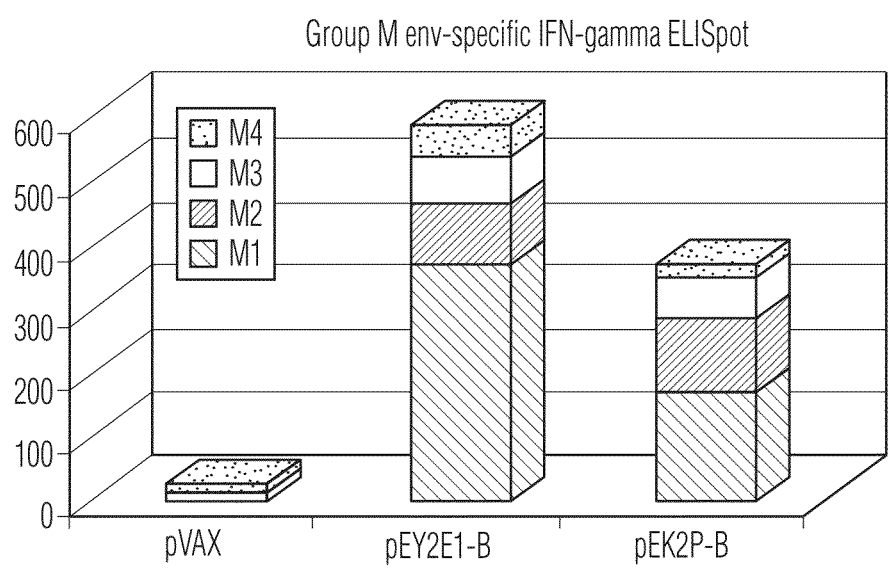
Figure 12C:
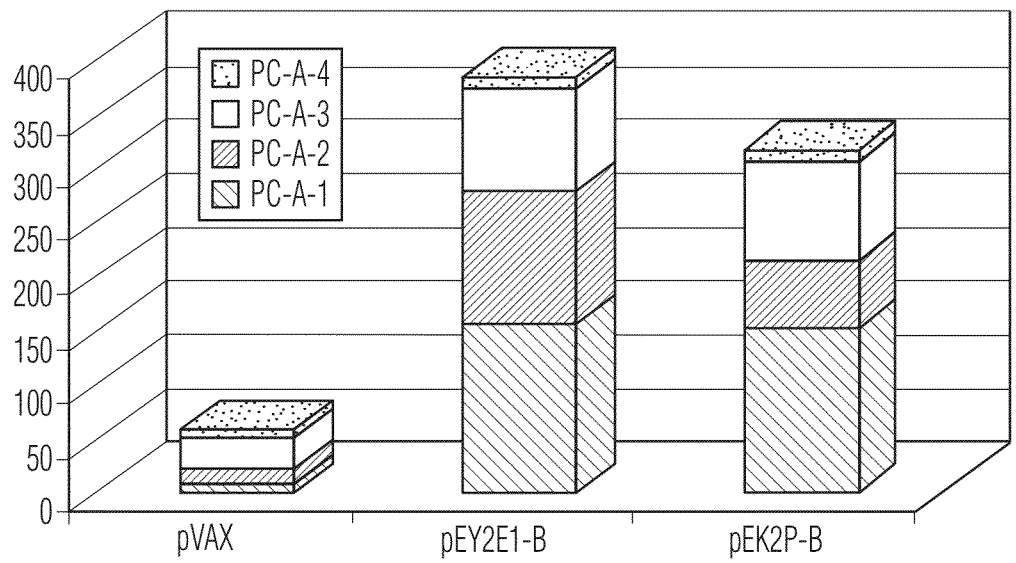
Figure 12D:
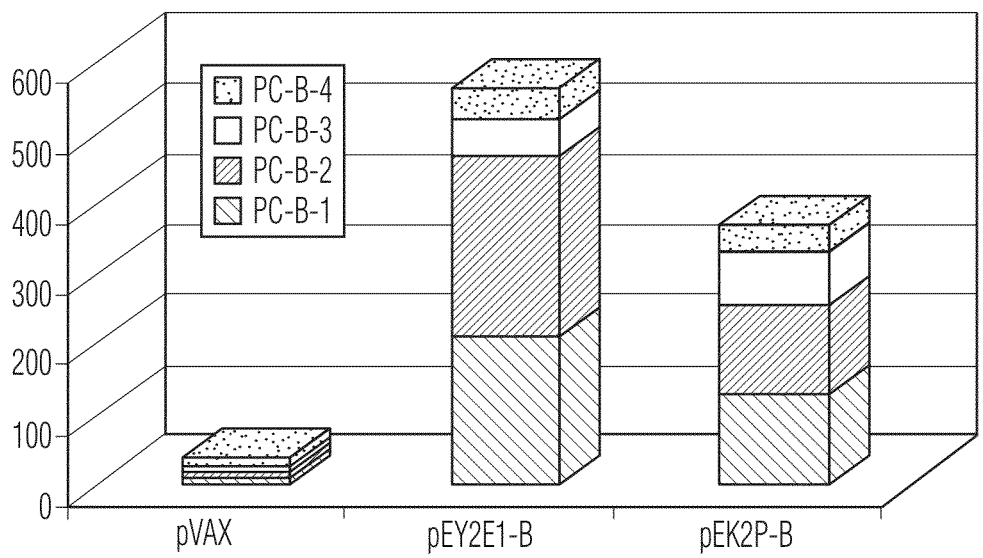
Figure 13:
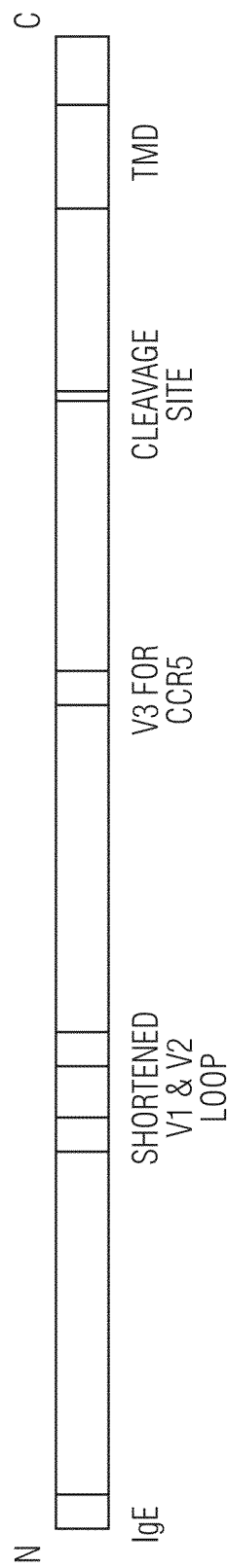
FIG. 13 depicts the immunogen designed for study in Example 2.

Finally, we determined whether there was also an increase in the breadth of cross-reactive cellular immune responses against subtype specific targets induced by the EY2E1-B immunogen by detailing the cellular immune responses against HIV-1 MN observed above both in BalB/C and HLA-A2 transgenic mice. An epitope mapping assay was performed against the library of peptides spanning the subtype B MN envelope protein. The results suggested that there was no clear dominant epitope induced by the synthetic envelope in both mouse strains. However, IFN-γ ELISpot analysis of splenocytes derived from the pEY2E1-B-vaccinated BalB/C mice revealed that there were 14 pools out of 29 pools showing more than 50 spots, while there were only 9 pools in pEK2P-B vaccinated BalB/C mice (FIG. 7A). Similarly, in transgenic mice, there were 18 pools out of 29 pools showing more than 50 spots in pEY2E1-B immunized transgenic mice, while there were only 6 pools in pEK2P-B vaccinated transgenic mice (FIG. 7B). These data indicated that there is a significant increase in the breadth and magnitude of cross reactive cellular immune responses induced by the EY2E1-B immunogen both in BalB/C and HLA-A2 transgenic mice.

Discussion

Worldwide HIV-1 DNA vaccine efforts have been guided by the principle that HIV-specific T-cell responses may provide some contribution to protection from infection or control of replication post-infection. DNA vaccines can impact viral replication although in general they are not as potent in immune induction as attenuated live viral vectors (Almond, N., et al. 1995. Protection by attenuated simian immunodeficiency virus in macaques against challenge with virus-infected cells. Lancet 345:1342-1344; Berman, P. W., et al. 1996. Protection of MN-rgp120-immunized chimpanzees from heterologous infection with a primary isolate of human immunodeficiency virus type 1. J Infect Dis 173:52-9; Boyer, J., et al. 1997. Protection of chimpanzees from high-dose heterologous HIV-1 challenge by DNA vaccination. Nat Med 3:526-532; Daniel, M. C., et al. 1992. Protective effects of a live attenuated SIV vaccine with a deletion in the nef gene. Science 258:1938-1941). Strategies aimed at improving the breadth and magnitude of the cellular immune responses are therefore important. The present invention provides a novel antigen using several features of immunogens that have been reported in the literature as separate approaches, but have not been previously assembled together in one vaccine modality. As proof of concept, a synthetic engineered consensus-based envelope immunogen was developed and compared with an optimized primary sequence immunogen for induction of cell-mediated immune responses. Expression data showed that this engineered new envelope gene could be efficiently expressed in mammalian cell lines although the expression levels of these two immunogens were very similar (FIG. 3A). We observed in the immunogenicity studies that the cellular immune responses induced by this functional immunogen exhibited increased diversity and magnitude compared to the primary envelope vaccine. Epitope mapping data obtained in both BalB/C and HLA-A2 transgenic mice demonstrated that this diversity and magnitude improvement was maintained across these haplotypes. To further confirm this finding, we also developed a consensus-based subtype C envelope immunogen and compared it with a primary subtype C immunogen, again the synthetic consensus-based subtype C envelope immunogen exhibited enhanced diversity and magnitude of cellular immune responses compared to the primary C immunogen (unpublished data).

From the point of view of vaccine design strategy, sequence homology between the vaccine candidate and the infecting or challenging virus may be an important consideration. An effective approach to minimize the degree of sequence dissimilarity between a vaccine strain and contemporary circulating viruses is to create artificial sequences that are "central" to these viruses. One strategy to design such a sequence is to use a consensus sequence derived from the most common amino acid in every position in an alignment. In this study, we developed a consensus-based subtype B envelope vaccine and thought this synthetic immunogen would have higher cross reactivity. Our results did show that there was a diversity of cellular immune responses induced by the pEY2E1-B vaccine. Peptide mapping results in both Balb/c and transgenic mice as well indicated that the EY2E1-B immunogen broadened the immune responses. Moreover, the results of cross-reactive cellular immune responses study indicated that pEY2E1-B could elicit significantly stronger and broader cross-reactive cellular immune responses. Therefore, the artificial consensus envelope immunogens contain more conserved epitopes than found in any individual natural isolate and they induce broader cross-clade CTL responses.

A consensus sequence theoretically has advantages and disadvantages. Since a consensus sequence is generated based on contemporary isolates, it may be genetically closer to current circulating viral strains than any given natural virus isolate. However, since global sequencing is generally conducted with viruses sampled during chronic infections instead of viruses sampled during acute infection, developing a consensus vaccine response on epitopes that for the most part have escaped may be a disadvantage. To minimize this disadvantage, one useful strategy for vaccine design would be to take early transmitter sequences into account. Envelope proteins are among the most difficult HIV proteins to construct artificially because the hypervariable regions in HIV-1 envelope gene evolve by rapid insertion and deletion and not by point mutation. The difference of hypervariable regions in length makes it hard to generate the consensus sequences of these regions. Recently, Gao et al. (Gao, F., E et al. 2005. Antigenicity and immunogenicity of a synthetic human immunodeficiency virus type I group m consensus envelope glycoprotein. J Virol 79:1154-63) generated a group M consensus envelope sequence, however, the nonconsensus sequences from corresponding regions of a CRF08 BC recombinant strain were used in these variable regions. Studies have indicated that subtype C viruses encoding envelope glycoproteins with shorter V1, V2 and V4 regions are transmitted in recipients with a frequency significantly greater than would be expected by chance. The subtype A envelope sequences from early infection also had significant shorter V1 and V2 loop sequences and fewer potential N-linked glycosylation sites (Chohan, B., D. et al. 2005. Selection for Human Immunodeficiency Virus Type 1 envelope glycosylation variants with shorter V1-V2 loop sequences occurs during transmission of certain genetic subtypes and may impact viral RNA levels. J. Virol. 79:6528-6531). In contrast, recently transmitted subtype B variants didn't have shorter V1 and V2 loops. However, it may be important to note the subtype B infection cases were primarily the result of homosexual transmission or drug injection use. Moreover, studies have suggested that a possible functional consequence of having a compact V1, V2 region is to increase exposure of the CD4 binding domain, and then to enhance susceptibility to neutralization (Edwards, T. G., et al. 2001. Relationships between CD4 independence, neutralization sensitivity, and exposure of a CD4-induced epitope in a Human Immunodeficiency Virus type 1 envelope protein. J. Virol. 75:5230-5239; Kolchinsky, P., et al. 2001. Increased neutralization sensitivity of CD4-independent Human Immunodeficiency Virus variants. J. Virol. 75:2041-2050; Pickora, C., et al. 2005. Identification of two N-linked glycosylation sites within the core of the Simian Immunodeficiency virus glycoprotein whose removal enhances sensitivity to soluble CD4. J. Virol. 79:12575-12583; Puffer, B. A., et al. 2002. CD4 independent of Simian Immunodeficiency Virus Envs is associated with macrophage tropism, neutralization sensitivity, and attenuated pathogenicity. J. Virol. 76:2595-2605). We shortened the V1 and V2 regions when we generated the subtype B consensus sequence.

The early phase of HIV-1 infection is dominated by non-syncytium-inducing (NSI) viruses, which replicate slowly and use CCR5 as their main coreceptor. Syncytium-inducing (SI) viruses, which emerge in about 50% of infected individuals preceding an accelerated CD4 cell decline and progressive clinical course of infection, use CXCR4 as the main coreceptor. A differential coreceptor usage of HIV variants has been demonstrated for all subtypes. Subtype C viruses appear to be different from most other subtypes because an underrepresentation of CXCR4 using HIV variants in subtype C has frequently been reported. Therefore, CCR5 utilization should be a very crucial consideration for a vaccine design. Previous reports showed that the V3 region of gp120 plays an important role in coreceptor utilization. Six residues in V3 loop has been identified to be critical for CCR5 interaction: arginine307, lysine314, isoleucine316, arginine322, phenylalanine324 and alanine337. However, based on the sequences of subtype C early transmitters, the residue at position 322 should be glutamine instead of arginine. In summary, based on the previous studies showing residues important for CCR5 utilization and the sequences of early transmitters, we designed the subtype B consensus envelope immunogen that could drive immune responses that may in theory target CCR5 coreceptor To maximize potential cross-reactivity, a HIV-1 group M consensus envelope sequence has been created. However, it is possible that subtype-specific envelope consensus vaccines may represent a compromise for the overall sequence similarity of the vaccine antigen relative to circulating viruses at least at the level of cellular immune responses. Studies have shown that there were high rates of selection identified in different regions of subtype B and C envelope proteins. This may be caused by different immune pressure on different regions of the envelope protein in subtype B and C. Therefore, there may be advantages in using a subtype-specific envelope vaccine, as the immune responses to the vaccine and the circulating virus would share antigenic domains. More experiments comparing group M and subtype-specific envelope vaccines are needed to further clarify this issue.

Another important concern about using a consensus sequence is that its sequence may associate polymorphisms in combinations not found in any natural virus, thus potentially resulting in improper protein conformations. Previous studies has indicated that a group M consensus immunogen could fold into native conformation, preserve envelope antigenic epitopes and elicit weak neutralizing antibody response. Based on the facts that the synthetic protein could bind to antibodies 2G12, ID6 and F105, we think that the pEY2E1-B may have somewhat native structural confirmations. Importantly, our data also demonstrated that EY2E1-B immunogen could induce a higher-titer subtype B envelope-specific antibody, indicating this synthetic immunogen may preserve more Class II epitopes as well. More studies in this area will be important.

With the generation of new HIV-1 vaccine strategies, there is also an increasing demand to predict the efficacy of these vaccines in human using preclinical models. In our study, HLA-A2 transgenic mice were used to study the cellular immune responses elicited by the synthetic immunogen. Studies have shown that this transgenic strain is an important preclinical model for design and testing of vaccines for infectious diseases involving optimal stimulation of human CD8+ cytolytic T cells. In this model the results indicated that EY2E1-B could elicit much broader and stronger cellular immune responses compared to EK2P-B, suggesting that this new vaccine may have more potential to induce HLA-A2-restricted cellular responses. Further study of this immunogen in non-human primates are being planned.

Taken together, our results suggest that EY2E1-B could serve as an immunogen that increases both the magnitude and breadth of CTL responses as a DNA vaccine cassette. In more general terms, this construct may be useful in other platforms for induction of stronger and broader cellular immune responses against HIV strains in non-DNA vector approaches.

Example 2

Development of a Novel Engineered HIV-1 Clade C Envelope DNA Vaccine that Enhances Diversity and Breadth of the Elicited Cellular Immune Response Strong HIV-1 specific CTL responses have an important role in managing viral load during acute and asymptomatic infection. However, recent studies on consensus immunogens have not been able to noticeably demonstrate improved cellular immune responses. Here we test a novel engineered Clade C consensus-based envelope immunogen for improved cellular immune response. The novel vaccine (pEY3E1-C) was created from the HIV-1 Clade C consensus envelope sequence. Several modifications were performed including shortening the highly variable V1 and V2 regions based on early transmitter sequence, retention of the V3 loop for CCR5 utilization, removal of the cytoplasmic tail region from the C-terminus to prevent envelope recycling, and retention of the cleavage site and TMD for proper folding. Also, an IgE leader sequence was added to the N-terminus. This consensus DNA vaccine was also RNA optimized and codon optimized. The cellular immune response was studied in BalB/C mice via ELiSpot and epitope mapping assays. When studied as a DNA vaccine, compared to pEK3P-C (derived from a primary isolate of Clade C env), our construct (pEY3E1-C) was more effective at driving a cellular immune response. pEY3E1-C elicited a cellular immune response greater in magnitude than pEK3P-C when stimulated by Consensus Clade C peptides. Additionally, the consensus immunogen elicited an increase in the magnitude of the cellular immune response when stimulated by two other sets of primary isolate peptides also from Clade C. In addition to augmented magnitude, enhanced breadth of the CTL response was supported by the pEY3E1-C's ability to induce at least 15 out of 29 strongly reactive peptide pools (having more than 50 spots/per million splenocytes), white pEK3P-C only induced 3 out of 29 pools and 9 out of 29 pools with strong reactivity in response to two primary isolate peptide sets, which were selected for their uniqueness and ability to serve as a stringent control for evaluating breadth. Furthermore, pEY3E1-C elicited a stronger Cross-Clade cellular immune response when stimulated with Clade B peptides. The consensus immunogen pEY3E1-C enhances both the magnitude and breadth of CTL responses as a DNA vaccine cassette, suggesting that the potential for consensus immunogens to serve as a component antigen in a HIV vaccine cocktail merits further examination.

With wide genetic diversity, rapid mutation, and recombination of the existing strains, the difficulty of generating an effective vaccine is tremendous. A candidate DNA vaccine derived from an individual isolate may not be able to elicit the cross-reactivity necessary for protection against the diverse circulating strains of HIV-1.

Additionally, it has been reported that DNA vaccines expressing the HIV-1 envelope glycoprotein are not very immunogenic.

We have used a multiphase strategy to increase the potency of the CTL response elicited by the DNA vaccine to possibly provide protection against circulating strains of the virus.

Recent studies have shown that a consensus immunogen may overcome the diversity obstacle created by the rapidly evolving HIV-1 virus.

Derdeyn et al. found that a shorter V1-V4 region is characteristic of early transmitting subtype C virus and our construct has been designed to carry this feature which might be useful in producing a immune response resulting from early transmitted viruses.

Furthermore, the expression levels of our DNA vaccine have been enhanced by codon optimization, RNA optimization, and the addition of an immunoglobulin leader sequence.

HIV-1 specific CTL responses have been shown to be important in controlling viral load during acute and asymptomatic infection and the development of AIDS, thus the following data focuses on the CTL responses elicited by our novel immunogen.

FIG. 13 depicts the immunogen design for development of a novel engineered HIV-1 clade C Envelope DNA Vaccine that enhances diversity and breadth of the elicited cellular immune responses.

FIG. 14 shows phylogenetic Relationships: Thirty-Six HIV-1 subtype C envelope sequences, EY3E1-C, EK3P-C, two subtype B, one subtype A and one subtype D sequences (outgroup) were included in the phylogenetic analysis. The subtype C envelope sequences representing a broad sample of diversity were from 12 countries.

Table 3 shows the average and range of percent similarity scores between potential envelope vaccine candidates and an alignment of subtype C envelope sequences.

TABLE 3

| | Average % Similarity Scores | Range of % Similarity Scores |
|---|---|---|
| pEY3E1-C | 85.3 | 82.7-93.1 |
| pEK3P-C | 87.4 | 83.6-90.2 |

Three groups of three Balb/C mice were immunized with 100 μg of DNA 3 times with two weeks between immunizations. On the seventh week, spleens were harvested for cellular studies.

As shown in FIG. 15 (FIG. 15A and FIG. 15B), strong cellular response elicited by pEY3E1-C.

FIG. 16 shows strong and broad cellular responses elicited by pEY3E 1-C. When stimulated with 29 pools of Consensus C env peptides: pEY3E1-C vaccinated mice elicited more than 50 spots/million splenocytes from 23 pools; pEK3P-C vaccinated mice elicited more than 50 spots/million splenocytes from 2 pools.

FIG. 17 FIG. (17A through 17D) show strong cross-reactive cellular responses elicited by pEY3E1-C within the same clade.

FIG. 18 (FIG. 18A and 18B) show strong and broad cross-reactive cellular responses elicited by pEY3E1-C. FIG. 18A shows data from subtype C (Uruguay) env-Specific IFN-γ ELISpot. When stimulated with 29 pools of Clade C (Uruguay) env peptides: pEY3E1-C vaccinated mice elicited more than 50 spots/million splenocytes from 12 pools; pEK3P-C vaccinated mice elicited more than 50 spots/million splenocytes from 3 pools. FIG. 18B shows data from Subtype C (S. Africa) env-Specific IFN-γ ELISpot. When stimulated with 29 pools of Clade C (S. Africa) env peptides: pEY3E1-C vaccinated mice elicited more than 50 spots/million splenocytes from 13 pools; pEK3P-C vaccinated mice elicited more than 50 spots/million splenocytes from 5 pools.

FIG. 19 (FIG. 19A through 19F) show strong cross-reactive cellular responses elicited by pEY3E1-C between clades.

There is a significant increase in the breath and magnitude of cellular immune responses induced by the EOC immunogen. Broader cross-clade reactivity appears as an additional benefit of this immunogen.

Example 3

Efficacy of a Novel Engineered HPV-16 DNA Vaccine Encoding a E6/E7 Fusion Protein The immunogen has been designed to be expressed as a polyprotein whereby E6 and E7 sequences are separated by a proteolytic cleavage site. The polyprotein is also expressed with an IgE leader sequence. The polyprotein design includes deletions or mutations in the E6 sequence which are important for p53 binding and degradation and mutations in Rb binding site on the E7 protein. FIG. 23 provides an illustration of the immunogen design.

Coding sequences encoding the polyprotein were inserted into the vector pVAX to produce plasmid p1667 FIG. 24 shows maps of pVax and p1667.

TC1 tumor cells were immortalized with HPV-16 E7 and transformed with the c-Ha-ras oncogene. These cells express low levels of E7 and are very tumorigenic.

In the immunogenicity study in mice, 3 mice/per group of C57BL6 mice were administered 100 μg DNA/per mouse. Groups included 1) control which were administered pVAX-control vector and 2) test which were administered p1667.

Mice were vaccinated on days 0, 14 and 28. On day 35, mice were sacrificed and ELISPOT was performed (Focus on CMI).

The data for cellular immune responses induced by the DNA Immunogen p1667 is shown on FIG. 25. HPV16 consensus E6 and E7 peptides (37, 15-mers overlapping by 9 aa) were used in two pools—pool 1: 18 peptides; pool 2: 19 peptides. FIG. 25A and FIG. 25C show data from total splenocytes. FIG. 25B and 25D show data from samples with CDS depletion.

Figure 26:
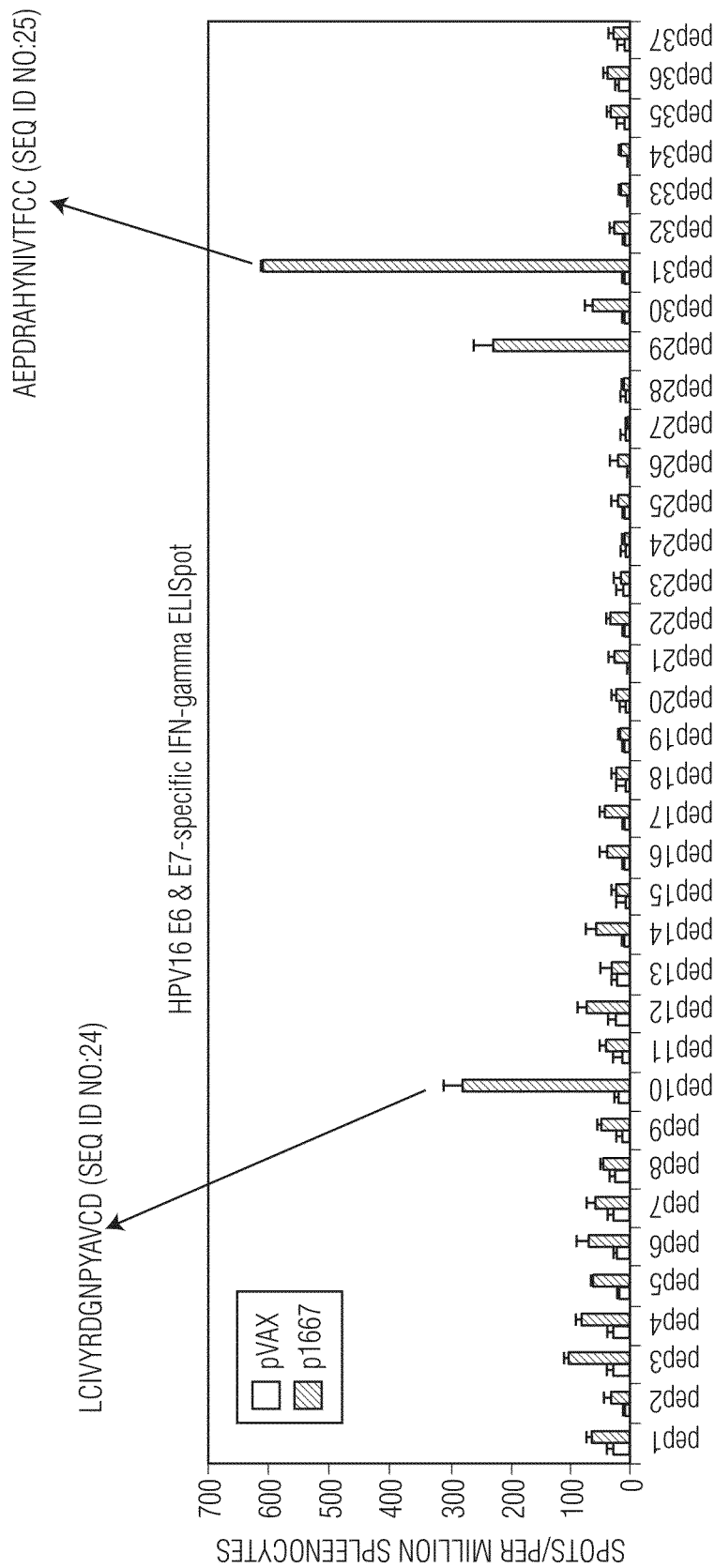
FIG. 26 shows results of immunodominant epitope mapping.

FIG. 26 shows results of immunodominant epitope mapping. Two sequences are noted.

Figure 27:
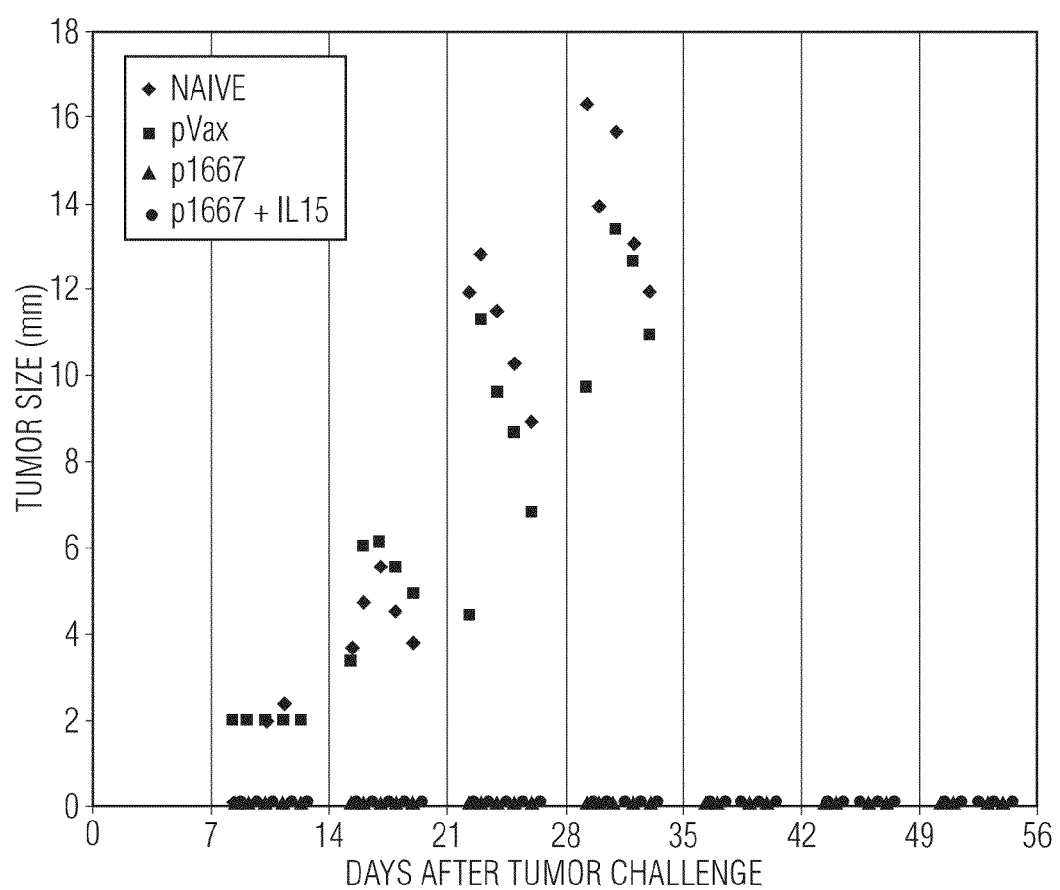
FIG. 27 shows results from the prophylactic experiments using E6/E7 DNA Vaccine to study protection in C57/BL6 Mice.

In prophylactic experiments in mice, 5 mice/per group of C57BL6 mice were administered 100 µg DNA/per mouse. Groups included 1) naïve (PBS injected), 2) control which were administered pVAX-control vector and 3) test which were administered p1667. Mice were vaccinated on days 0, 14 and 28. On day 35, mice were challenged with TC-1 cells and thereafter tumor size measurements were made. Results are shown in FIG. 27. Data from a group in which TL-15 construct was co-administered is also shown.

Figure 28:
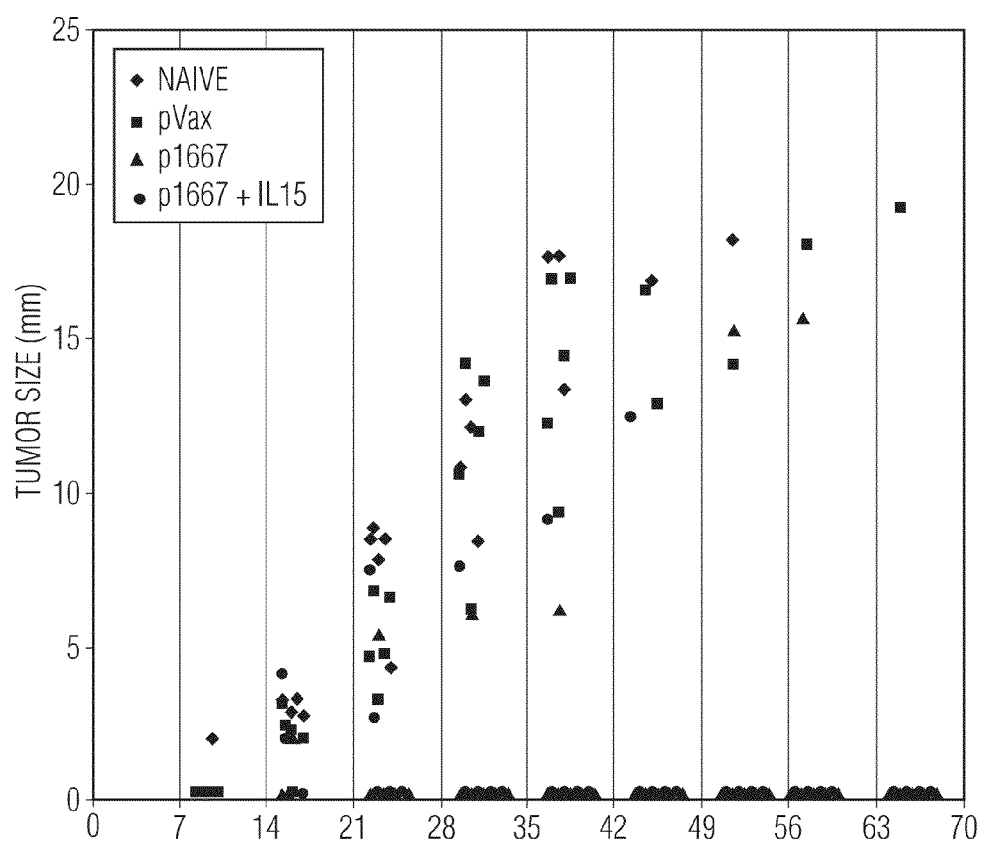
FIG. 28 shows results from the tumor regression experiments using E6/E7 DNA Vaccine to study protection in C57/BL6 Mice.

In tumor regression experiments in mice, 5 mice/per group of C57BL6 mice were administered 100 µg DNA/per mouse. Groups included 1) naïve (PBS injected), 2) control which were administered pVAX-control vector and 3) test which were administered p1667. Mice were challenged with 5×104 TC-1 cells at Day 0. Mice were administered DNA vaccine on days 3, 10 and 17. Tumors were measured starting at day 8. Results are shown in FIG. 28. Data from a group in which IL-15 construct was co-administered is also shown.

Figure 29:
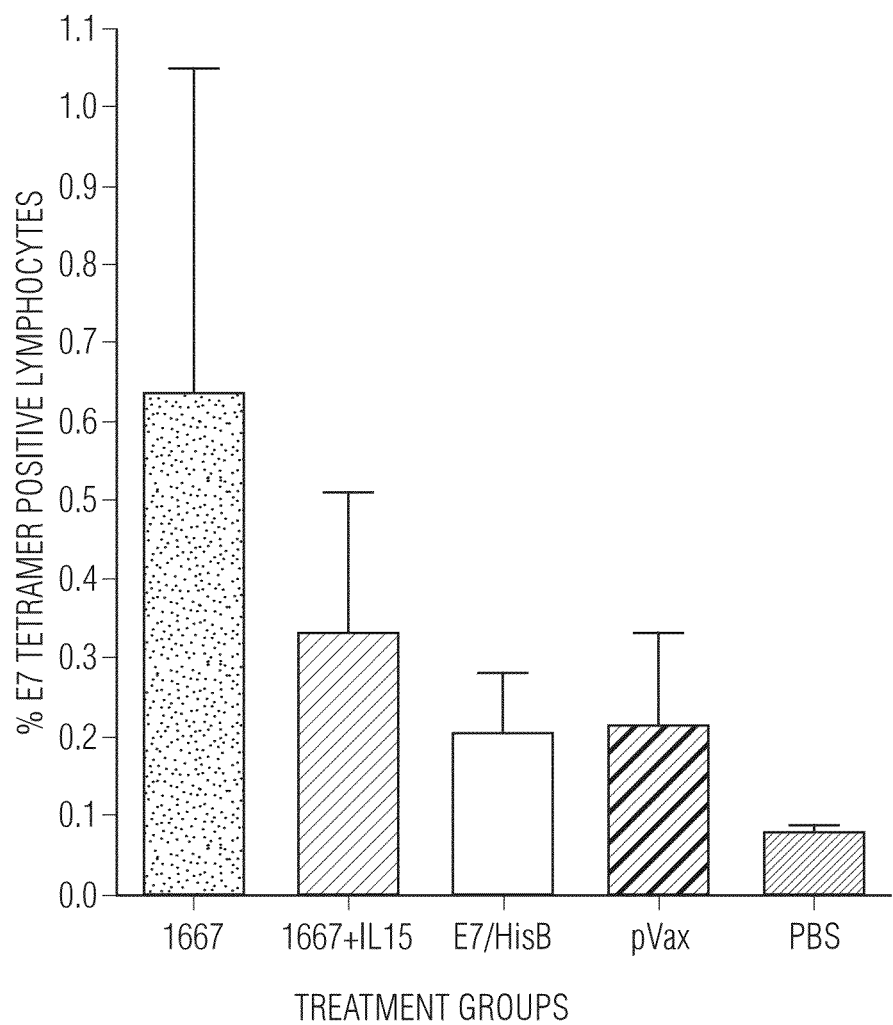
FIG. 29 shows the data from experiments detecting E7 Tetramer positive lymphocytes in spleens.

The level of E7 Tetramer positive lymphocytes in spleens was determined. FIG. 29 shows the data as the percent E7 Tetramer positive lymphocytes. DNA vaccine p1667 induces the activation of E7-specific CD8+ T cells that are CD62L$^{lo}$ within spleens.

Figure 30:
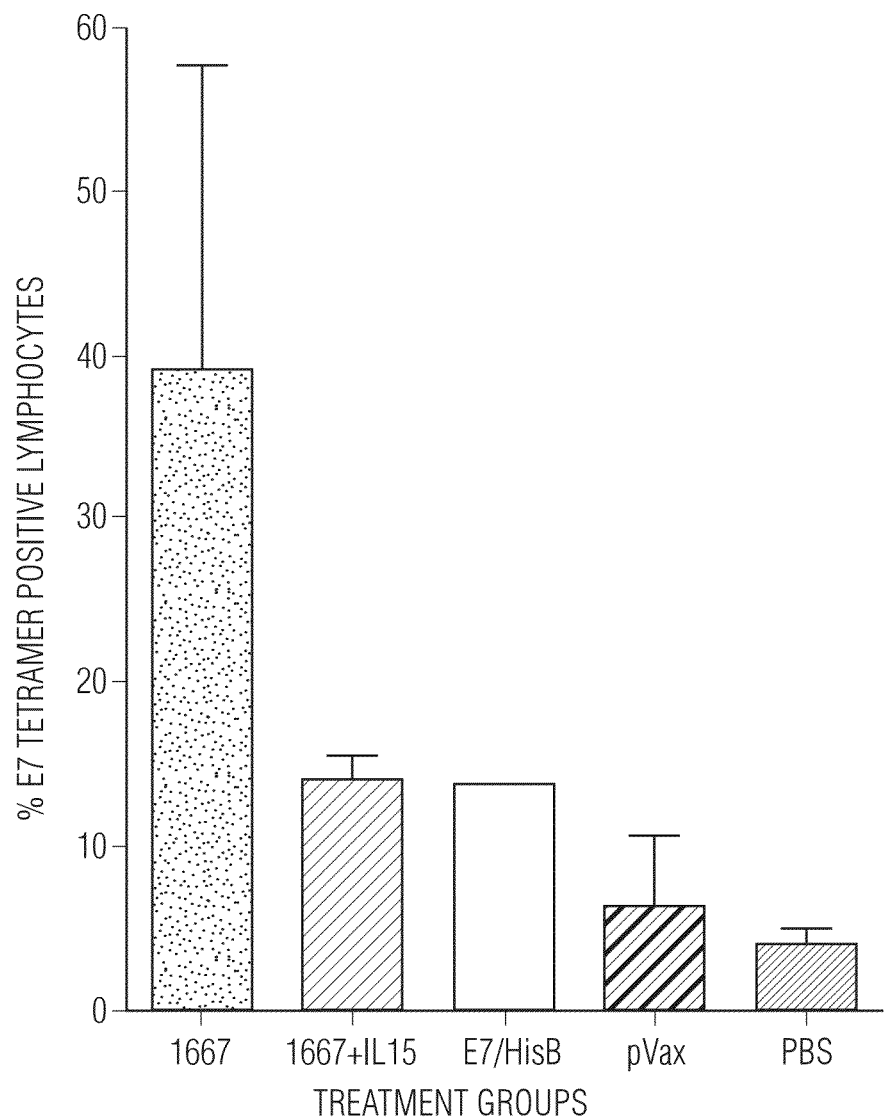
FIG. 30 shows the data from experiments detecting E7 Tetramer positive lymphocytes in tumors.
Figure 31:
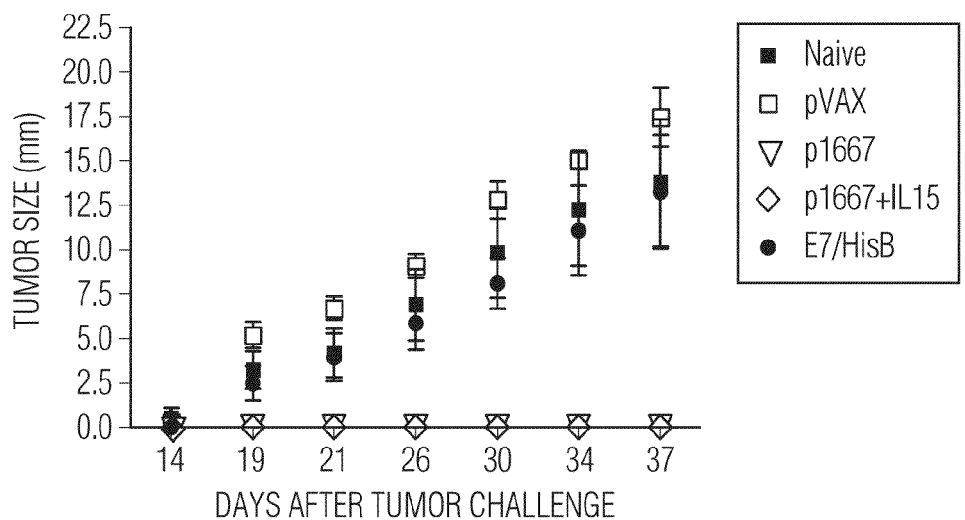
FIG. 31 shows data from a DNA Vaccine protection study in transgenic mice.
Figure 32:
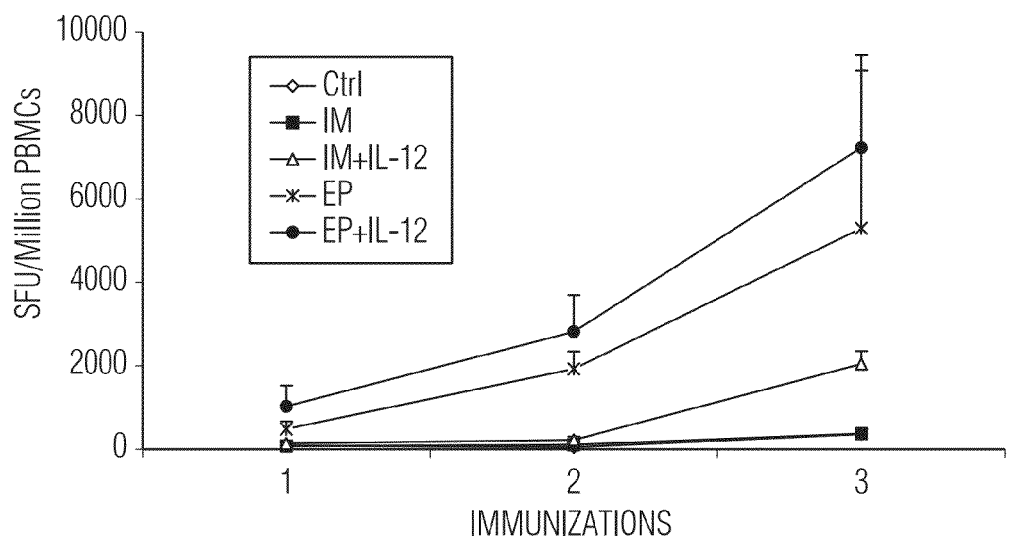
FIG. 32 shows enhanced cellular immune responses to HIV-1 consensus immunogens with IM co-injection of plasmid encoded IL-12 followed by electroporation (EP). IFNγ ELISpots were performed two weeks after the (a) first immunization, (b) second immunization, and (c) third immunization (as seen in comparison to the other three). Responses to env are depicted as black bars and gag are depicted as white bars with the data shown as stacked group mean responses±SEM.
Figure 33:
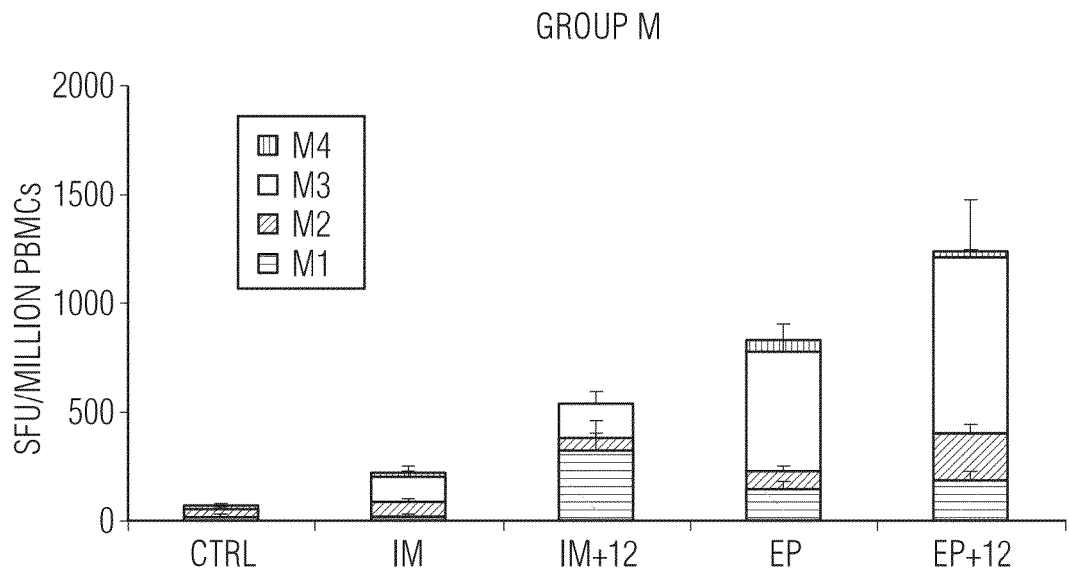
FIG. 33 shows enhanced cross-reactive cellular immune responses with intramuscular electroporation. After three immunizations, the total T-cell immune response in pEY2E1-B immunized macaques against four peptide pools of the HIV-1 group M peptides were determined by IFNγ ELISpot. The data are shown as stacked group means±SEM.
Figure 34:
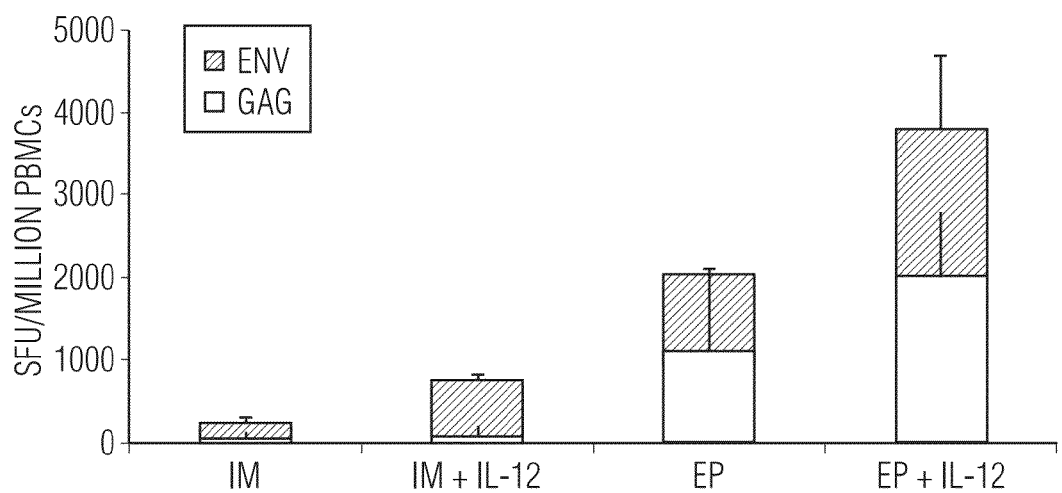
FIG. 34 shows Enhanced memory responses to HIV-1 immunogens with IM electroporation and plasmid IL-12. Five months after the last immunization, ELISpot assays were performed to determine antigen-specific memory responses to gag and env in the IM and EP immunized groups with and without co-immunization with the IL-12 plasmid. The data are shown as group mean responses±SEM.

The level of E7 Tetramer positive lymphocytes in tumors was determined. FIG. 30 shows the data as the percent E7 Tetramer positive lymphocytes. DNA vaccine p1667 induces the activation of E7-specific CD8+ T cells that are CD62L$^{lo}$ within tumors A E6/E7 DNA Vaccine protection study in transgenic mice was undertaken. A comparison was made among naive, pVAX, p1667, P1667+IL-15 and E7/HisB. Data is shown in FIG. 31. p1667 and p1667 IL-15 protected completely.

The data presented herein support the following conclusions. The p1667 construct induces a strong cellular immune response capable of inducing E7-specific CD8+ lymphocytes that mediate the elevated IFN-g responses. We have identified both dominant and novel sub-dominant HPV-16 epitopes against which antigen-specific CTL are generated after administration of the DNA construct. The p1667 construct is capable of preventing tumor growth and causing the regression of tumors in both C57/BL6 and transgenic mice. DNA vaccine p1667 shows great potential for a novel therapeutic strategy to target microscopic HPV-associated cancer.

Example 4

Nucleic acid sequences encoding HIV Env consensus sequences may be administered as DNA vaccines in combination with nucleic acid sequences encoding various other HIV proteins such as Gag, Pol, Gag/Pol, Nef, Vif, and Vpr using for example electroporation technology for intramuscular or intradermal delivery. Multivalent/polyvalent HIV vaccine constructs may provide enhanced immune responsed and be particularly useful. In some embodiments, IL-12 coding sequences are additional provided. U.S. Patent application publication number 20070106062, which is incorporated herein by reference, discloses an HIV Vif DNA vaccine. U.S. Patent application publication number 20040106100, which is incorporated herein by reference, discloses HIV vaccines comprising HIV accessory proteins as well as the sequences of such proteins which may be used to prepare additional vaccine constructs. U.S. Pat. Nos. 6,468,982, 5,817,637, and 5,593,972, which are incorporated herein be reference disclose DNA vaccines including HIV gag, HIV pol and HIV gag/pol constructs. Electroporation is described in U.S. Pat. No. 7,245,963, which is incorporated by reference. PCT application PCT/US97119502, which is incorporated herein be reference, discloses IL-12 constructs. U.S. Application Publication No. 20070041941 which is incorporated herein be reference, discloses constructs encoding IL-15.

Example 5

Two groups of macaques were IM immunized three times with optimized plasmid gag and env constructs with or without plasmid IL-12. The same immunization strategy was used for two additional groups but the plasmids were delivered with or without in vivo electroporation.

Cellular responses were determined by IFNγ ELISpot after each immunization and five months later for memory responses. Throughout the study humoral responses were evaluated by recombinant p24 and gp160 ELISA. The proliferative capacity of antigen-specific T cells were determined by CFSE staining. Intracellular cytokine staining was done to further characterize the functional characteristics of the induced T-cell response.

Plasmid IL-12 enhanced cellular responses to our optimized constructs. However the use of electroporation to enhance the delivery of plasmids was able to improve both the cellular and humoral response compared to IM immunization with plasmid IL-12. The combination of plasmid IL-12 and electroporation resulted in the best immune responses, both primary and memory, as measured by a variety of parameters.

Optimized DNA constructs encoding HIV gag and env in rhesus macaques in the presence or absence of plasmid IL-12 as a DNA adjuvant was compared. IL-12 could substantially increase T cell responses 5-fold in a quantitative ELISpot format resulting in substantially better memory T cell responses. However, EP delivered DNA was more efficient at generating T cell responses and memory that were 2-fold higher compared to the IL-12 IM adjuvanted DNA vaccine. The best responses were observed in the combination arm of EP+IL-12 adjuvant. Memory responses in this arm were 10-fold higher than the IM DNA alone and almost 2-fold higher than EP alone. We also observed 4-fold better immune expansion by CFSE in the EP+IL-12 arm compared to EP alone. The presence of polyfunctional T cells also suggested that the DNA+cytokine+EP arm is most effective.

Materials and Methods
Animals:
Rhesus macaques (*Macaca mulatta*) were housed at BIOQUAL, Inc. (Rockville, Md.), in accordance with the standards of the American Association for Accreditation of Laboratory Animal Care. Animals were allowed to acclimate for at least 30 days in quarantine prior to any experimentation.
Immunization:
Five rhesus macaques were immunized at weeks 0, 4, and 11 with 1.0 mg of pGag4Y and pEY2E 1-B. The DNA at each immunization time point was delivered into two injection sites, one in each quadriceps muscle. Three of the macaques were electroporated following IM injection. Another group of five macaques were immunized at weeks 0, 4, and 8 with 1.0 mg of pGag4Y, pEY2E1-B, and WLV104. Of the five animals, two animals received the immunization by IM injection and three animals were electroporated following IM injection. All electroporation procedures were performed using the constant current Cellectra™ device (VGX Immune Therapeutics Division of VGX Pharmaceuticals, The Woodlands, Tex.). Electroporation conditions were 0.5 Amps, 3 pulses, 52 msec pulse length with 1 sec between pulses. This software-controlled device was designed to measure the tissue resistance immediately prior to plasmid delivery and generation of constant current square wave pulses, eliminating the risk of delivery outside the muscle tissue and potential plasmid loss.

Blood Collection:

Animals were bled every two weeks for the duration of the study. 10 mL of blood were collected in EDTA tubes. PBMCs were isolated by standard Ficoll-hypaque centrifugation and then resuspended in complete culture medium (RPMI 1640 with 2 mM/L L-glutamine supplemented with 10% heat-inactivated fetal bovine serum, 100 IU/mL penicillin, 100 μg/mL streptomycin, and 55 μM/L β-mercaptoethanol.) RBCs were lysed with ACK lysis buffer (Cambrex Bio Science, East Rutherford, N.J.).

Plasmids and Plasmid Products:

Gag4Y contains an expression cassette encoding for a consensus sequence of the gag protein of HIV clades A, B, C, and D with several modifications including: the addition of a kozak sequence, a substituted IgE leader sequence, codon and RNA optimization for expression in mammalian cells (SEQ ID NO: 11 discloses HIV Gag consensus sequence.). The Gag4Y gene was subcloned into the expression vector, pVax, for further study. pEY-2E1-B contains an expression cassette encoding for a consensus sequence of the envelope of HIV clade B. (SEQ ID NO:3 discloses HIV Env consensus sequence.) WLV104M is a plasmid encoding a rhesus IL-12 gene. Plasmids were produced at Aldevron (Fargo, N. Dak.), and re-formulated at VGX Immune Therapeutics (The Woodlands, Tex.), in sterile water for injection with low molecular weight 0.1% poly-L-glutamate sodium salt CFSE of Cryo-Preserved PBMCs Cryo-preserved PBMCs were quick-thawed in a 37° C. water bath and washed with complete media. Cells were incubated overnight in a 37° C. incubator and cell counts were obtained the following day. Cells were pelleted and resuspended in 1 ml CFDA SE (Molecular Probes, Eugene, Oreg.) in PBS (1:2000 dilution). Cells were incubated at 37° C. for 10 min. Cells were washed with complete media and resuspended to a concentration of 1×10$^6$ cells/100 ul and plated in 96 well round bottom plates with 100 ul of 2 μg/ml recombinant HIV-1 p24 or gp120 (ImmunoDiagnostics, Woburn, Mass.) plus peptide pools. 5 μg/ml Concavalin A (positive) and complete media (negative) were used as controls. Cultures were incubated for 5 days. Cells were first stained with Vivid dye violet, a live/dead cell marker, for 15 min on ice. Cells were washed once with PBS. Cells were then stained using anti-human CD3-PE (clone SP34-2) (BD Pharmingen) and anti-human CD4-PerCP (clone L200), anti-human CD8-APC (SK1) for 1 hour at 4° C. Cells were then washed twice with PBS and fixed with 1% paraformaldehyde. Data was collected using a LSRII flow cytometer (BD Biosciences, Franklin Lakes, N.J.). Flow cytometry data was analyzed using FlowJo software (Tree Star, Ashland, Oreg.), gating on CD3$^+$ lymphocytes. Thirty to fifty thousand CD3$^+$ lymphocytes were collected per sample.

Enzyme Linked Immunosorbant Assay (ELISA):

Ninety-six well plates were coated overnight with 100 ng/well of recombinant HIV-1 IIIB p24 or gp120 (ImmunoDiagnostics) to determine HIV gag and env responses respectively. Plates coated with 100 ng/well of bovine serum albumin served as a negative control. Plates were blocked with 3% BSA-PBST for 1 hour at 37° C. Plates were then incubated with four-fold serial serum dilutions for 1 hour at 37° C. Goat anti-monkey IgG horseradish peroxidase conjugated antibody was then added at a 1:10,000 dilution (MP Biomedicals, Aurora, Ohio) to the plates and incubated for 1 hour at 37° C. Tetramethylbenzidine (R&D systems, Minneapolis, Minn.) was used to develop the plates and reactions were stopped with 2N $H_2SO_4$. Optical densities (OD) were then measured.

IgG end-point titers were defined as the reciprocal serum dilution that resulted in OD values that were greater than twice the average OD value of the BSA wells.

Enzyme Linked Immunospot Assay (ELISpot)

Antigen specific responses were determined by subtracting the number of spots in the negative control wells from the wells containing peptides. Results are shown as the mean value (spots/million splenocytes) obtained for triplicate wells.

1. Intracellular Cytokine Staining

Antibody Reagents

Directly conjugated antibodies were obtained from the following: BD Biosciences (San Jose, Calif.): IL-2 (PE), CD3 (Pacific Blue), IFN-γ (PE-Cy7), and TNF-α (Alexa Fluor 700), CD8 (APC) and CD4 (PerCP).

Cell Stimulation and Staining

PBMCs were resuspended to 1×10$^6$ cells/100 ul in complete RPMI and plated in 96 well plates with stimulating peptides 100 ul of 1:200 dilutions. An unstimulated and positive control (Staphylococcus enterotoxin B, 1 μg/mL; Sigma-Aldrich) was included in each assay. Cells were incubated for 5 hours at 37° C. Following incubation, the cells were washed (PBS) and stained with surface antibodies. The cells were washed and fixed using the Cytofix/Cytoperm kit (BD PharMingen, San Diego, Calif.) according to instructions. Following fixation, the cells were washed twice in the perm buffer and stained with antibodies against intracellular markers. Following staining, the cells were washed, fixed (PBS containing 1% paraformaldehyde), and stored at 4° C. until analysis.

Flow Cytometry

Cells were analyzed on a modified LSR II flow cytometer (BD Immunocytometry Systems, San Jose, Calif.). Fifty thousand CD3+ events were collected per sample. Data analysis was performed using FlowJo version 8.4.1 (TreeStar, San Carlos, Calif.). Initial gating used a forward scatter area (FSC-A) versus height (FSC-H) plot to remove doublets. The events were subjected to a lymphocyte gate by a FSC-A versus SSC plot. Following this, events are sequentially gated on CD3$^+$, CD8$^+$, and CD4$^−$ events versus IFN-γ to account for down-regulation. Following identification of CD8$^+$ T cells, a gate was made for each respective function using combinations that provided optimal separation. After the gates for each function were created, we used the Boolean gate platform to create the full array of possible combinations, equating to 8 response patterns when testing 3 functions. Data are reported after background correction. Thresholds for positive responses were 10 events or 0.05%.

Statistical Analysis

Data are analyzed using Prism Graphpad software, and is expressed as means±SEM.

Results

ELISpot Analysis the induction of the cellular immune response was evaluated after each immunization by IFNγ ELISpot. After a single immunization (FIG. 1), the group receiving plasmid DNA by IM injection alone displayed weak cellular responses (74±29 SFU/10⁶ PBMCs). Co-immunization with rhesus IL-12 plasmid resulted in a higher response (136±51.4 SFU/10⁶ PBMCs). The electroporated (EP) group had an average response that was six times higher than the IM group (482±181 SFU/10⁶ PBMCs). The combination of IL-12 co-immunization with EP further doubled the number of IFNγ-producing cells (1030±494 SFU/10⁴ PBMCs).

After two immunizations (FIG. 1), the IM and IM+IL-12 groups had a modest increase in ELISpot counts (104±67.9 SFU/10⁶ PBMCs and 223±76.6 SFU/10⁶ PBMCs, respectively). EP group had responses that were almost four fold higher (1924±417 SFU/10⁶ PBMCs) than the previous immunization and the EP+IL-12 group had again doubled the number of IFNγ-producing cells (2819±872 SFU/10⁶ PBMCs) compared to the EP arm alone.

After the third immunization (FIG. 1), the number of antigen specific cells in the EP group was more than a log higher than that of the IM group (5300±3781 and 370±110 SFU/10⁶ PBMCs, respectively). The IM+IL-12 group also had a dramatic increase in cellular responses with ELISpot counts that were nearly a log higher than the previous immunization (2042±311 SFU/10⁶ PBMCs). As with the other two immunizations, the EP+IL-12 group was the most potent of all the vaccination groups (7228±2227 SFU/10⁶ PBMCs).

Induction of Cross-Reactive Envelope Responses

A successful HIV vaccine will require the induction of a cross-reactive immune responses in this regard it was interesting to see if EP+IL-12 could improve the magnitude of cross-reactivity to divergent peptide libraries. We compared the cross-reactive CTL responses induced by the env antigen using a peptide library from a consensus group M. Cross-reactivity was observed in all groups. However the results displayed the same magnitude differences observed in the subtype B ELISpot analysis (FIG. 2). After 3 immunizations, the IM group had the lowest response to the group M envelope peptides (222±SEM SFU/10⁶ PBMCs). The addition of IL-12 doubled the response (540±SEM SFU/10⁶ PBMCs). Higher group M envelope responses were induced with EP (830±SEM SFU/10⁶ PBMCs), which were further enhanced with IL-12 co-injection (1238±SEM SFU/10⁶ PBMCs).

1. Memory T Cell Responses

An important issue is to be able to improve the generation of memory responses with the DNA platform. We performed ELISpot analysis five months after the last DNA vaccination (FIG. 3). In the IM groups, the addition of plasmid IL-12 resulted in nearly a 10-fold increase in memory cells (751±11.1 and 78.6±16.9 SFU/10⁶ PBMCs). It is clear that IL-12 can positively impact this important T cell phenotype. The number of antigen-specific IFNγ producing cells was substantial in the EP group as well, however the IL-12 adjuvant EP resulted in the most robust memory response (1231±523.5 and 3795±1336 SFU/10⁶ PBMCs respectively), a response showing that the combined technology drives very strong T cell memory responses.

Humoral Immune Responses to DNA Vaccines

A weakness of IM DNA vaccine technology lies in its inability to induce clear antibody responses in non-human primates and in human clinical studies. We evaluated each group's ability to induce both HIV-1 gag and env specific antibody titers to recombinant p24 and gp160 antigens in an ELISA format. For both antigens, the IM and IM+IL-12 groups did not show significant antibody titers (<1:50 endpoint titer). The electroporated groups exhibited dramatically higher gag antibody titers that were able to bind to recombinant p24. Although both the EP and the EP+IL-12 groups had similar endpoint titers at week 12 (22,400 and 12,800 respectively), the EP+IL-12 group generated a more efficient antibody response. That response appeared earlier in the immunization scheme and rose to the maximum level quickest. The env antibody responses also reflected the results we observed with the gag antigen, albeit with Lower endpoint titers.

CD4⁺ and CD8⁺ T Cell Proliferation

Having observed substantial ELISpot responses, we next examined additional parameters of cellular immunity. We examined the ability of gag specific CD4⁺ and CD8⁺ T cells to proliferate in vitro following peptide stimulation among the different immunization arms. Cryo-preserved samples, collected two weeks after the final immunization, were stimulated and analyzed by CFSE assay. The average CD4⁺ response increased similar to that observed in the ELISpot assay. By comparison, the CD8 proliferation induction was much more dramatic in magnitude. We observed that IL-12 increased CD8⁺ T cell proliferation over IM alone and EP was substantially higher. The EP+IL-12 group had the highest percentage of CD8⁺ cells that were able to proliferate after in vitro stimulation (2.51±SEM % and 4.88±SEM %, respectively). Obvious CD8 T cell proliferation bands were observed in the EP+IL-12 arm, demonstrating the potent proliferative potential of this combined immunization.

Polyfunctional CD8⁺ T Cell Responses

Although we have clearly observed the induction of a robust IFNγ effector response following EP and IL-12 co-immunization, we wanted to further characterize the functions of the antigen specific CD8⁺ T cell responses in the various arms. Samples taken three months following the final immunization were stimulated with gag peptides and stained for intracellular cytokine production of IFNγ, TNFα and IL-2. Out of all groups, only one animal in the IM+IL-12 and one animal in the EP only group had a detectable IFNγ response. However two out of the three animals in the EP+IL-12 immunized group had gag-specific IFNγ producing CD8⁺ T cells. The IM+IL-12 responder had a small percentage of polyfunctional cells that stained for all three cytokines as well as a population that had lost its ability to produce IL-2. The EP responder had slightly higher polyfunctional responses that were comprised of four different populations. The most dramatic response was seen in the second EP+IL-12 animal. More than 2% of its CD8⁺ T cells were able to produce all three cytokines and 2% were able to produce both IFNγ and TNFα. Clearly the number of animals in each group is low and requires additional primate studies to confirm these results, however collectively the trends observed appear clear and encouraging.

Discussion

IL-12 as a DNA vaccine adjuvant improved ELISpot responses several fold over plasmid alone. In addition proliferation was clearly enhanced. The EP group exhibited a higher average response than either IM group alone or the IM+IL-12 arm exhibiting a combined ELISpot response that was 3× higher than the IM+IL-12 group. The best ELISpot responses were observed in the EP+IL-12 arm, which was almost 4× over the IM+IL-12 arm 19×IM alone.

After each immunization the magnitude of the antigen-specific response by IFNγ ELISpot was determined. After a single immunization all of the animals in the EP and EP+IL-12 groups not only had detectable responses, they had averages that were higher than those seen in the IM group after three immunizations. After two immunizations, IFNγ responses in the EP and EP+IL-12 groups were comparable to responses that have been reported in studies using viral vectors. Substantial memory responses were observed in the IM+IL-12 and both EP groups five months after the last immunization.

IM immunization, with or without IL-12, did not result in a significant amount of antibody. Electroporation was able to enhance the humor immune response as reported previously. All of the animals in the electroporated groups seroconverted.

Although the EP and the EP+IL-12 groups had similar endpoint titers after three immunizations the kinetics of antibody induction was slightly faster in the EP+IL-12 group.

The proliferative capacity of CD8 T cells appeared to be enhanced with EP and plasmid IL-12. This data supports the memory expansion observed in the ELISpot assay where expansion of antigen specific T cell is likely a result of the enhanced proliferative potential of the EP+IL-12 arm.

The invention claimed is:

1. A nucleic acid molecule comprising a nucleotide sequence selected from the group consisting of: SEQ ID NO:34; and a nucleotide sequence having at least 90% homology to SEQ ID NO:34.

2. The nucleic acid molecule of claim 1, wherein the nucleic acid molecule comprises the nucleotide sequence of SEQ ID NO:34.

3. The nucleic acid molecule of claim 1 selected from the group consisting of: a nucleic acid molecule comprising a nucleotide sequence having at least 95% homology to SEQ ID NO:34; a nucleic acid molecule comprising a nucleotide sequence having at least 98% homology to SEQ ID NO:34; and a nucleic acid molecule comprising a nucleotide sequence having at least 99% homology to SEQ ID NO:34.

4. A nucleic acid molecule comprising a nucleotide sequence that encodes SEQ ID NO:35.

5. The nucleic acid molecule of claim 1 wherein said molecule is a plasmid.

6. A pharmaceutical composition comprising a nucleic acid molecule of claim 1.

7. An injectable pharmaceutical composition comprising a nucleic acid molecule of claim 1.

8. A recombinant vaccine comprising a nucleic acid molecule of claim 1.

9. The recombinant vaccine of claim 8 wherein said recombinant vaccine is a recombinant vaccinia vaccine.

10. A live attenuated pathogen comprising a nucleic acid molecule of claim 1.

11. A method of inducing an immune response in an individual against hTERT comprising administering to said individual a composition comprising a nucleic acid molecule of claim 1.

12. A method of inducing an immune response in an individual against hTERT comprising administering to said individual a composition comprising a nucleic acid molecule of claim 4.

* * * * *